United States Patent
Yoon et al.

(10) Patent No.: US 12,060,372 B2
(45) Date of Patent: Aug. 13, 2024

(54) COMPOUND AND ORGANIC LIGHT EMITTING DEVICE COMPRISING THE SAME

(71) Applicant: LG CHEM, LTD., Seoul (KR)

(72) Inventors: Jung Min Yoon, Daejeon (KR); Kongkyeom Kim, Daejeon (KR); Ki Dong Koo, Daejeon (KR); Young Seok Kim, Daejeon (KR); Joongsuk Oh, Daejeon (KR); Min Woo Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 802 days.

(21) Appl. No.: 17/267,560

(22) PCT Filed: Aug. 26, 2019

(86) PCT No.: PCT/KR2019/010852
§ 371 (c)(1),
(2) Date: Feb. 10, 2021

(87) PCT Pub. No.: WO2020/045924
PCT Pub. Date: Mar. 5, 2020

(65) Prior Publication Data
US 2022/0017544 A1   Jan. 20, 2022

(30) Foreign Application Priority Data

Aug. 29, 2018 (KR) .......... 10-2018-0102199
Aug. 23, 2019 (KR) .......... 10-2019-0103963

(51) Int. Cl.
*C07F 7/08* (2006.01)
*C07C 211/61* (2006.01)
(Continued)

(52) U.S. Cl.
CPC .......... *C07F 7/0812* (2013.01); *C07C 211/61* (2013.01); *C07D 403/12* (2013.01);
(Continued)

(58) Field of Classification Search
None
See application file for complete search history.

(56) References Cited

U.S. PATENT DOCUMENTS

2003/0096117 A1   5/2003  Kawabata et al.
2004/0251816 A1  12/2004  Leo et al.
(Continued)

FOREIGN PATENT DOCUMENTS

CN           106397398         2/2017
JP             4157245         10/2008
(Continued)

OTHER PUBLICATIONS

Chen, C.-H., et al., "Synthesis and characterization of spiro(adamantane-2,9'-fluorene)-based triaryldiamines: 1 thermally stable hole-transporting materials," Synthetic Metals 143(2):215-220 (2004).

*Primary Examiner* — Long Pham
(74) *Attorney, Agent, or Firm* — Bryan Cave Leighton Paisner LLP

(57) ABSTRACT

Provided is a compound of Chemical Formula 1:

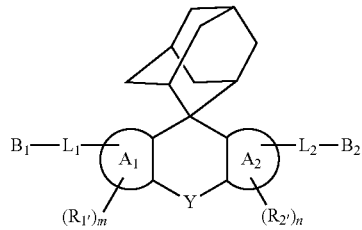

Chemical Formula 1 wherein:
Y is a direct bond, O or S;
(Continued)

$A_1$ and $A_2$ are each independently a benzene ring, a naphthalene ring, or

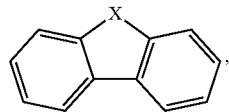

, with the proviso that at least one of them is a naphthalene ring or

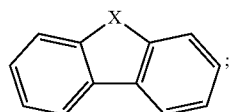

;

each X is independently $CR_1R_2$, $SiR_3R_4$, $NR_5$, O, S, or $SO_2$;

$R_1$ to $R_5$ are each independently hydrogen, deuterium, or a substituted or unsubstituted: $C_{1-60}$ alkyl, $C_{3-60}$ cycloalkyl, or $C_{6-60}$ aryl;

$L_1$ and $L_2$ are each independently a direct bond, or a substituted or unsubstituted $C_{6-60}$ arylene or $C_{2-60}$ heteroarylene;

$B_1$ and $B_2$ are each independently *—$NR_6R_7$; and $R'_1$ and $R'_2$ are each independently hydrogen, deuterium, halogen, cyano, or a substituted or unsubstituted: $C_{1-60}$ alky, $C_{1-60}$ alkoxy, $C_{1-60}$ haloalkyl, $C_{1-60}$ haloalkoxy, tri($C_{1-60}$ alkyl)silyl, or $C_{6-60}$ aryl; and and an organic light emitting diode comprising: a first electrode; a second electrode opposite to the first electrode; and at least one organic material layer between the first electrode and the second electrode, wherein the organic material layer contains the compound of Chemical Formula 1.

11 Claims, 1 Drawing Sheet

(51) Int. Cl.
| | | |
|---|---|---|
| *C07D 403/12* | (2006.01) | |
| *C07D 405/12* | (2006.01) | |
| *C07D 493/04* | (2006.01) | |
| *C07D 495/04* | (2006.01) | |
| *H10K 85/40* | (2023.01) | |
| *H10K 85/60* | (2023.01) | |
| *H10K 50/11* | (2023.01) | |
| *H10K 101/10* | (2023.01) | |

(52) U.S. Cl.
CPC ......... *C07D 405/12* (2013.01); *C07D 493/04* (2013.01); *C07D 495/04* (2013.01); *H10K 85/40* (2023.02); *H10K 85/622* (2023.02); *H10K 85/623* (2023.02); *H10K 85/624* (2023.02); *H10K 85/626* (2023.02); *H10K 85/633* (2023.02); *H10K 85/636* (2023.02); *H10K 85/6574* (2023.02); *H10K 85/6576* (2023.02); *H10K 50/11* (2023.02); *H10K 2101/10* (2023.02)

(56) References Cited

U.S. PATENT DOCUMENTS

| | | | |
|---|---|---|---|
| 2014/0346483 A1 | 11/2014 | Yu et al. | |
| 2016/0351818 A1 | 12/2016 | Kim et al. | |
| 2022/0017544 A1* | 1/2022 | Yoon | H10K 85/636 |

FOREIGN PATENT DOCUMENTS

| | | |
|---|---|---|
| KR | 10-2013-0073537 | 7/2013 |
| KR | 10-2016-0141359 | 12/2016 |
| KR | 10-2016-0141360 | 12/2016 |
| KR | 10-2017-0121575 | 11/2017 |
| KR | 10-2017-0136980 | 12/2017 |
| WO | 2001-060811 | 8/2001 |
| WO | 2003-012890 | 2/2003 |

* cited by examiner

【FIG. 1】
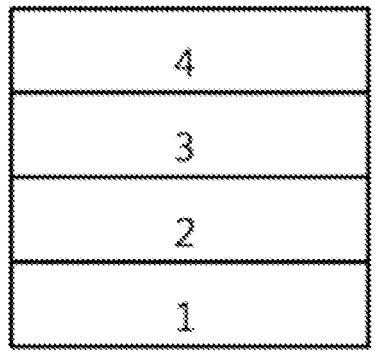
【FIG. 2】
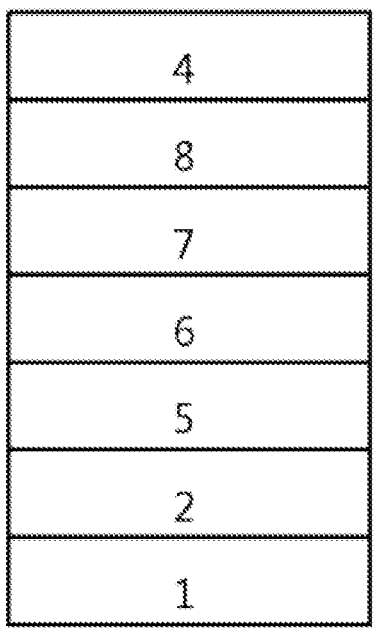

COMPOUND AND ORGANIC LIGHT EMITTING DEVICE COMPRISING THE SAME

CROSS-REFERENCE TO RELATED APPLICATIONS

This application is a National Stage Application of International Application No. PCT/KR2019/010852, filed on Aug. 26, 2019, which claims priority to or the benefit of Korean Patent Application No. 10-2018-0102199 filed with the Korean Intellectual Property Office on Aug. 29, 2018 and Korean Patent Application No. 10-2019-0103963 filed with the Korean Intellectual Property Office on Aug. 23, 2019, the disclosures of which are incorporated herein by reference in their entirety.

TECHNICAL FIELD

The present invention relates to a novel compound and to an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 0001) Korean Unexamined Patent Publication No. 10-2013-073537

BRIEF DESCRIPTION

Technical Problem

It is an object of the present invention to provide a novel compound and an organic light emitting device including the same.

Technical Solution

In one aspect of the invention, there is provided a compound of the following Chemical Formula 1.
A compound of the following Chemical Formula 1:

Chemical Formula 1

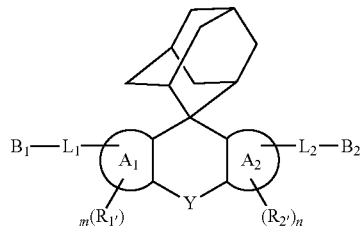

wherein, in Chemical Formula 1:
Y is a direct bond, O or S;
$A_1$ and $A_2$ are each independently a benzene ring, a naphthalene ring, or

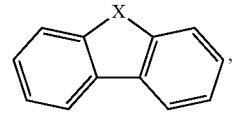

with the proviso that at least one of $A_1$ and $A_2$ is a naphthalene ring or

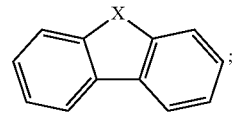

each X is independently $CR_1R_2$, $SiR_3R_4$, $NR_5$, O, S, or $SO_2$;
$R_1$ to $R_5$ are each independently hydrogen, deuterium, a substituted or unsubstituted $C_{1-60}$ alkyl, a substituted or unsubstituted $C_{3-60}$ cycloalkyl, or a substituted or unsubstituted $C_{6-60}$ aryl;
$L_1$ and $L_2$ are each independently a direct bond, a substituted or unsubstituted $C_{6-60}$ arylene, or a substituted or unsubstituted $C_{2-60}$ heteroarylene containing one or more heteroatoms selected from the group consisting of N, O and S;
$B_1$ and $B_2$ are each independently *—$NR_6R_7$;
$R_6$ and $R_7$ are each independently a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, a tri ($C_{1-60}$ alkyl) silyl, a substituted or unsubstituted $C_{6-60}$ aryl, a tri ($C_{6-60}$ aryl) silyl, a substituted or unsubstituted $C_{2-60}$ heteroaryl containing one or more heteroatoms selected from the group consisting of N, O and S, or are bonded to adjacent groups to form a substituted or unsubstituted condensed ring;
$R'_1$ and $R'_2$ are each independently hydrogen, deuterium, halogen, cyano, a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, a tri ($C_{1-60}$ alkyl) silyl, or a substituted or unsubstituted $C_{6-60}$ aryl; and
m and n are each independently an integer of 0 to 3.

In another aspect of the prevent invention, there is provided an organic light emitting device including a first electrode; a second electrode that is opposite to the first electrode; and one or more organic material layers that are between the first electrode and the second electrode, wherein one or more layers of the organic material layers include the compound of the present invention described above.

Advantageous Effects

The compound of Chemical Formula 1 described above can be used as a material of an organic material layer of an organic light emitting device, and can improve the efficiency, achieve low driving voltage and/or improve lifetime characteristics in the organic light emitting device. In particular, the compound of Chemical Formula 1 can be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8 and a cathode 4.

DETAILED DESCRIPTION

Hereinafter, embodiments of the present invention will be described in more detail to facilitate understanding of the invention.

The present invention provides a compound of Chemical Formula 1.

As used herein, the notation

and *— means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulas, but is not limited thereto:

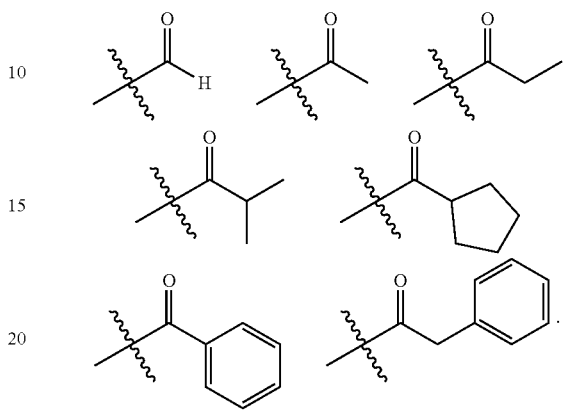

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having the following structural formulas, but is not limited thereto:

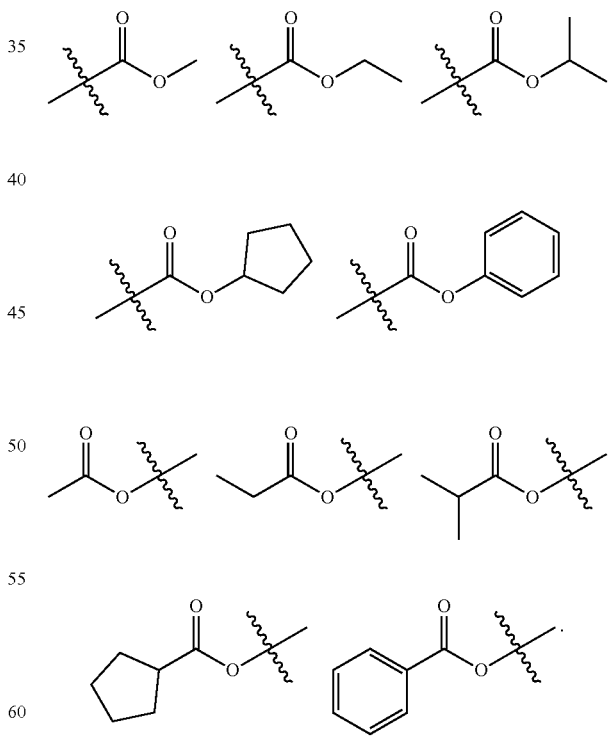

In the present specification, the number of carbon atoms of an imide group is not particularly limited, but is preferably 1 to 25. Specifically, the imide group can be a compound having the following structural formulas, but is not limited thereto:

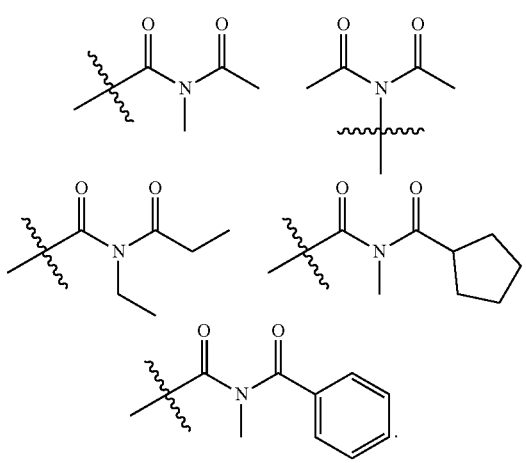

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group can be straight-chain or branched-chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexyl-methyl, octyl, n-octyl, tert-octyl, 1-methylheptyl, 2-ethylhexyl, 2-propylpentyl, n-nonyl, 2,2-dimethyl-heptyl, 1-ethyl-propyl, 1,1-dimethyl-propyl, iso-hexyl, 4-methylhexyl, 5-methylhexyl, and the like, but are not limited thereto.

In the present specification, the alkenyl group can be straight-chain or branched-chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and it can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group or the like, but is not limited thereto.

In the present specification, a fluorenyl group can be substituted, and two substituent groups can be bonded to each other to form a spiro structure. In the case where the fluorenyl group is substituted,

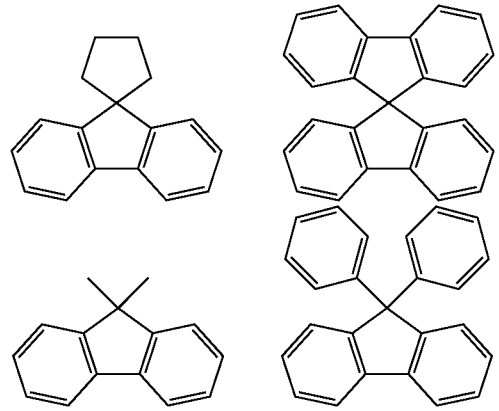

and the like can be formed. However, the structure is not limited thereto.

In the present specification, a heterocyclic group is a heterocyclic group including one or more of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heterocylic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocyclic group is not a monovalent group but formed by combining two substituent groups.

Preferably, the compound of Chemical Formula 1 is any one of the compounds of the following Chemical Formulas 1-1 to 1-3:

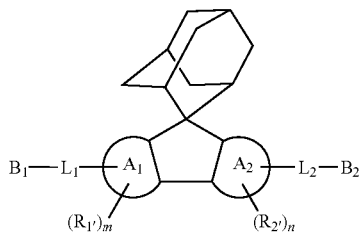

Chemical Formula 1-1

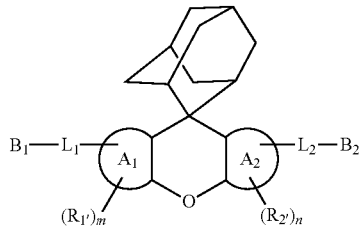

Chemical Formula 1-2

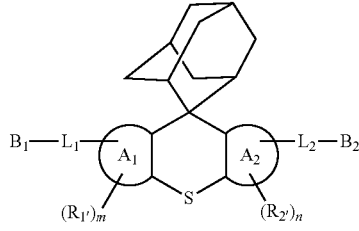

Chemical Formula 1-3 wherein:
$A_1$, $A_2$, $B_1$, $B_2$, $L_1$, $L_2$, $R'_1$, $R'_2$, m and n are as defined above.

Preferably, in Chemical Formula 1:
$A_1$ is a benzene ring, and $A_2$ is a naphthalene ring; or
$A_1$ is a naphthalene ring, and $A_2$ is a benzene ring; or
$A_1$ is a benzene ring, and $A_2$ is

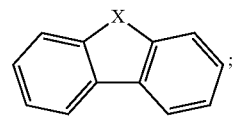

or
$A_1$ is

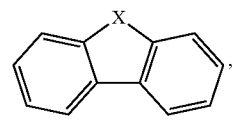

and $A_2$ is a benzene ring; or
$A_1$ is a naphthalene ring, and $A_2$ is

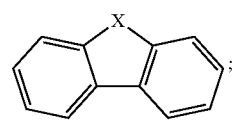

or
$A_1$ is

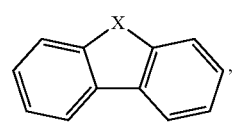

and $A_2$ is a naphthalene ring; or
$A_1$ is a naphthalene ring, and $A_2$ is a naphthalene ring; or
$A_1$ is

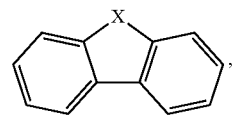

and $A_2$ is

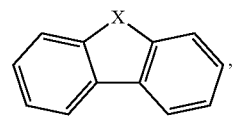

where X is as defined above.

Preferably, the compound of Chemical Formula 1 is any one selected from the group consisting of the following:

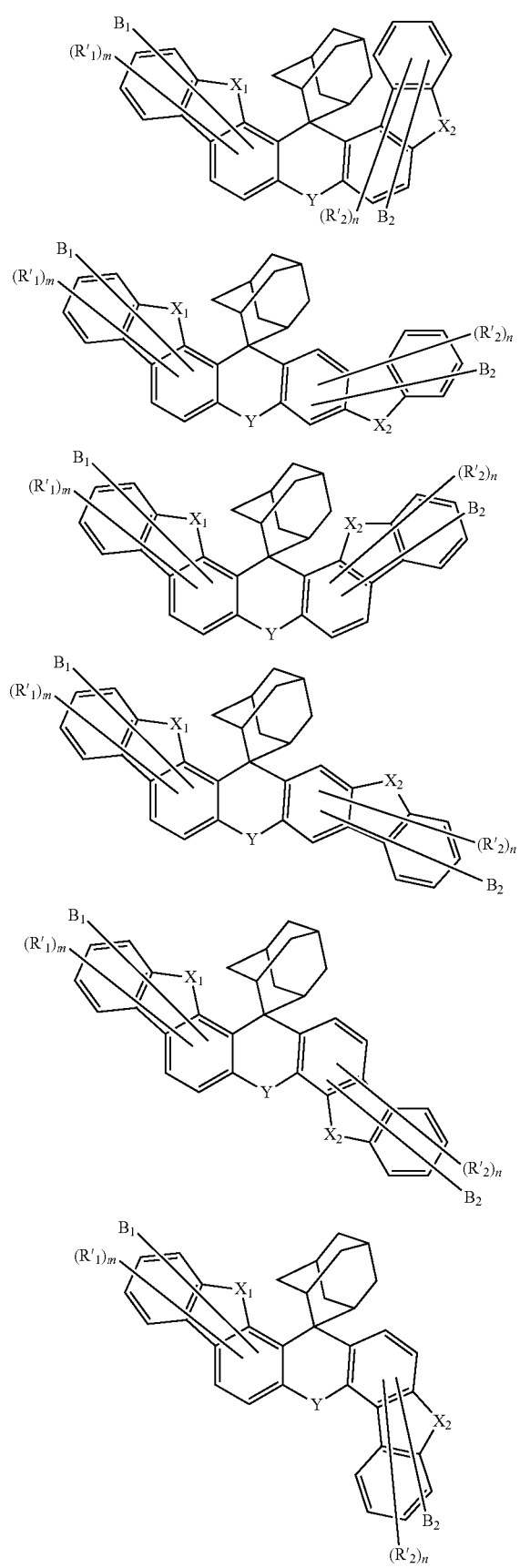
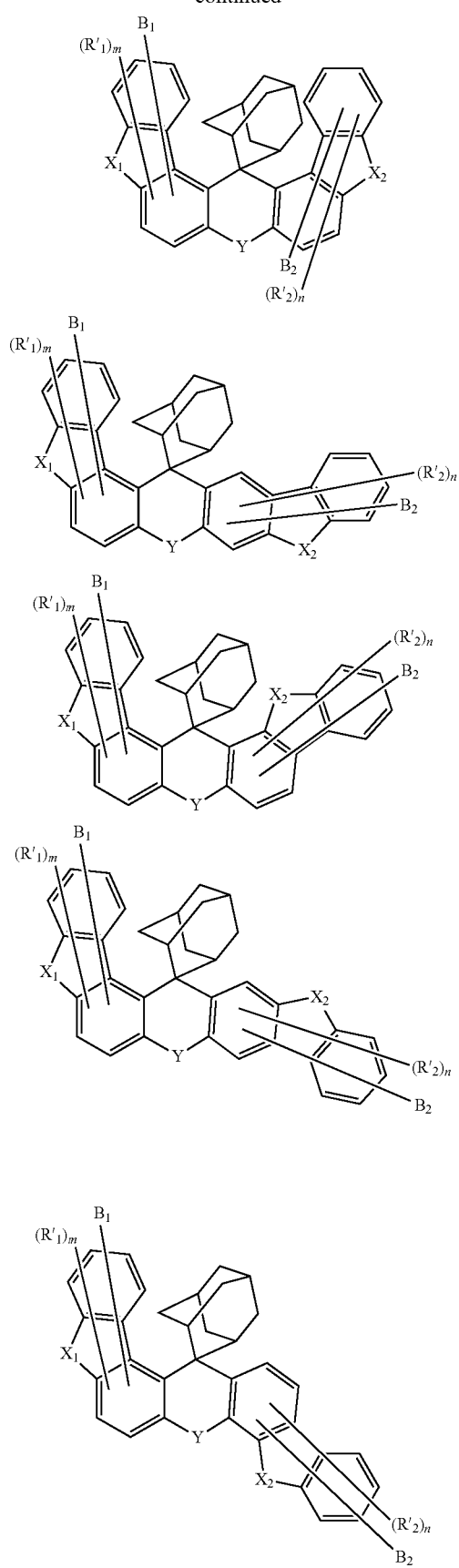

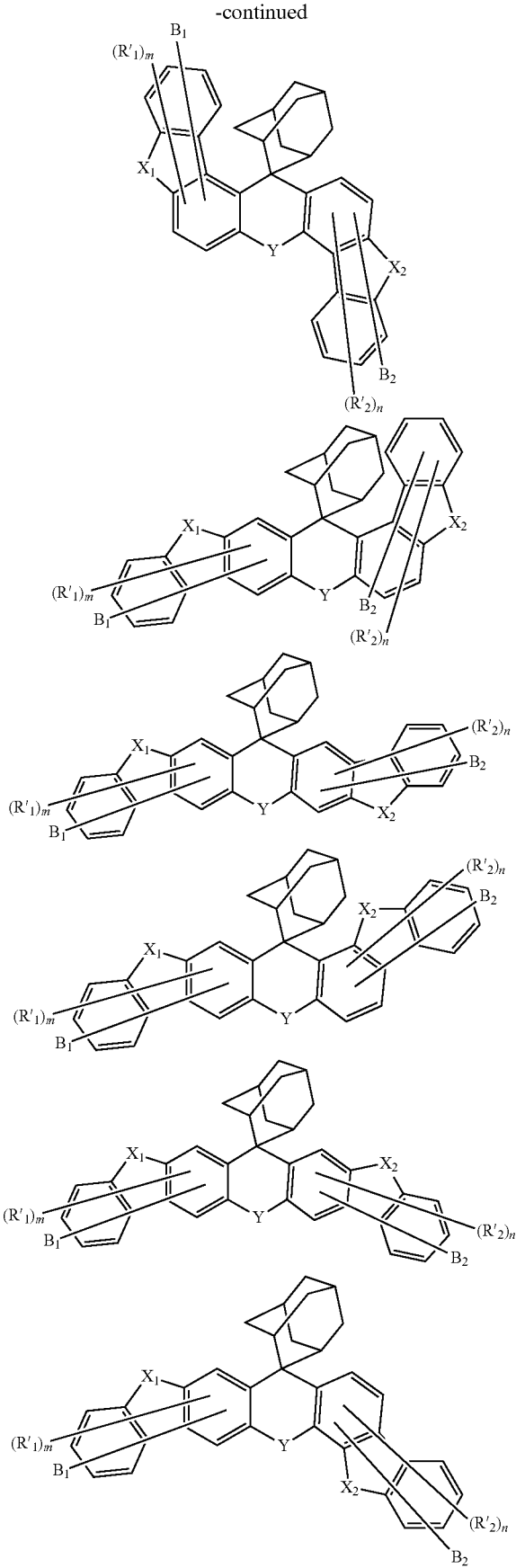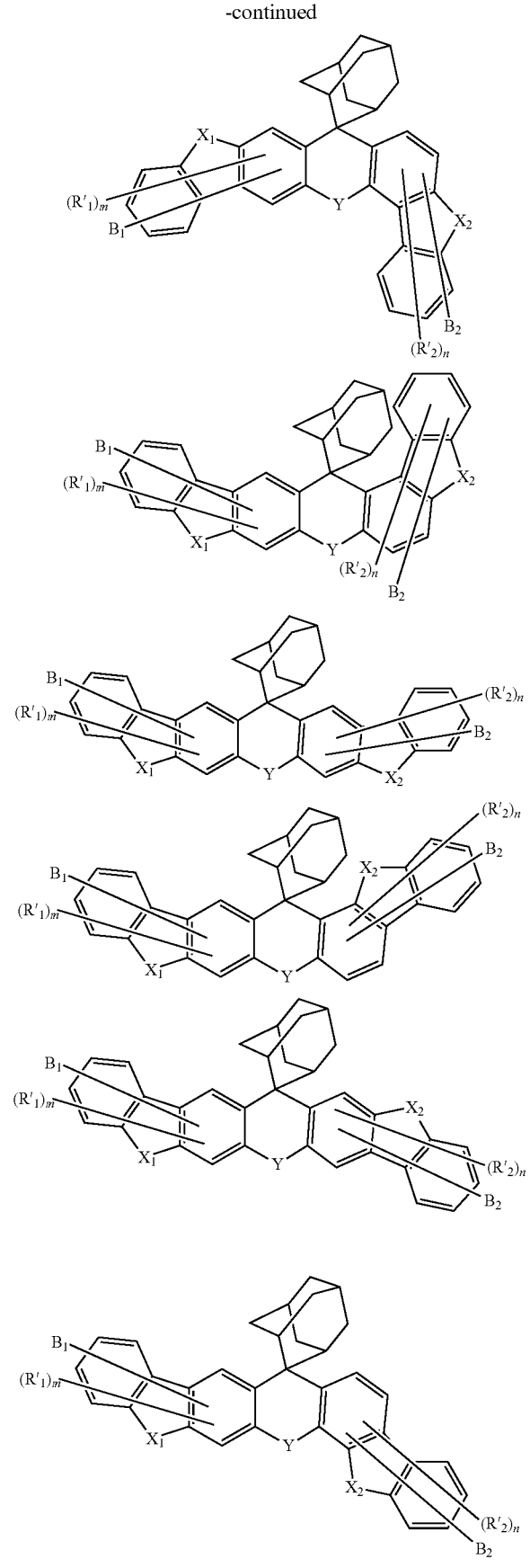

-continued
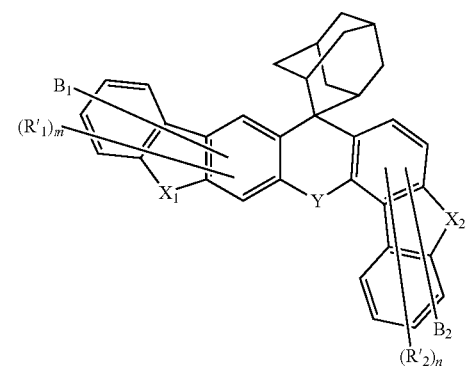
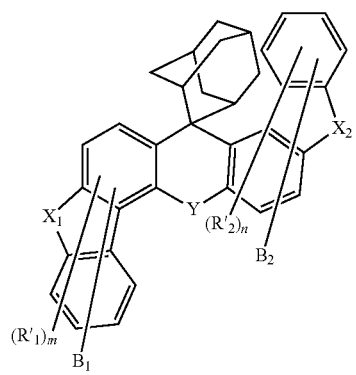
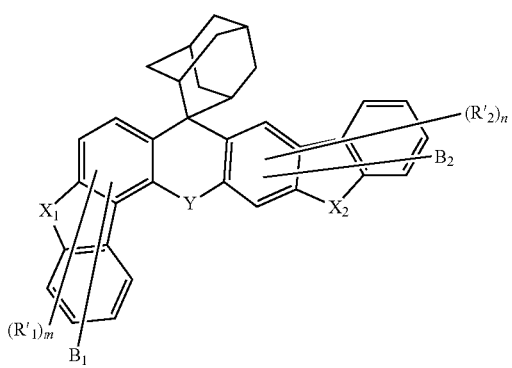
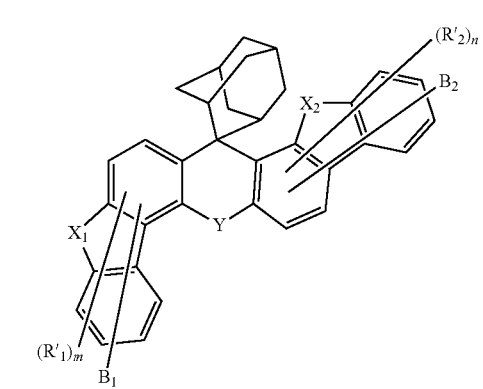
-continued
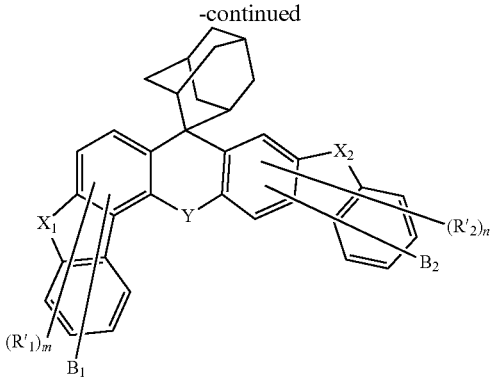
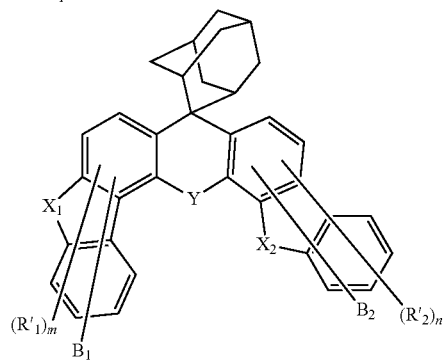
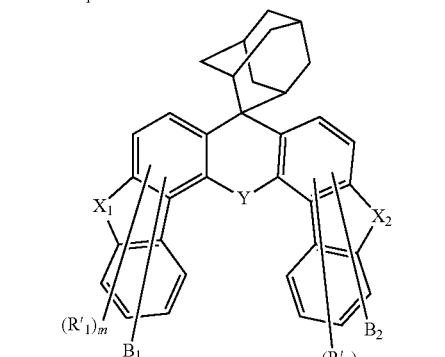
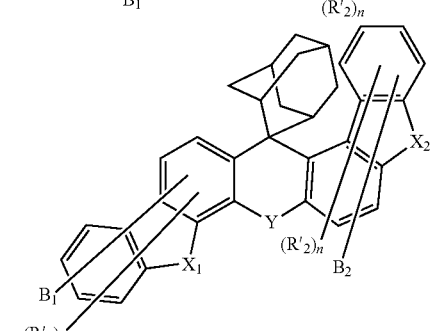
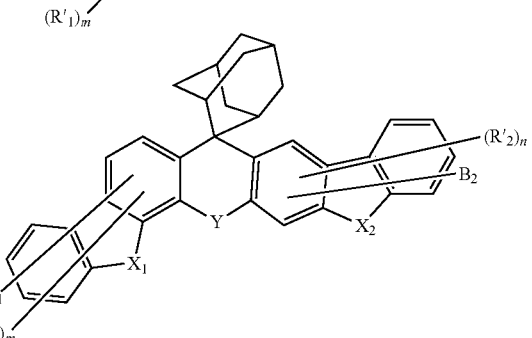

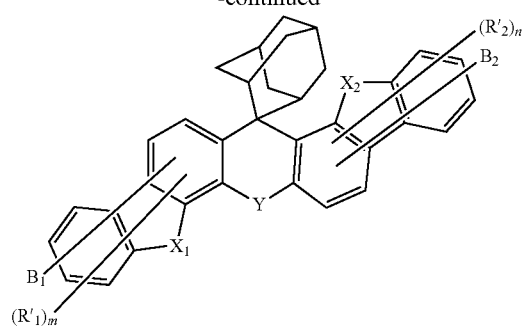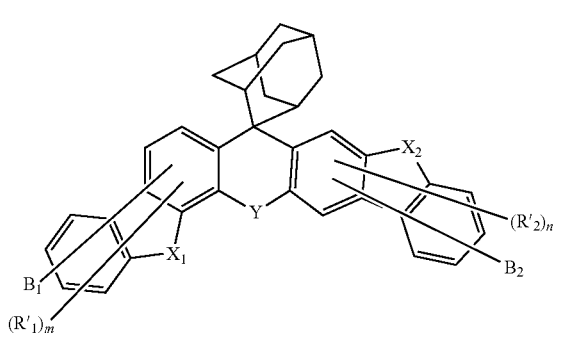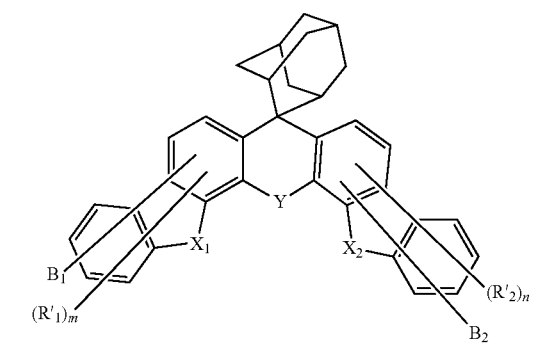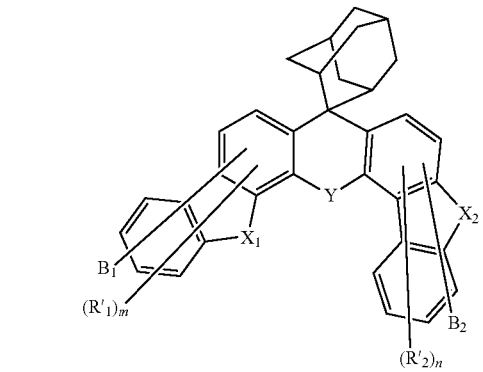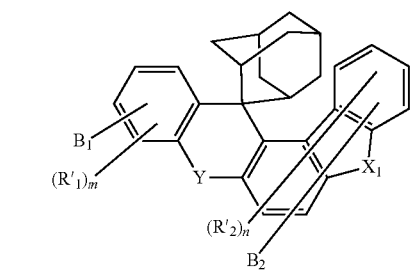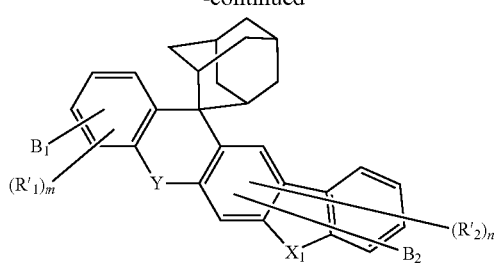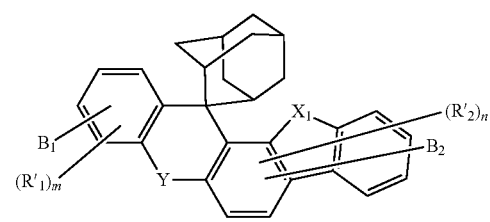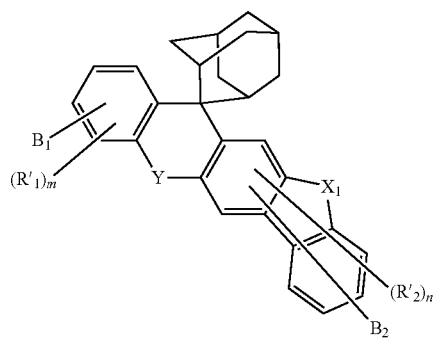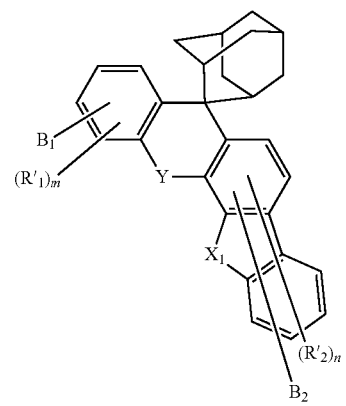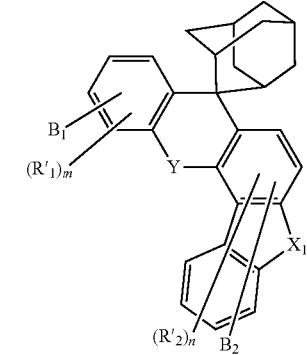

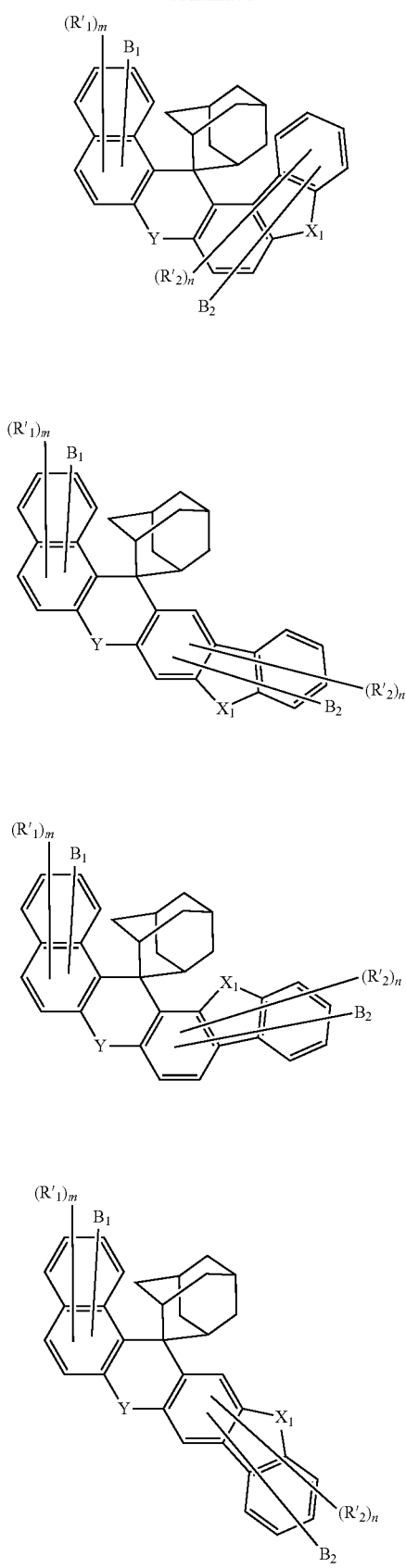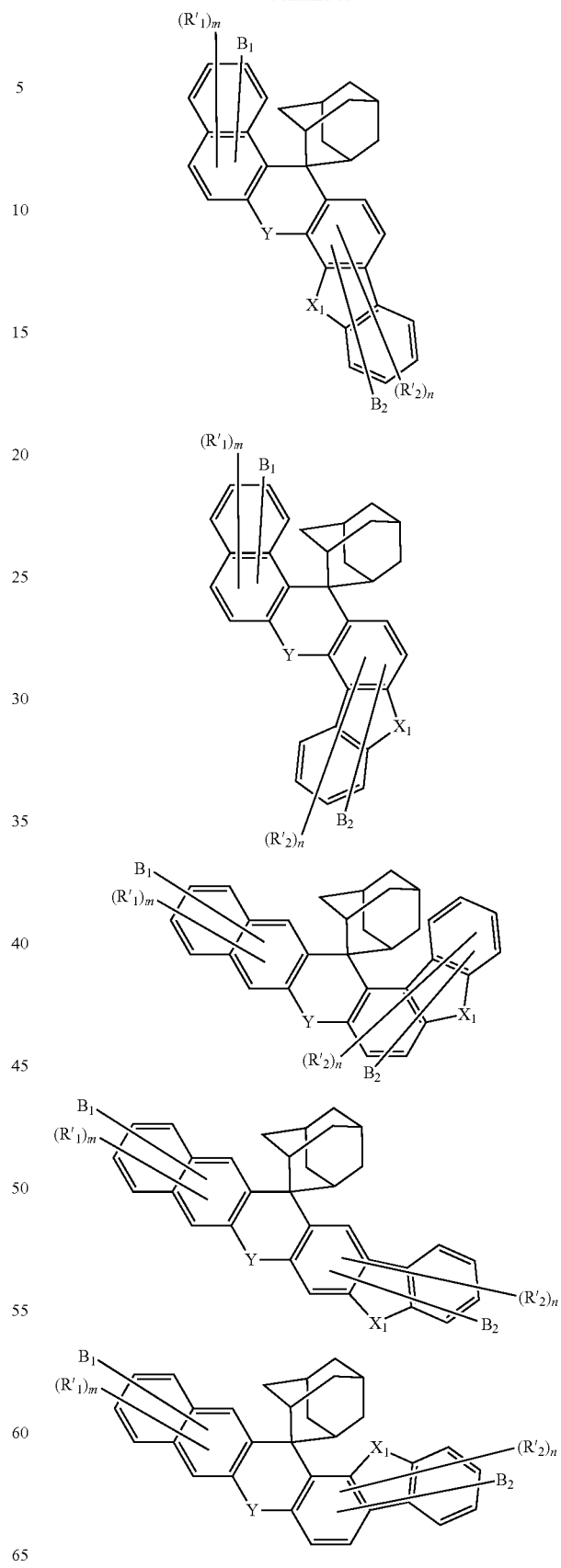

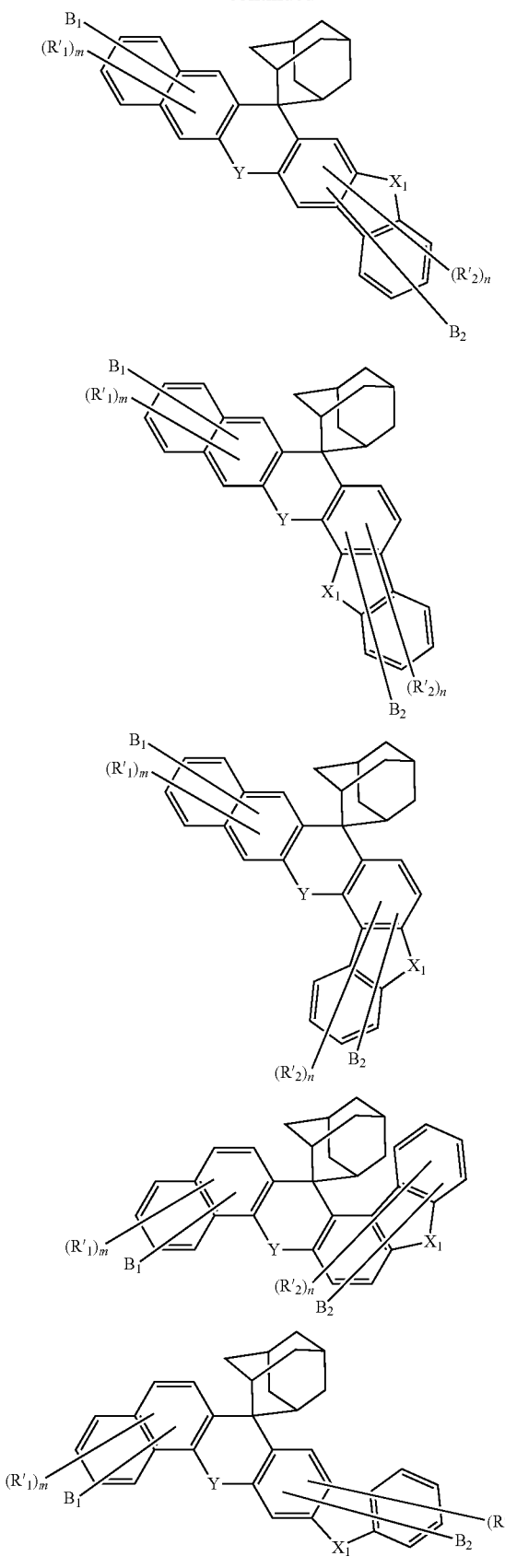
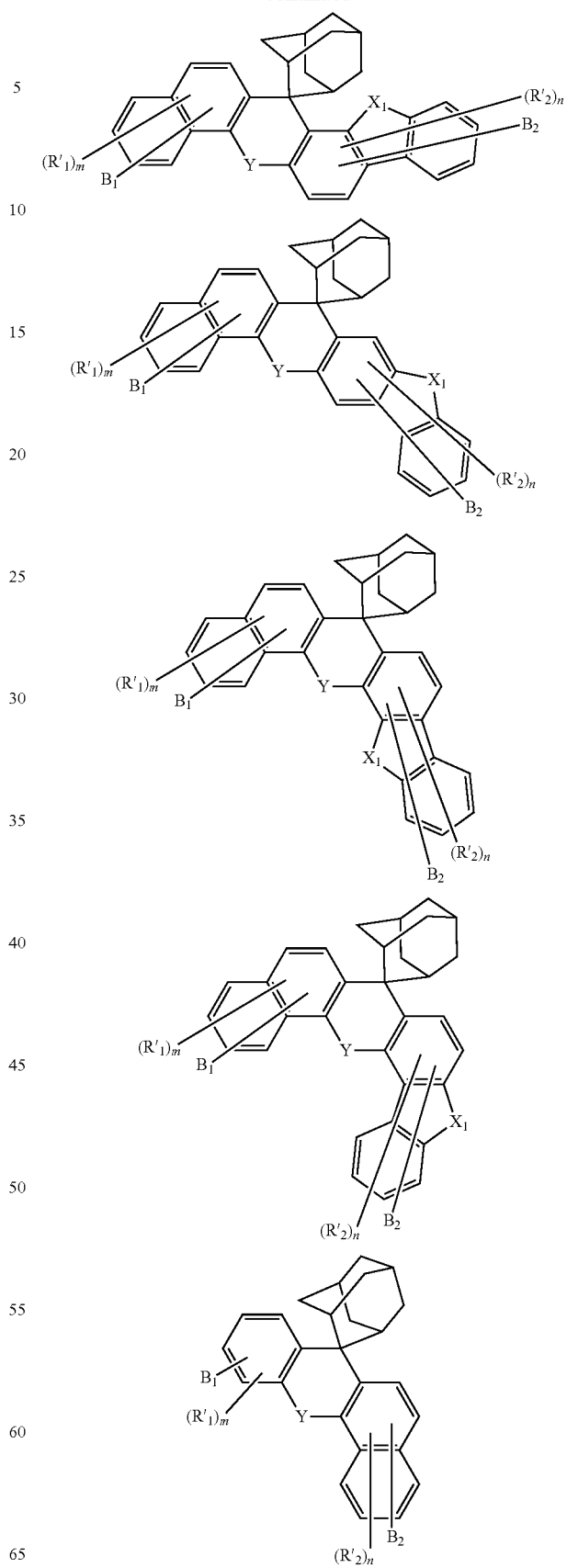

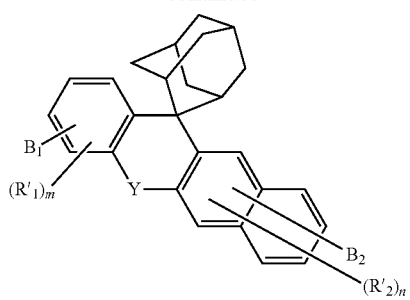
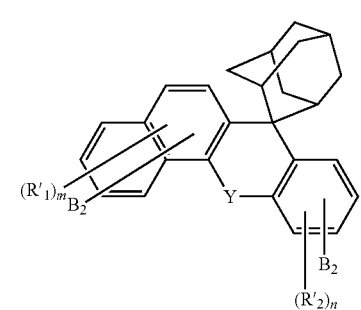
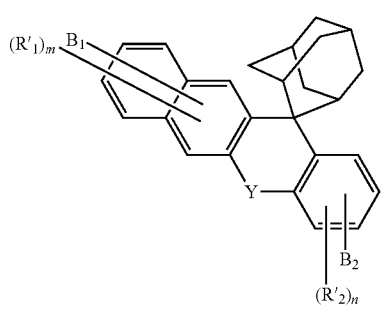
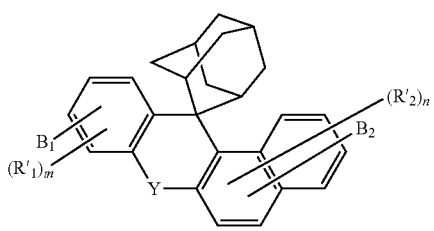
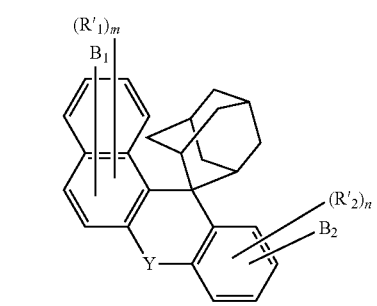
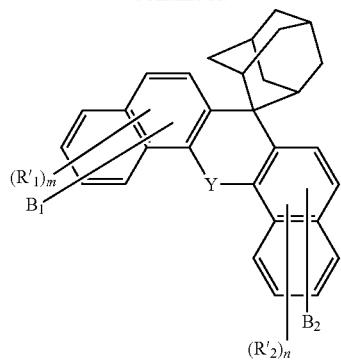
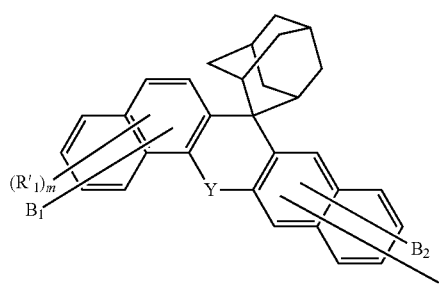
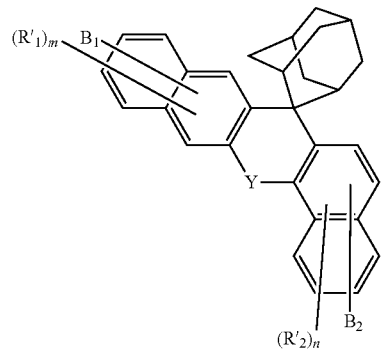
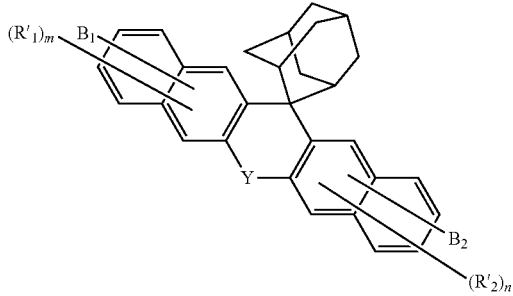
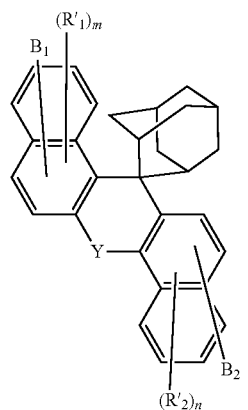

-continued

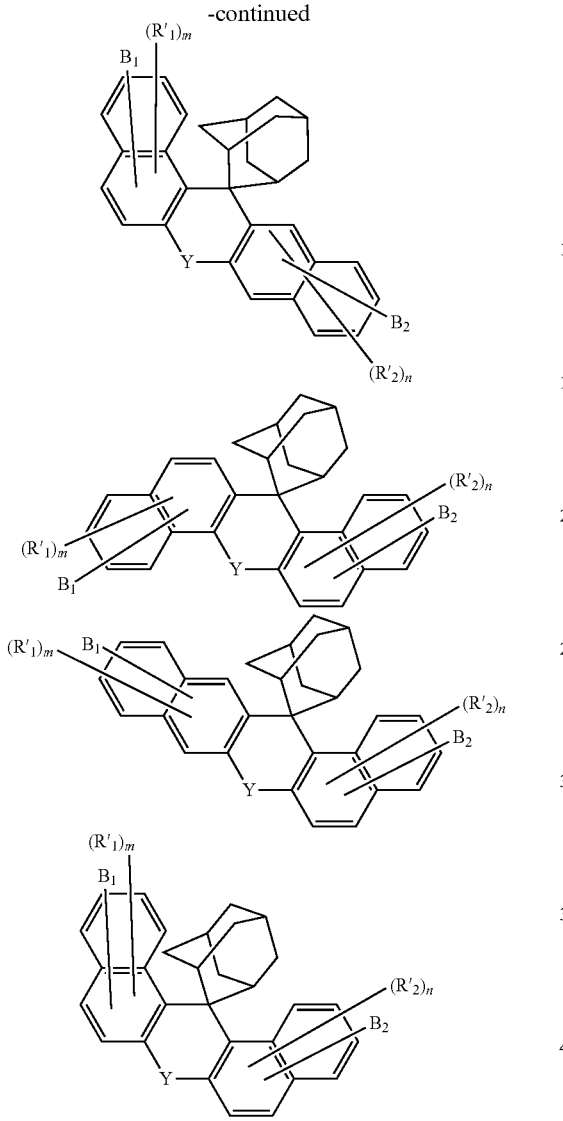

wherein:
$X_1$ and $X_2$ are each independently $CR_1R_2$, $SiR_3R_4$, $NR_5$, O, S, or $SO_2$; and
Y, $R_1$, $R_2$, $R_3$, $R_4$, $R_5$, $B_1$, $B_2$, $R'_1$, $R'_2$, m and n are as defined above.

Preferably, each X is independently $CR_1R_2$, O, or S, where $R_1$ and $R_2$ are each independently methyl or ethyl.

Preferably, $L_1$ and $L_2$ are each independently a direct bond or phenylene.

Preferably, $R_6$ and $R_7$ are each independently phenyl, biphenylyl, terphenylyl, naphthyl, phenanthrenyl, cyclohexenyl, dibenzofuranyl, dibenzothiophenyl, dimethylfluorenyl, benzonaphthofuranyl, benzonaphthothiophenyl, benzodimethylfluorenyl, or are bonded to adjacent substituents to form a substituted or unsubstituted condensed ring, and
they are each unsubstituted or independently substituted with deuterium, *—$CD_3$, $C_{1-4}$ alkyl, *—($C_{1-4}$ alkyl) phenyl, $C_{3-10}$ cycloalkyl, phenyl, halogen, cyano, or *—$SiR_{11}R_{12}R_{13}$, where $R_{11}$, $R_{12}$ and $R_{13}$ are each independently methyl, ethyl, tertbutyl or phenyl.

Here, $R_6$ and $R_7$ are structures formed including a nitrogen atom when bonded to an adjacent substituent to form a substituted or unsubstituted condensed ring.

Preferably, $B_1$ and $B_2$ are each independently any one selected from the group consisting of the following:

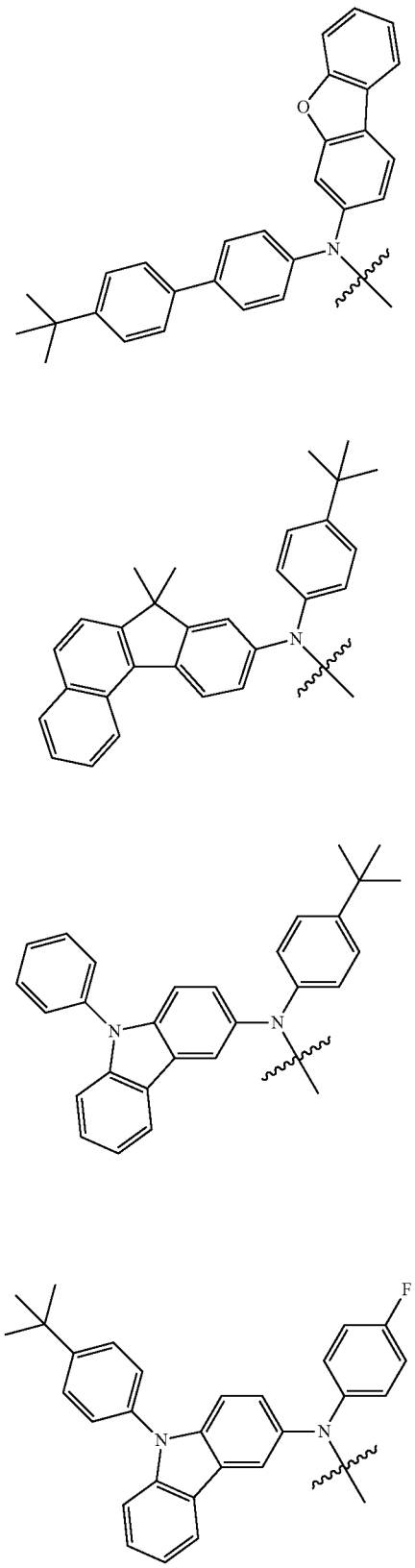

25
-continued
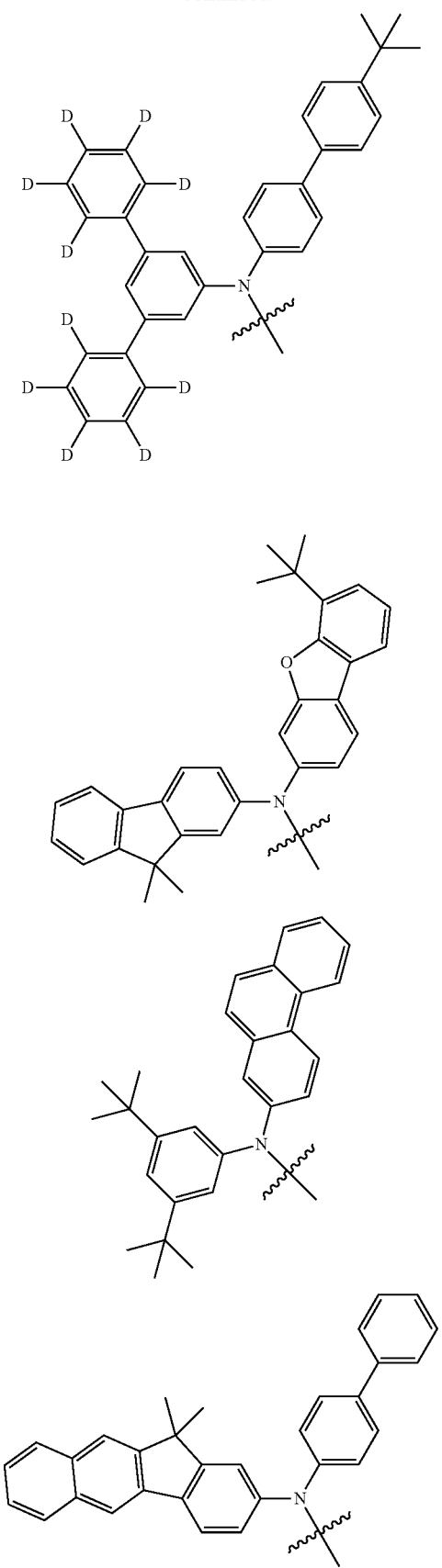
26
-continued
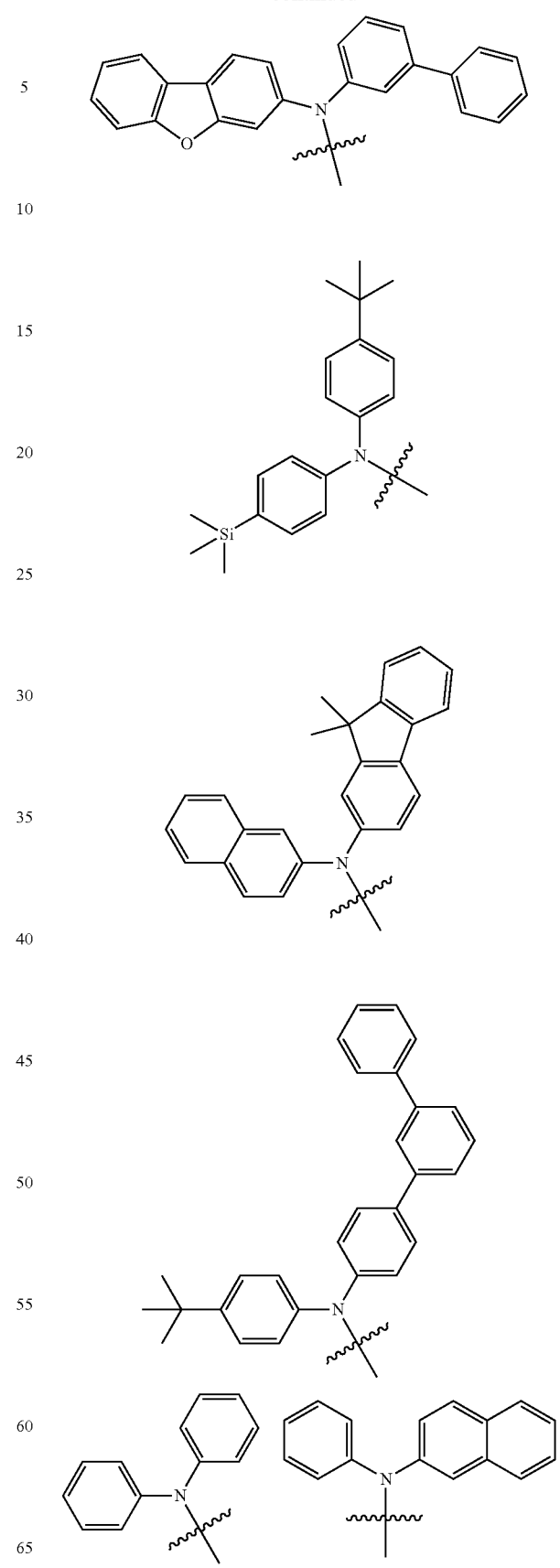

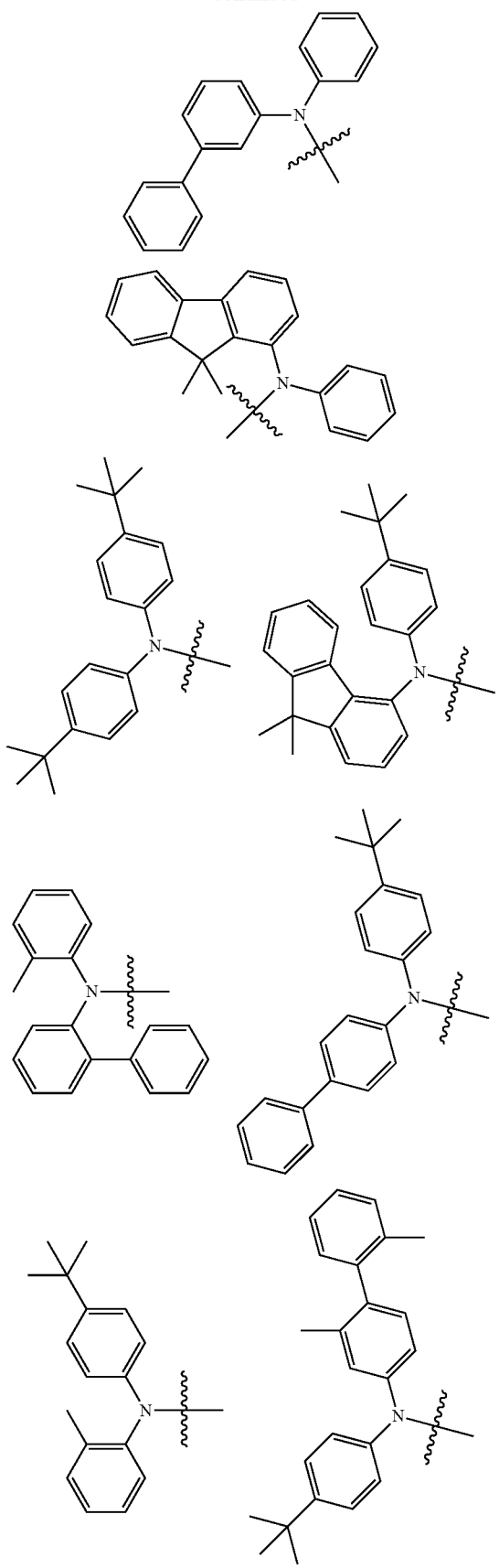
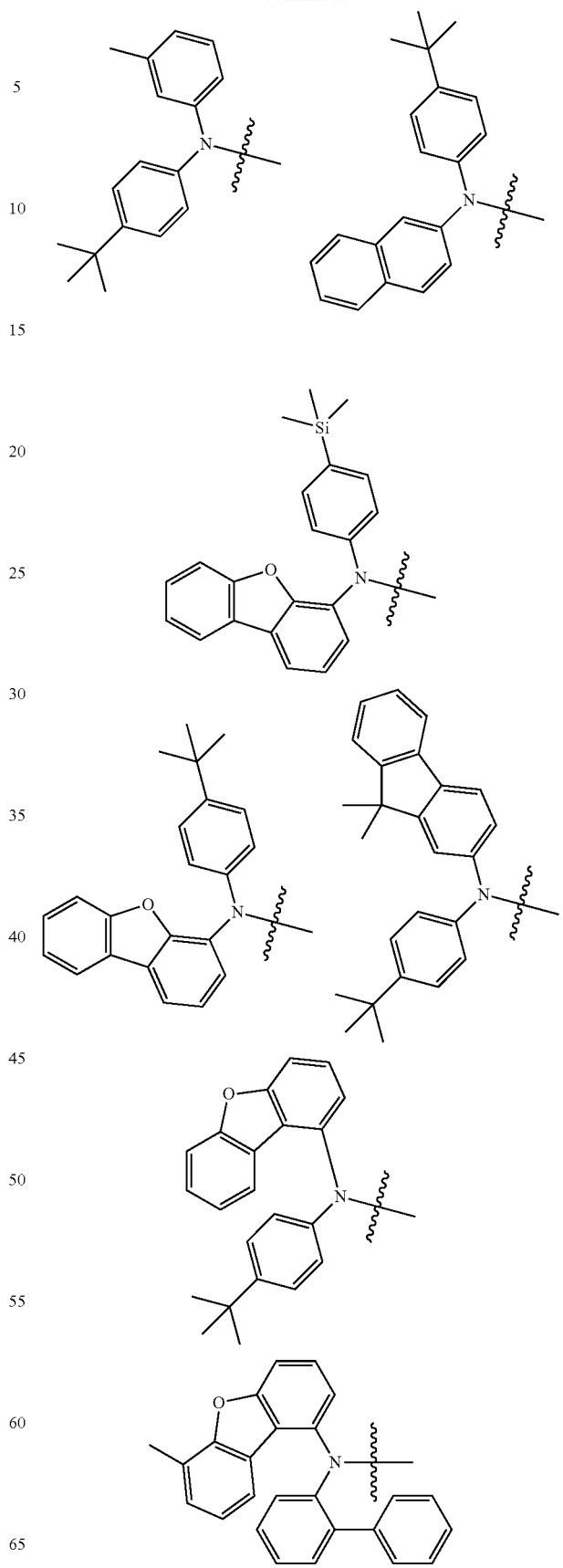

-continued
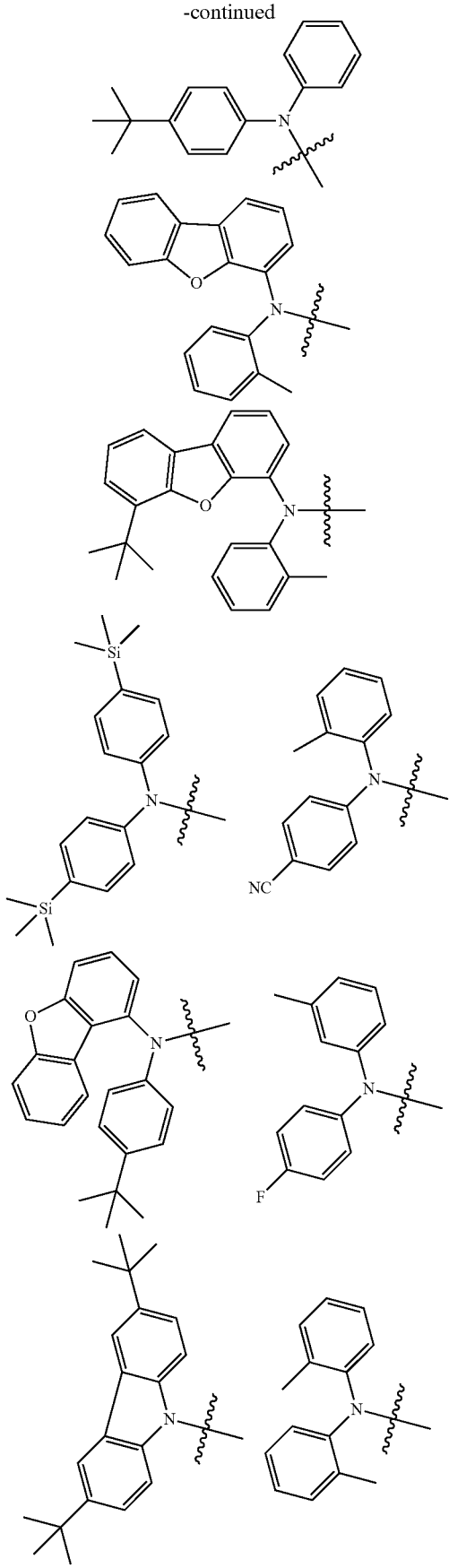
-continued
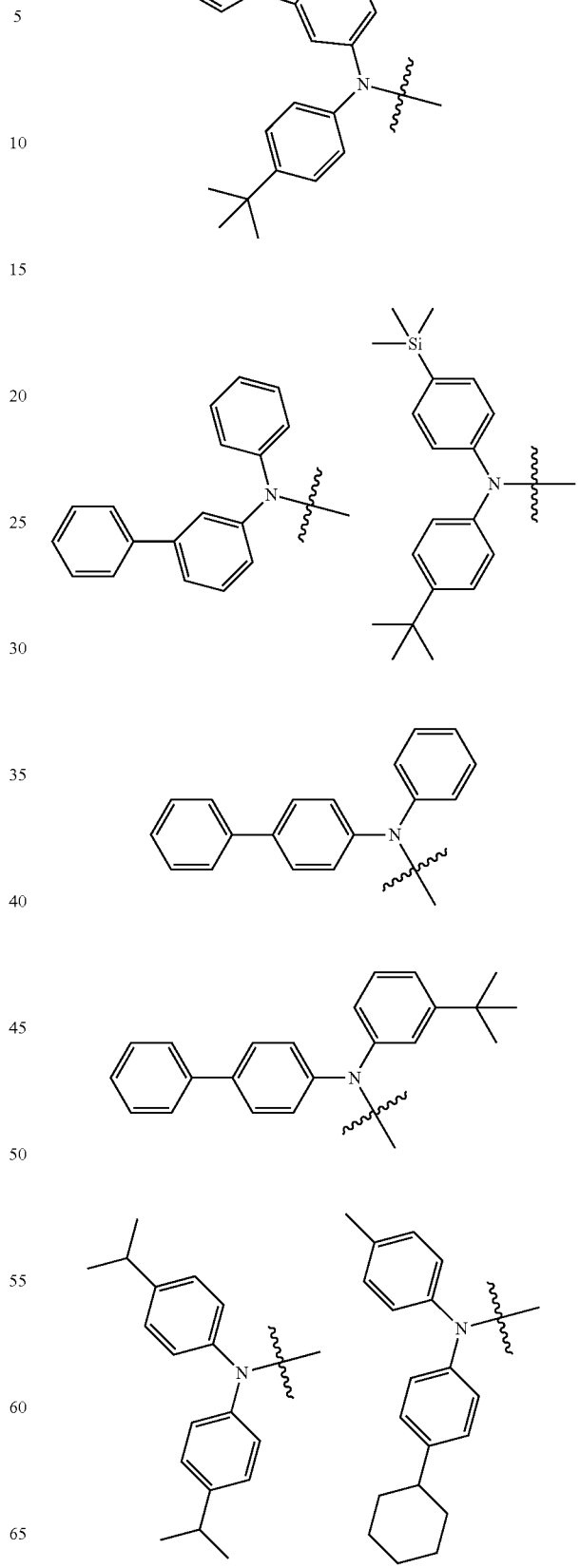

31
-continued
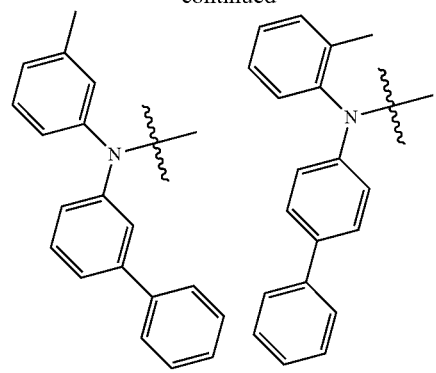
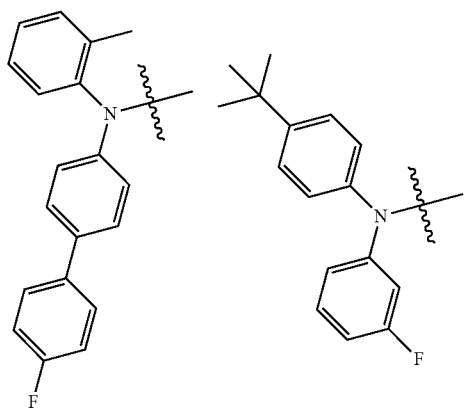
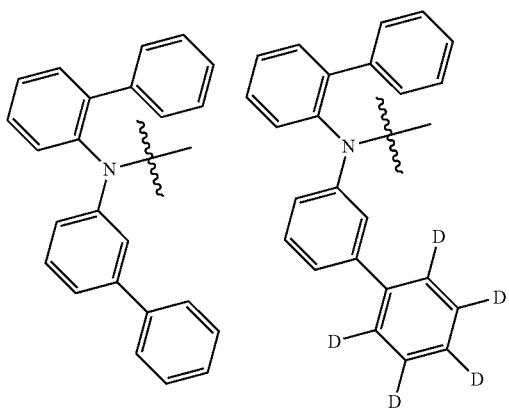
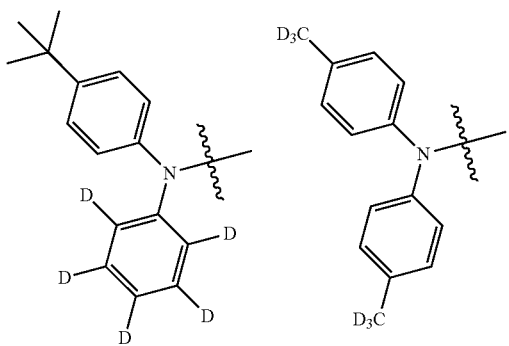
32
-continued
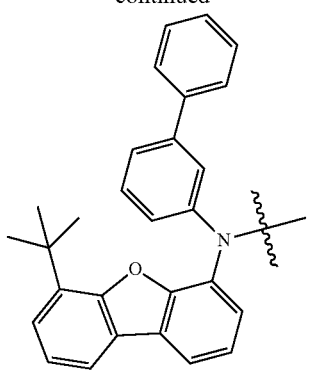
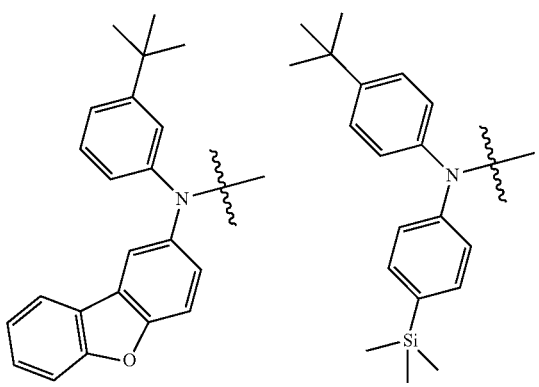
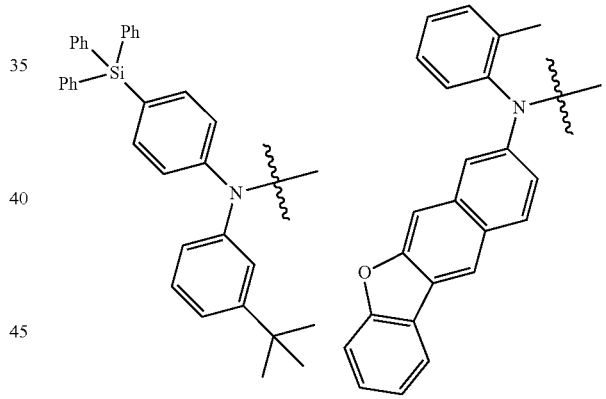
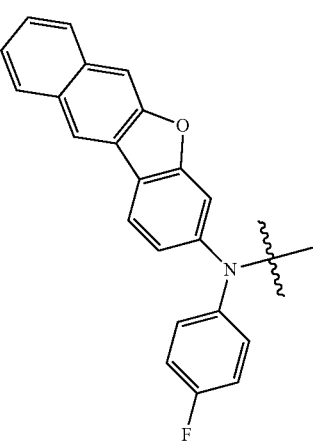

-continued
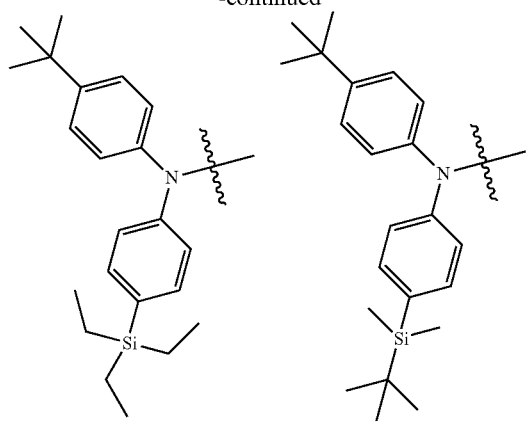
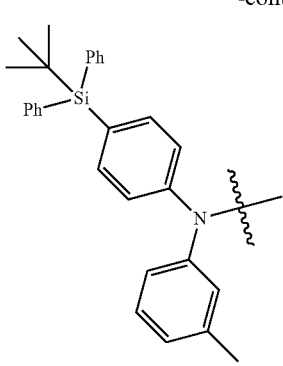
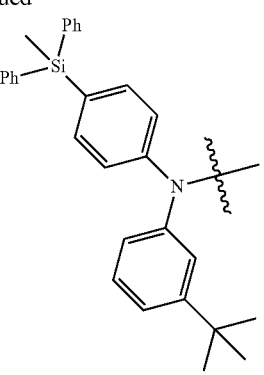
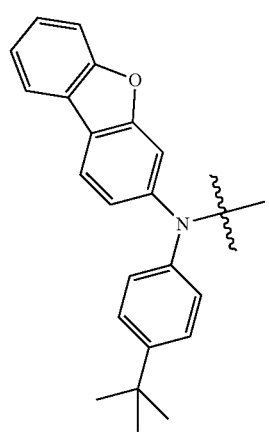
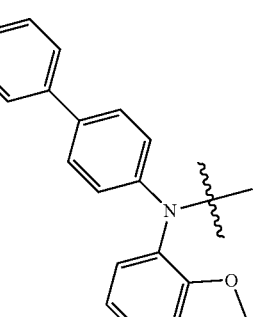
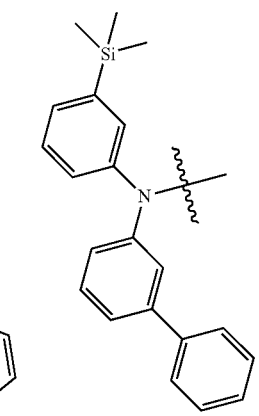
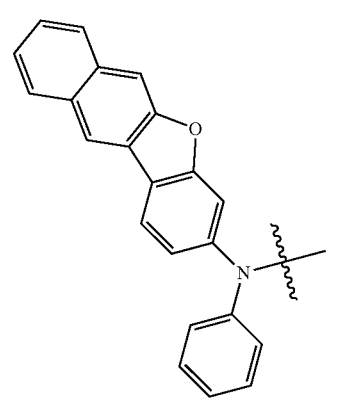
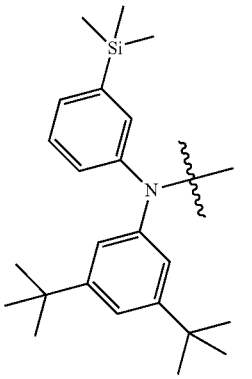
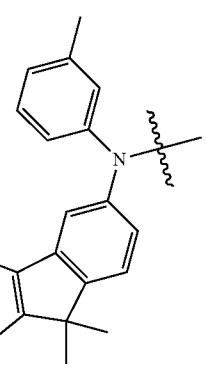
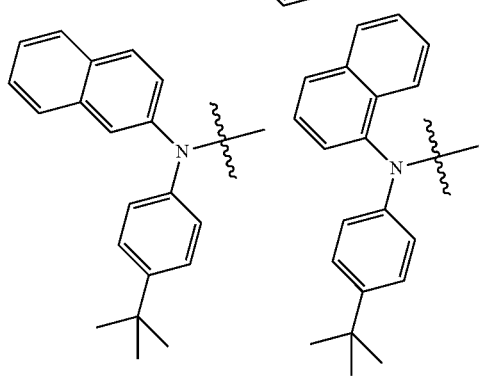
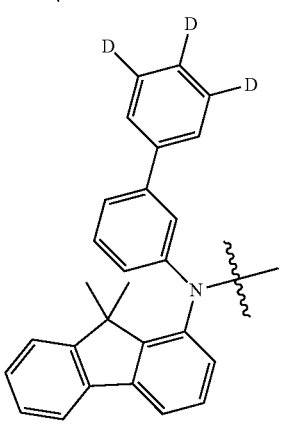

-continued
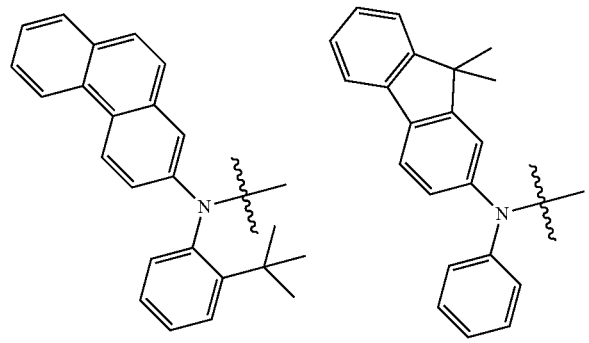
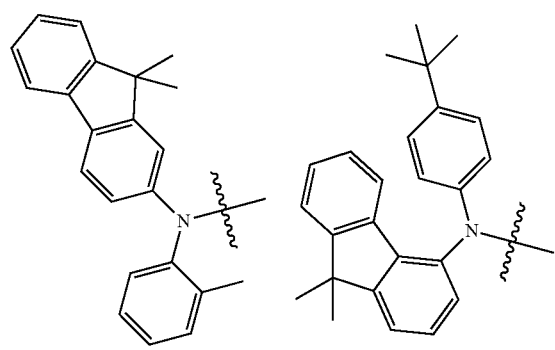
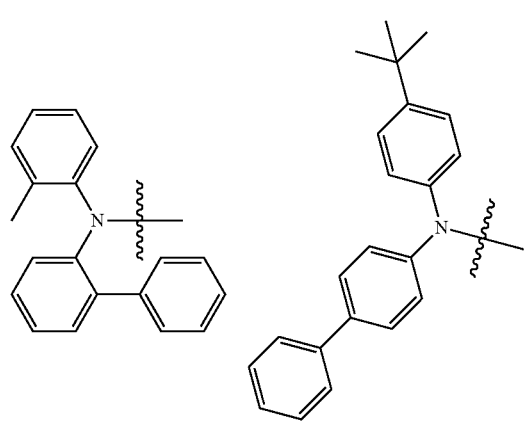
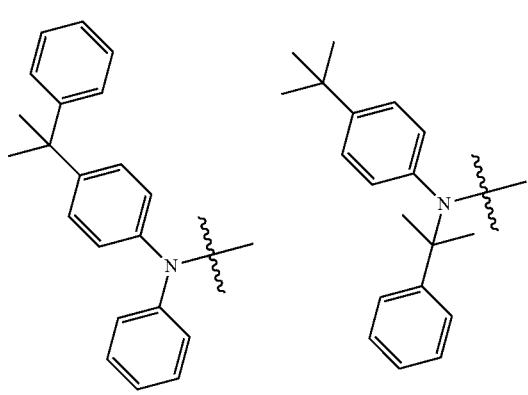
-continued
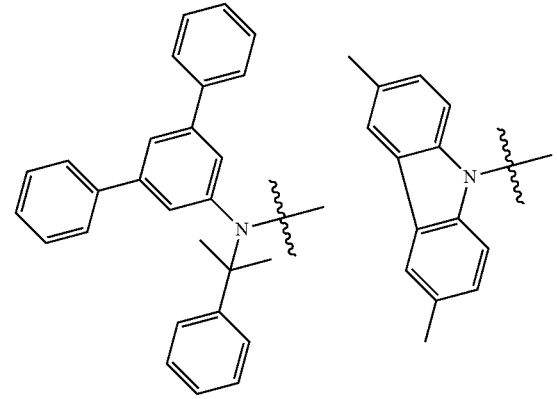
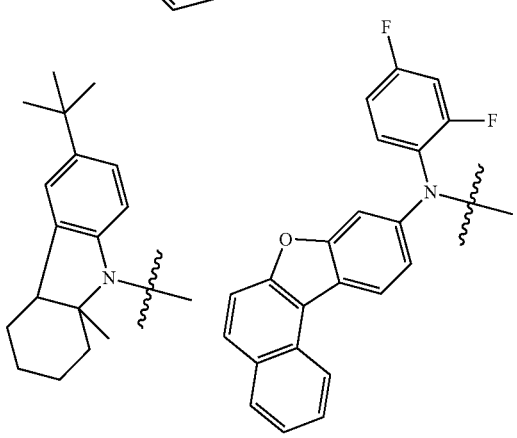
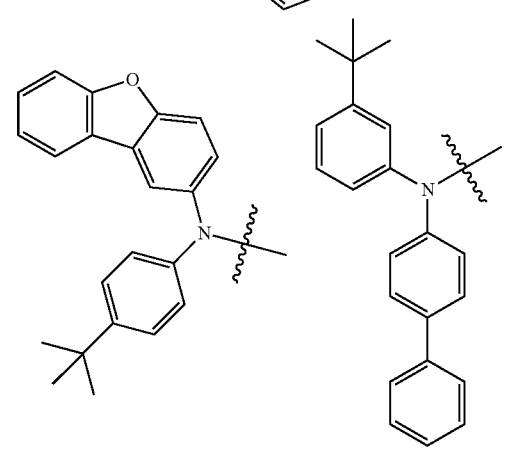
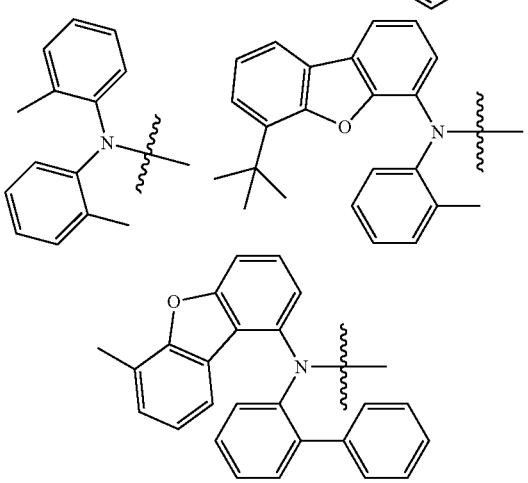

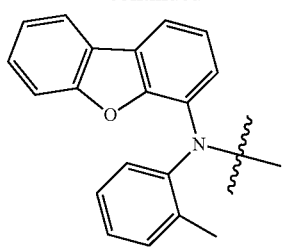
Preferably, R'$_1$ and R'$_2$ are each independently hydrogen or deuterium.
Preferably, the compound of Chemical Formula 1 is any one compound selected from the group consisting of the following compounds:
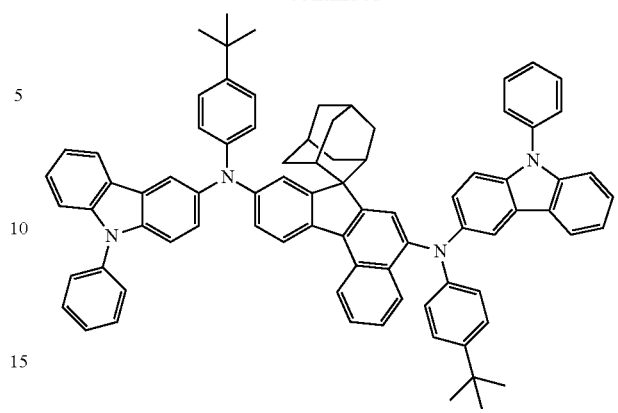
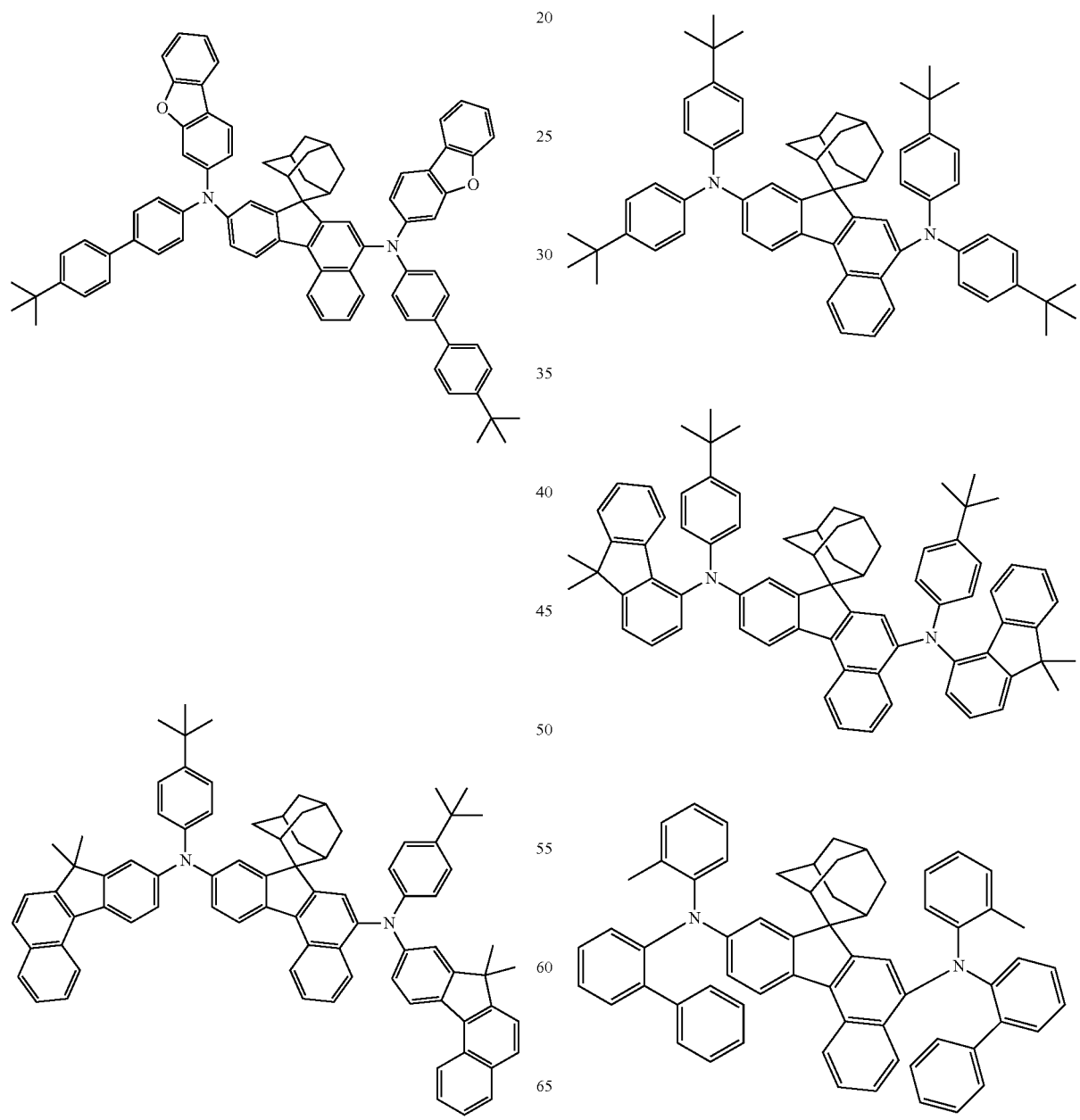

39
-continued
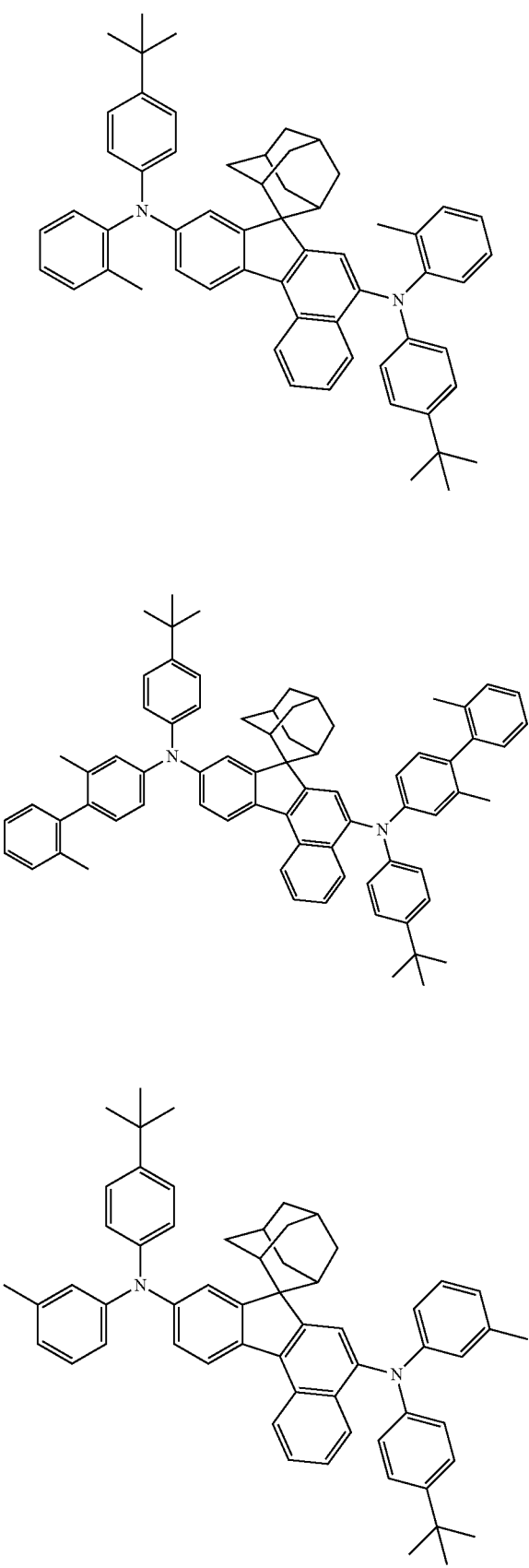
40
-continued
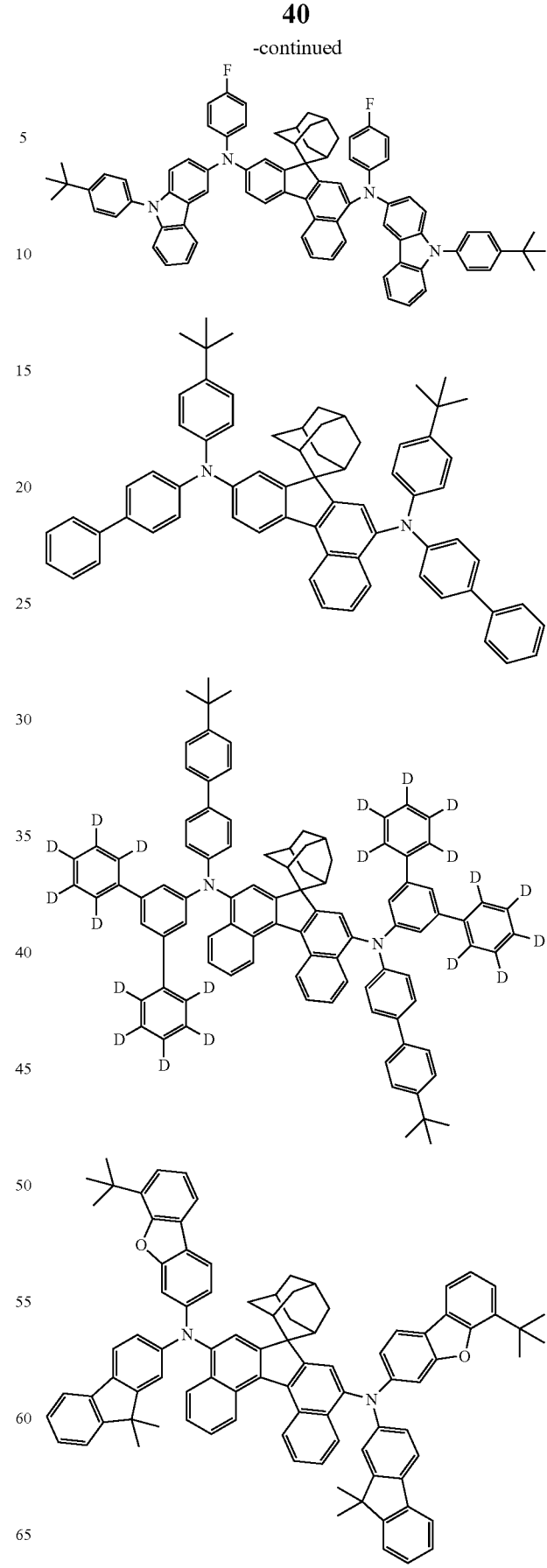

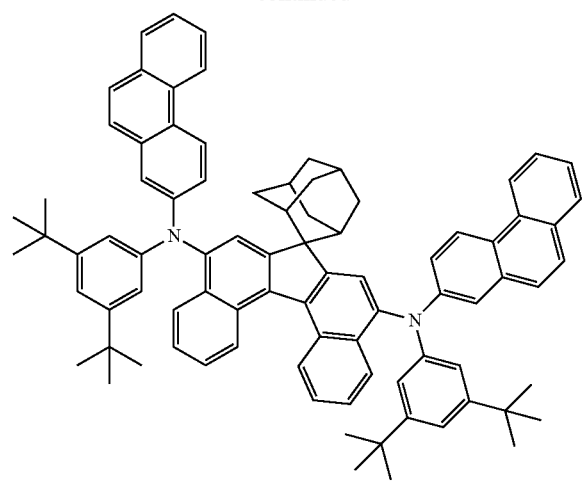
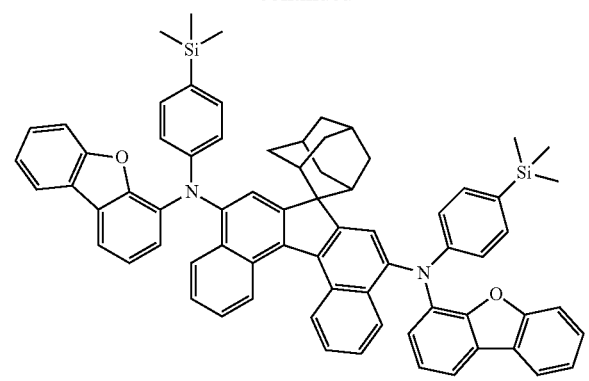
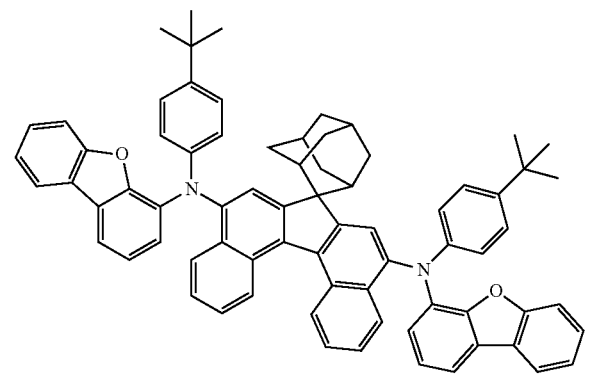
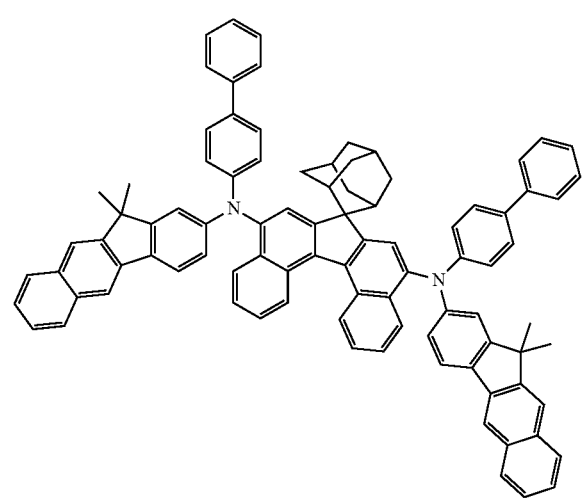
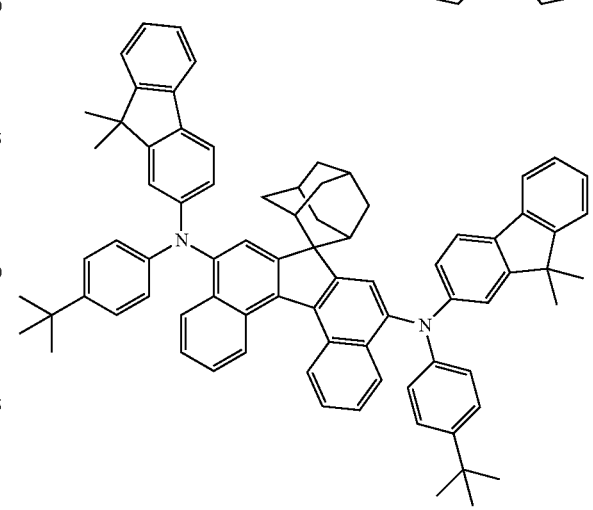
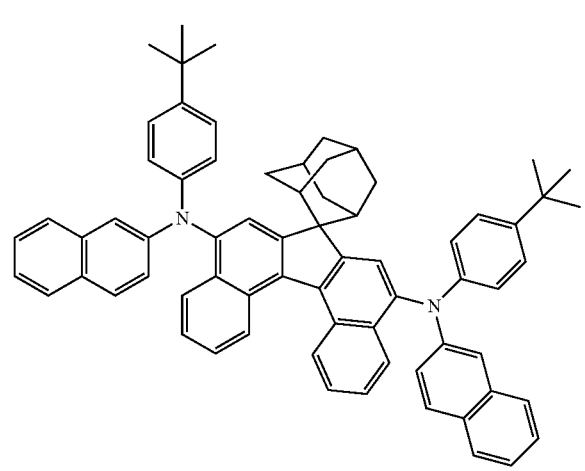
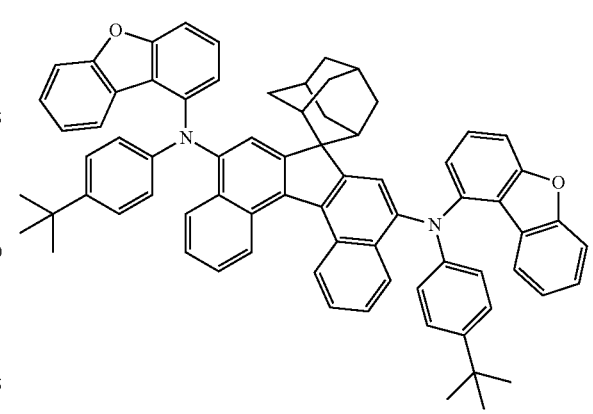

43
-continued
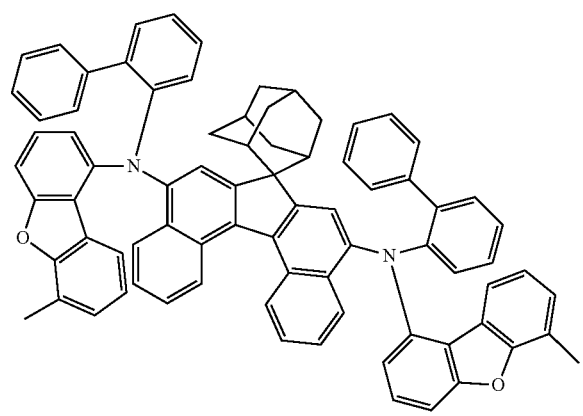
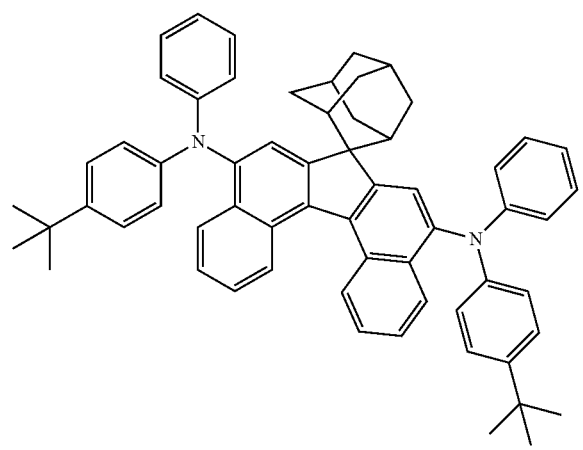
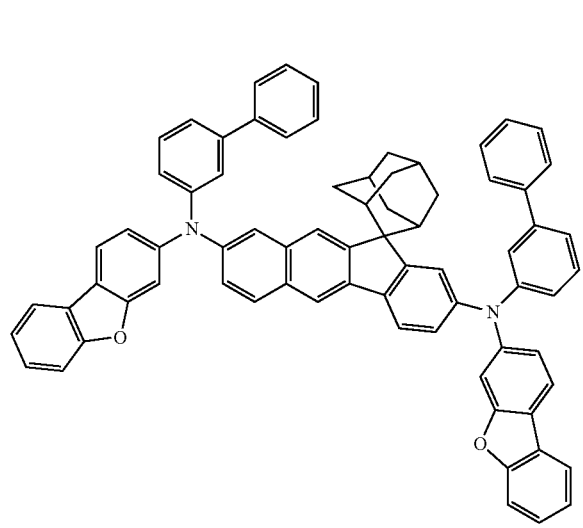
44
-continued
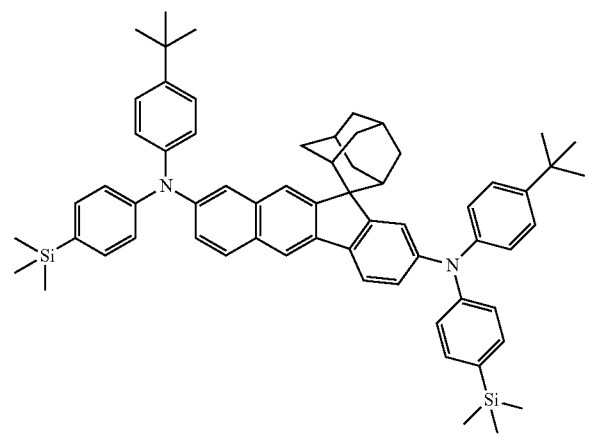
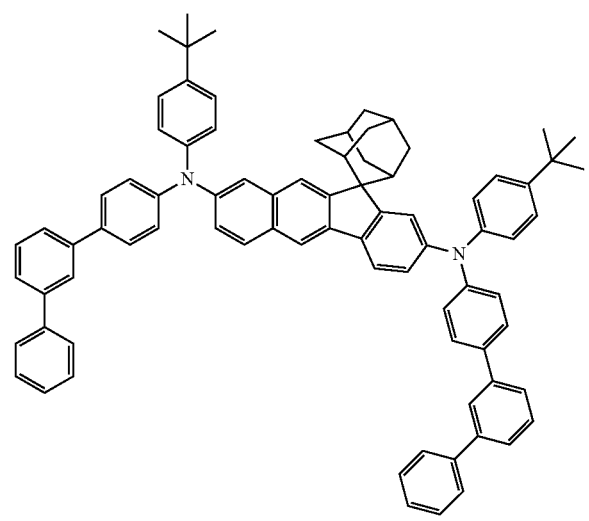

-continued
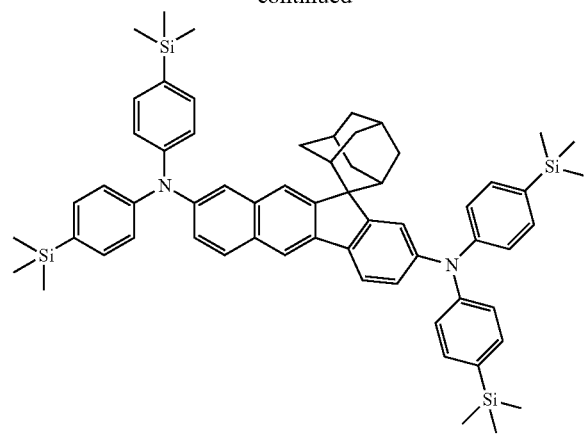
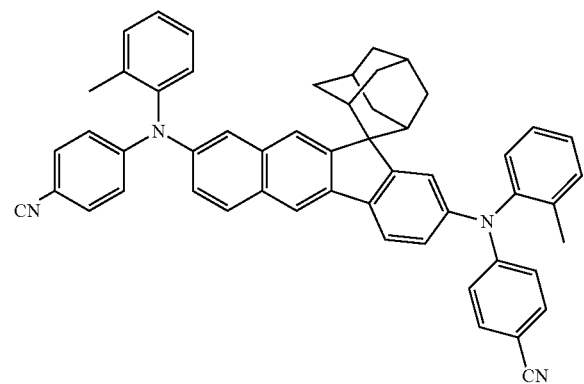
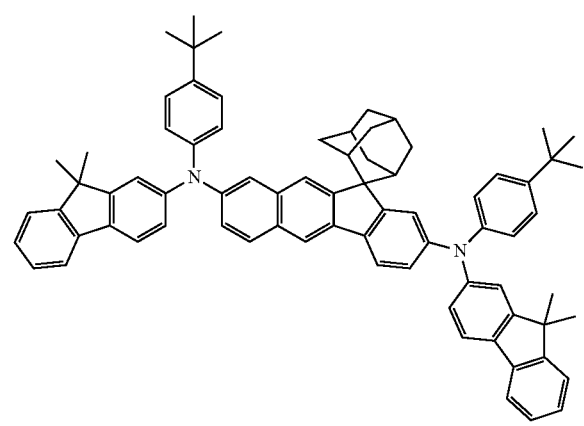
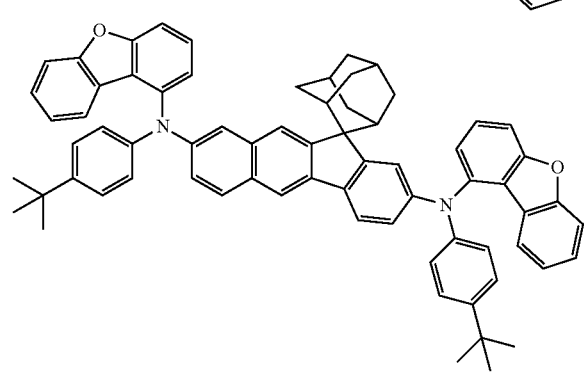
-continued
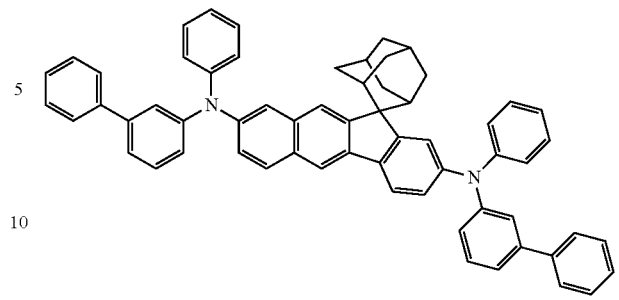
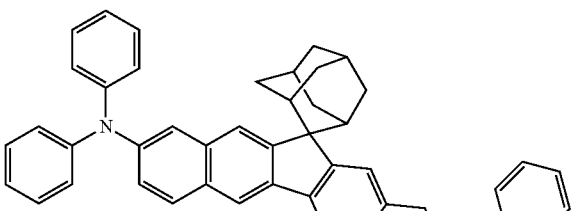
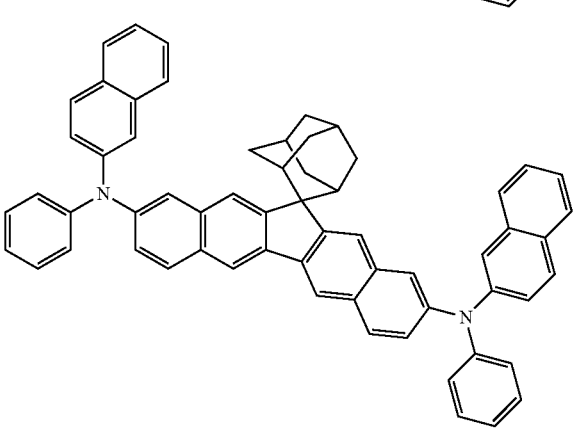

47
-continued
48
-continued
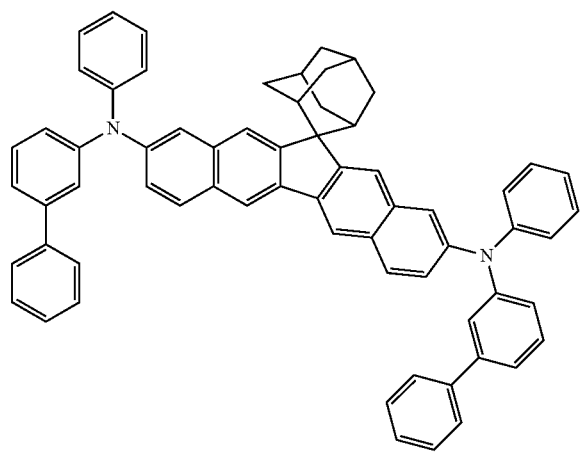
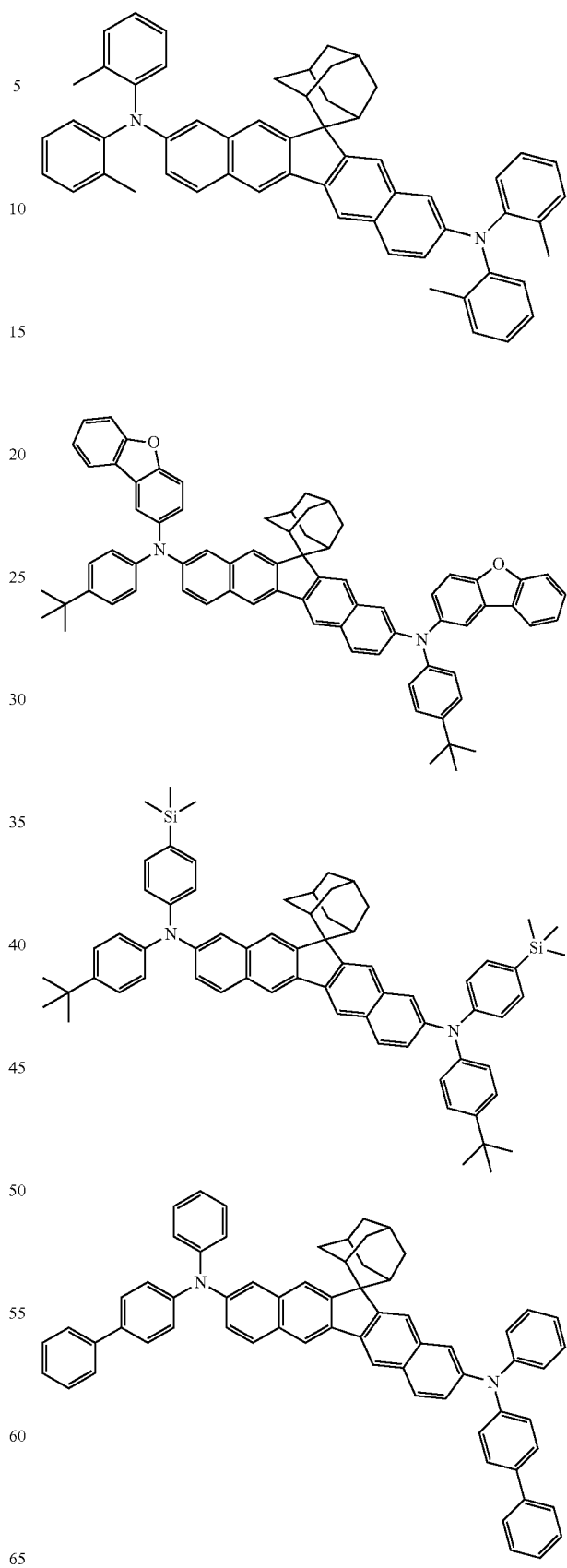

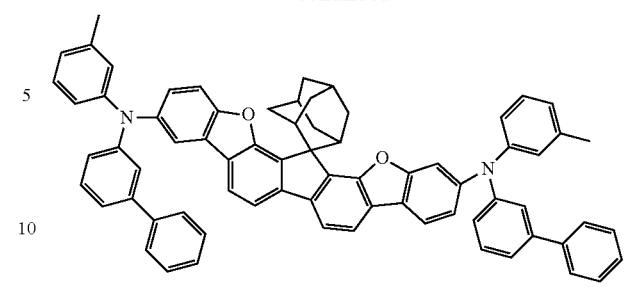
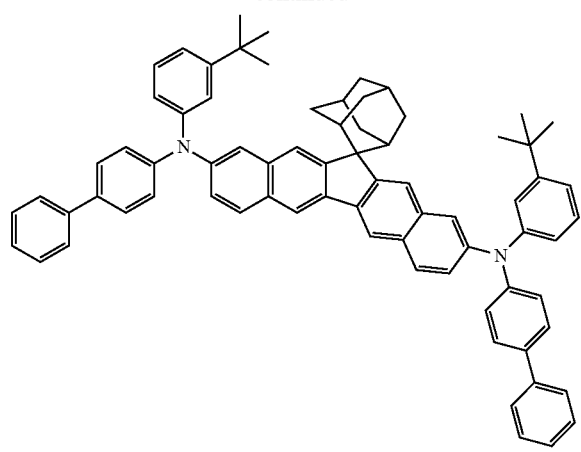
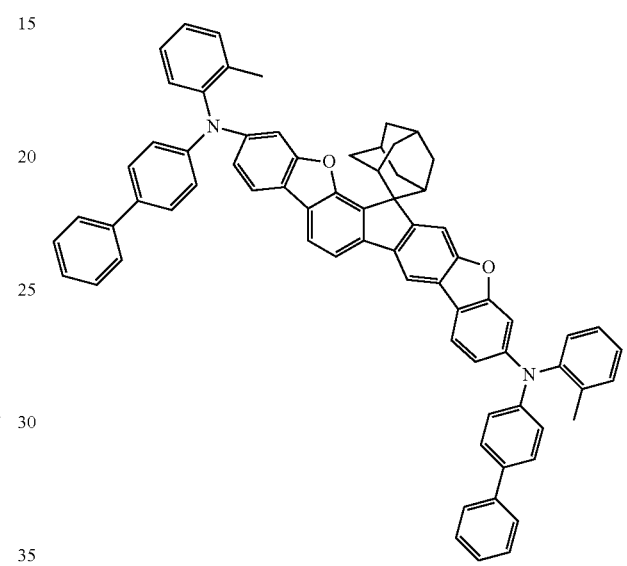
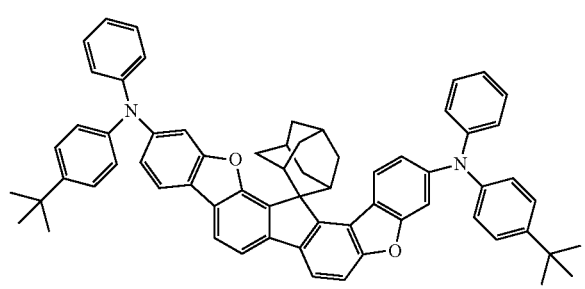
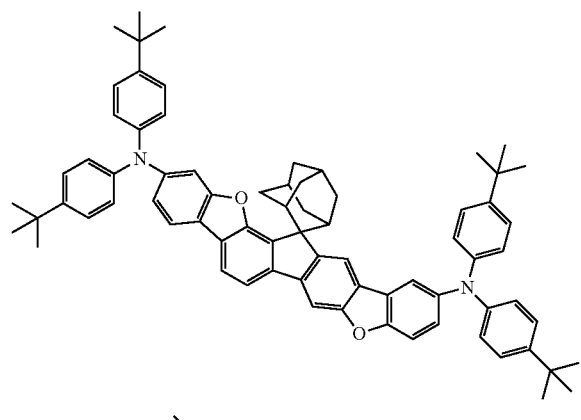
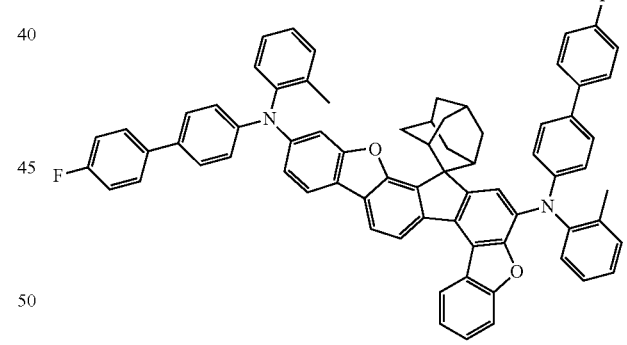
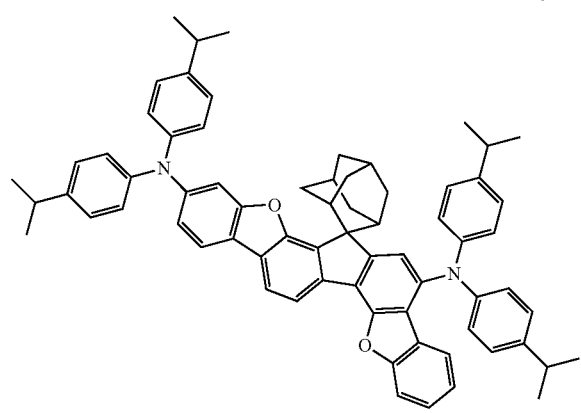
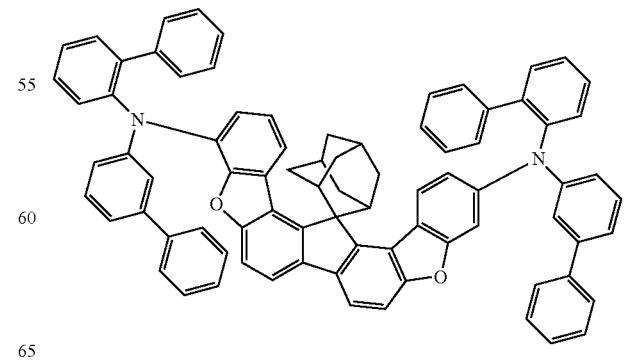

51
-continued
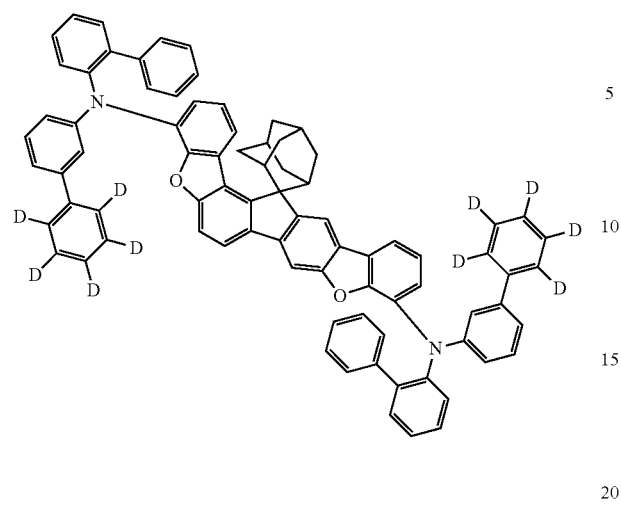
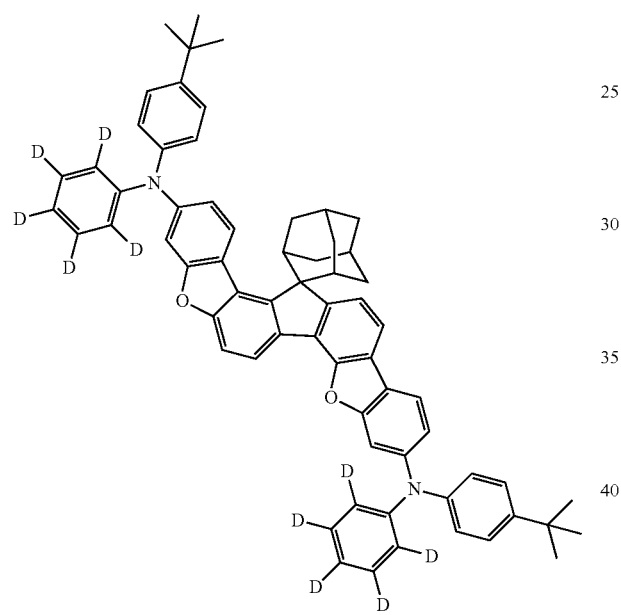
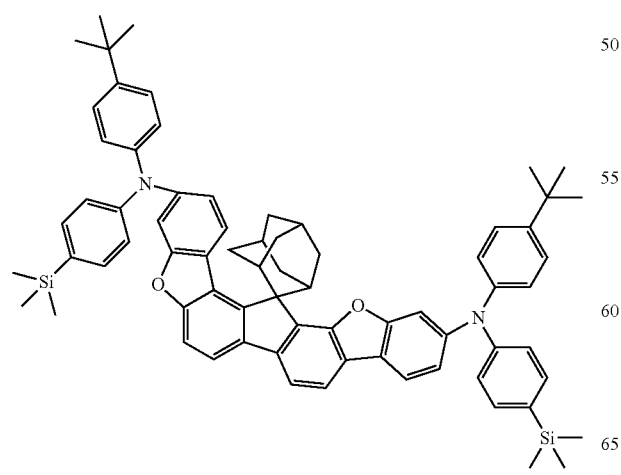
52
-continued
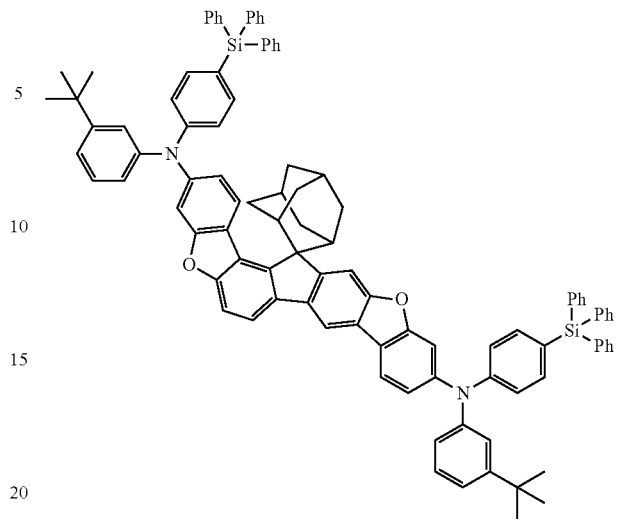
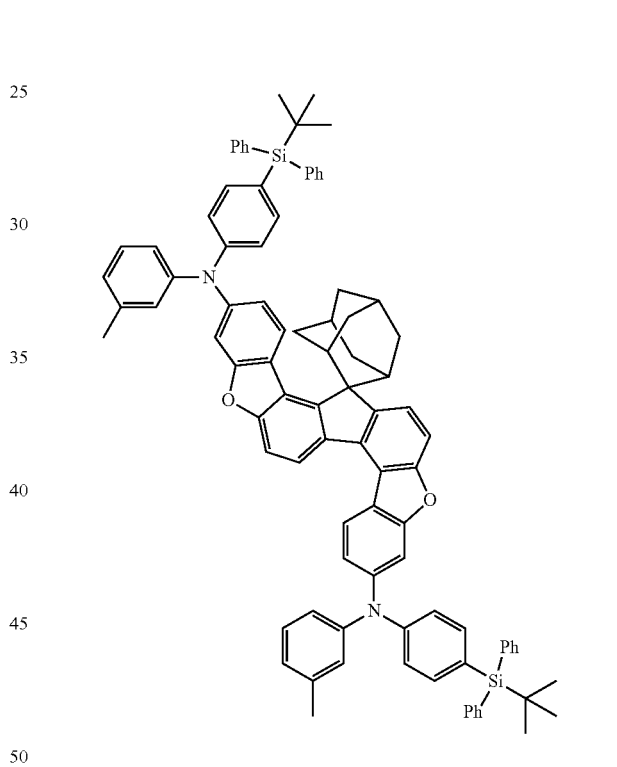
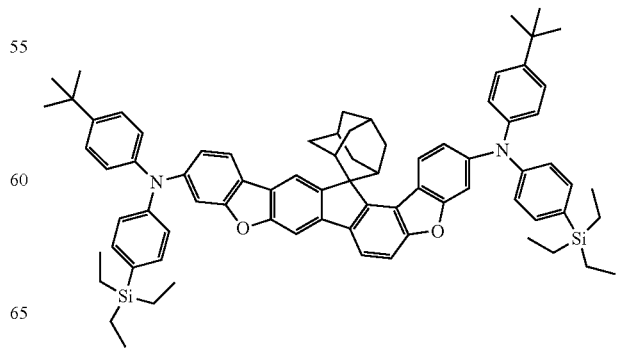

53
-continued
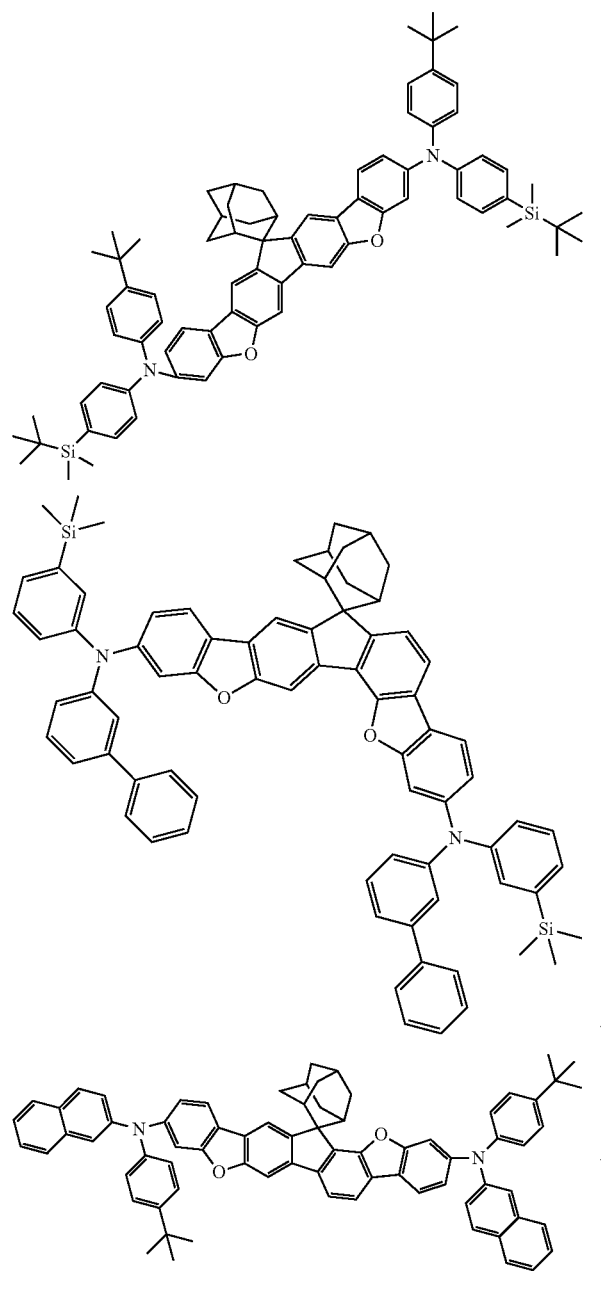
54
-continued
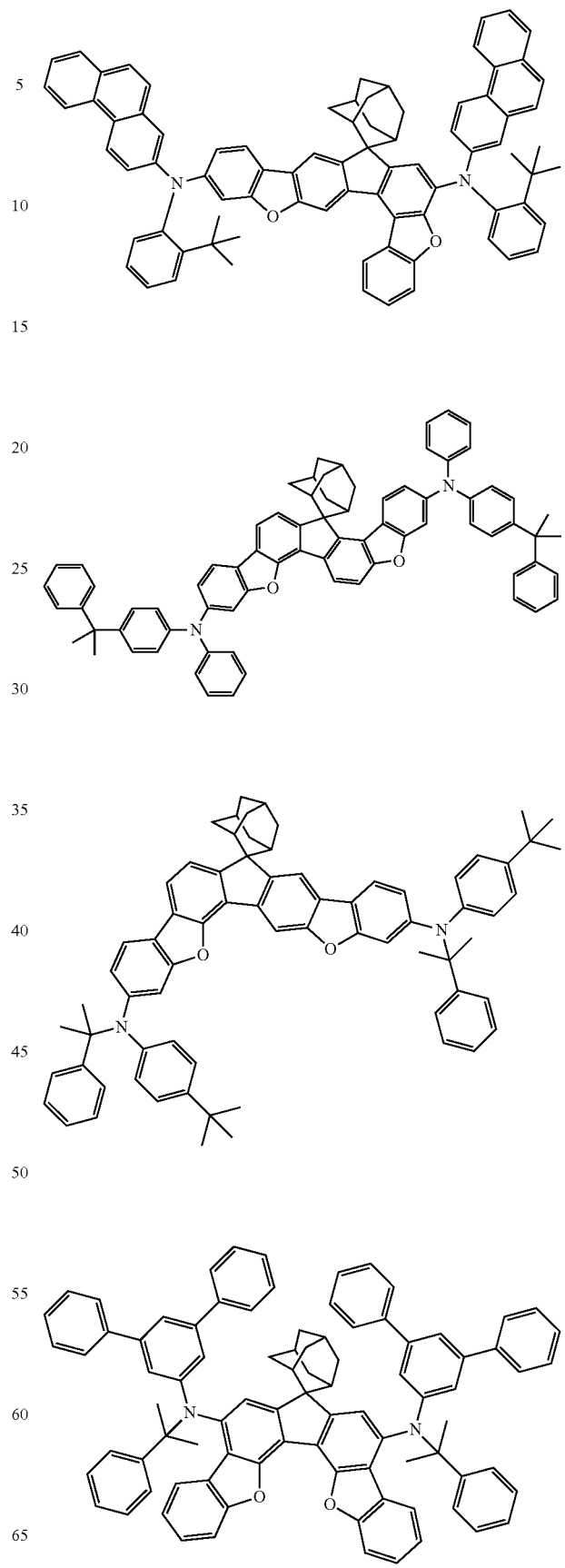

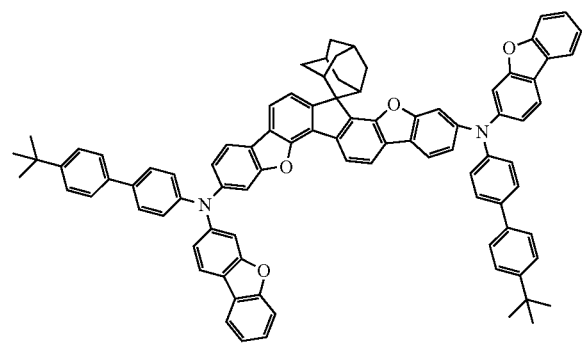
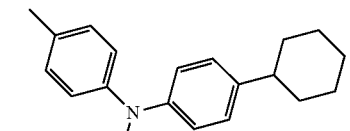
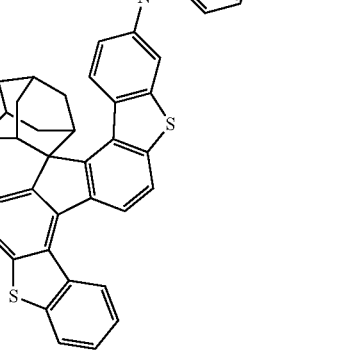
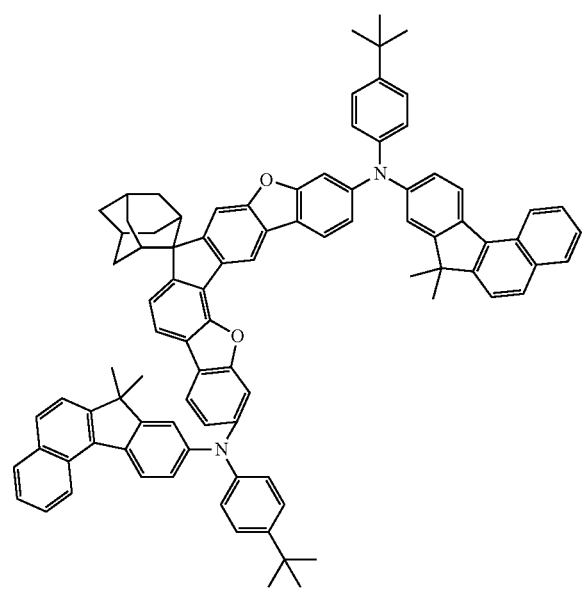
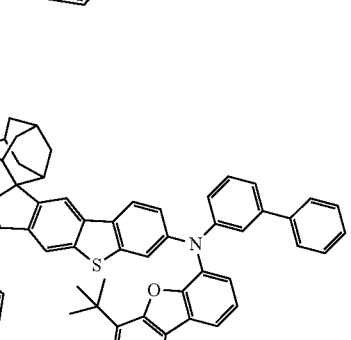
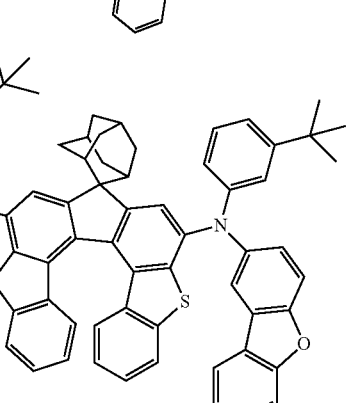
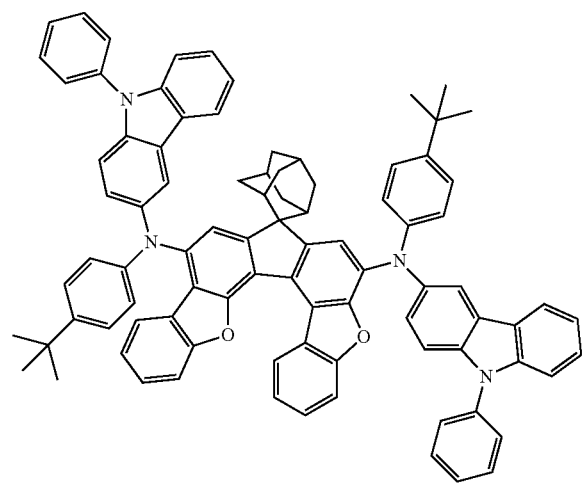
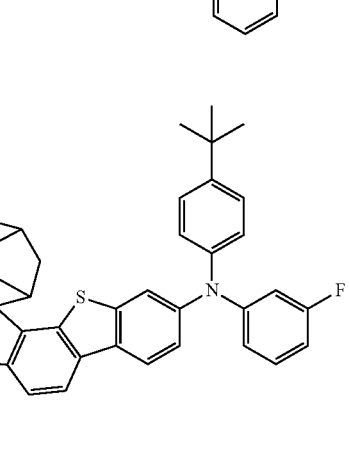

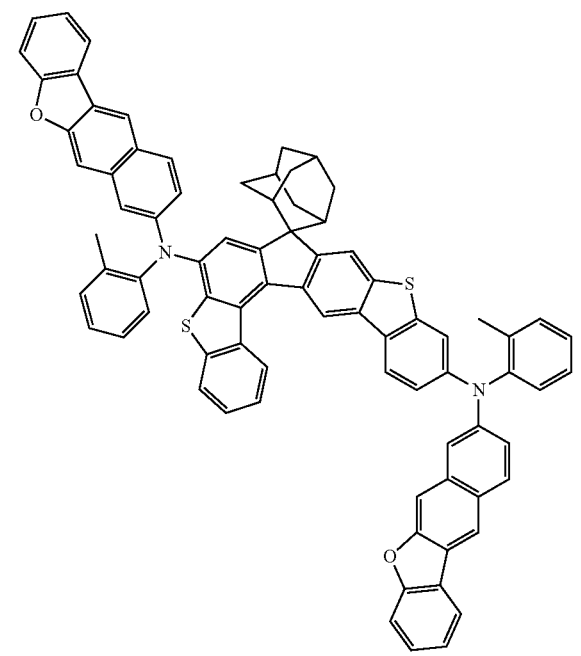
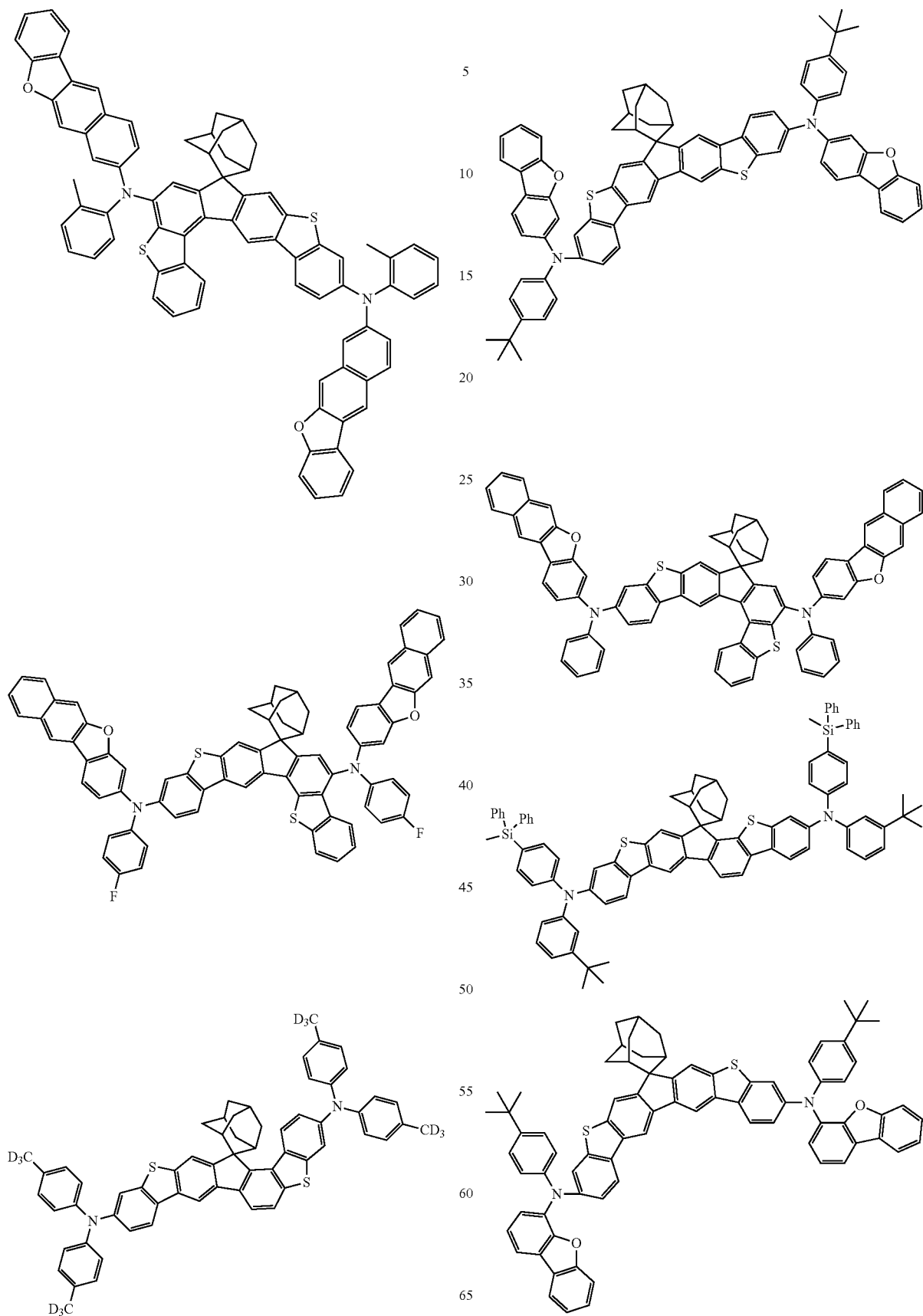

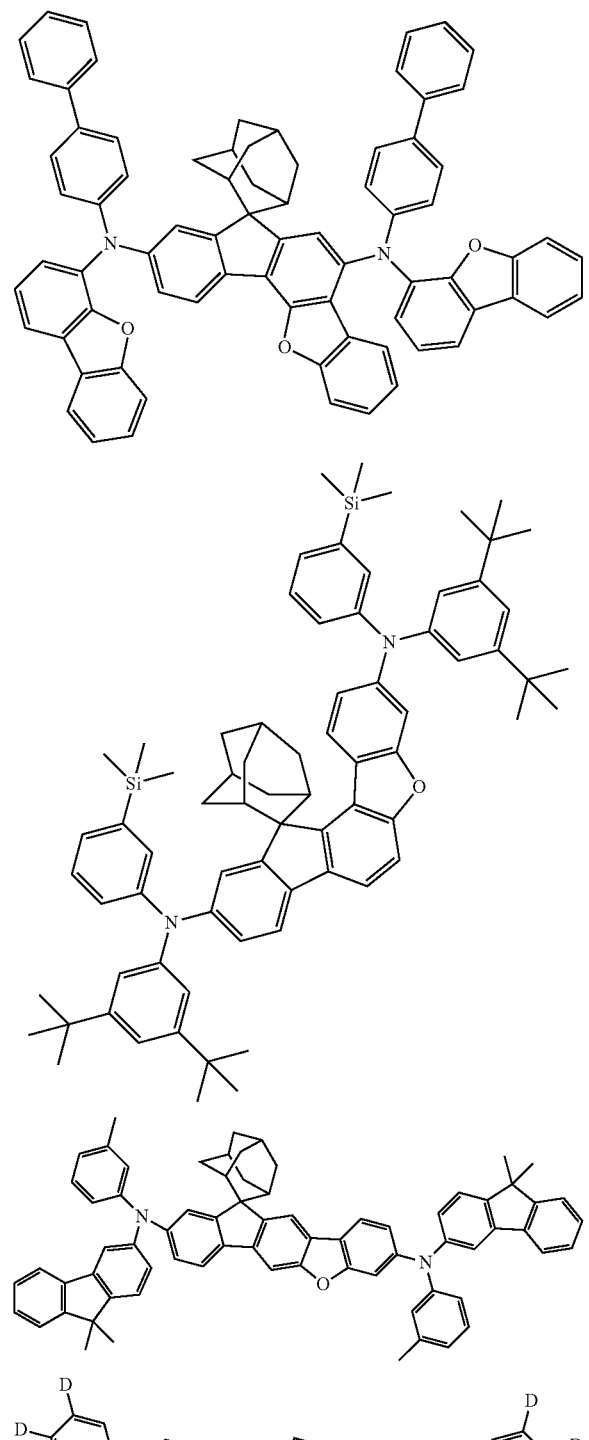
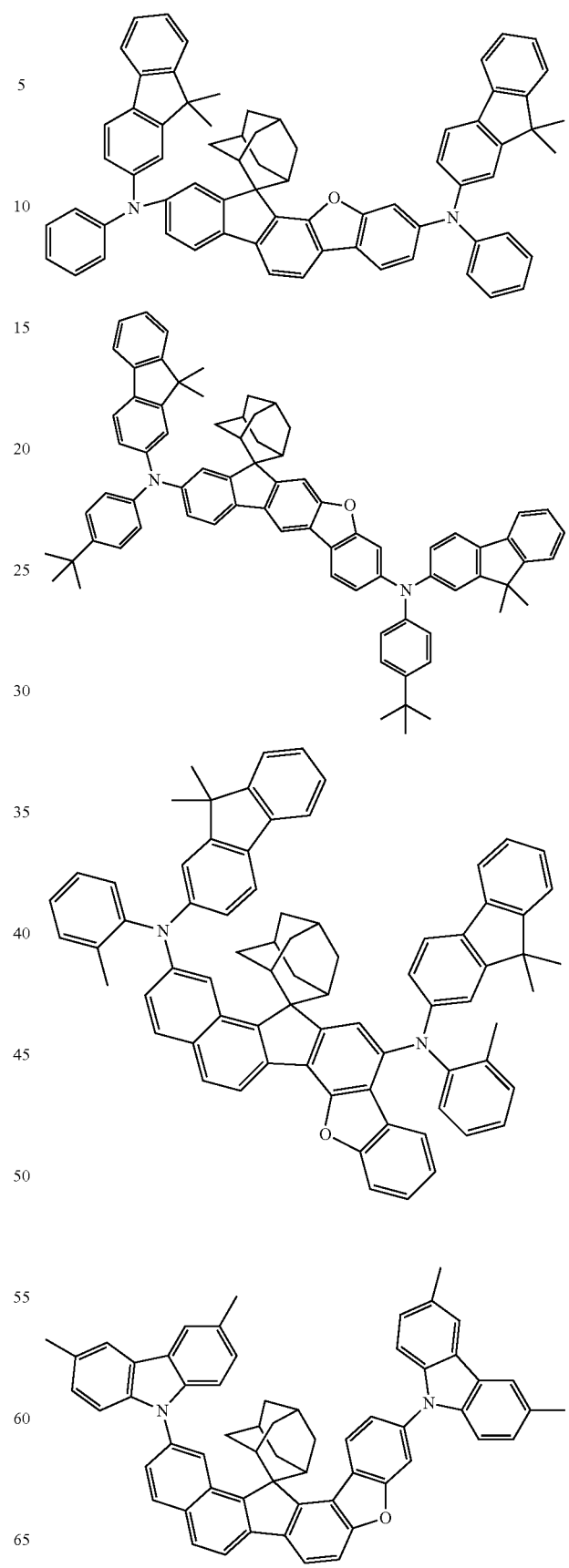

61
-continued
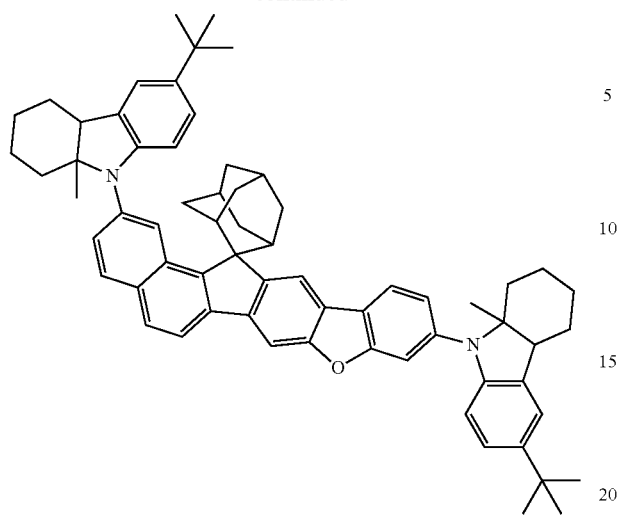
62
-continued
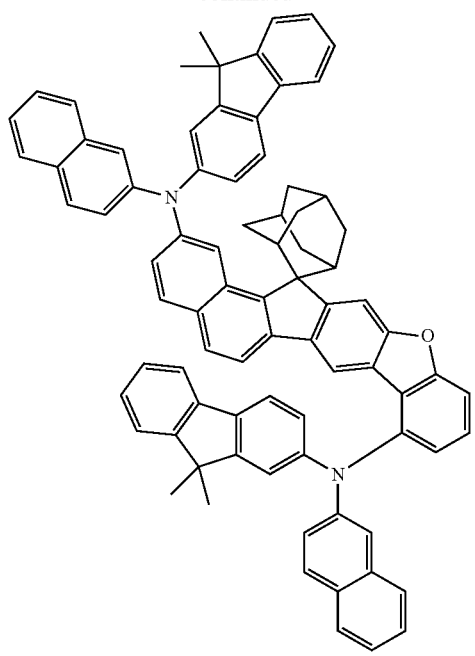
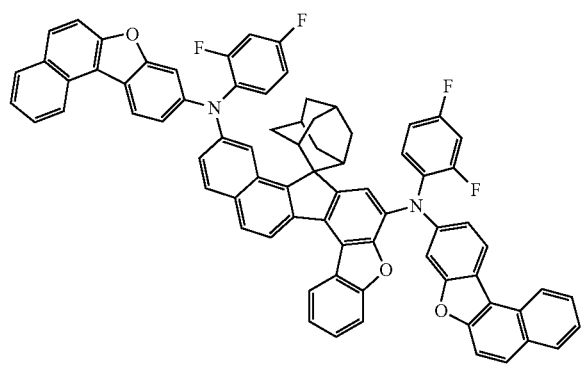
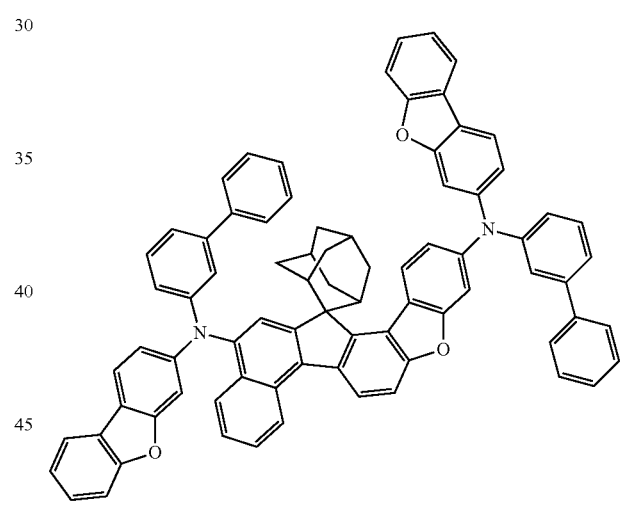
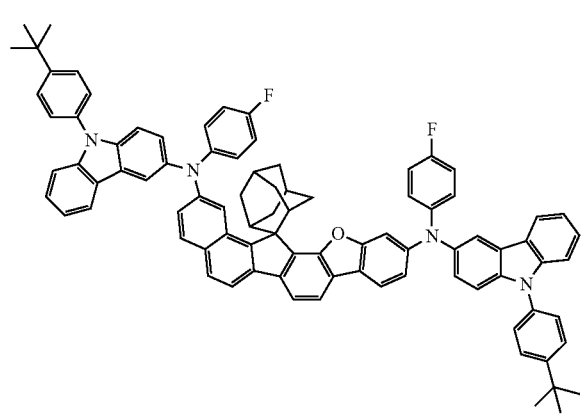
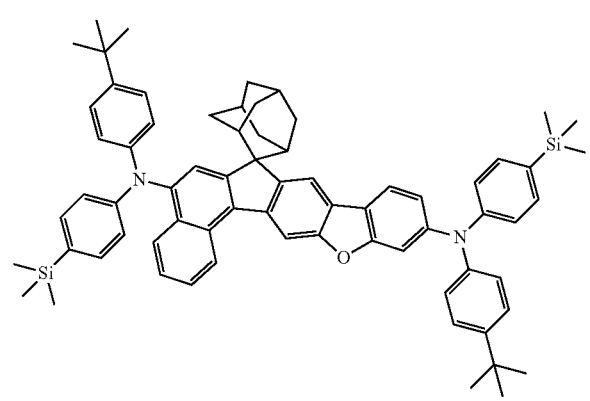

63
-continued
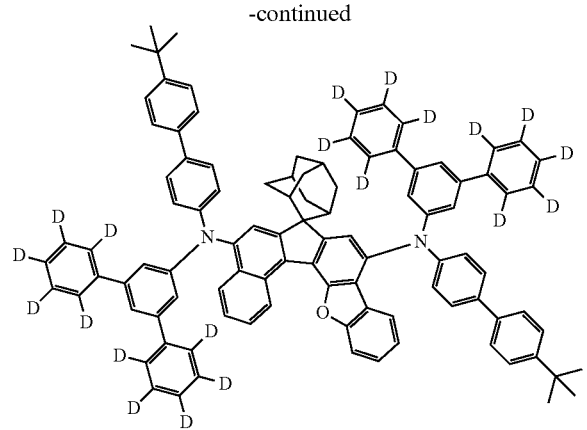
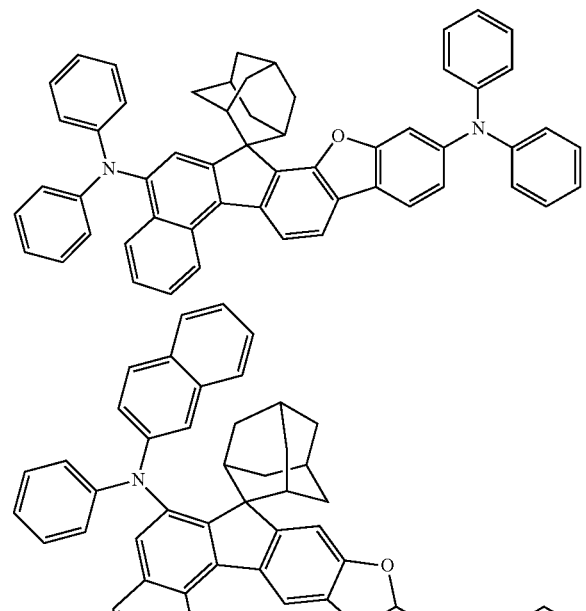
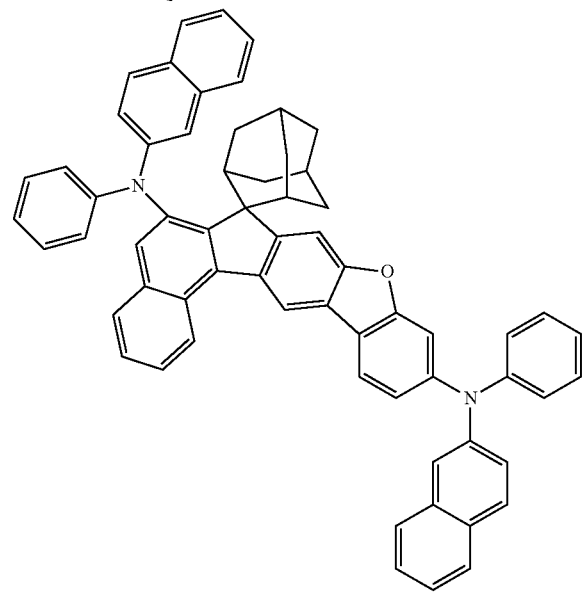
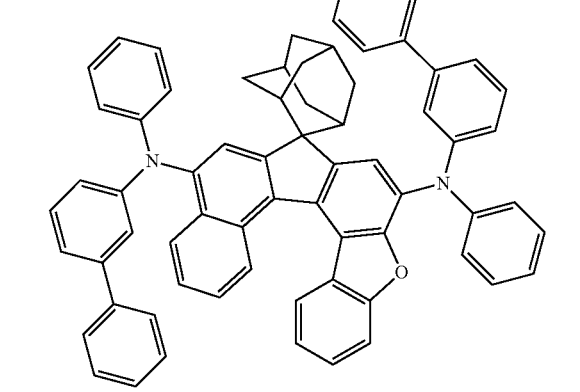
64
-continued
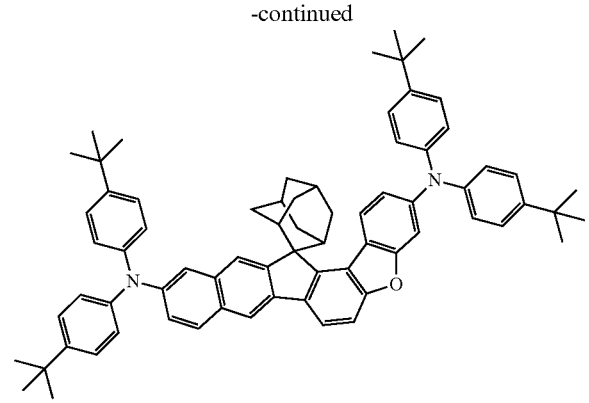
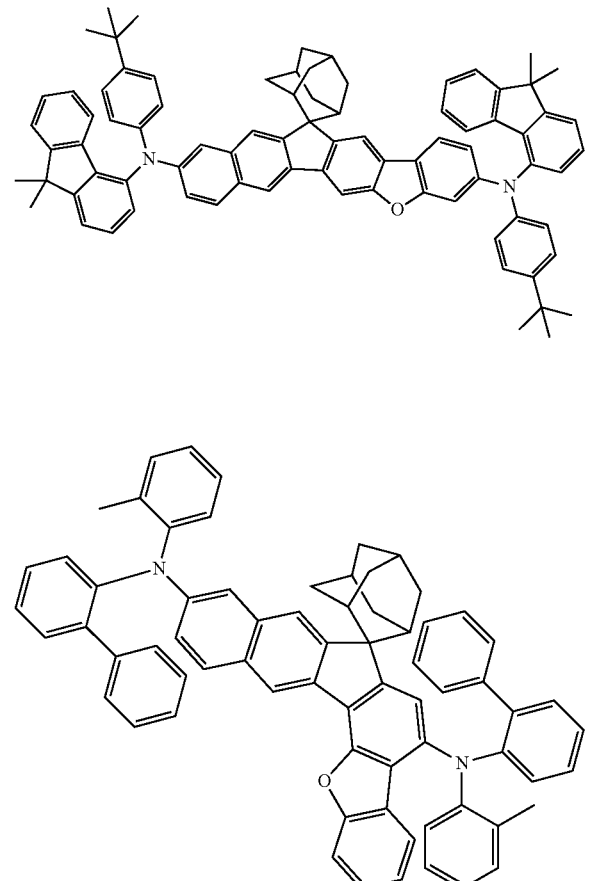
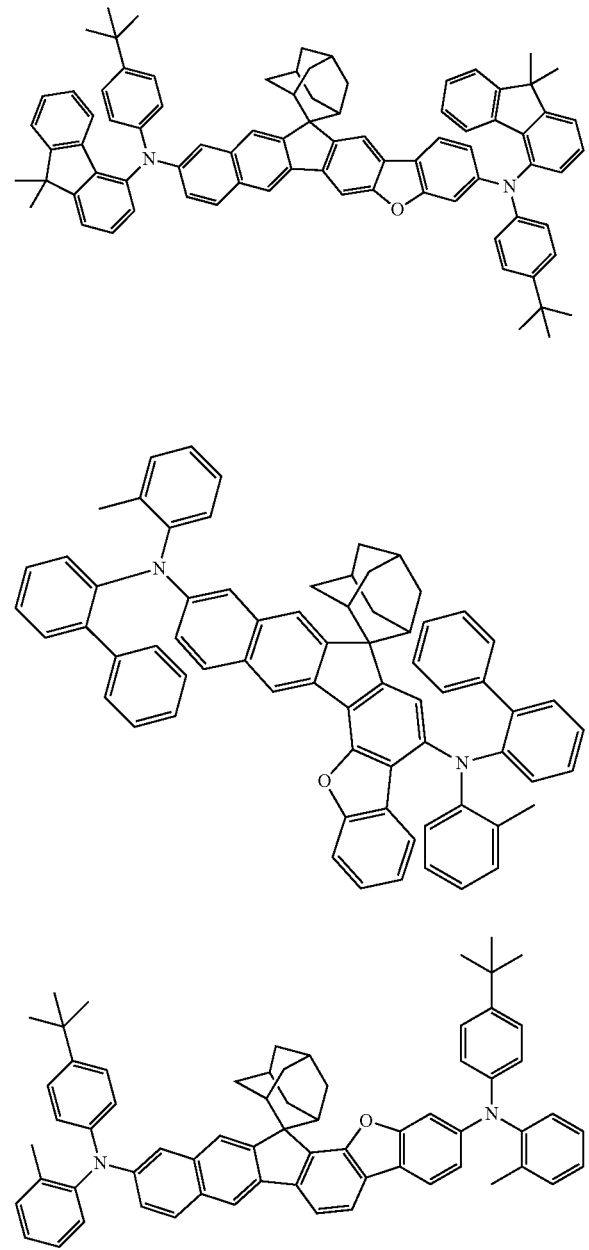

65
-continued
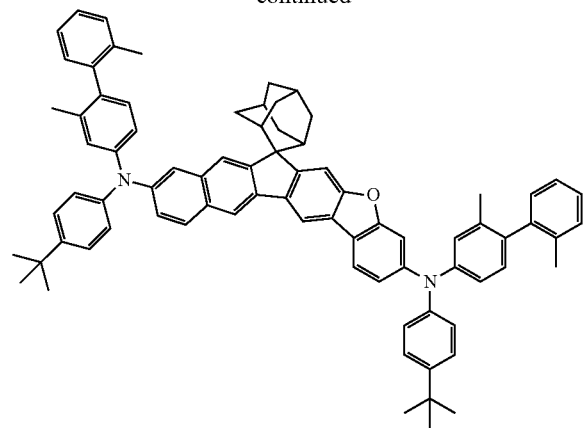
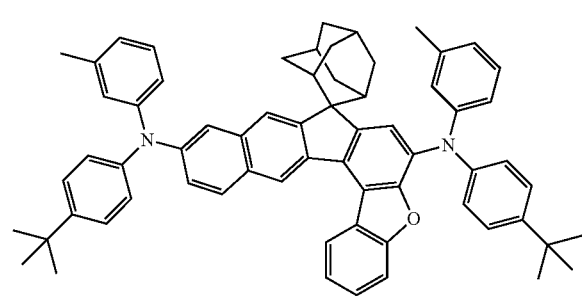
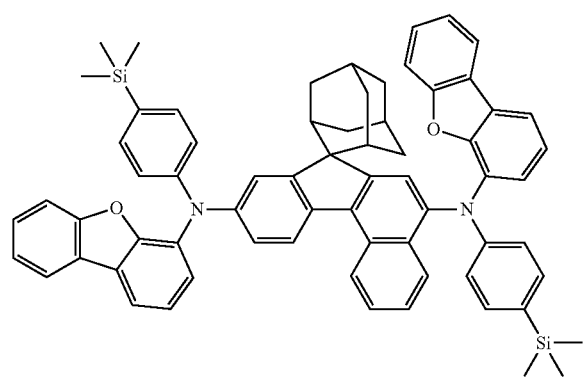
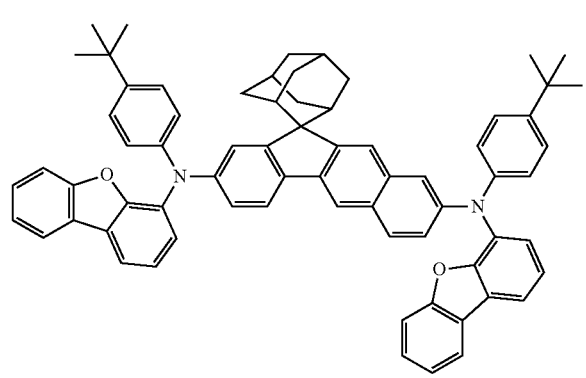
66
-continued
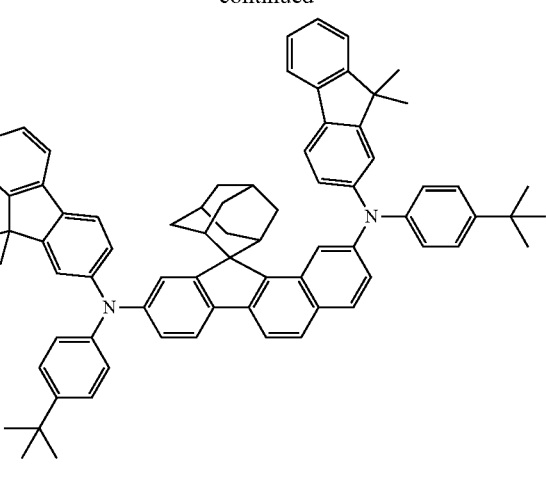
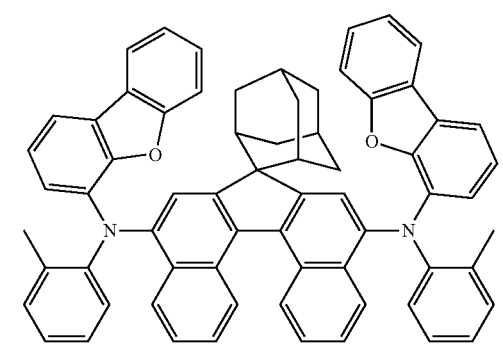
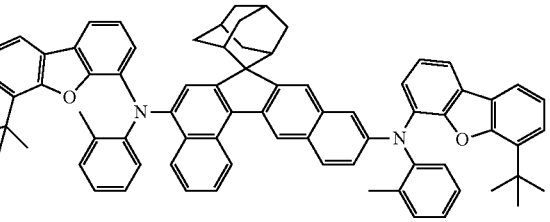
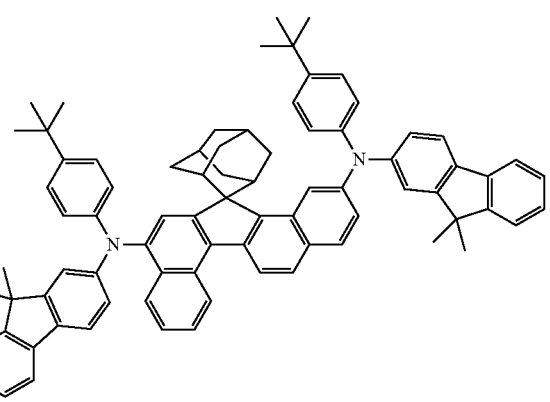

-continued
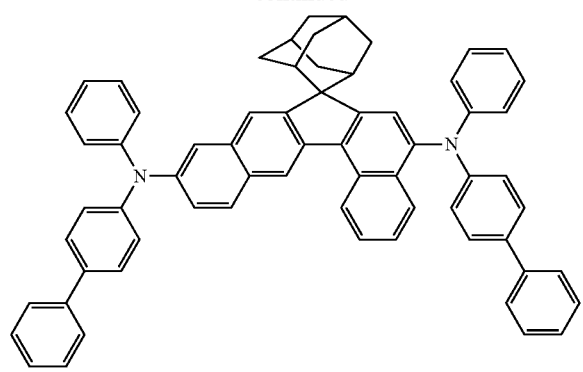
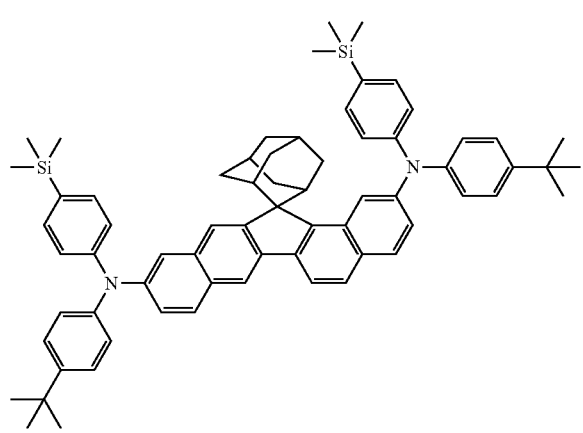
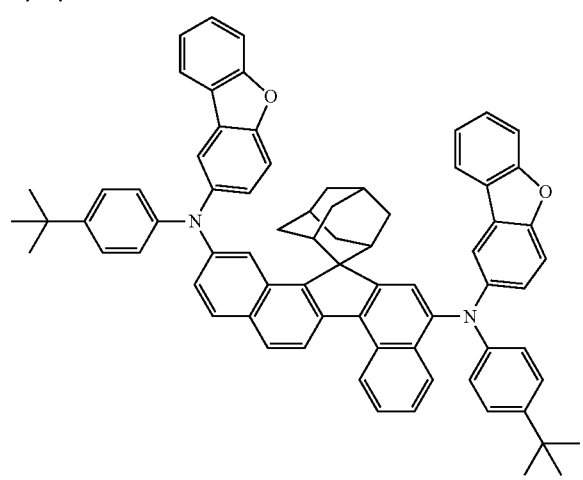
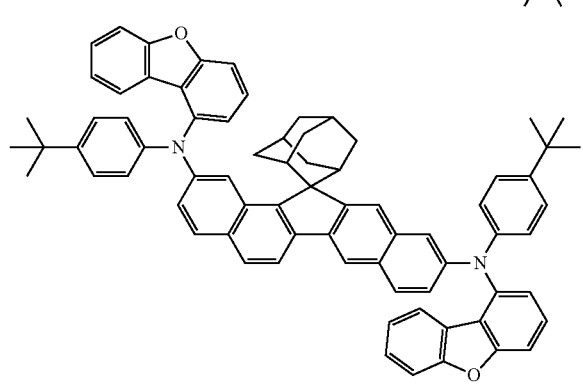
-continued
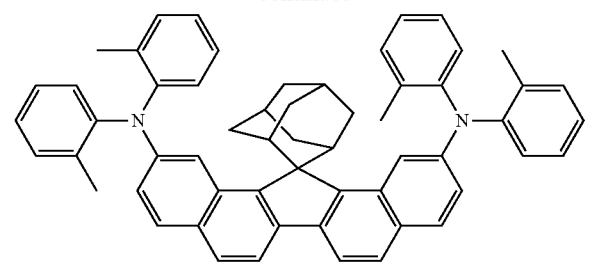
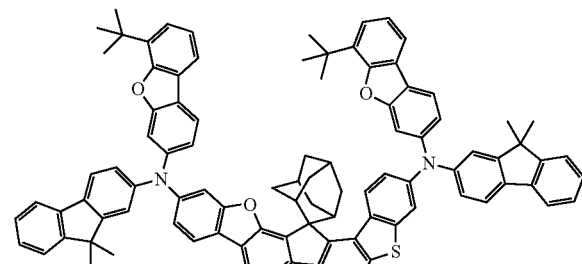
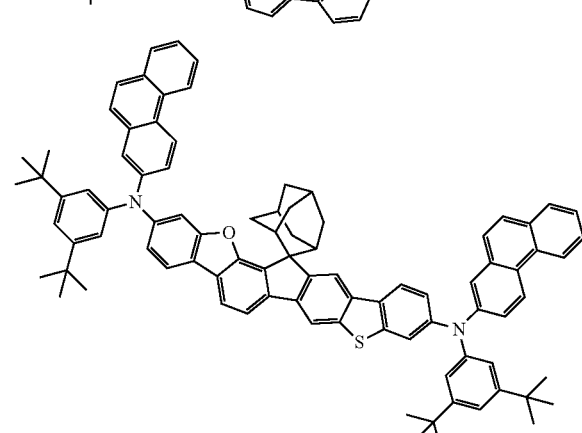
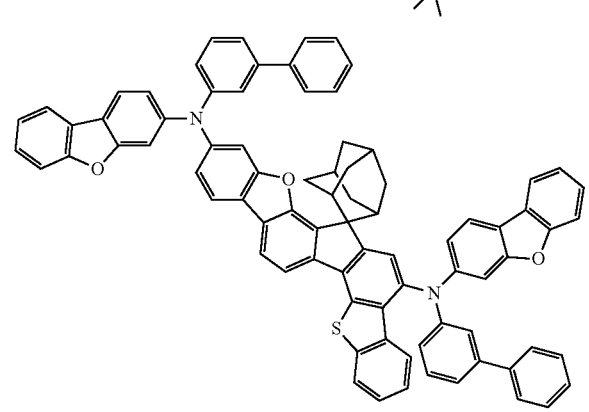
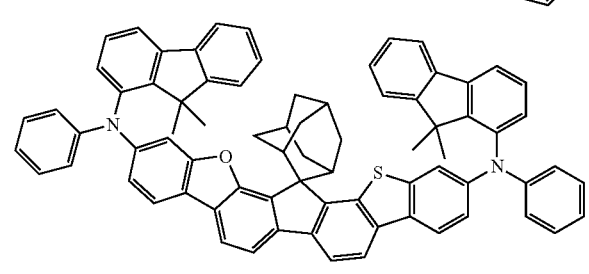

69
-continued
70
-continued
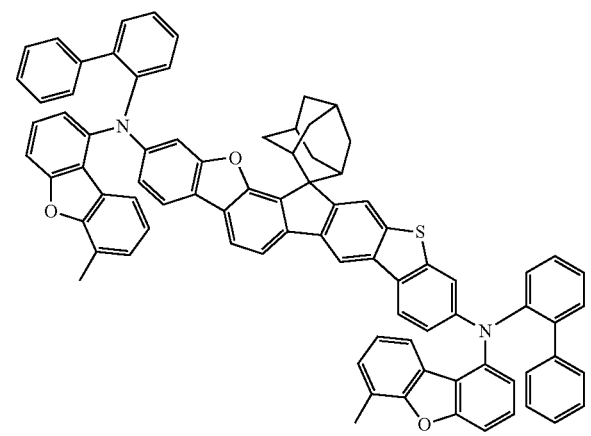
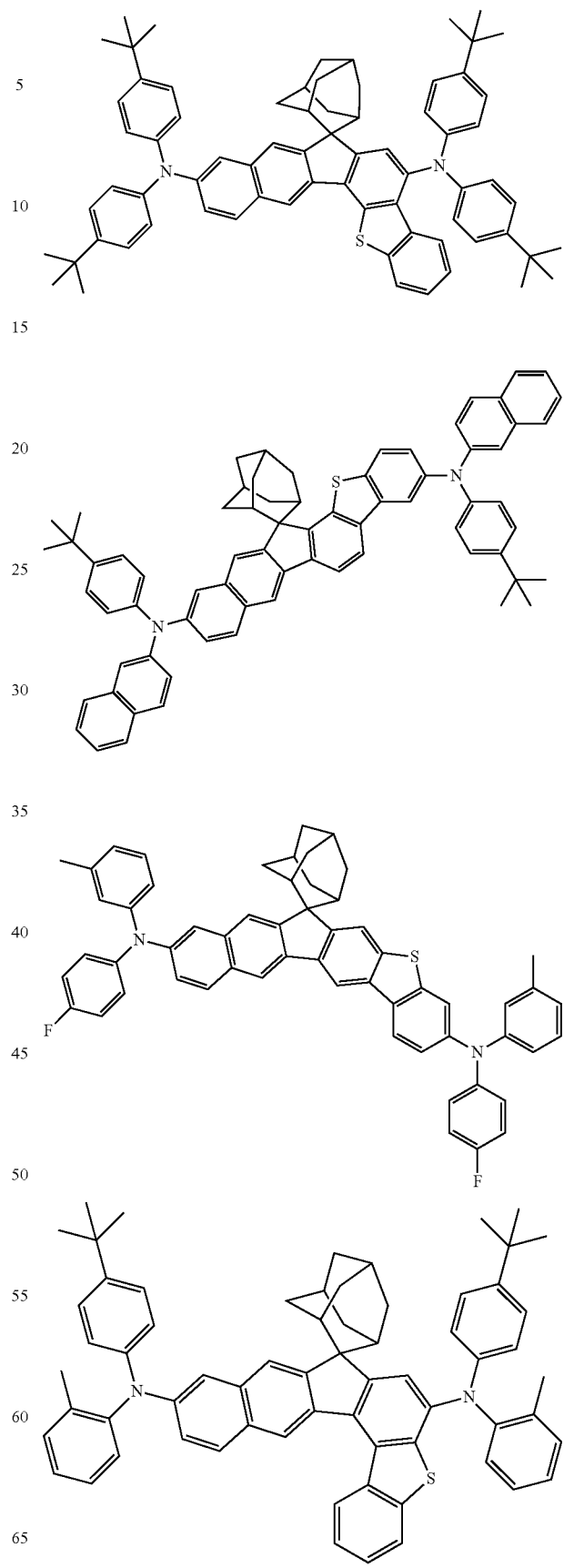

71
-continued
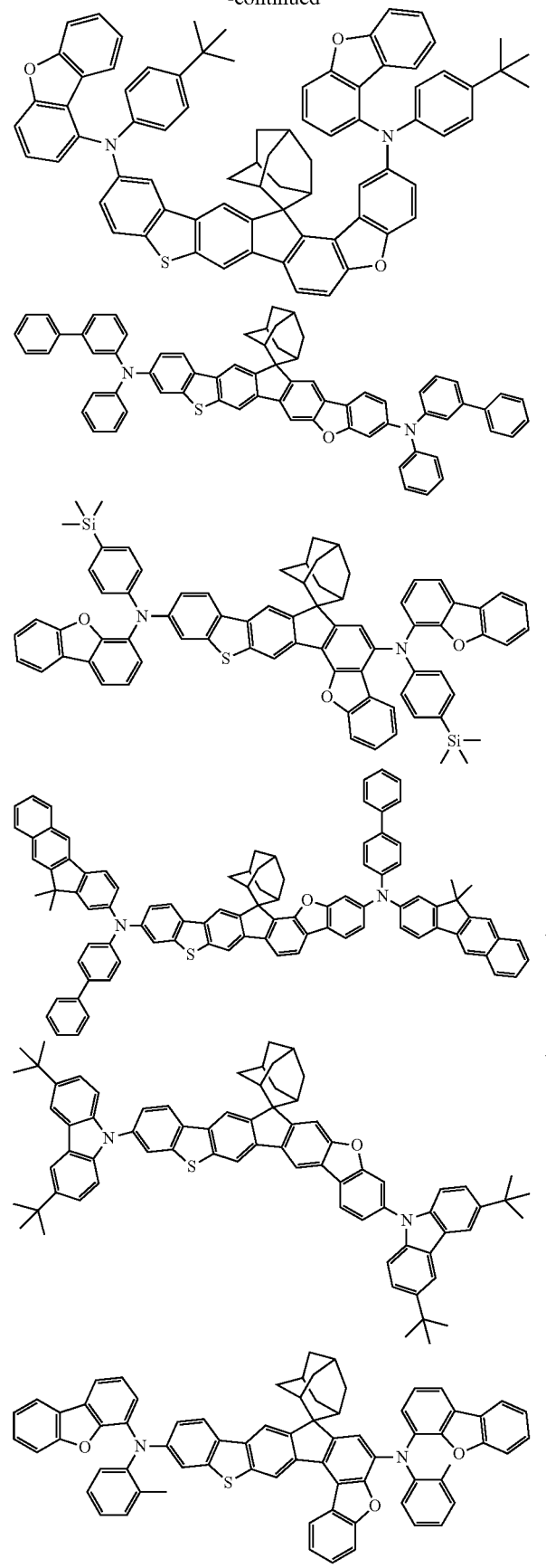
72
-continued
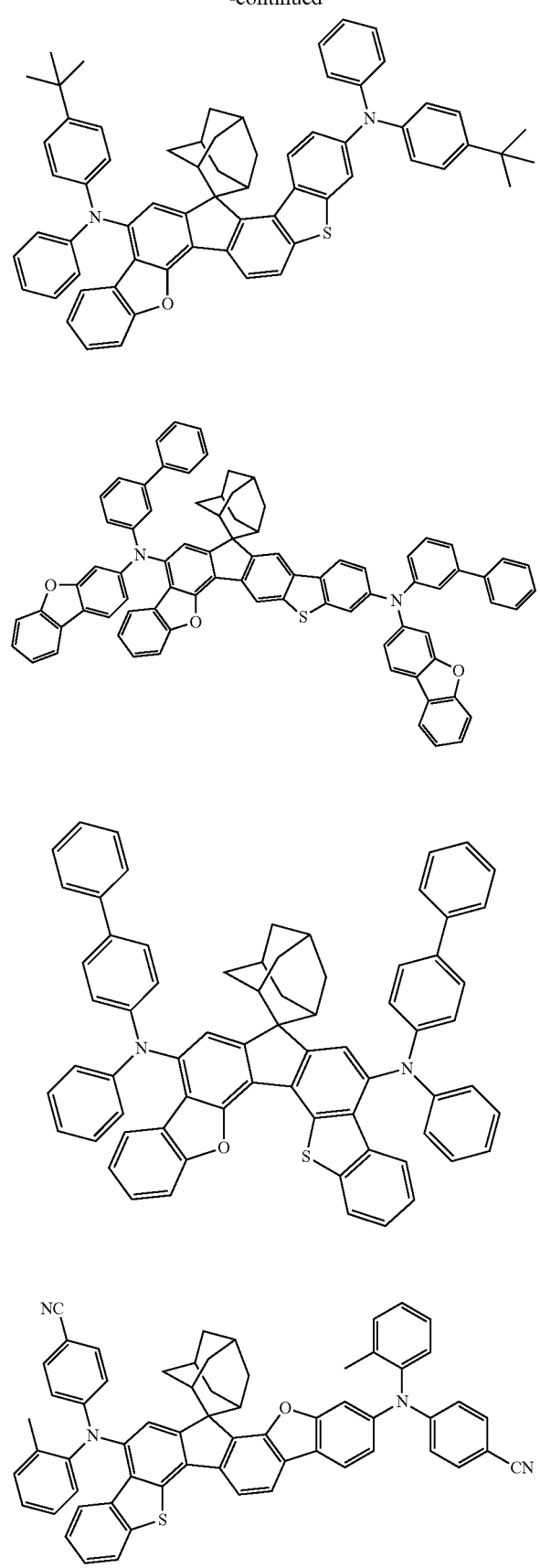

73
-continued
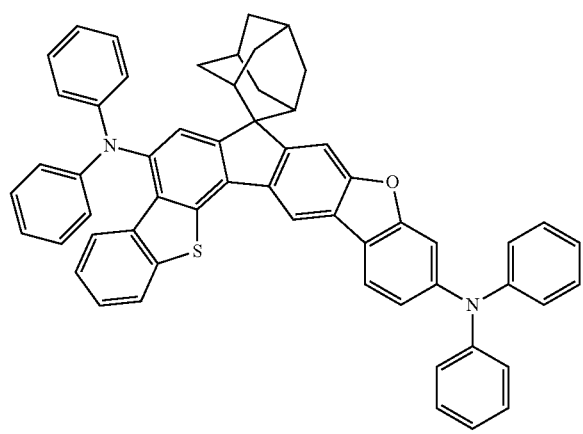
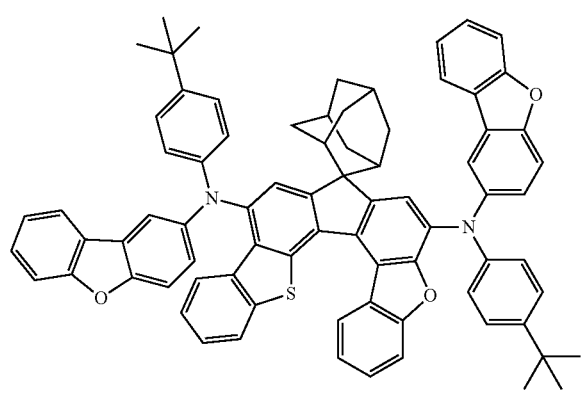
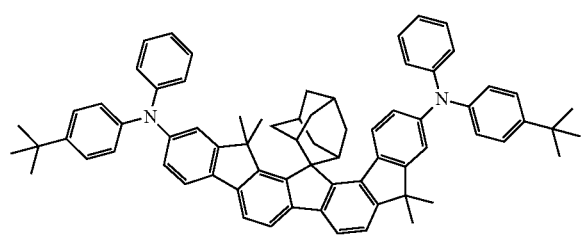
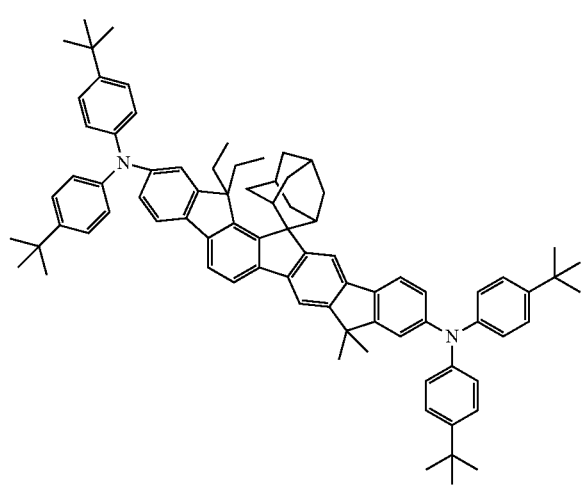
74
-continued
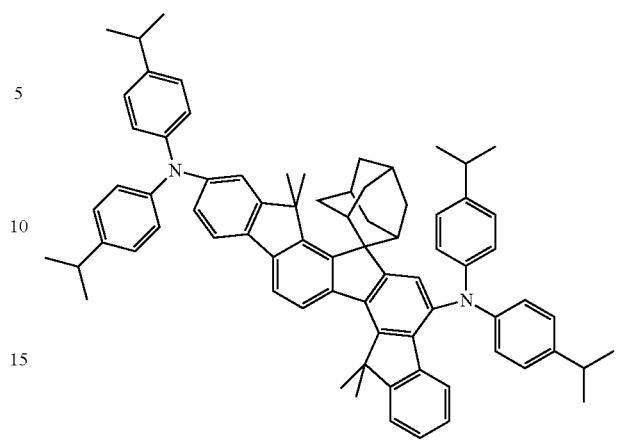
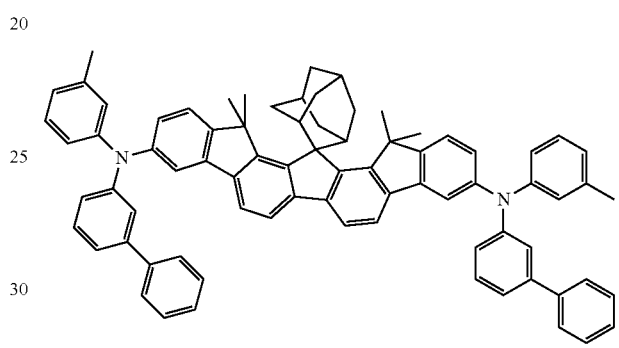
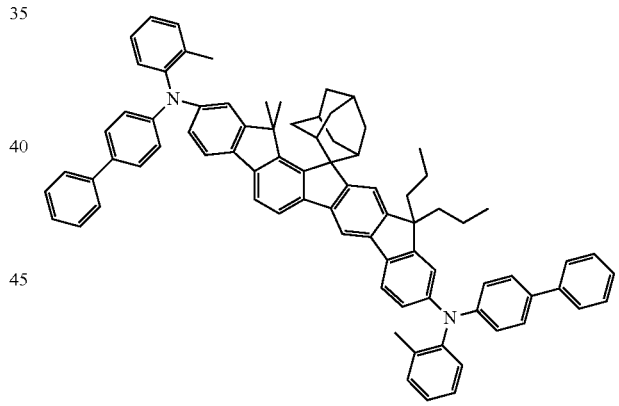
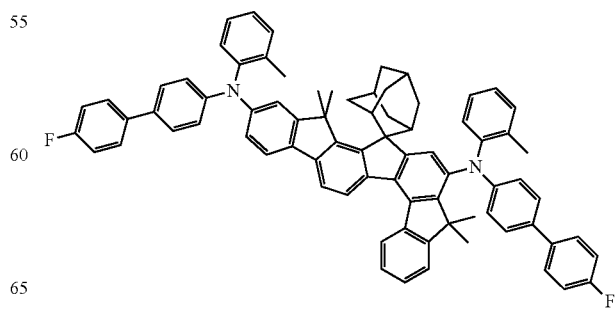

75
-continued
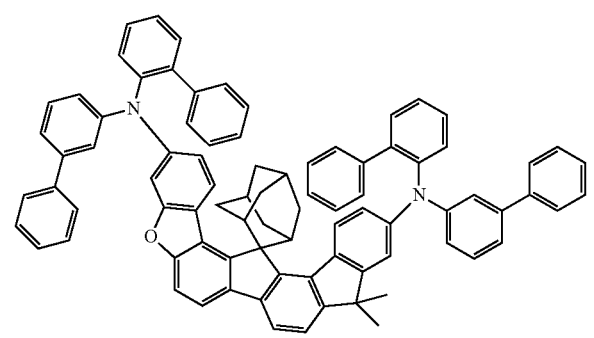
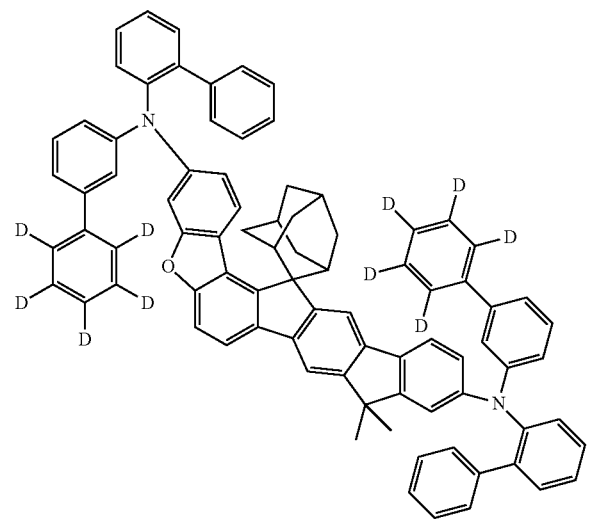
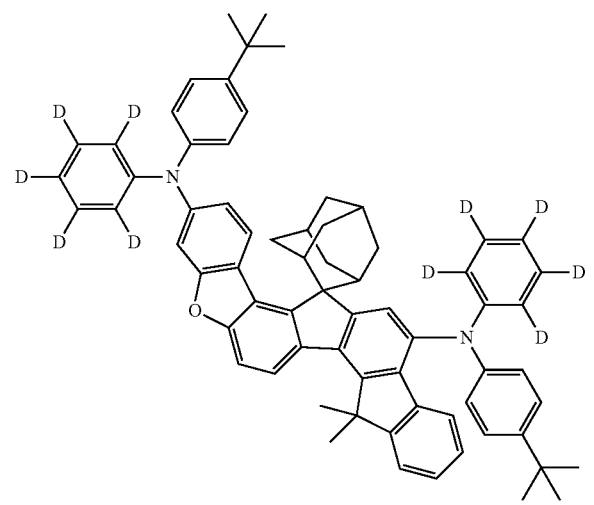
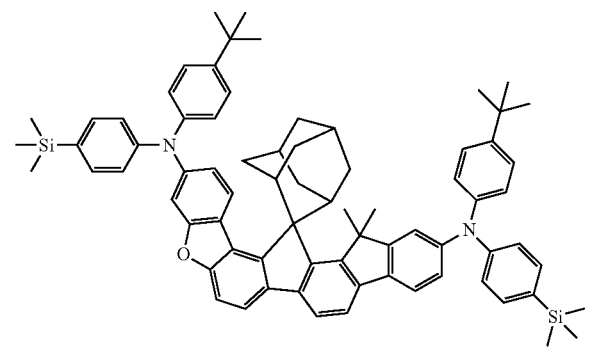
76
-continued
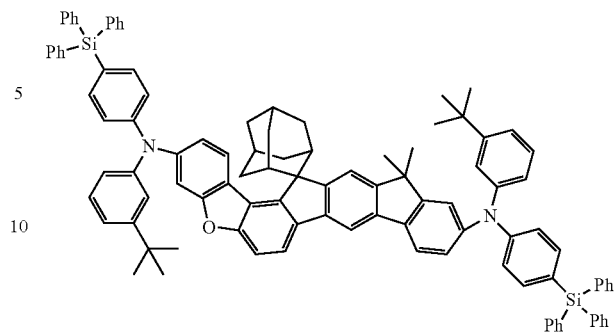
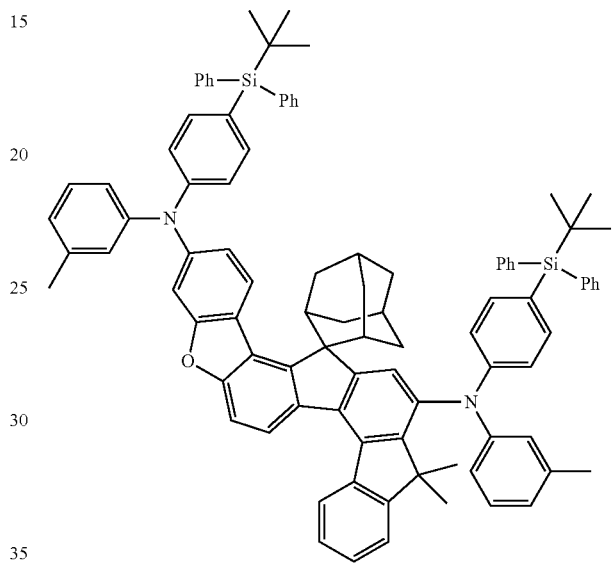
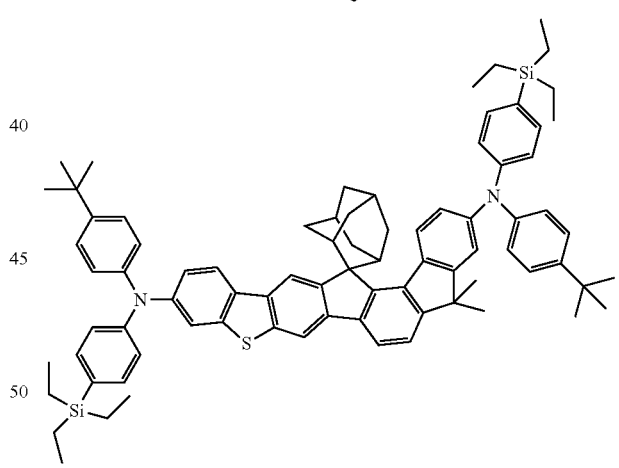
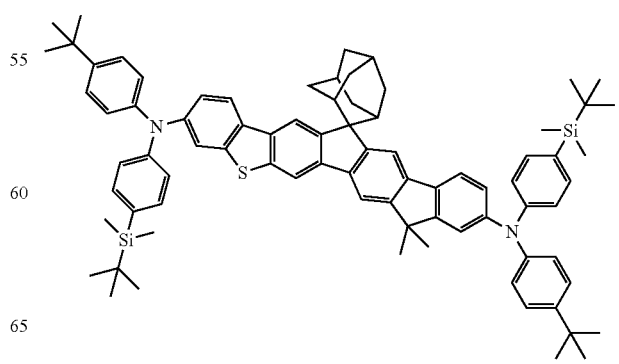

77
-continued
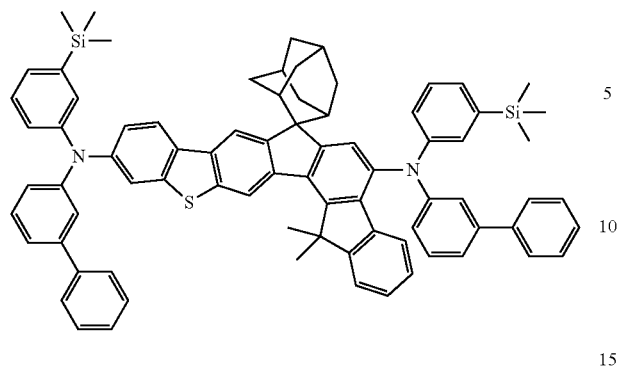
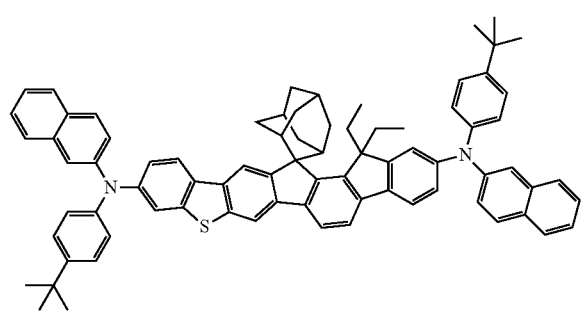
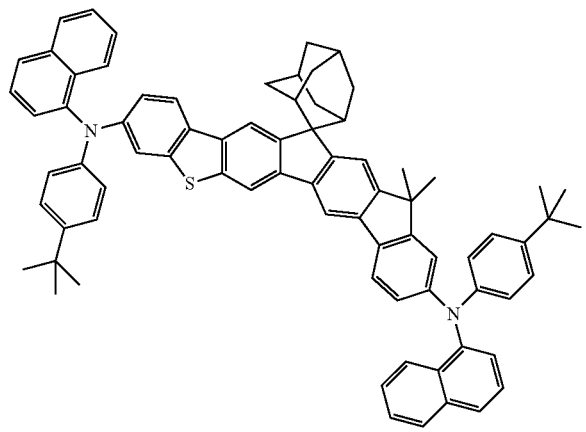
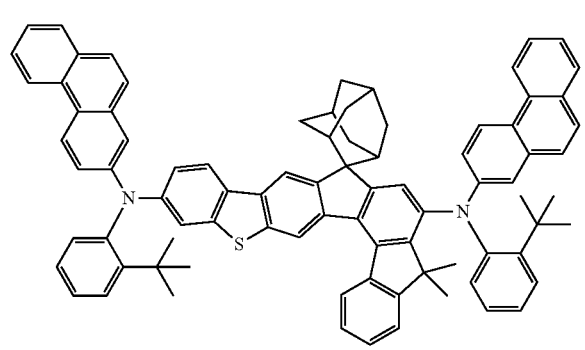
78
-continued
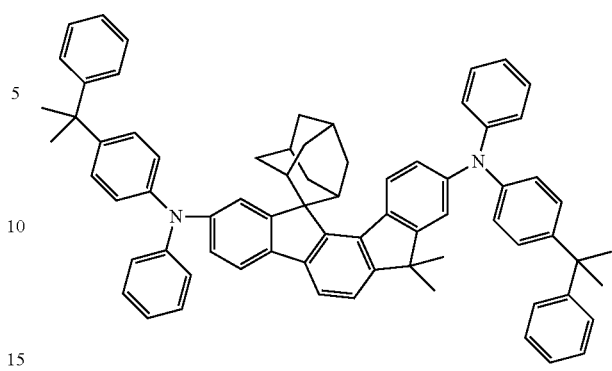
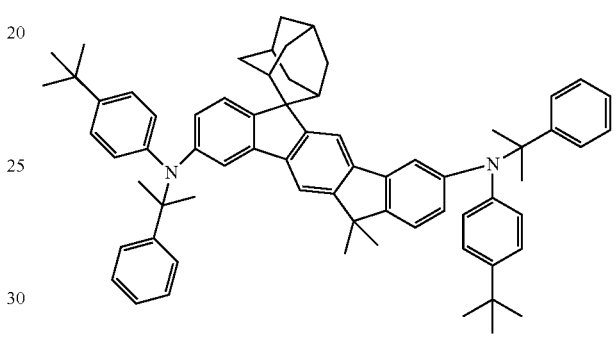
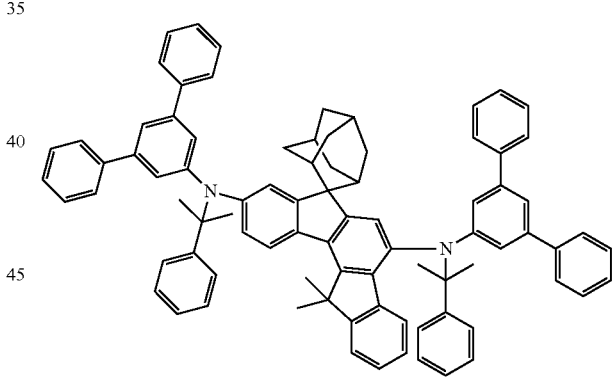
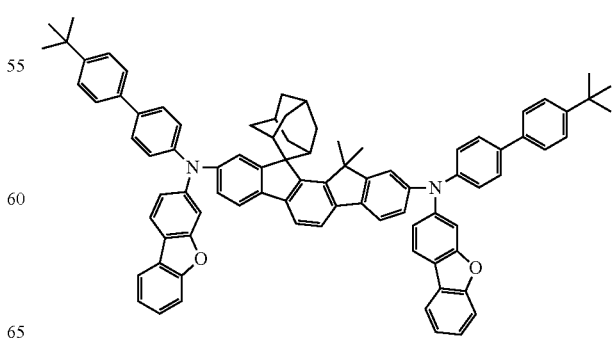

-continued
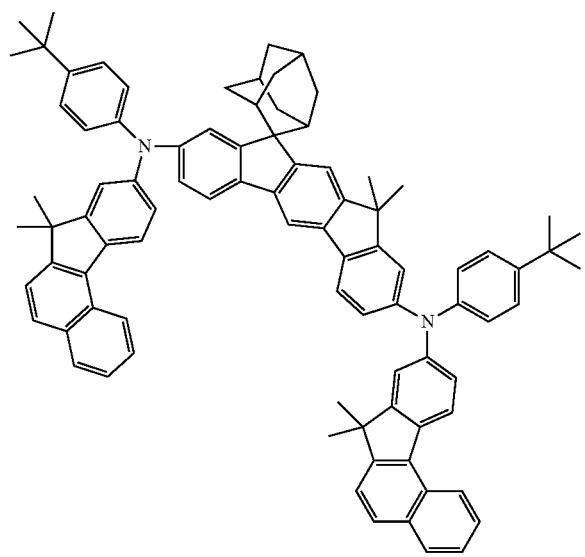
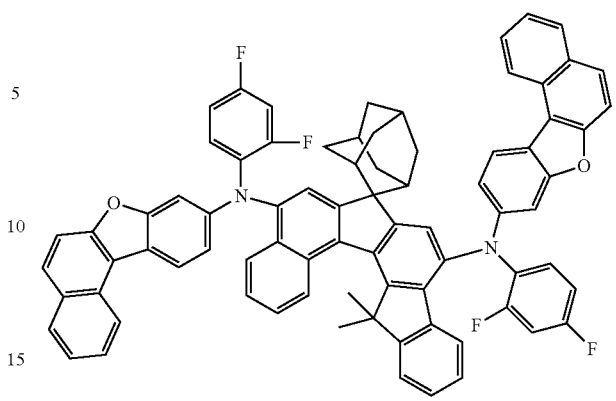
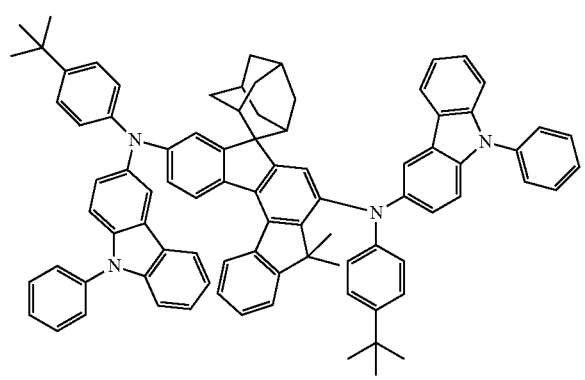
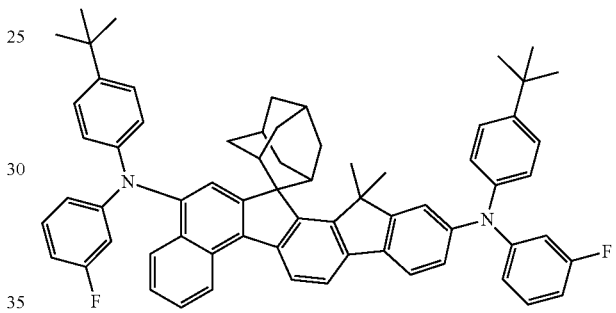
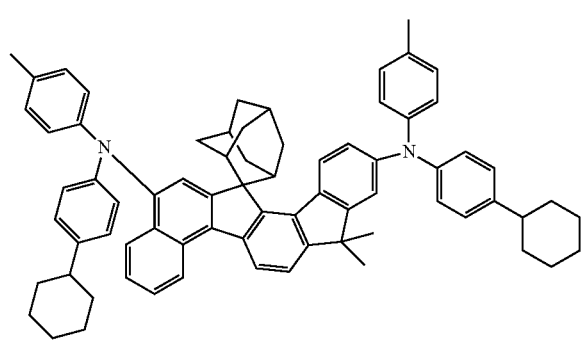
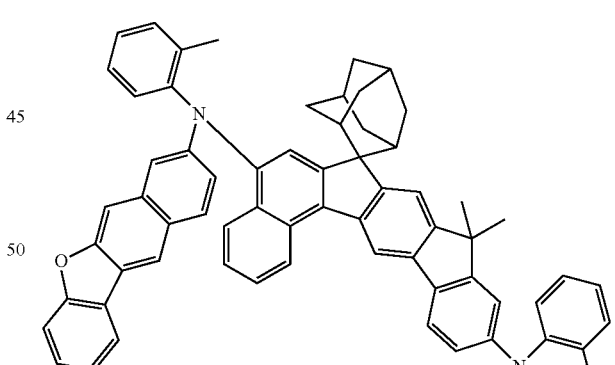
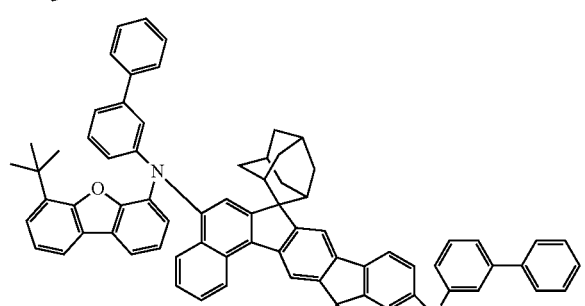

81
-continued
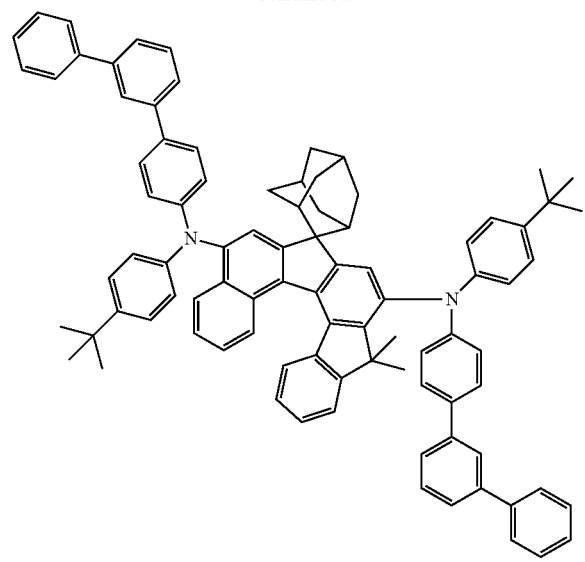
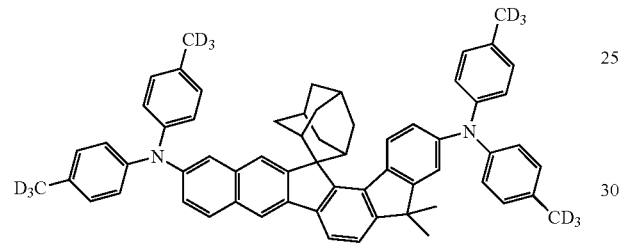
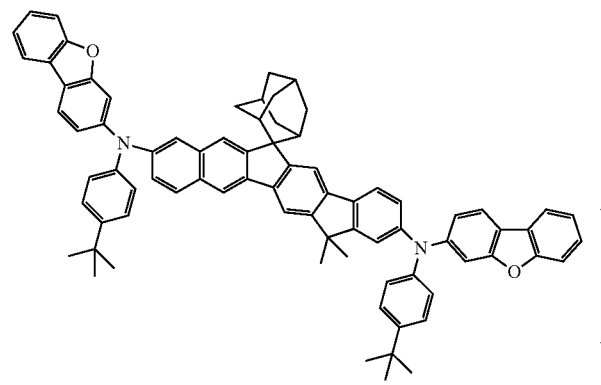
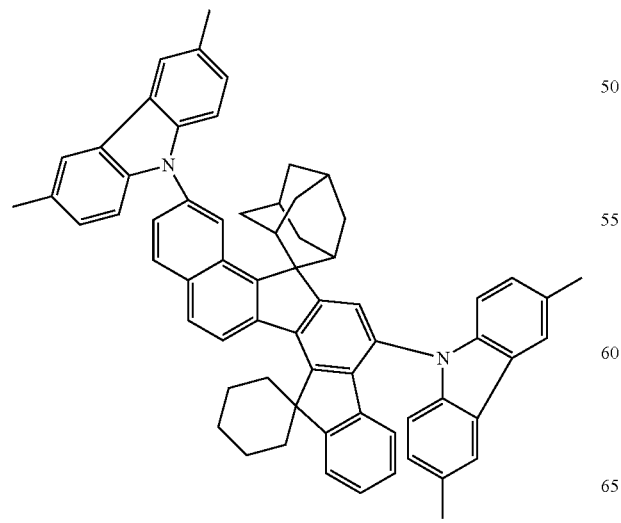
82
-continued
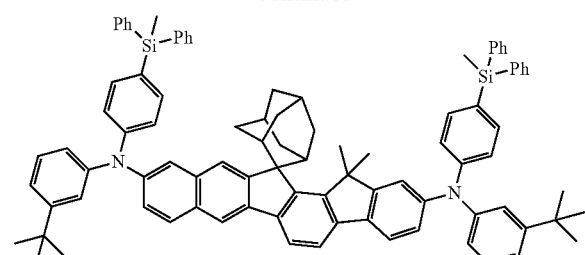
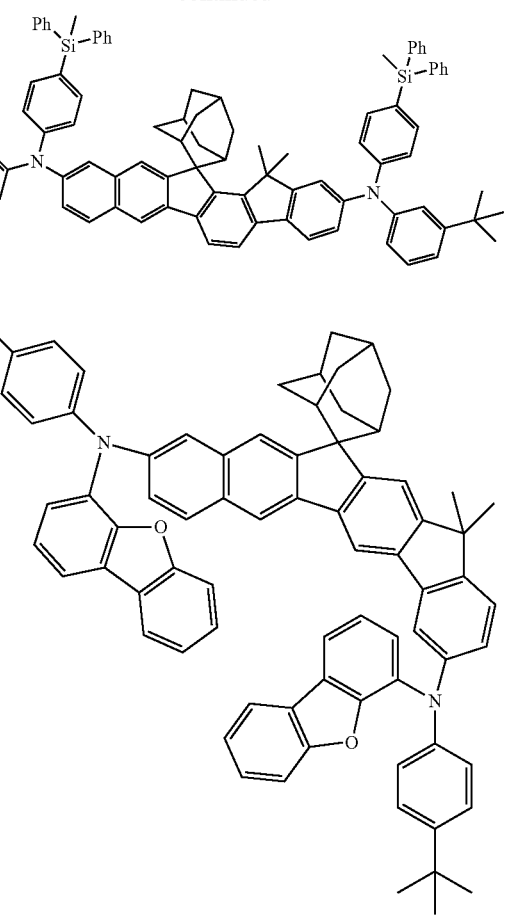
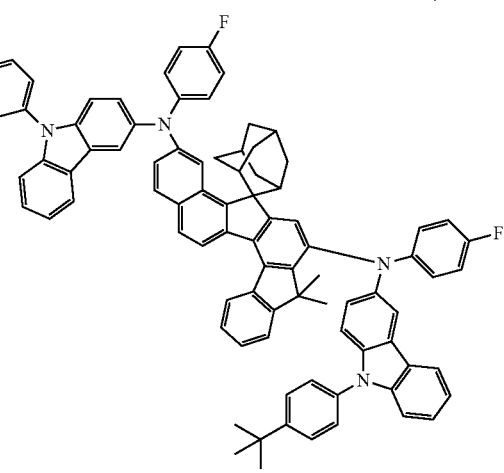
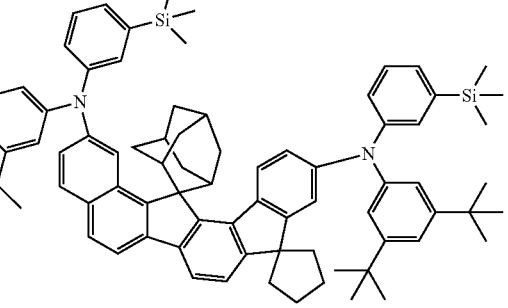

83
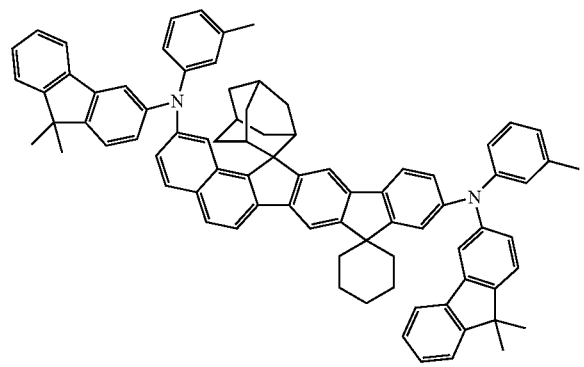
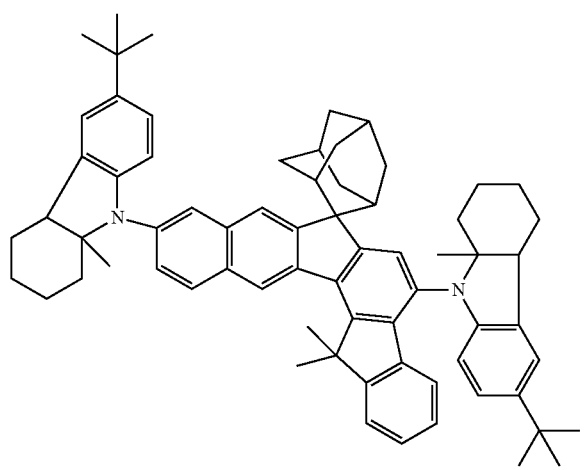
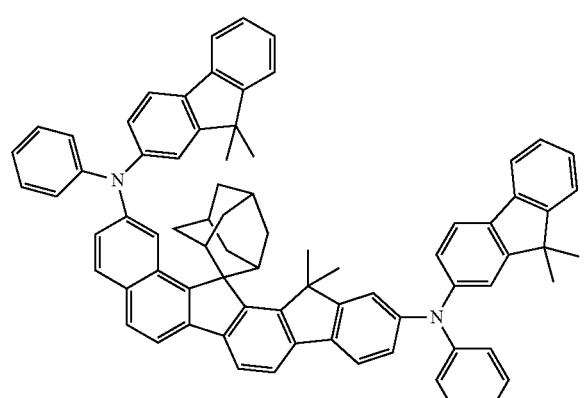
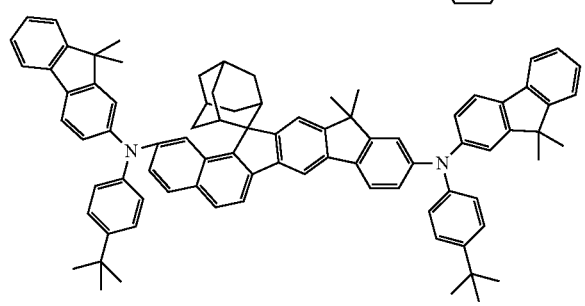
84
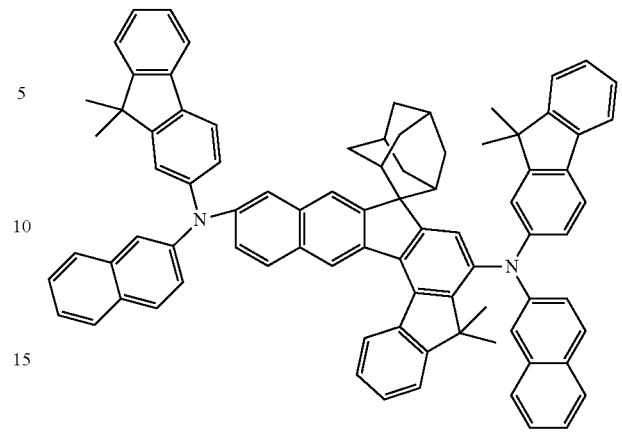
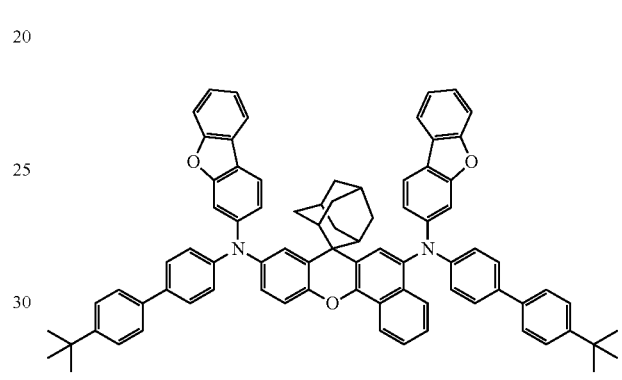
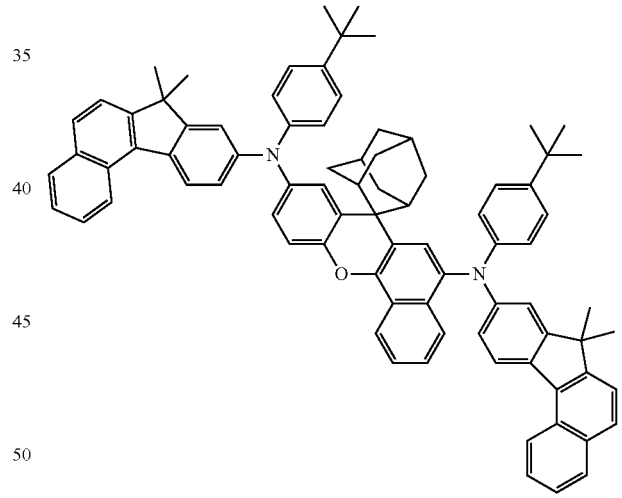
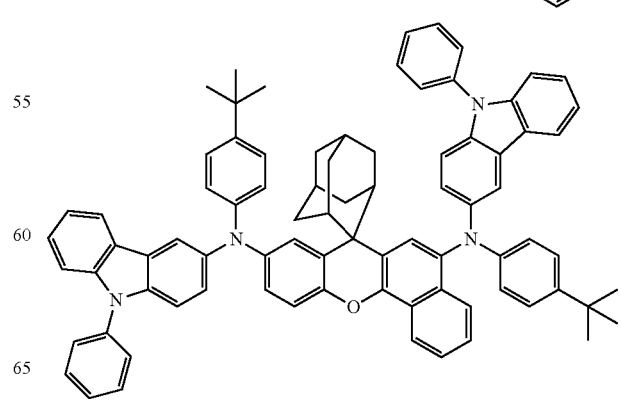

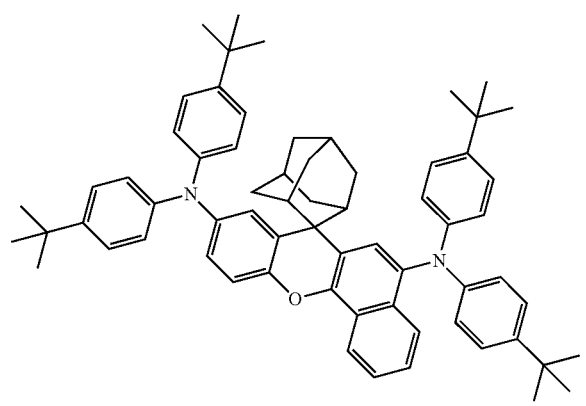
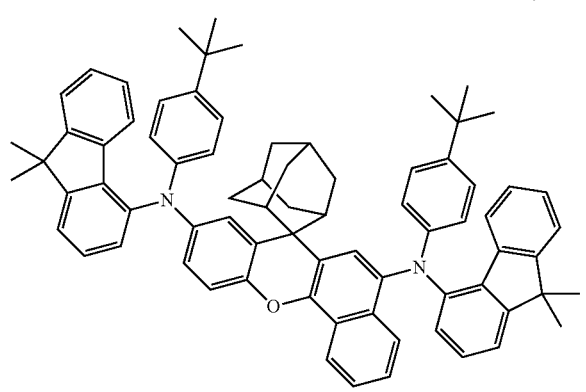
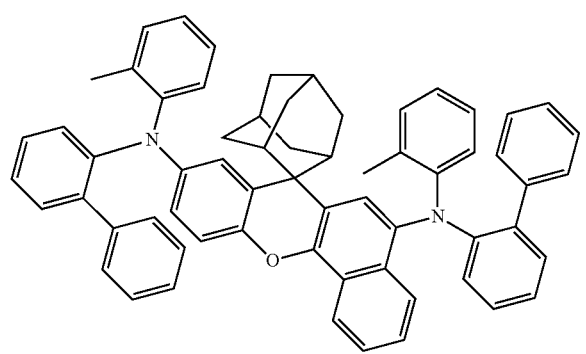
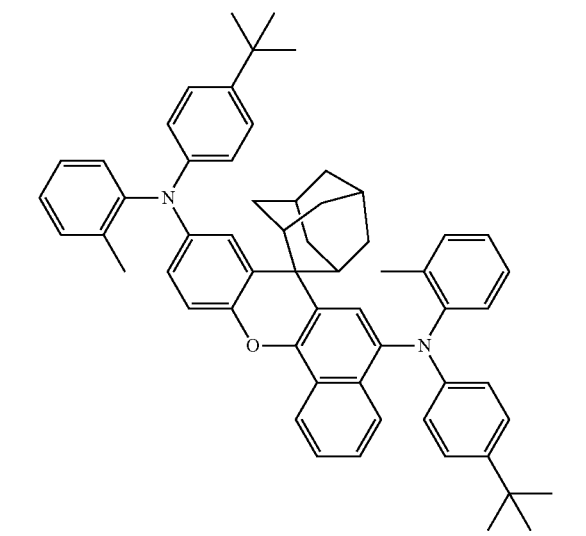
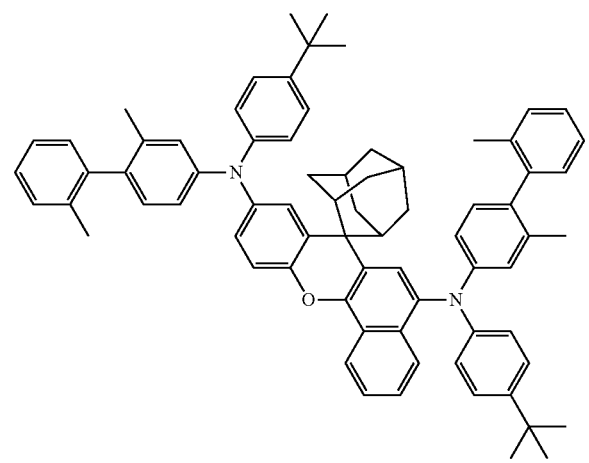
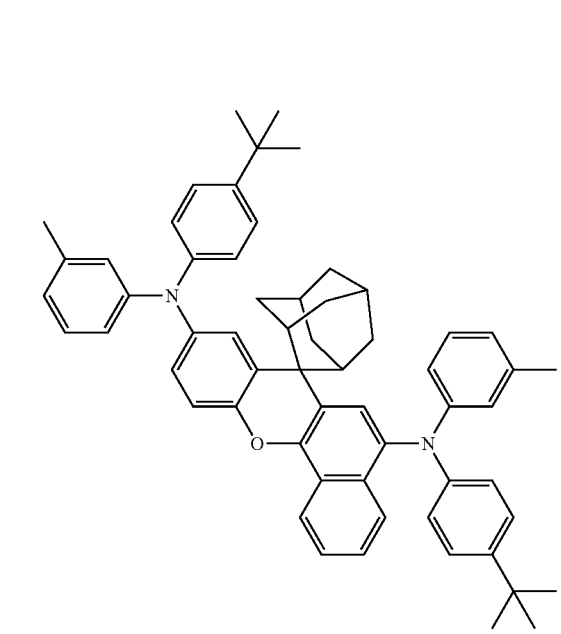
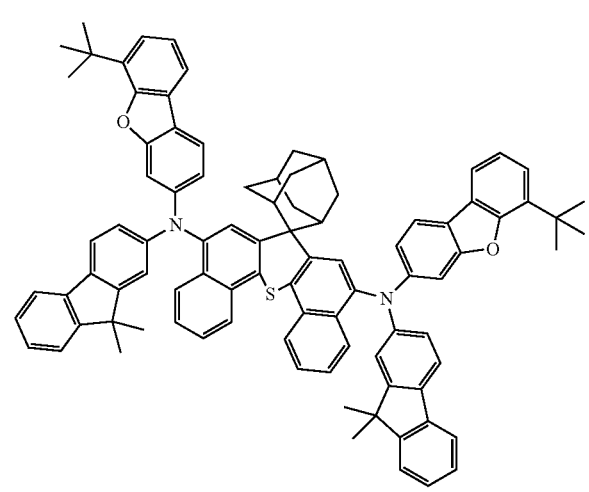

-continued
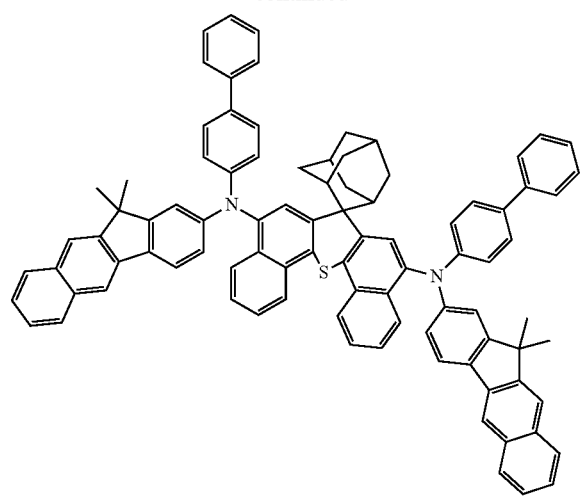
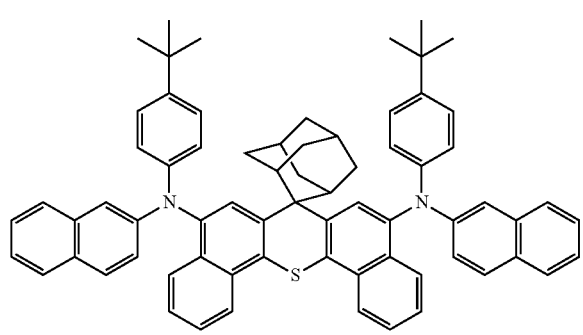
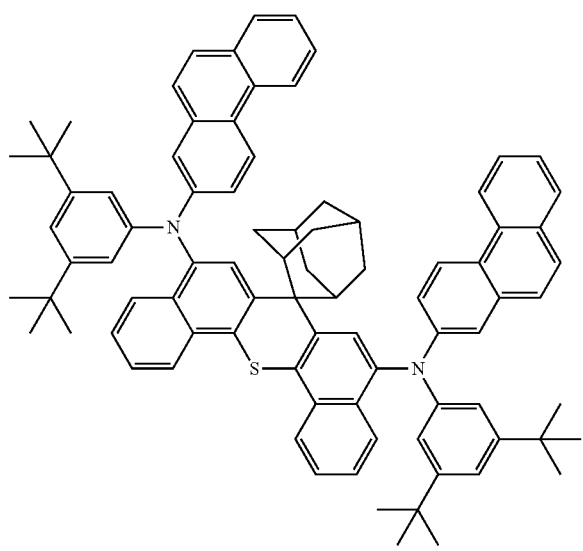
-continued
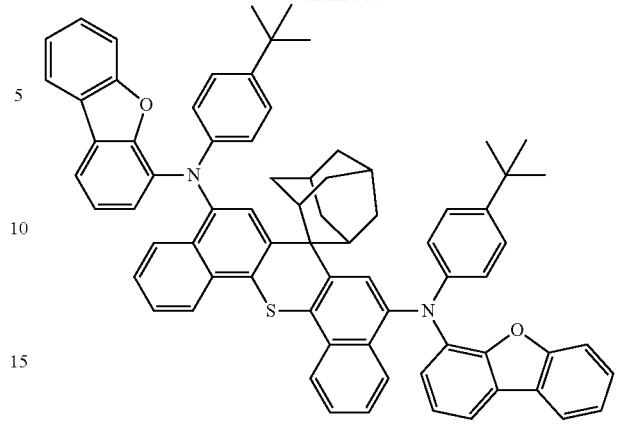

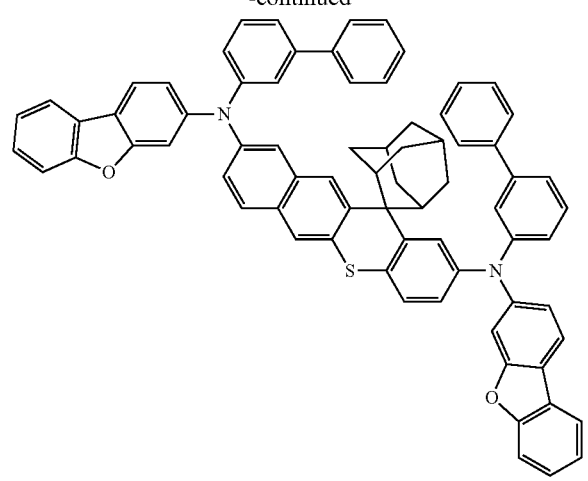
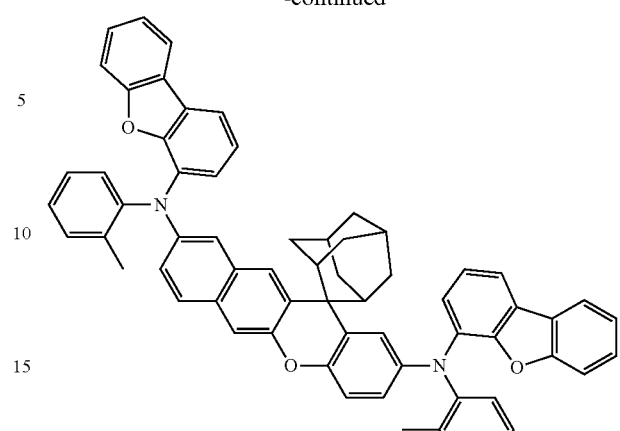
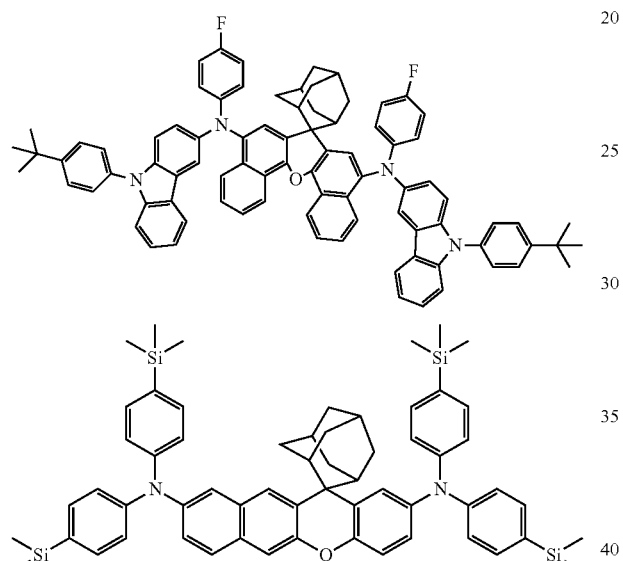
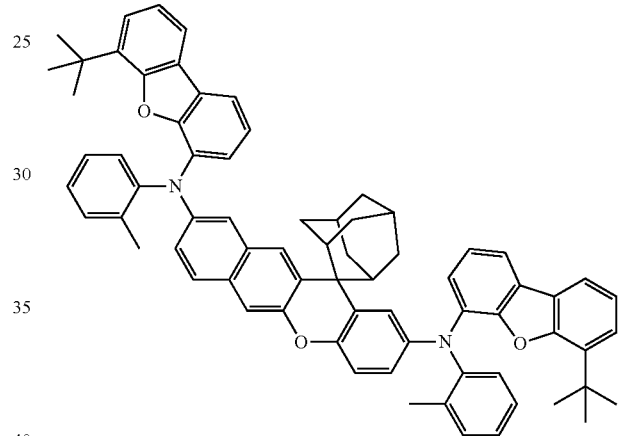
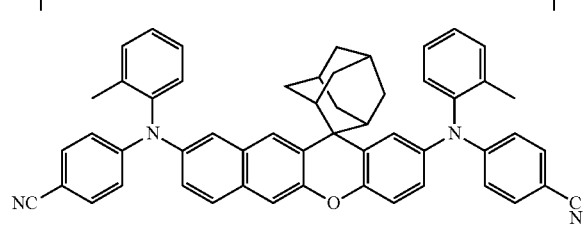
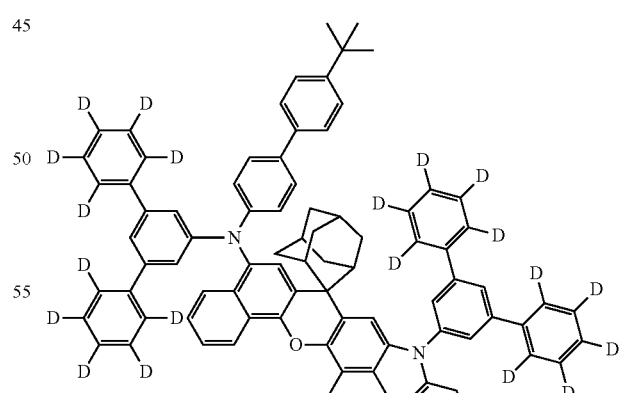
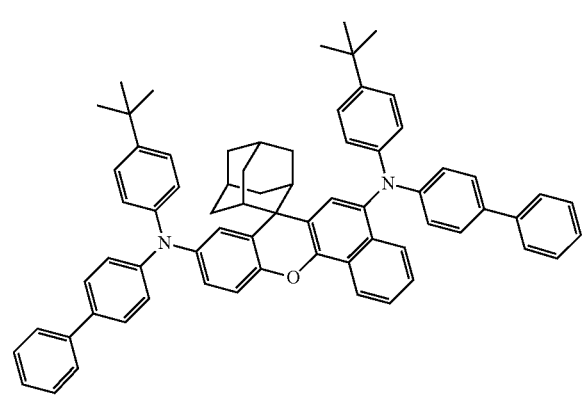

91
-continued
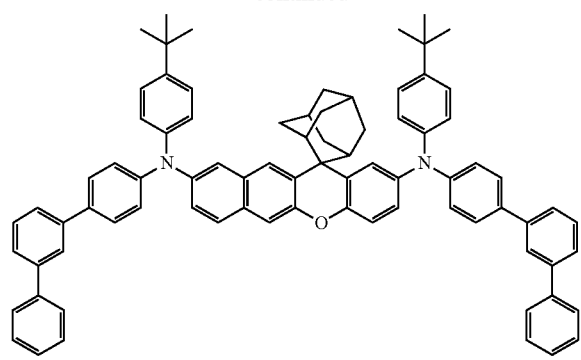
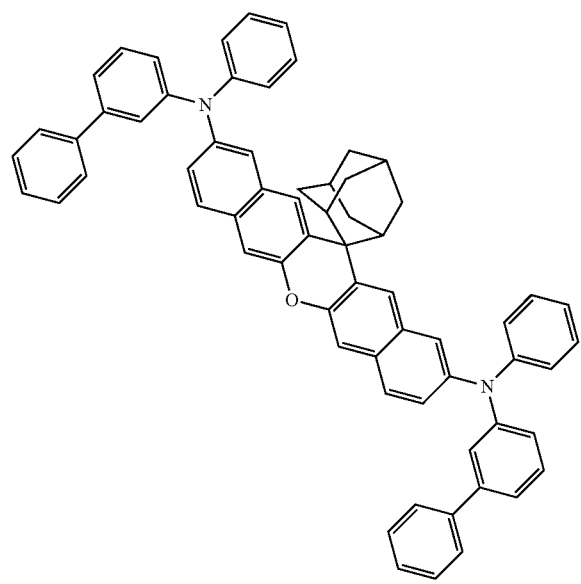
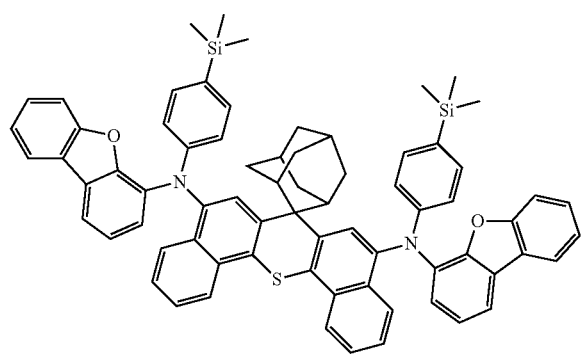
92
-continued
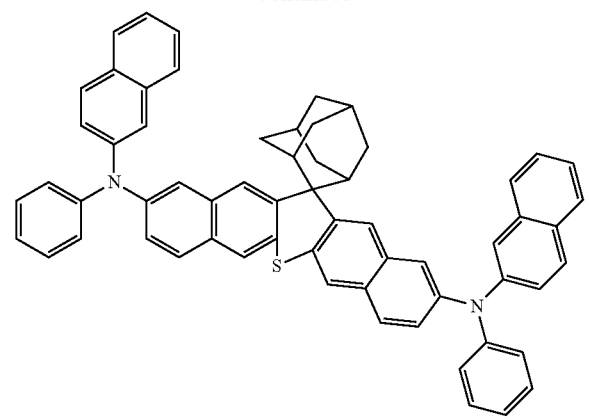
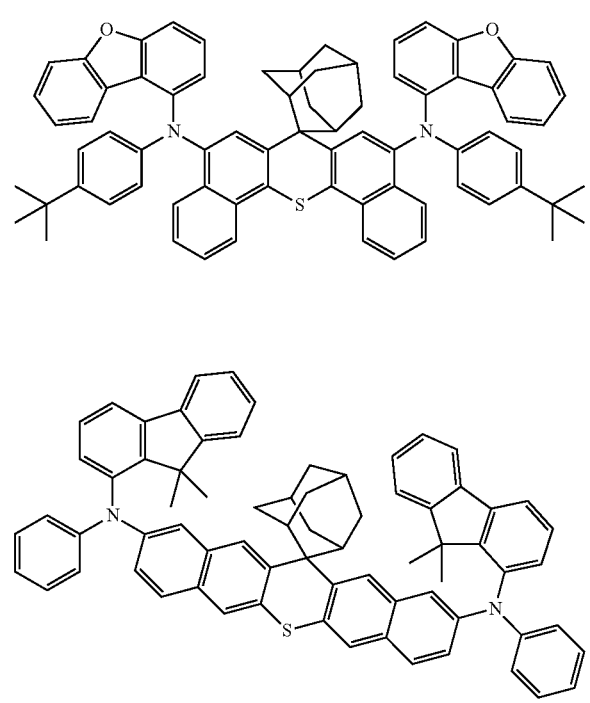
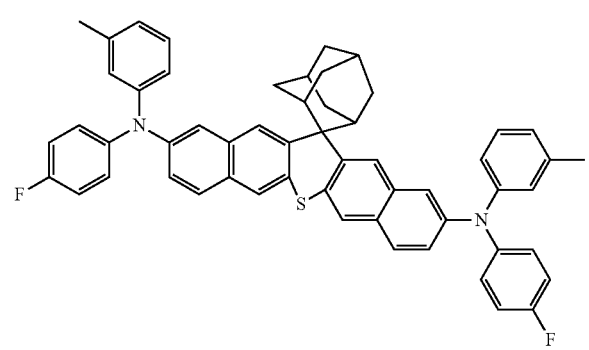

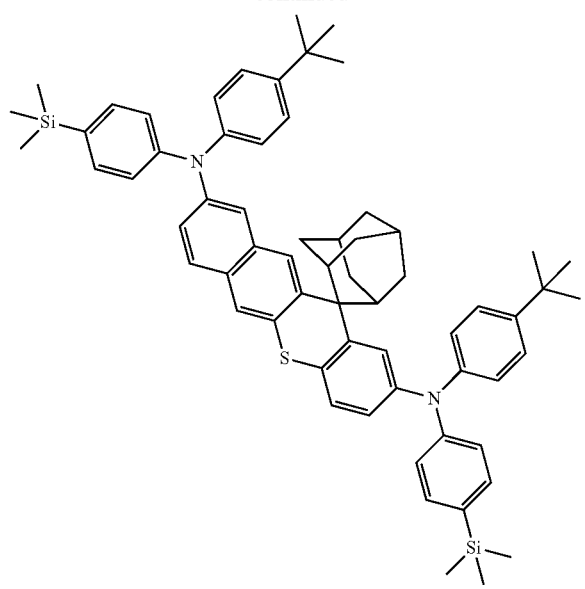

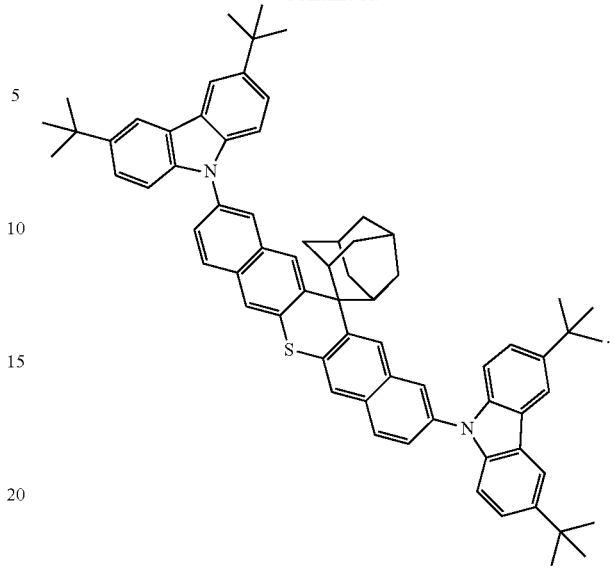

The compound of Chemical Formula 1 according to the present invention includes a core structure of fluorene in which adamantane is substituted. Thereby, due to the bulkiness and rigidity of the core structure, the sublimation property is excellent, the chemical structure is stable, the luminous efficiency is increased, and the thermal stability is excellent. In particular, since the compound of Chemical Formula 1 includes an amine substituent having a specific structure, it is possible to control the electrical characteristics and the light emission characteristics at the same time, thereby improving the efficiency and lifetime of the OLED device. Therefore, the organic light emitting device employing the present compound can have high efficiency, low driving voltage, high luminance, long lifetime, and the like as compared with a conventional organic light emitting device employing the compound (e.g., dimethyl fluorene, etc.) having a simple spiro structure.

The compound of Chemical Formula 1 can be prepared by a manufacturing method according to the multi-step reaction of Reaction Scheme 1 below. The preparation method can be further embodied in the Preparation Examples described hereinafter.

<Reaction Scheme 1>

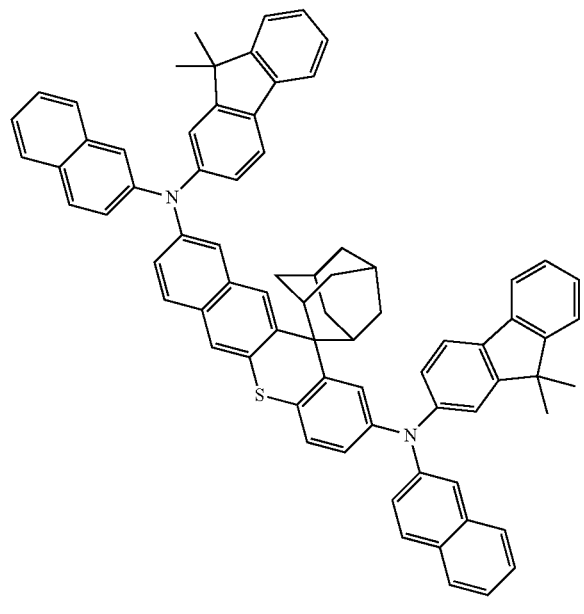

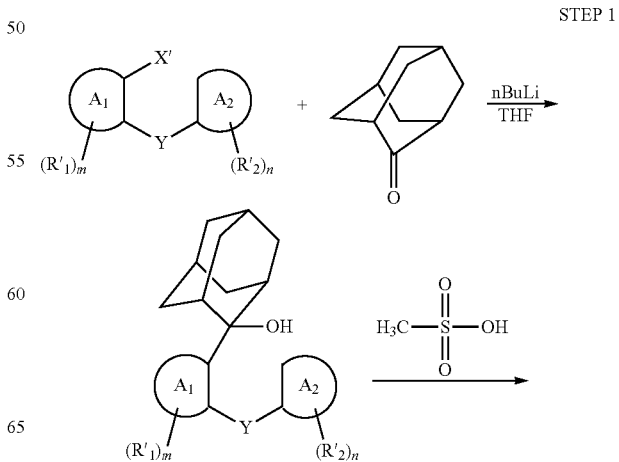

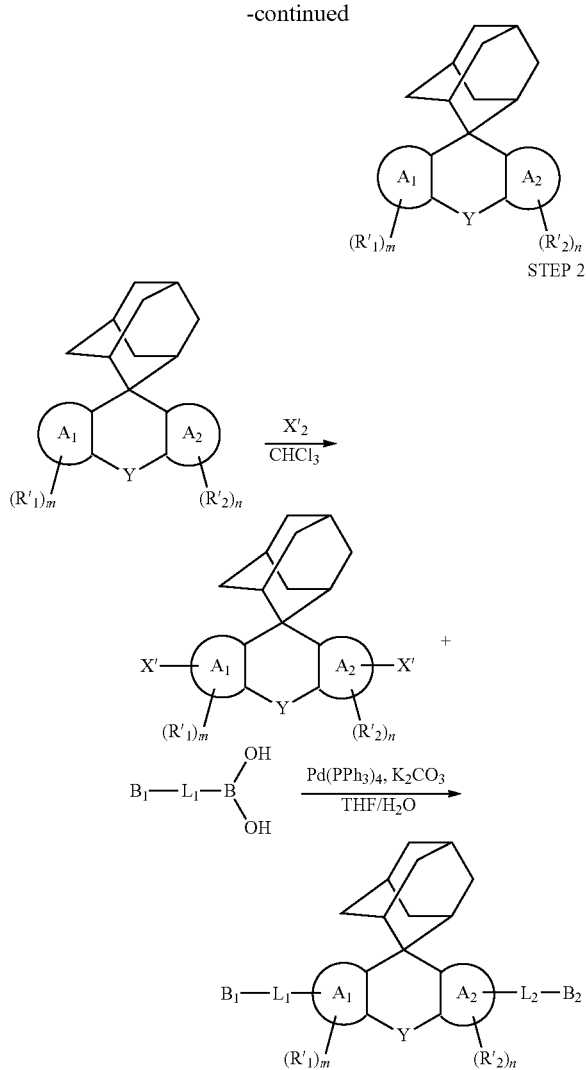

wherein, the remaining variables excluding X' are as defined above, each X' is independently halogen, preferably chloro or bromo, more preferably bromo.

In Reaction Scheme 1, the reactants, catalysts, solvents, and the like used can be modified to conform to the desired product.

The reaction of STEP 2 is a Suzuki coupling reaction, which is preferably carried out in the presence of a palladium catalyst and a base, and a reactive group for the Suzuki coupling reaction can be modified as known in the art.

On the other hand, the synthesis of asymmetric compounds having amine substituents (*-$L_1$-$B_1$/*-$L_2$-$B_2$) in the final product can proceed with two Suzuki coupling reactions for intermediate compounds having different structures in STEP 2. The preparation method of the compound can be further embodied in the Preparation Examples described hereinafter.

In another embodiment of the invention, there is provided an organic light emitting device including a compound of Chemical Formula 1 described above. As an example, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

The organic material layer of the organic light emitting device of the present invention can have a single-layer structure, or it can have a multilayered structure in which two or more organic material layers are stacked. For example, the organic light emitting device of the present invention can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic layers.

Further, the organic material layer can include a hole injection layer, a hole transport layer, or a layer for simultaneously performing hole injection and transport, wherein the hole injection layer, the hole transport layer, or the layer for simultaneously performing hole injection and transport include the compound of Chemical Formula 1.

Further, the organic material layer can include a light emitting layer, wherein the light emitting layer includes the compound of Chemical Formula 1.

Further, the organic material layer can include an electron transport layer, or an electron injection layer, wherein the electron transport layer, or the electron injection layer includes the compound of Chemical Formula 1.

Further, the electron transport layer, the electron injection layer, or the layer for simultaneously performing electron injection and electron transport includes the compound of Chemical Formula 1. In particular, the compound of Chemical Formula 1 according to one embodiment of the present specification has excellent thermal stability, a deep HOMO level of 6.0 eV or higher, high triplet energy (ET) and hole stability. Further, when using the compound of Chemical Formula 1 in an organic material layer performing electron injection and electron transfer at the same time, an n-type dopant used in the art can be mixed thereto.

Further, the organic material layer includes a light emitting layer and an electron transport layer, wherein the electron transport layer can include the compound of Chemical Formula 1.

Further, the organic light emitting device according to the present invention can be a normal type organic light emitting device in which an anode, one or more organic material layers and a cathode are sequentially stacked on a substrate. Further, the organic light emitting device according to the present invention can be an inverted type organic light emitting device in which a cathode, one or more organic material layers and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 can be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound of Chemical Formula 1 can be included in one or more layers of the hole injection layer, the hole transport layer, the light emitting layer and the electron transport layer.

The organic light emitting device according to the present invention can be manufactured by materials and methods known in the art, except that one or more layers of the organic material layers include the compound of Chemical Formula 1. Moreover, when the organic light emitting device includes a plurality of organic material layers, the organic material layers can be formed of the same material or different materials.

For example, the organic light emitting device according to the present invention can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

Further, the compound of Chemical Formula 1 can be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or SnO$_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO$_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole-injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples thereof include an 8-hydroxy-quinoline aluminum complex (Alq$_3$), a carbazole-based compound, a dimerized styryl compound, BAlq; a 10-hydroxybenzoquinoline-metal compound, a benzoxazole, benzothiazole and benzimidazole-based compound; a poly(p-phenylenevinylene) (PPV)-based polymer, a spiro compound, polyfluorene, rubrene, and the like, but are not limited thereto.

The light emitting layer can include a host material and a dopant material. The host material can be a fused aromatic ring derivative, a heterocyclic-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

The dopant material can be an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer and has large mobility for electrons. Specific examples thereof include: an Al complex of 8-hydroxyquinoline, a complex including Alq₃, an organic radical compound, a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxy-quinolinato)zinc, bis(8-hydroxyquinolinato)copper, bis(8-hydroxyquinolinato)manganese, tris(8-hydroxy-quinolinato)aluminum, tris(2-methyl-8-hydroxy-quinolinato)aluminum, tris(8-hydroxyquinolinato)-gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium, and the like, but are not limited thereto.

The organic light emitting device according to the present invention can be a front side emission type, a backside emission type, or a double-sided emission type according to the used material.

In addition, the compound of Chemical Formula 1 can be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only and are not intended to limit the scope of the present invention.

Preparation Example 1: Synthesis of Compound 1

(1) Preparation Example 1-1: Synthesis of Intermediate Compound C

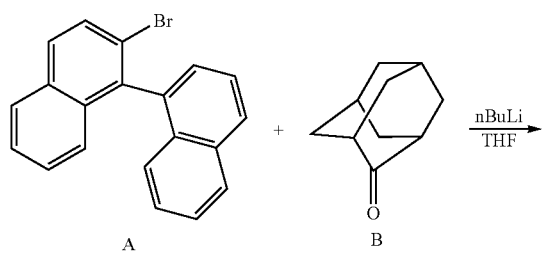

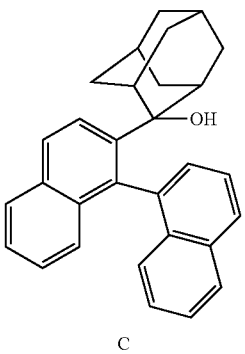

Compound A (30 g, 90.0 mmol) was added to tetrahydrofuran (900 mL). 2.5M nBuLi (36 mL) was added thereto at 0° C. and then stirred for 5 hours under nitrogen condition. After raising the temperature to room temperature, Compound B (13.5 g, 90.0 mmol) was added and then stirred for 12 hours. After the reaction, 3M NH₄Cl (300 mL) was added thereto, and the organic layer was extracted and recrystallized from ethanol to give Compound C (32.0 g, yield: 88%, MS: [M+H]⁺=405).

(2) Preparation Example 1-2: Synthesis of Intermediate Compound D

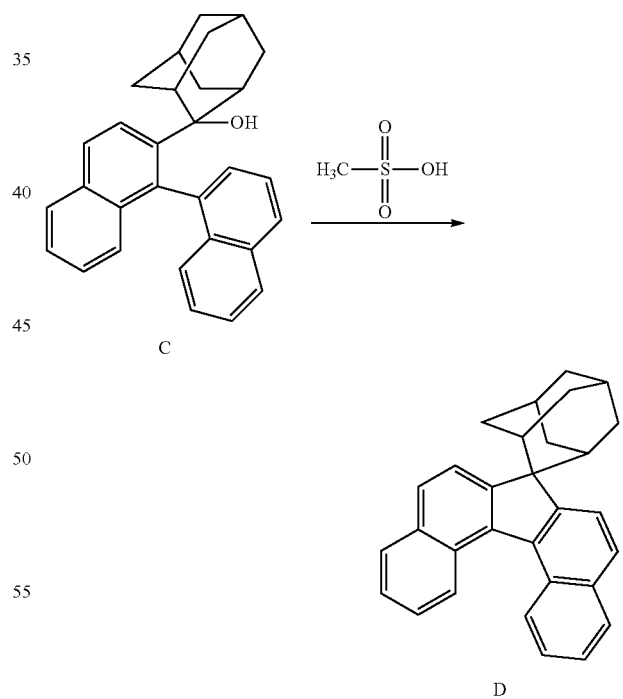

Compound C (32 g, 79.10 mmol) and CH₃SO₂OH (64 mL) were added and then stirred for 5 hours. After cooling to room temperature, the reaction mixture was poured into water then filtered, and the resulting solid was recrystallized from chloroform and ethanol to give Compound D (23.3 g, yield: 76%, MS: [M+H]⁺=387).

(3) Preparation Example 1-3: Synthesis of Intermediate Compound E

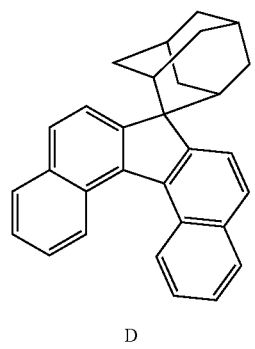

D

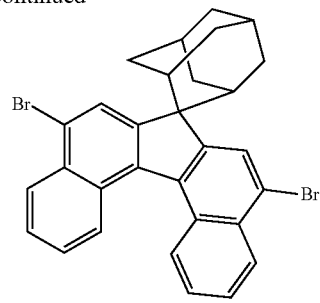

E

Compound D (23.3 g, 60.3 mmol) was added to chloroform (400 mL). Br$_2$ (19.3 g) was slowly added dropwise thereto and then stirred for 5 hours. After the reaction was completed, the mixture was filtered and the resulting solid was recrystallized from tetrahydrofuran and ethanol to give Compound E (17.4 g, yield: 53%, MS: [M+H]$^+$=545).

(4) Preparation Example 1-4: Synthesis of Compound

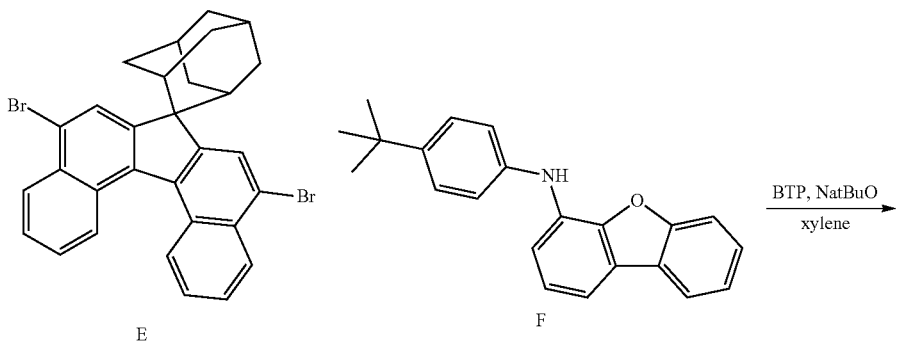

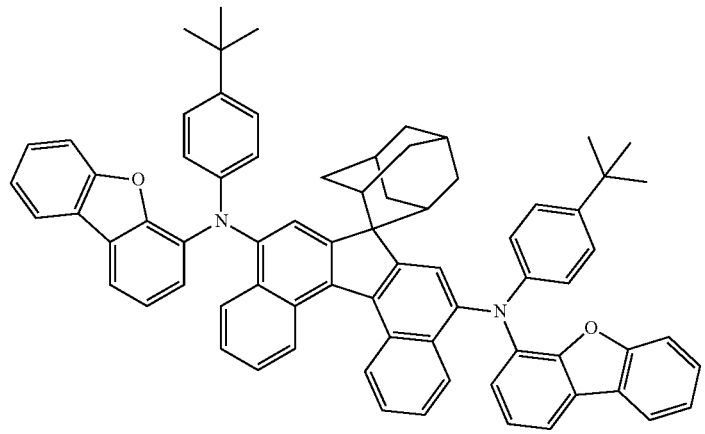

Compound 1

Compound E (17.4 g, 32.0 mmol) and Compound F (20.2 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 1 (16.2 g, yield: 50%, MS: [M+H]$^+$=1014).

Preparation Example 2: Synthesis of Compound 2

(1) Preparation Example 2-1: Synthesis of Intermediate Compound H

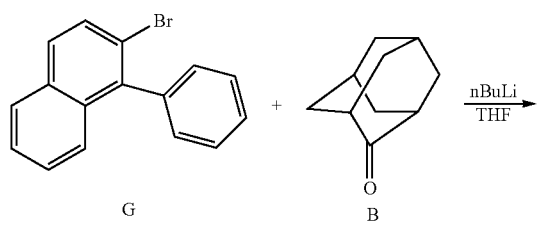

G   B

Compound G (30 g, 106 mmol) was added to tetrahydrofuran (900 mL). 2.5M nBuLi (42.4 mL) was added thereto at 0° C. and then stirred for 5 hours under nitrogen condition. After raising the temperature to room temperature, Compound B (15.9 g, 106 mmol) was added thereto and then stirred for 12 hours. After the reaction, 3M NH$_4$Cl (300 mL) was added, the organic layer was extracted and then recrystallized from ethanol to give Compound H (31.9 g, yield: 85%, MS: [M+H]$^+$=355).

(2) Preparation Example 2-2: Synthesis of Intermediate Compound I

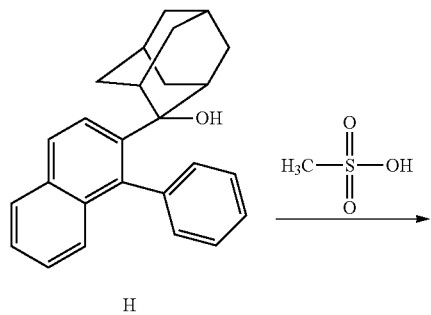

H

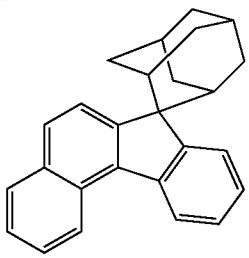

I

Compound H (31.9 g, 90.1 mmol) and CH$_3$SO$_2$OH (73 mL) were added and then stirred for 5 hours. After cooling to room temperature, the reaction mixture was poured into water and then filtered, and the resulting solid was recrystallized from chloroform and ethanol to give Compound I. (21.2 g, yield: 70%, MS: [M+H]$^+$=337).

(3) Preparation Example 2-3: Synthesis of Intermediate Compound J

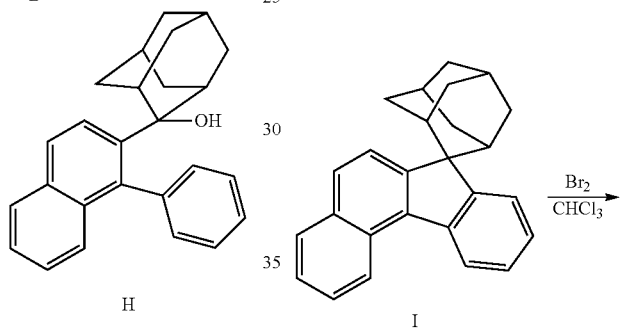

I

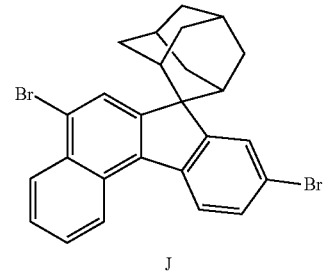

J

Compound I (21.2 g, 63.1 mmol) was added to chloroform (400 mL). Br$_2$ (20.2 g) was slowly added dropwise thereto and then stirred for 5 hours. After the reaction was completed, the mixture was filtered and the resulting solid was recrystallized from tetrahydrofuran and ethanol to give Compound J (15.0 g, yield: 48%, MS: [M+H]$^+$=495).

(4) Preparation Example 2-4: Synthesis of Compound

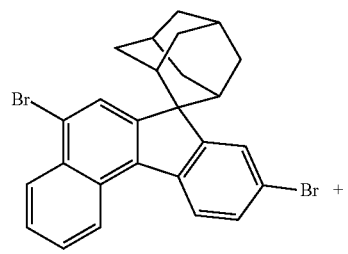

J

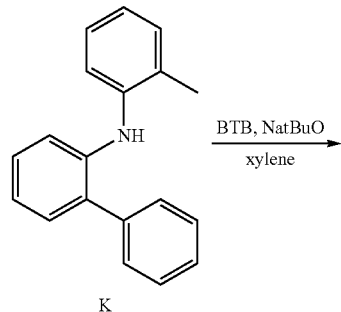

K

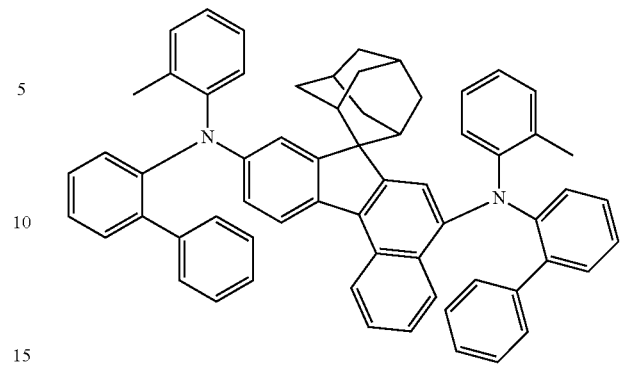

Compound 2

Compound J (15.0 g, 30.3 mmol) and Compound K (15.7 g, 60.6 mmol) were added to xylene (400 mL). NatBuO (17.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 2 (10.1 g, yield: 39%, MS: [M+H]$^+$=852).

Preparation Example 3: Synthesis of Compound 3

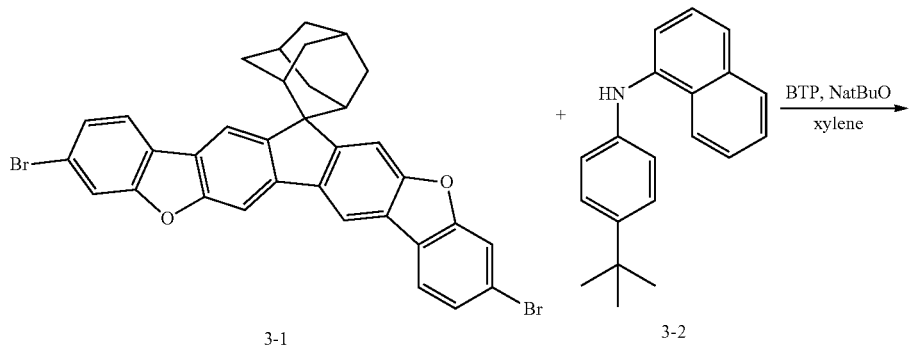

3-1    3-2

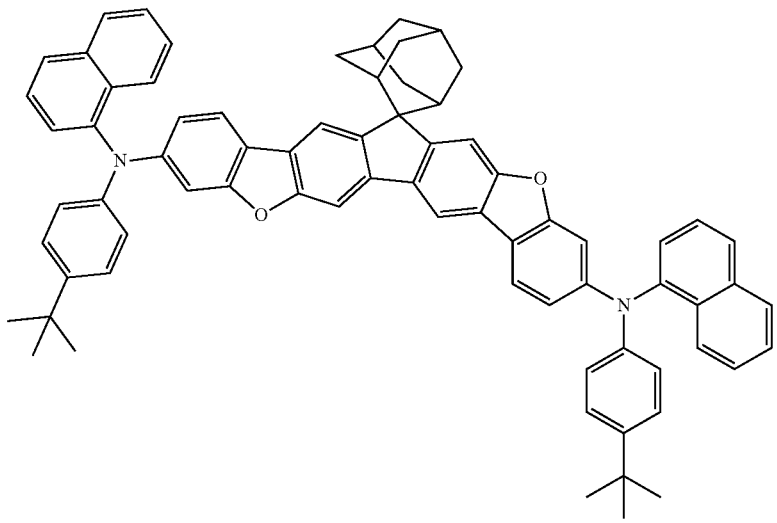

Compound 3

Compound 3-1 (20.0 g, 32.0 mmol) and Compound 3-2 (17.63 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 3 (23.02 g, yield: 71%, MS: [M+H]$^+$=1014).

Preparation Example 4: Synthesis of Compound 4

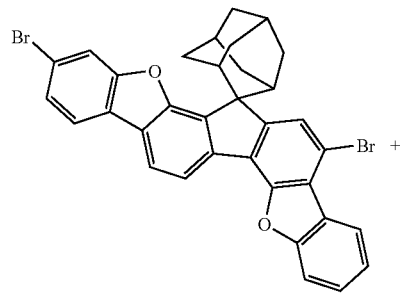

4-1

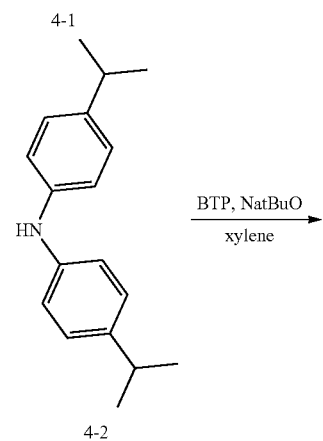

4-2

BTP, NatBuO
xylene
→

-continued

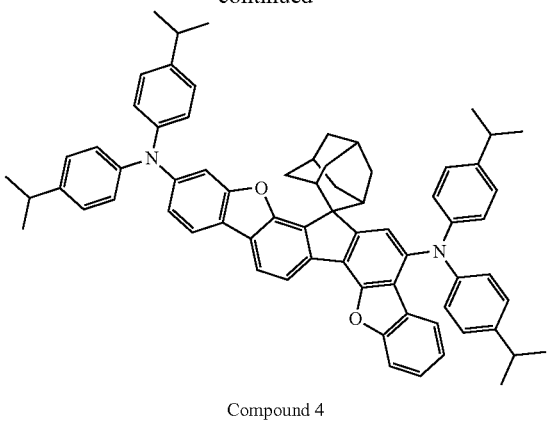

Compound 4

Compound 4-1 (20.0 g, 32.0 mmol) and Compound 4-2 (16.22 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 4 (20.16 g, yield: 65%, MS: [M+H]$^+$=970).

Preparation Example 5: Synthesis of Compound 5

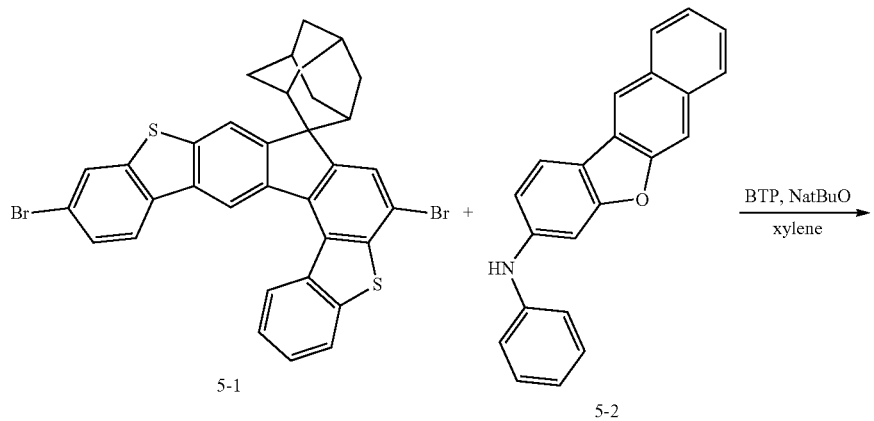

5-1

5-2

BTP, NatBuO
xylene
→

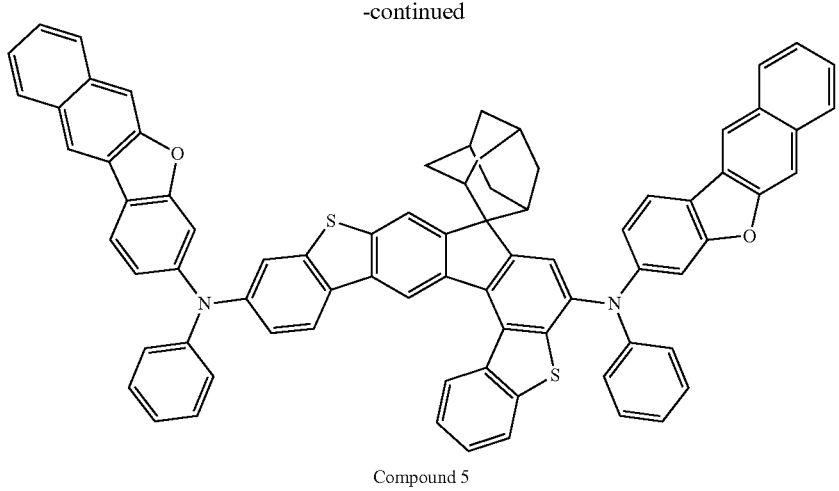

Compound 5

Compound 5-1 (21.0 g, 32.0 mmol) and Compound 5-2 (19.80 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 5 (28.86 g, yield: 81%, MS: [M+H]$^+$=1114).

Preparation Example 6: Synthesis of Compound 6

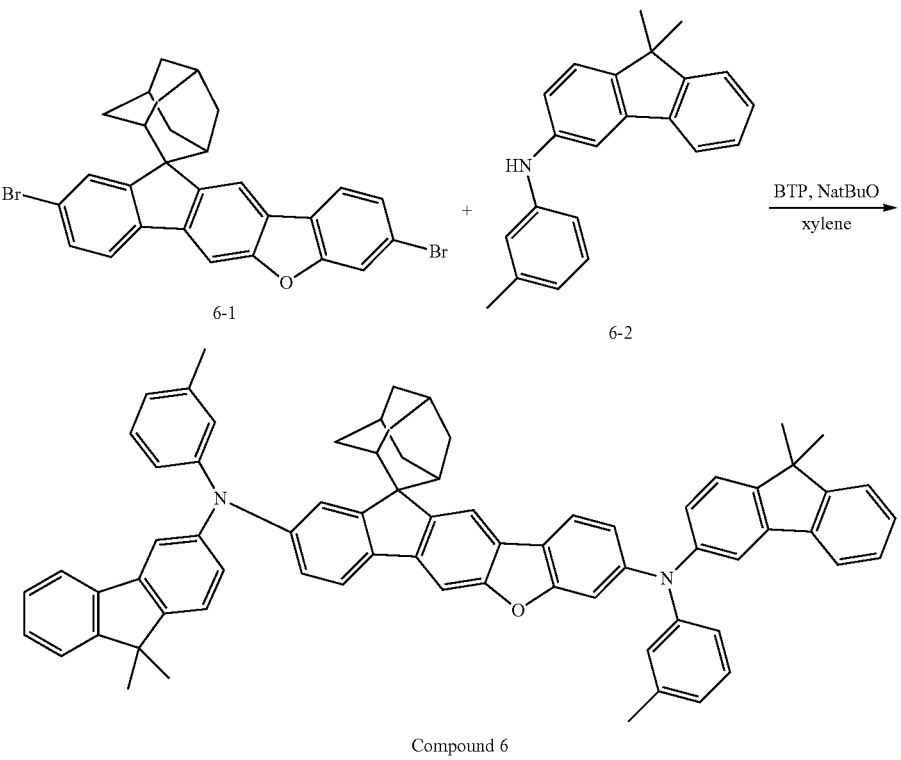

Compound 6

Compound 6-1 (17.1 g, 32.0 mmol) and Compound 6-2 (19.16 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 6 (23.93 g, yield: 77%, MS: [M+H]$^+$=972).

Preparation Example 7: Synthesis of Compound 7

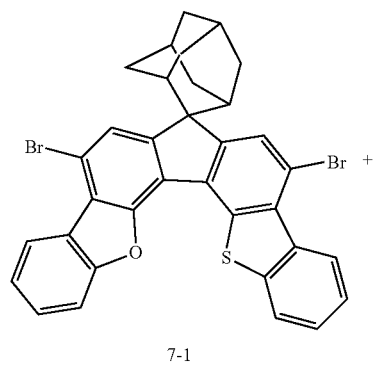

7-1

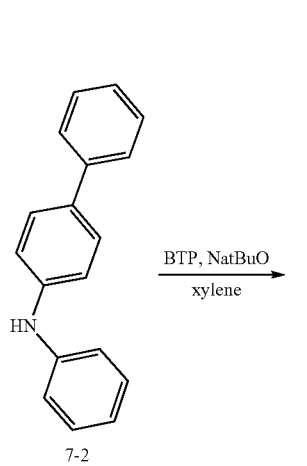

7-2

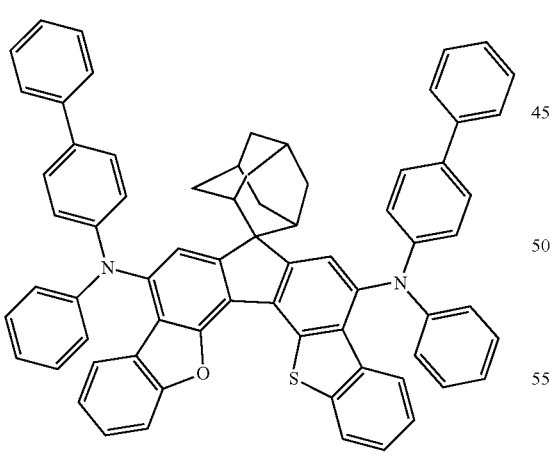

Compound 7

Compound 7-1 (20.5 g, 32.0 mmol) and Compound 7-2 (15.70 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 7 (24.19 g, yield: 78%, MS: [M+H]$^+$=970).

Preparation Example 8: Synthesis of Compound 8

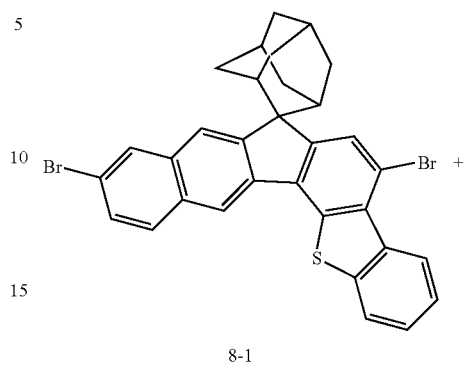

8-1

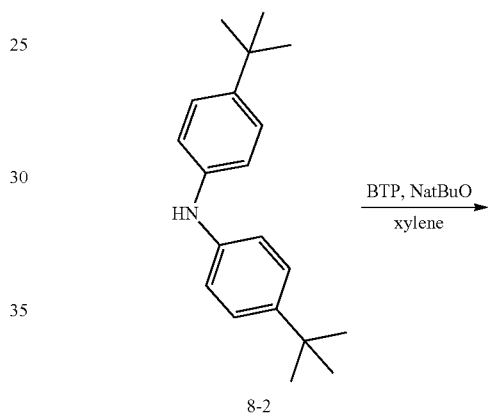

8-2

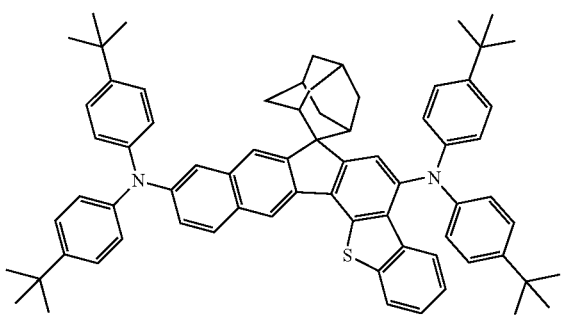

Compound 8

Compound 8-1 (19.2 g, 32.0 mmol) and Compound 8-2 (18.01 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 8 (22.11 g, yield: 69%, MS: [M+H]$^+$=765).

Preparation Example 9: Synthesis of Compound 9

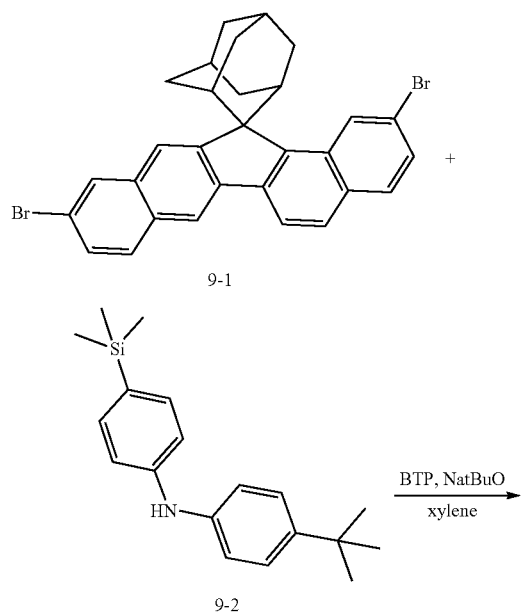

9-1

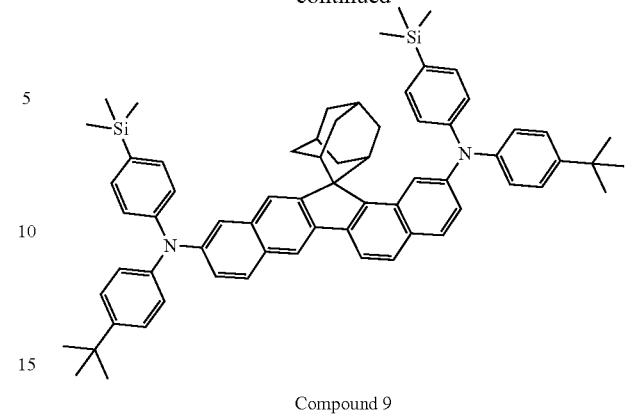

Compound 9

Compound 9-1 (17.4 g, 32.0 mmol) and Compound 9-2 (19.04 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 9 (20.65 g, yield: 66%, MS: $[M+H]^+=978$).

Preparation Example 10: Synthesis of Compound 10

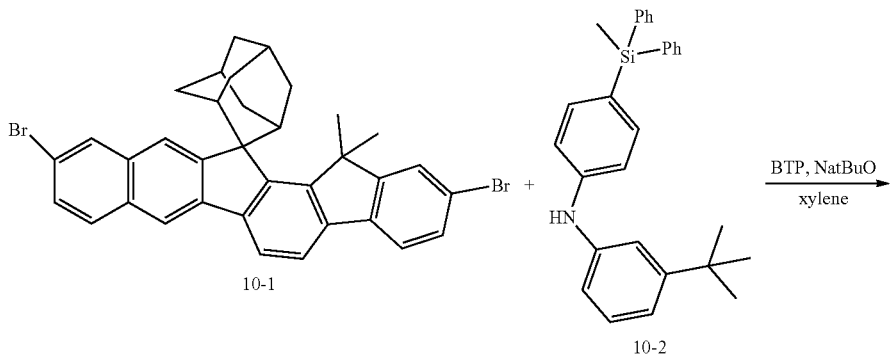

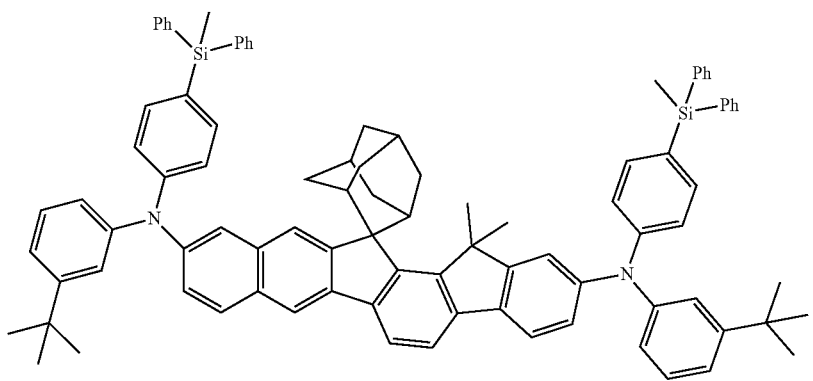

Compound 10

Compound 10-1 (19.5 g, 32.0 mmol) and Compound 10-2 (26.99 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 10 (33.49 g, yield: 81%, MS: [M+H]$^+$=1292).

Preparation Example 11: Synthesis of Compound 11

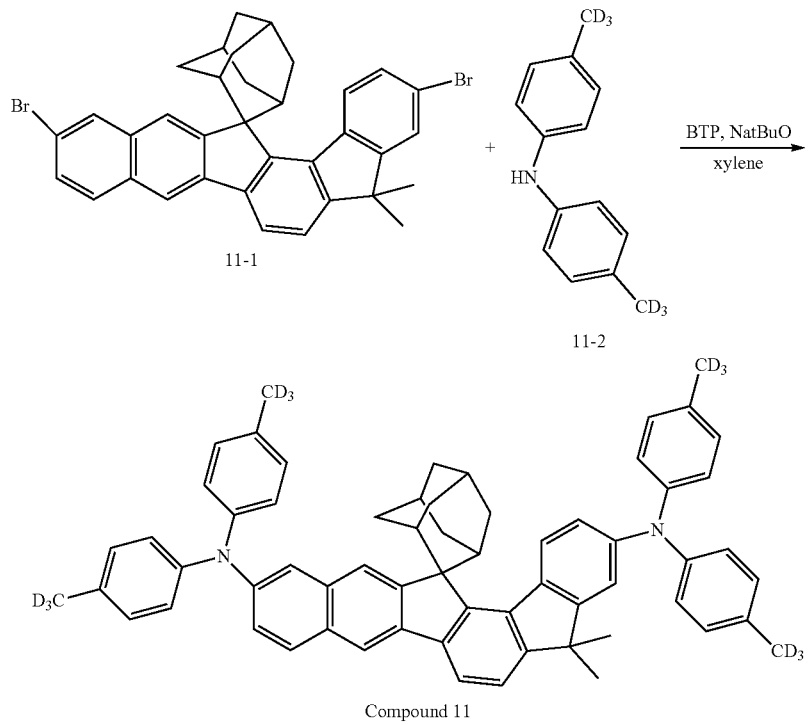

Compound 11-1 (19.5 g, 32.0 mmol) and Compound 11-2 (13.01 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 11 (19.16 g, yield: 70%, MS: [M+H]$^+$=856).

Preparation Example 12: Synthesis of Compound 12

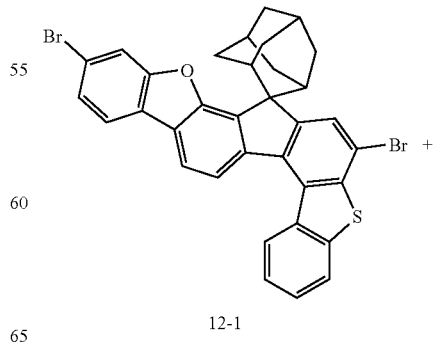

117
-continued

118
-continued

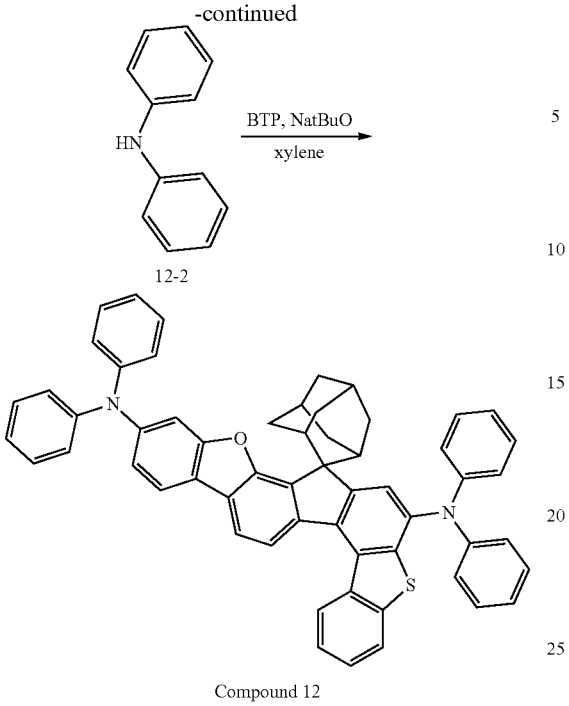

Compound 12

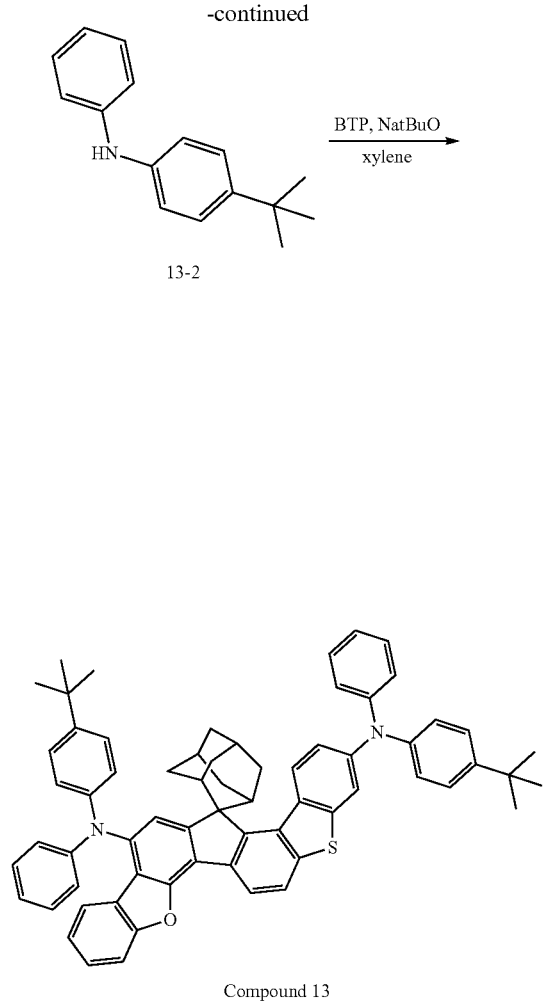

Compound 13

Compound 12-1 (20.5 g, 32.0 mmol) and Compound 12-2 (10.83 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 12 (19.87 g, yield: 76%, MS: [M+H]$^+$=818).

Preparation Example 13: Synthesis of Compound 13

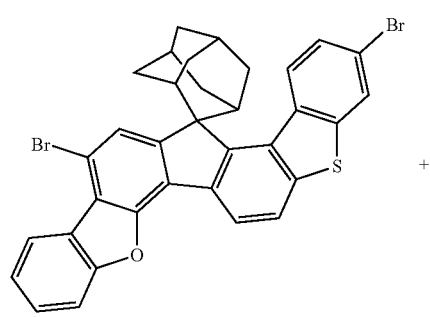

13-1

Compound 13-1 (20.5 g, 32.0 mmol) and Compound 13-2 (14.42 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 13 (19.92 g, yield: 67%, MS: [M+H]$^+$=930).

Preparation Example 14: Synthesis of Compound 14

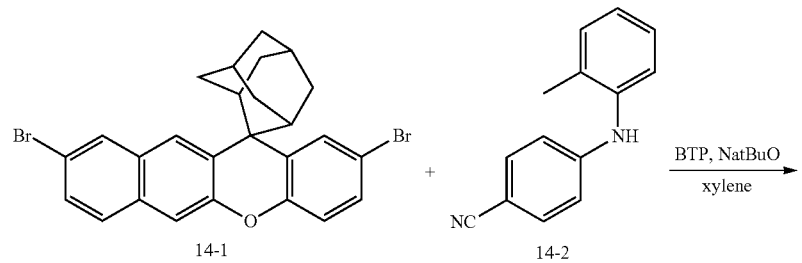

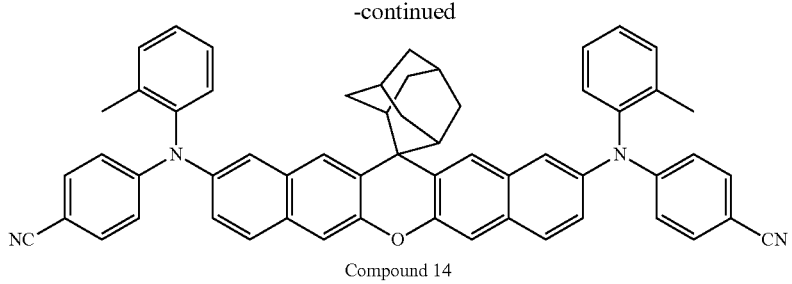
Compound 14

Compound 14-1 (16.3 g, 32.0 mmol) and Compound 14-2 (13.3 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 14 (14.9 g, yield: 61%, MS: $[M+H]^+=765$).

Preparation Example 15: Synthesis of Compound 15

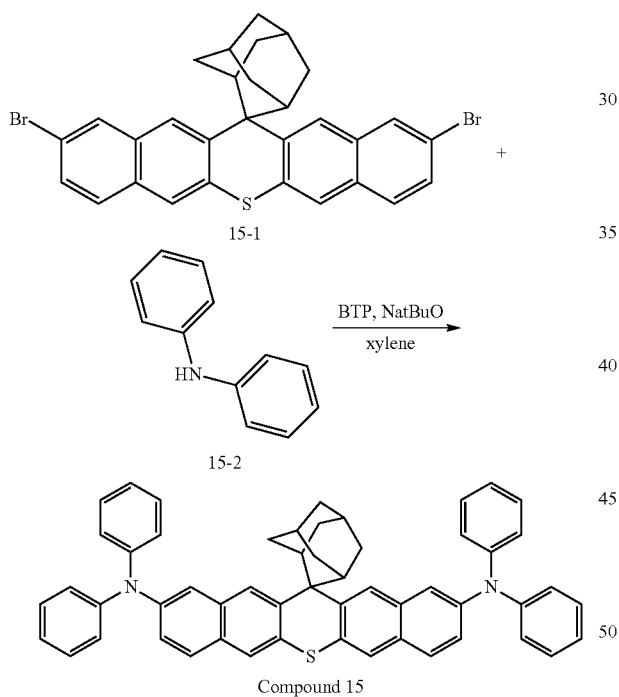
Compound 15

Compound 15-1 (18.4 g, 32.0 mmol) and Compound 15-2 (10.8 g, 64.0 mmol) were added to xylene (400 mL). NatBuO (18.5 g) and BTP (0.2 g) were added thereto, and the mixture was stirred and refluxed for 5 hours. After cooling to room temperature, the mixture was filtered and the resulting solid was recrystallized three times from ethyl acetate to give Compound 15 (18.8 g, yield: 78%, MS: $[M+H]^+=754$).

Example 1: Manufacture of Organic Light Emitting Device

A glass substrate (Corning 7059 glass) on which ITO (indium tin oxide) was coated as a thin film to a thickness of 1,000 Å was put into distilled water in which a detergent was dissolved, and ultrasonically cleaned. A product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the completion of cleaning with distilled water, the substrate was ultrasonically cleaned in the order of isopropyl alcohol, acetone, and methanol solvent, and then dried.

On the ITO transparent electrode thus prepared, the following compound HAT was thermally vacuum deposited to a thickness of 50 Å to form a hole injection layer. The following compound HT-A (1000 Å) was vacuum deposited thereon and the following compound HT-B (100 Å) was deposited as a hole transport layer. 4 wt % of Compound 3 of Preparation Example 3 as a dopant was doped to the following compound H-A as a host and vacuum deposited to a thickness of 200 Å as a light emitting layer. Then, the following compound ET-A and the following compound Liq were deposited in a ratio of 1:1 to a thickness of 300 Å, and magnesium (Mg) doped with 10 wt % of silver (Ag) in a thickness of 150 Å and aluminum in a thickness of 1,000 Å were sequentially deposited thereon to form a cathode, thereby manufacturing an organic light emitting device.

In the above-mentioned process, the vapor deposition rate of the organic material was maintained at 1 Å/sec, the deposition rate of LiF was maintained at 0.2 Å/sec, and the deposition rate of aluminum was maintained at 3 Å/sec to 7 Å/sec.

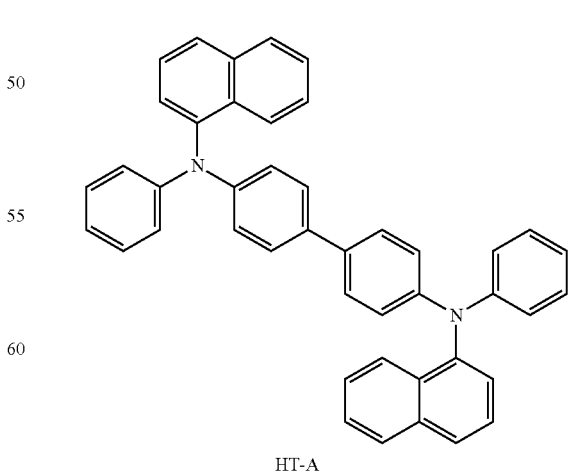
HT-A

-continued

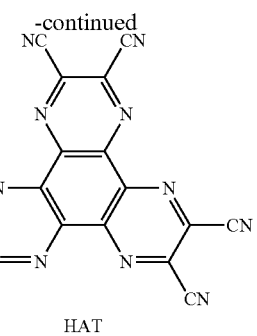
HAT

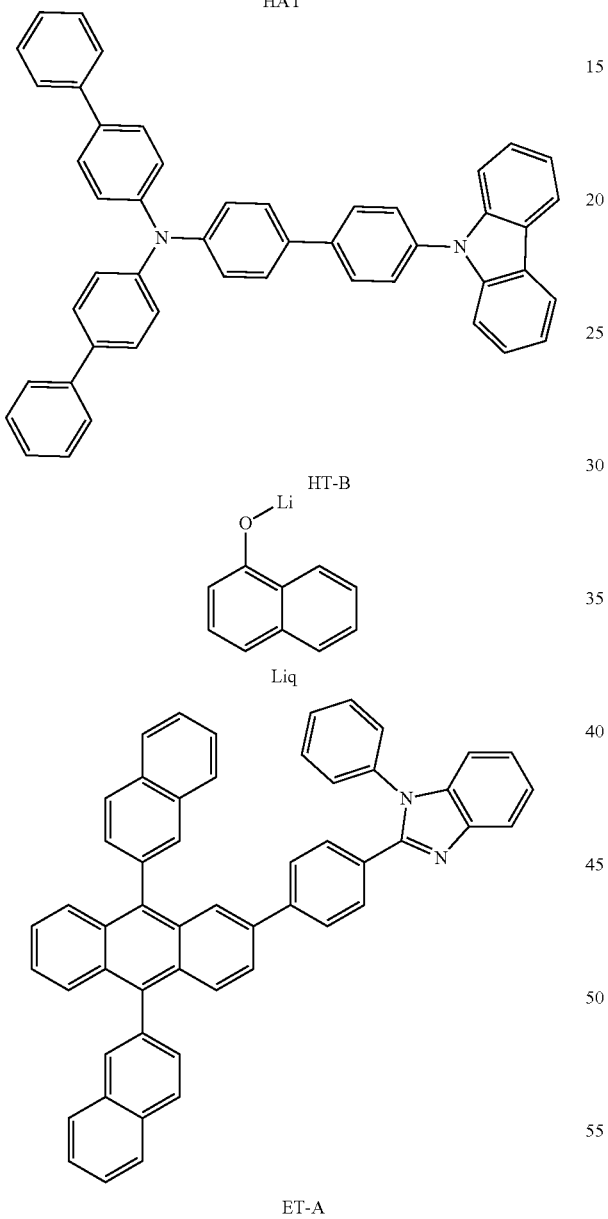

HT-B

Liq

ET-A

Examples 2 to 39 and Comparative Examples 1 to 12: Manufacture of Organic Light Emitting Device The organic light emitting devices were manufactured in the same manner as in Example 1, except that the compounds shown in Tables 1 to 3 below were used instead of H-A as a host of the light emitting layer, and the compounds shown in Tables 1 to 3 below were used instead of Compound 3 of Preparation Example 3 as a dopant of the light emitting layer, in the manufacture of the organic light emitting device of Example 1.

Experimental Example

For the organic light emitting devices manufactured in Examples 1 to 37 and Comparative Experimental Examples 1 to 12, the driving voltage and light emitting efficiency were measured at a current density of 10 mA/cm$^2$, and the time (LT95) required for the luminance to be reduced to 95% of the initial luminance was measured at a current density of 20 mA/cm$^2$. The results are shown in Tables 1 to 3 below.

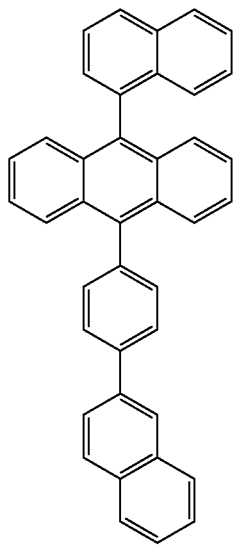

H-A

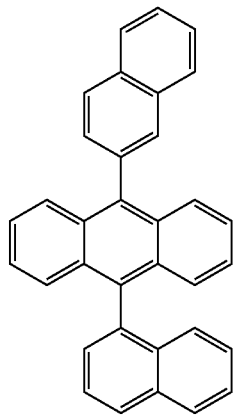

H-B

H-C

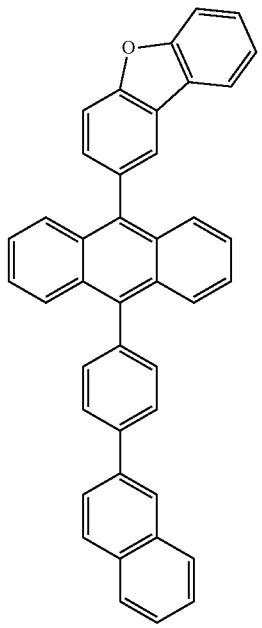

D-4

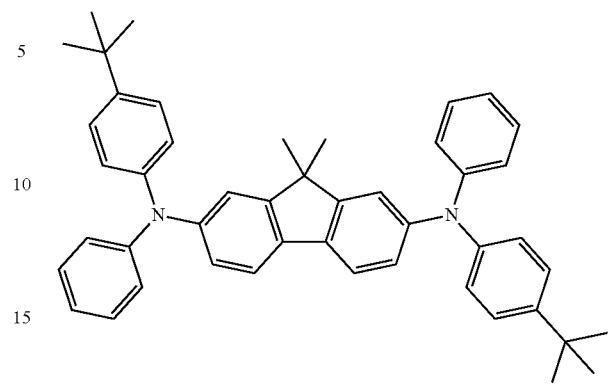

D-1

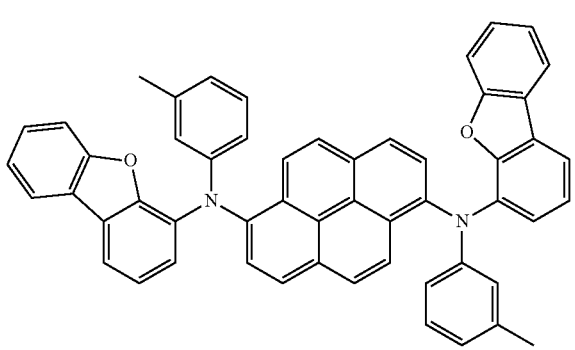

D-2

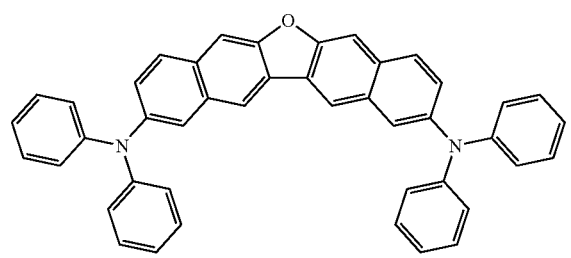

D-3

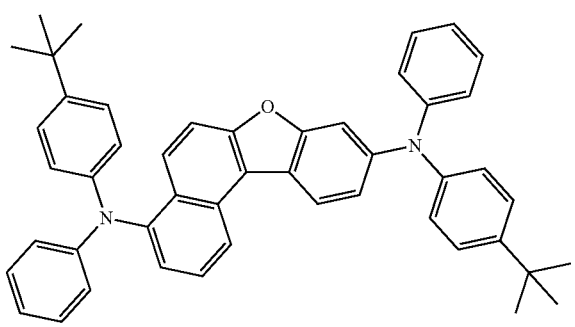

TABLE 1

| | | | @ 10 mA/cm² | | | LT95 |
|---|---|---|---|---|---|---|
| Category | Host | Dopant | Voltage (V) | Efficiency (cd/A) | color | Life-time (hr) |
| Example 1 | H-A | Compound 3 | 4.21 | 6.28 | blue | 100 |
| Example 2 | H-A | Compound 4 | 4.22 | 5.84 | blue | 110 |
| Example 3 | H-A | Compound 5 | 4.25 | 6.81 | blue | 120 |
| Example 4 | H-A | Compound 6 | 4.26 | 6.50 | blue | 120 |
| Example 5 | H-A | Compound 7 | 4.31 | 6.70 | blue | 115 |
| Example 6 | H-A | Compound 8 | 4.19 | 6.68 | blue | 120 |
| Example 7 | H-A | Compound 9 | 4.21 | 6.98 | blue | 130 |
| Example 8 | H-A | Compound 10 | 4.18 | 6.28 | blue | 125 |
| Example 9 | H-A | Compound 11 | 4.23 | 6.29 | blue | 110 |
| Example 10 | H-A | Compound 12 | 4.10 | 6.27 | blue | 115 |
| Example 11 | H-A | Compound 13 | 4.00 | 6.78 | blue | 110 |
| Example 12 | H-A | Compound 14 | 4.10 | 6.28 | blue | 120 |
| Example 13 | H-A | Compound 15 | 4.20 | 6.10 | blue | 140 |
| Comparative Example 1 | H-A | D-1 | 4.39 | 5.31 | blue | 75 |
| Comparative Example 2 | H-A | D-2 | 4.42 | 3.50 | blue | 50 |
| Comparative Example 3 | H-A | D-3 | 4.40 | 4.88 | blue | 85 |
| Comparative Example 4 | H-A | D-4 | 4.54 | 5.12 | blue | 55 |

TABLE 2

| | | | @ 10 mA/cm² | | | LT95 |
|---|---|---|---|---|---|---|
| | Host | Dopant | Voltage (V) | Efficiency (cd/A) | color | Life-time (hr) |
| Example 14 | H-B | Compound 3 | 4.32 | 7.12 | blue | 120 |
| Example 15 | H-B | Compound 4 | 4.31 | 6.77 | blue | 120 |
| Example 16 | H-B | Compound 5 | 4.40 | 6.98 | blue | 130 |
| Example 17 | H-B | Compound 6 | 4.46 | 6.45 | blue | 125 |
| Example 18 | H-B | Compound 7 | 4.41 | 6.44 | blue | 115 |
| Example 19 | H-B | Compound 8 | 4.29 | 6.97 | blue | 120 |
| Example 20 | H-B | Compound 9 | 4.30 | 6.28 | blue | 130 |
| Example 21 | H-B | Compound 10 | 4.30 | 6.57 | blue | 125 |
| Example 22 | H-B | Compound 11 | 4.25 | 6.48 | blue | 115 |
| Example 23 | H-B | Compound 12 | 4.25 | 6.53 | blue | 125 |
| Example 24 | H-B | Compound 13 | 4.27 | 6.08 | blue | 125 |
| Example 25 | H-B | Compound 14 | 4.29 | 6.65 | blue | 115 |
| Example 26 | H-B | Compound 15 | 4.28 | 6.10 | blue | 140 |
| Comparative Example 5 | H-B | D-1 | 4.56 | 5.12 | blue | 80 |
| Comparative Example 6 | H-B | D-2 | 4.54 | 4.50 | blue | 60 |

TABLE 2-continued

| | Host | Dopant | @ 10 mA/cm² Voltage (V) | Efficiency (cd/A) | color | LT95 Lifetime (hr) |
|---|---|---|---|---|---|---|
| Comparative Example 7 | H-B | D-3 | 4.55 | 5.32 | blue | 95 |
| Comparative Example 8 | H-B | D-4 | 4.60 | 4.80 | blue | 70 |

TABLE 3

| Category | Host | Dopant | @ 10 mA/cm² Voltage (V) | Efficiency (cd/A) | color | LT95 Lifetime (hr) |
|---|---|---|---|---|---|---|
| Example 27 | H-C | Compound 3 | 4.00 | 7.10 | blue | 120 |
| Example 28 | H-C | Compound 4 | 4.10 | 6.64 | blue | 110 |
| Example 29 | H-C | Compound 5 | 4.11 | 6.91 | blue | 120 |
| Example 30 | H-C | Compound 6 | 4.01 | 6.28 | blue | 130 |
| Example 31 | H-C | Compound 7 | 4.05 | 6.31 | blue | 115 |
| Example 32 | H-C | Compound 8 | 4.09 | 6.22 | blue | 120 |
| Example 33 | H-C | Compound 9 | 4.11 | 6.90 | blue | 125 |
| Example 34 | H-C | Compound 10 | 4.12 | 6.24 | blue | 125 |
| Example 35 | H-C | Compound 11 | 4.07 | 6.24 | blue | 110 |
| Example 36 | H-C | Compound 12 | 4.01 | 6.22 | blue | 130 |
| Example 37 | H-C | Compound 13 | 4.07 | 6.61 | blue | 120 |
| Example 38 | H-C | Compound 14 | 4.05 | 6.25 | blue | 100 |
| Example 39 | H-C | Compound 15 | 4.10 | 6.22 | blue | 120 |
| Comparative Example 9 | H-C | D-1 | 4.32 | 5.10 | blue | 70 |
| Comparative Example 10 | H-C | D-2 | 4.33 | 4.50 | blue | 50 |
| Comparative Example 11 | H-C | D-5 | 4.40 | 4.78 | blue | 75 |
| Comparative Example 12 | H-C | D-6 | 4.44 | 4.01 | blue | 55 |

From Tables 1 to 3, it can be confirmed that Examples 1 to 39 of the present invention have a lower driving voltage of the device and are excellent in efficiency and lifetime characteristics as compared with Comparative Examples 1 to 12. Specifically, Comparative Examples 1, 3 to 5, 7 to 9, 11, and 12 each use, as a dopant of the light emitting layer, Compound D-1, Compound D-3, Compound D-4, Compound D-5, or Compound D-6, to which pyrene, naphthobenzofuran, fluorene, dibenzofluorene, or dinaphthofuran is bonded between two amine groups, but these structures do not contain adamantane, and thus it can be confirmed that the performance is significantly lower than that of the devices using the compounds of the present invention.

DESCRIPTION OF SYMBOLS

| | |
|---|---|
| 1: substrate | 2: anode |
| 3: light emitting layer | 4: cathode |
| 5: hole injection layer | 6: hole transport layer |
| 7: light emitting layer | |
| 8: electron transport layer | |

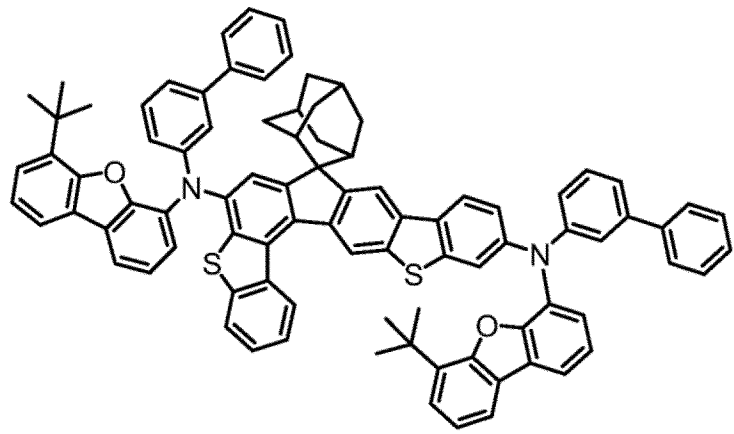

The invention claimed is:
1. A compound of Chemical Formula 1:

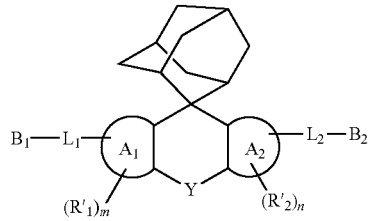

Chemical Formula 1 wherein, in Chemical Formula 1:
Y is a direct bond, O or S;
$A_1$ and $A_2$ are each independently a benzene ring, a naphthalene ring, or

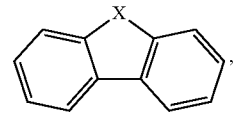

with the proviso that at least one of $A_1$ and $A_2$ is a naphthalene ring or

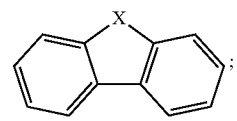

each X is independently $CR_1R_2$, $SiR_3R_4$, $NR_5$, O, S, or $SO_2$;
$R_1$ to $R_5$ are each independently hydrogen, deuterium, a substituted or unsubstituted $C_{1-60}$ alkyl, a substituted or unsubstituted $C_{3-60}$ cycloalkyl, or a substituted or unsubstituted $C_{6-60}$ aryl;
$L_1$ and $L_2$ are each independently a direct bond, a substituted or unsubstituted $C_{6-60}$ arylene, or a substituted or unsubstituted $C_{2-60}$ heteroarylene containing one or more heteroatoms selected from the group consisting of N, O and S;
$B_1$ and $B_2$ are each independently *—$NR_6R_7$ where *— means a bond linked to another substituent group;
$R_6$ and $R_7$ are each independently a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, a tri($C_{1-60}$ alkyl)silyl, a substituted or unsubstituted $C_{6-60}$ aryl, a tri($C_{6-60}$ aryl)silyl, a substituted or unsubstituted $C_{2-60}$ heteroaryl containing one or more heteroatoms selected from the group consisting of N, O and S, or are bonded to adjacent groups to form a substituted or unsubstituted condensed ring;
$R'_1$ and $R'_2$ are each independently hydrogen, deuterium, halogen, cyano, a substituted or unsubstituted $C_{1-60}$ alkyl, a substituted or unsubstituted $C_{1-60}$ alkoxy, a substituted or unsubstituted $C_{1-60}$ haloalkyl, a substituted or unsubstituted $C_{1-60}$ haloalkoxy, a tri($C_{1-60}$ alkyl)silyl, or a substituted or unsubstituted $C_{6-60}$ aryl; and
m and n are each independently an integer of 0 to 3.

2. The compound according to claim 1, wherein:
the compound of Chemical Formula 1 is any one of the compounds of the following Chemical Formulas 1-1 to 1-3:

Chemical Formula 1-1

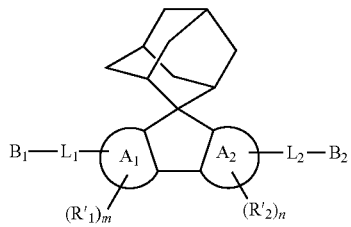

Chemical Formula 1-2

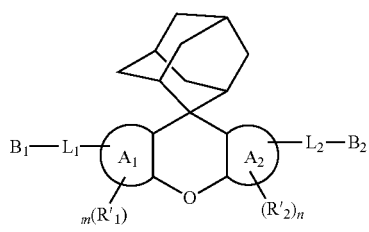

Chemical Formula 1-3

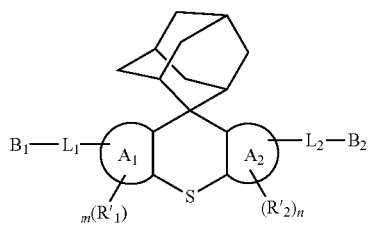

wherein:
$A_1$, $A_2$, $B_1$, $B_2$, $L_1$, $L_2$, $R'_1$, $R'_2$, m and n are as defined for Chemical Formula 1 in claim 1.

3. The compound according to claim 1, wherein:
$A_1$ is a benzene ring, and $A_2$ is a naphthalene ring; or
$A_1$ is a naphthalene ring, and $A_2$ is a benzene ring; or
$A_1$ is a benzene ring, and $A_2$ is

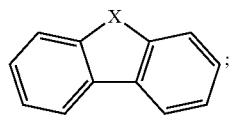;

or
$A_1$ is

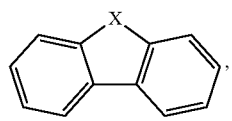, and $A_2$ is a benzene ring; or
$A_1$ is a naphthalene ring, and $A_2$ is

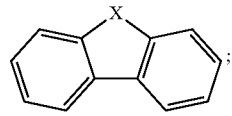;

or
$A_1$ is

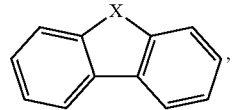, and $A_2$ is a naphthalene ring; or
$A_1$ is a naphthalene ring, and $A_2$ is a naphthalene ring; or
$A_1$ is

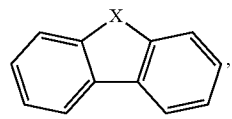, and $A_2$ is

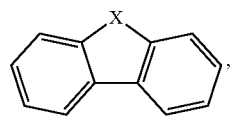, where X is as defined in claim 1.

4. The compound according to claim 1, wherein:
the compound of Chemical Formula 1 is any one compound selected from the group consisting of the following compounds:

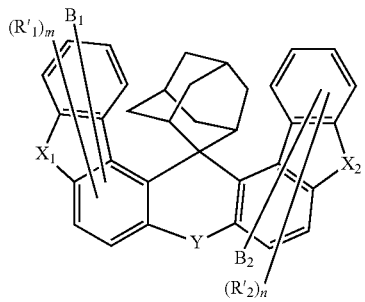

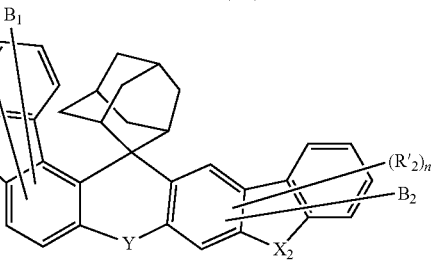

-continued
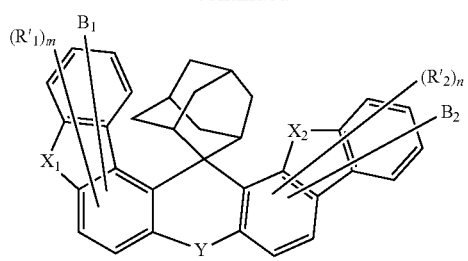
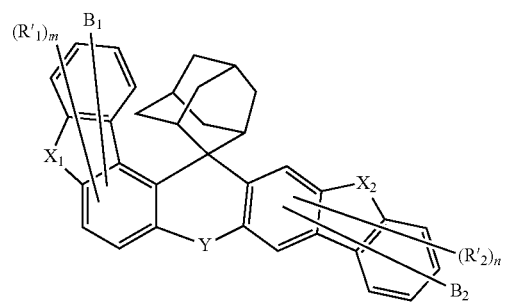
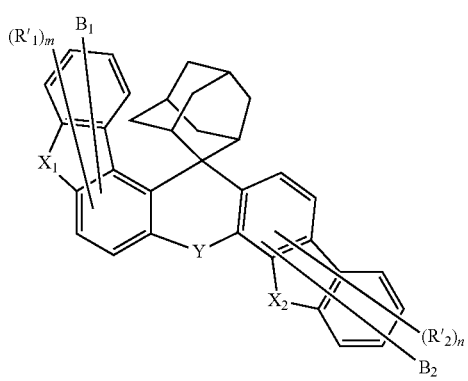
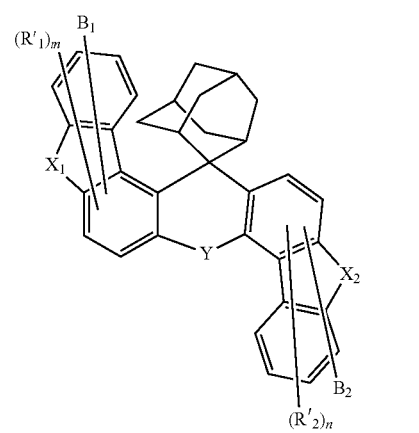
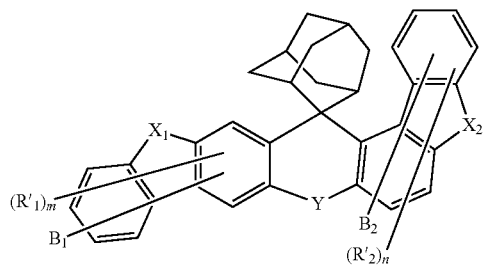
-continued
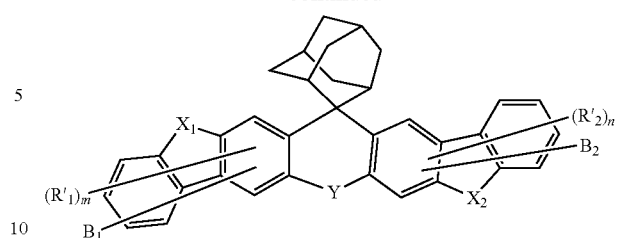
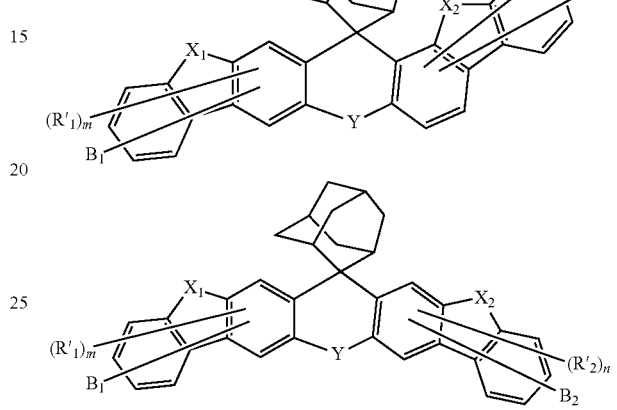
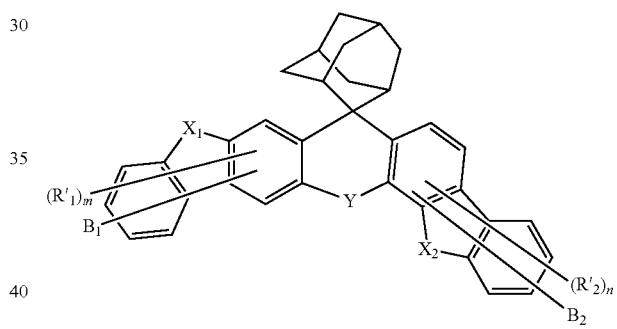
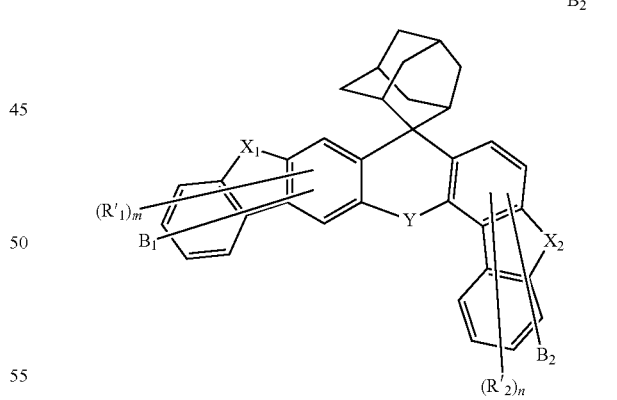
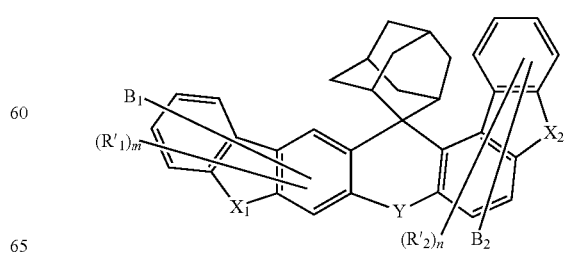

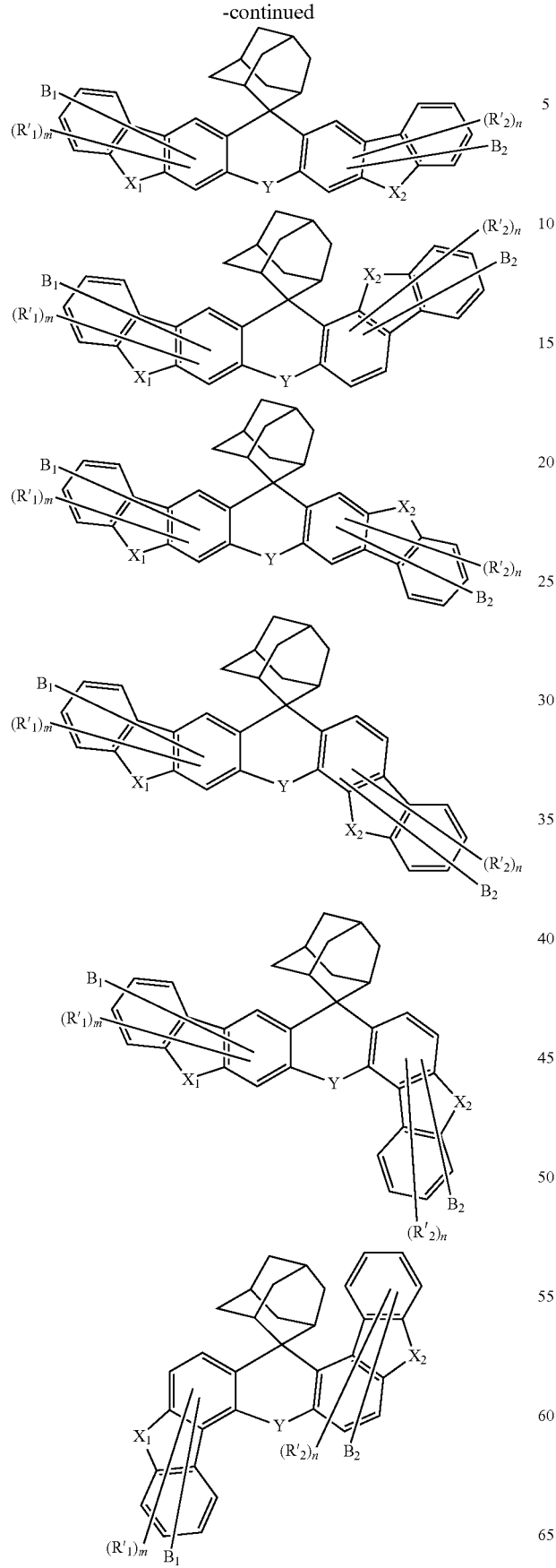
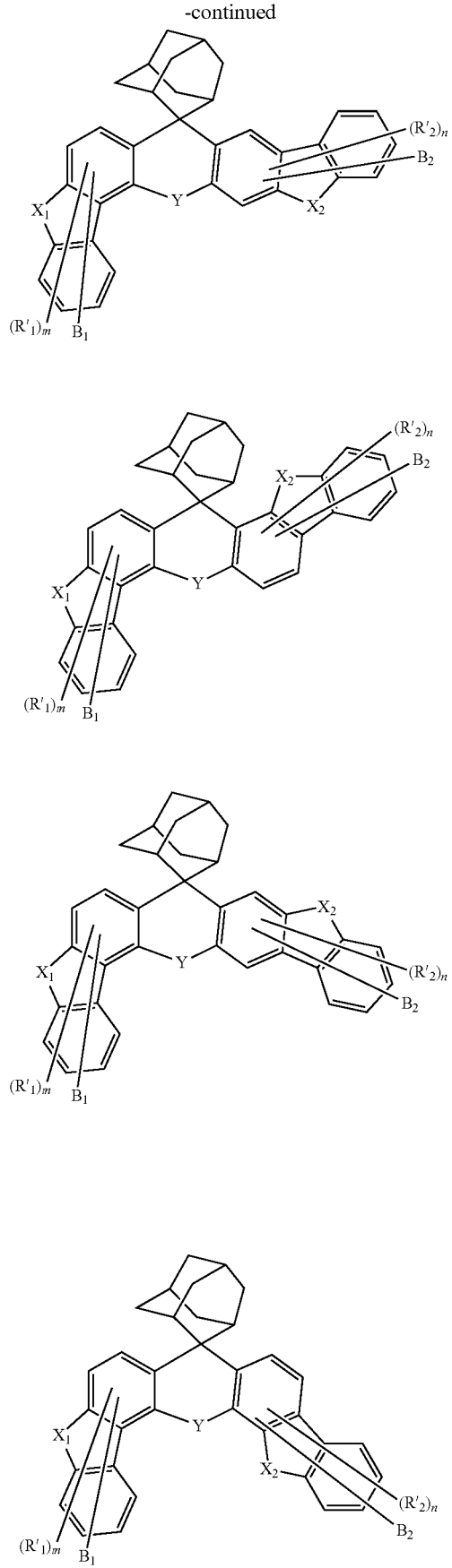

-continued
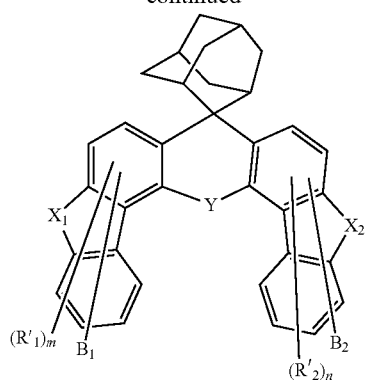
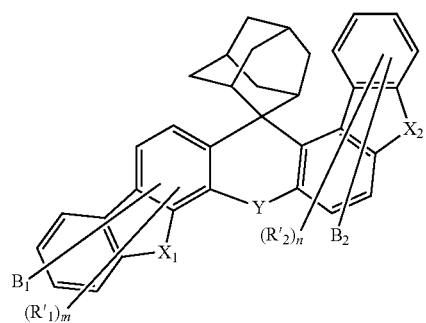
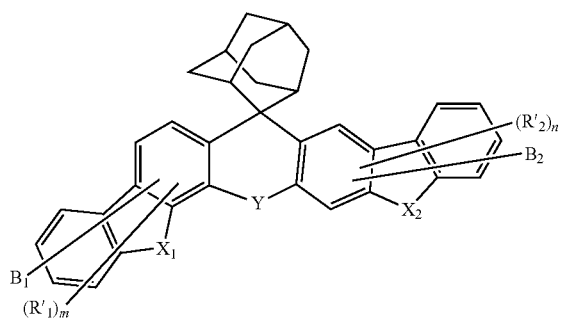
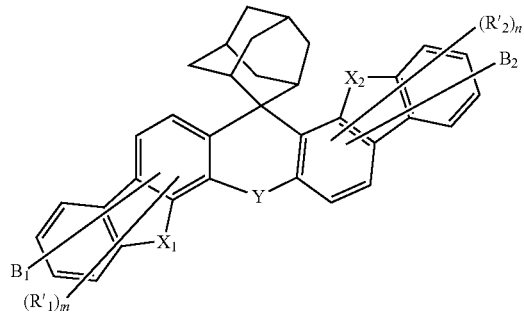
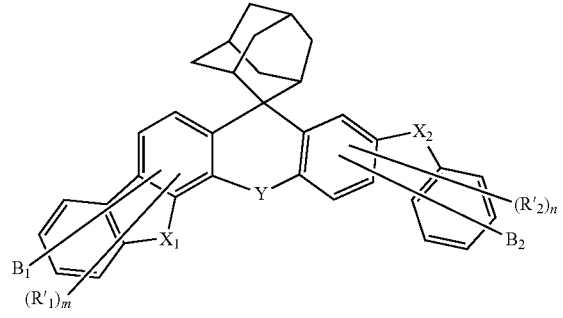
-continued
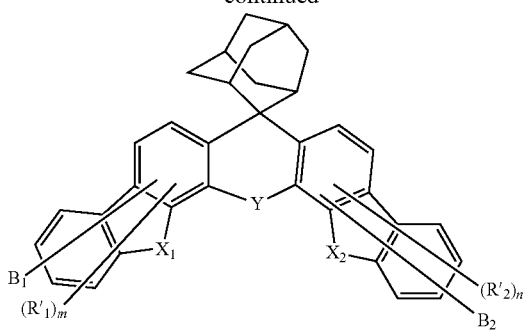
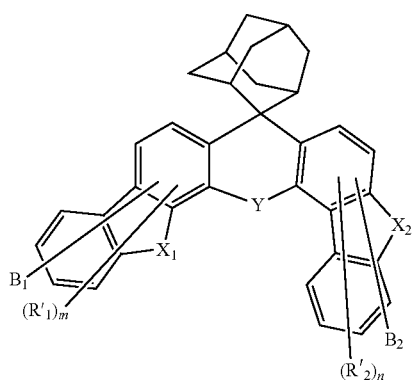
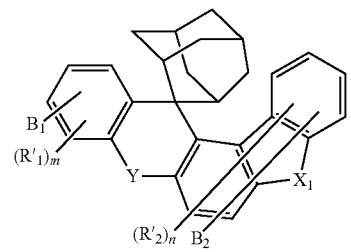
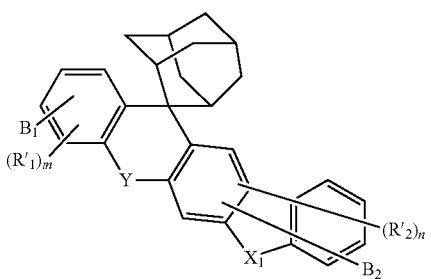
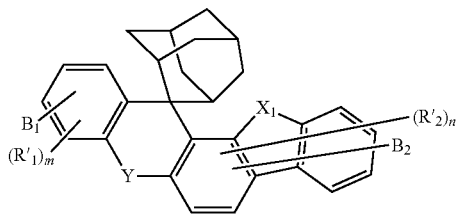

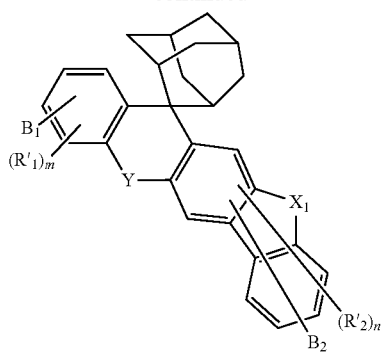
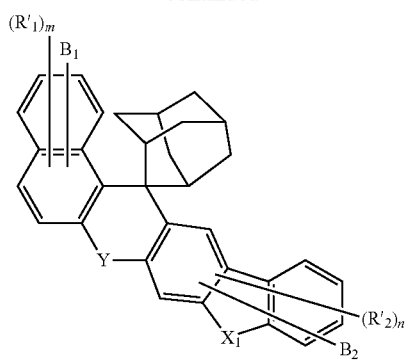
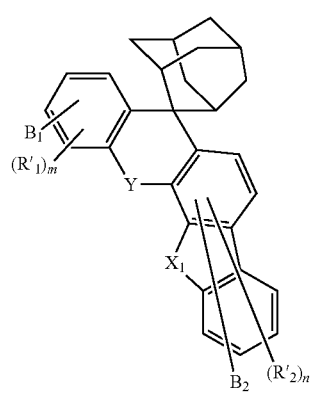
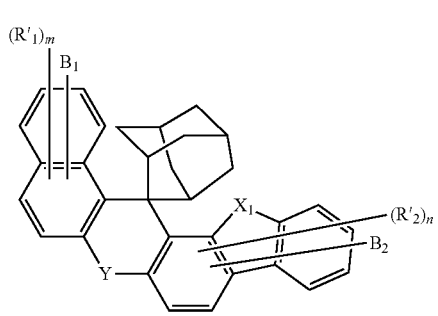
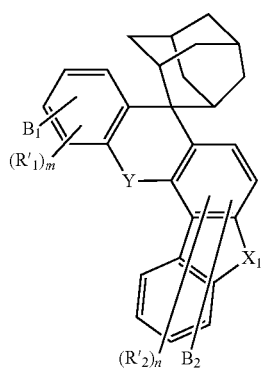
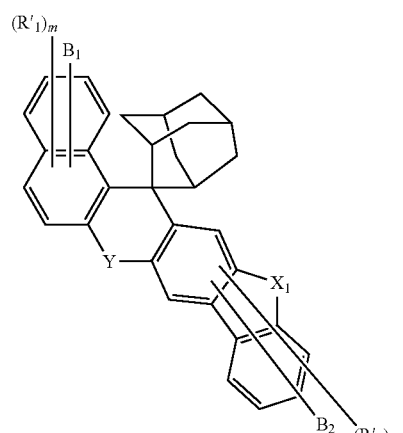
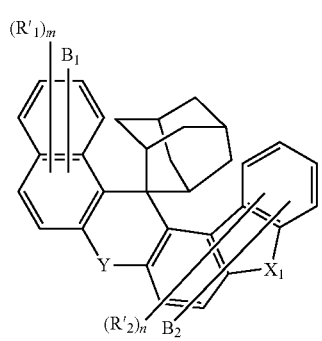
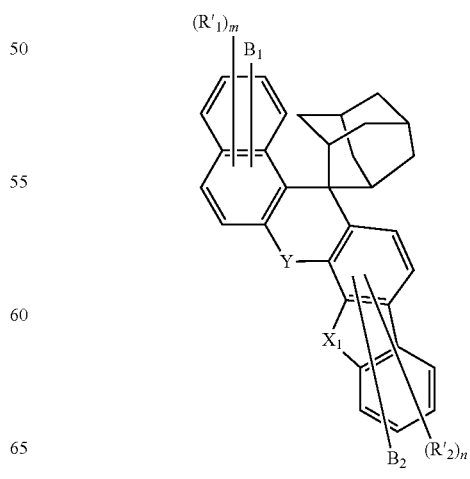

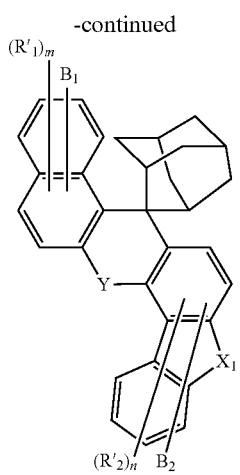
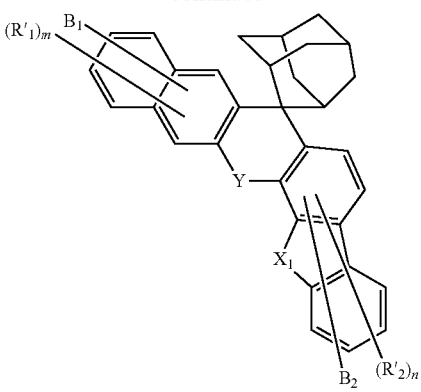

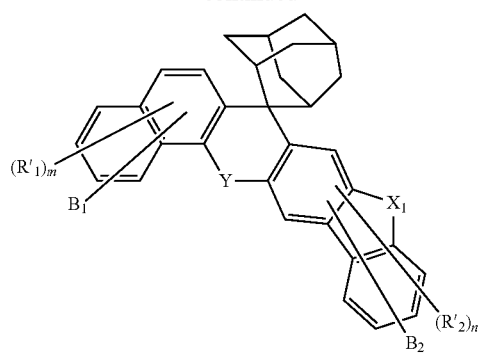
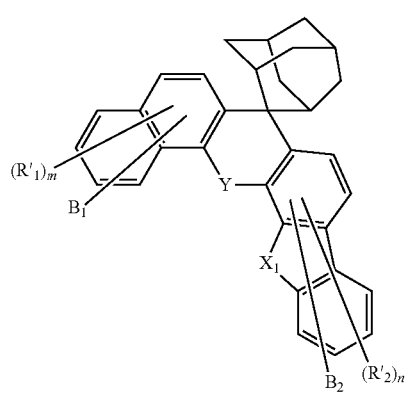
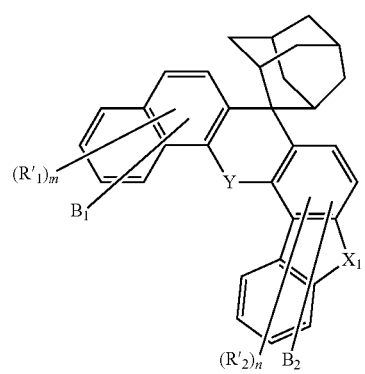
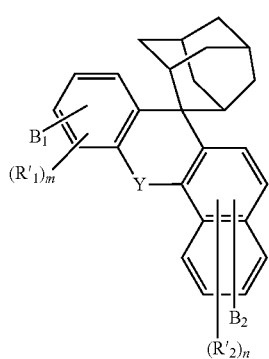
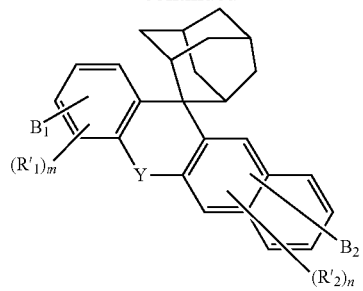
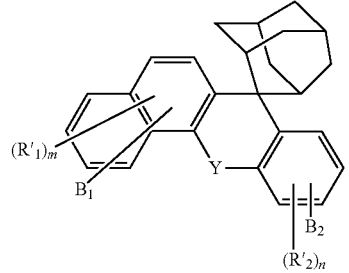
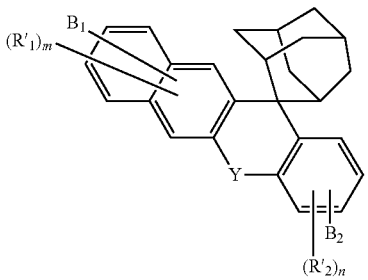
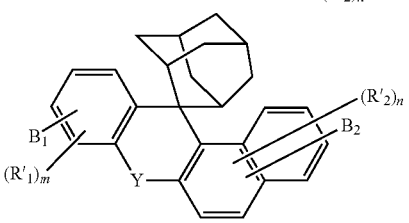
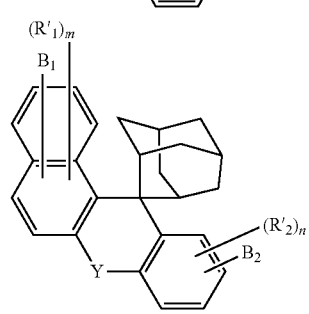
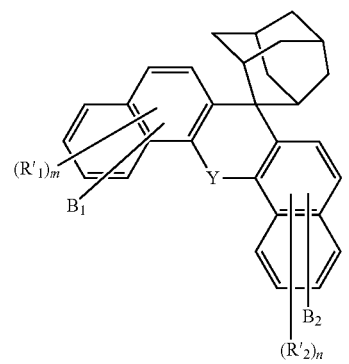

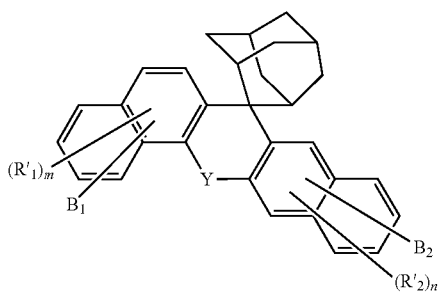

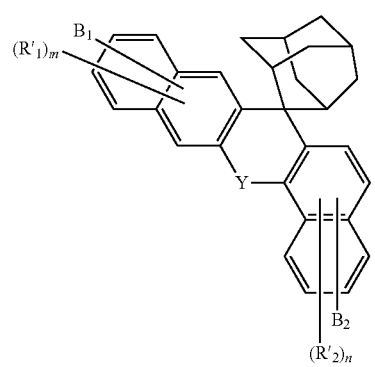

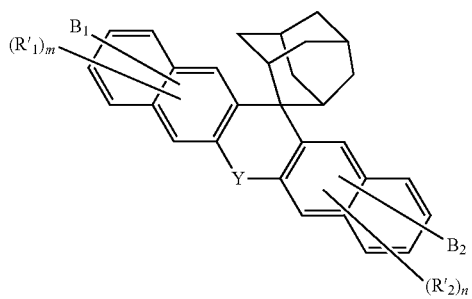

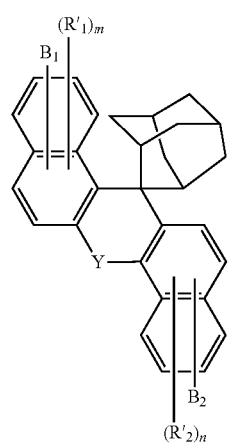

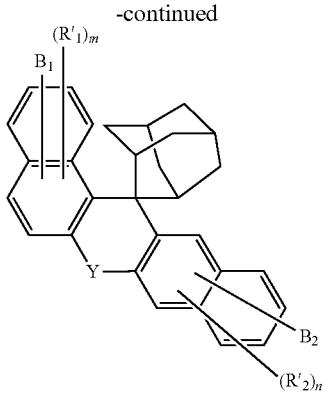

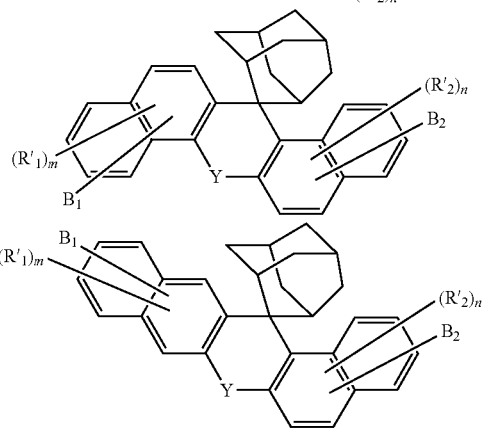

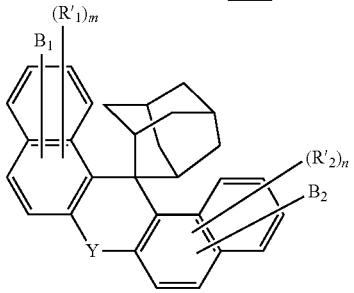

wherein:
$X_1$ and $X_2$ are each independently $CR_1R_2$, $SiR_3R_4$, $NR_5$, O, S, or $SO_2$; and
Y, $R_1$, $R_2$, $R_3$, $R_4$, $R_5$, $B_1$, $B_2$, $R'_1$, $R'_2$ m and n are as defined in claim 1.

5. The compound according to claim 1, wherein:
each X is independently $CR_1R_2$, O, or S,
where $R_1$ and $R_2$ are each independently methyl or ethyl.

6. The compound according to claim 1, wherein:
$L_1$ and $L_2$ are each independently a direct bond or phenylene.

7. The compound according to claim 1, wherein:
$R_6$ and $R_7$ are each independently phenyl, biphenylyl, terphenylyl, naphthyl, phenanthrenyl, cyclohexenyl, dibenzofuranyl, dibenzothiophenyl, dimethylfluorenyl, benzonaphthofuranyl, benzonaphthothiophenyl, or benzodimethylfluorenyl, or are bonded to adjacent substituents to form a substituted or unsubstituted condensed ring, and
they are each unsubstituted or independently substituted with deuterium, *—$CD_3$, $C_{1-4}$ alkyl, *—($C_{1-4}$ alkyl) phenyl, $C_{3-10}$ cycloalkyl, phenyl, halogen, cyano, or *—$SiR_{11}R_{12}R_{13}$, where $R_{11}$, $R_{12}$ and $R_{13}$ are each independently methyl, ethyl, tertbutyl or phenyl, and
*— means a bond linked to another substituent group.
8. The compound according to claim 1, wherein:
$B_1$ and $B_2$ are each independently any one selected from the group consisting of the following:
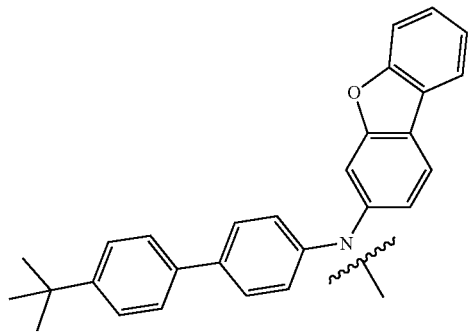
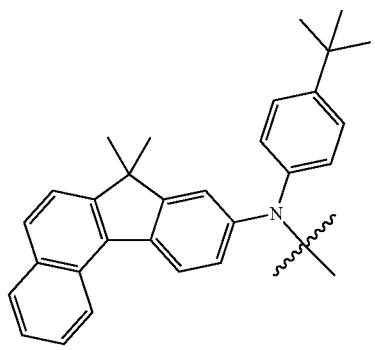
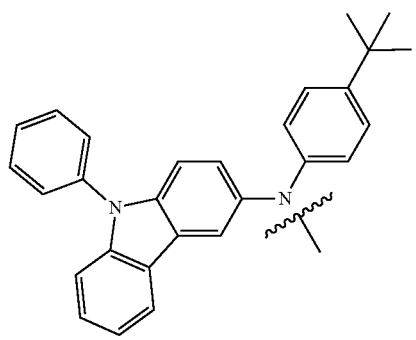
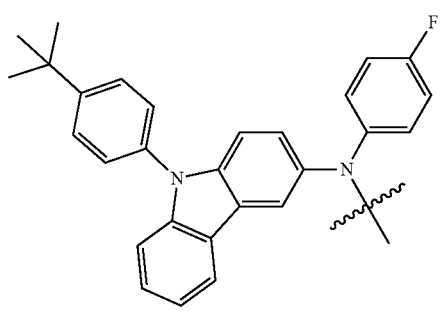
-continued
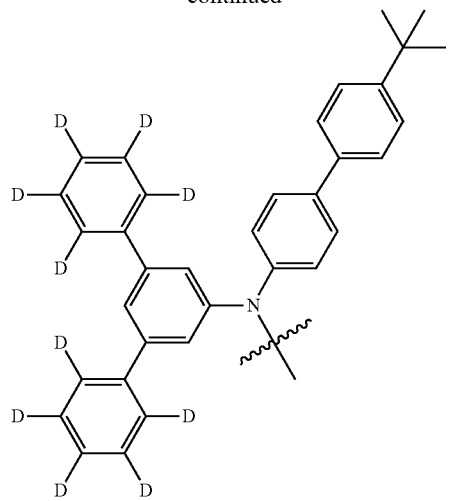
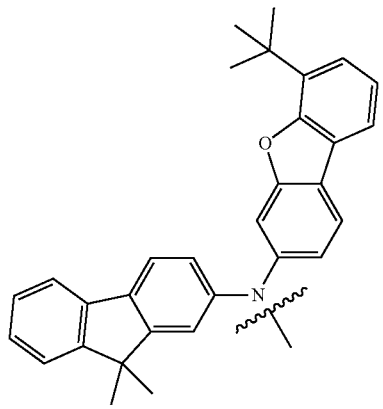
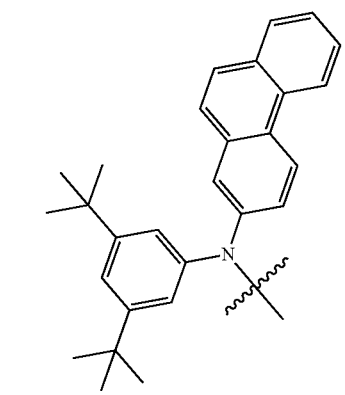
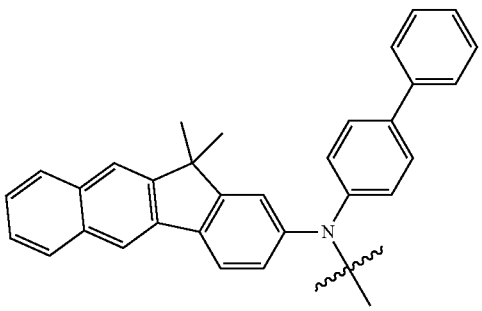

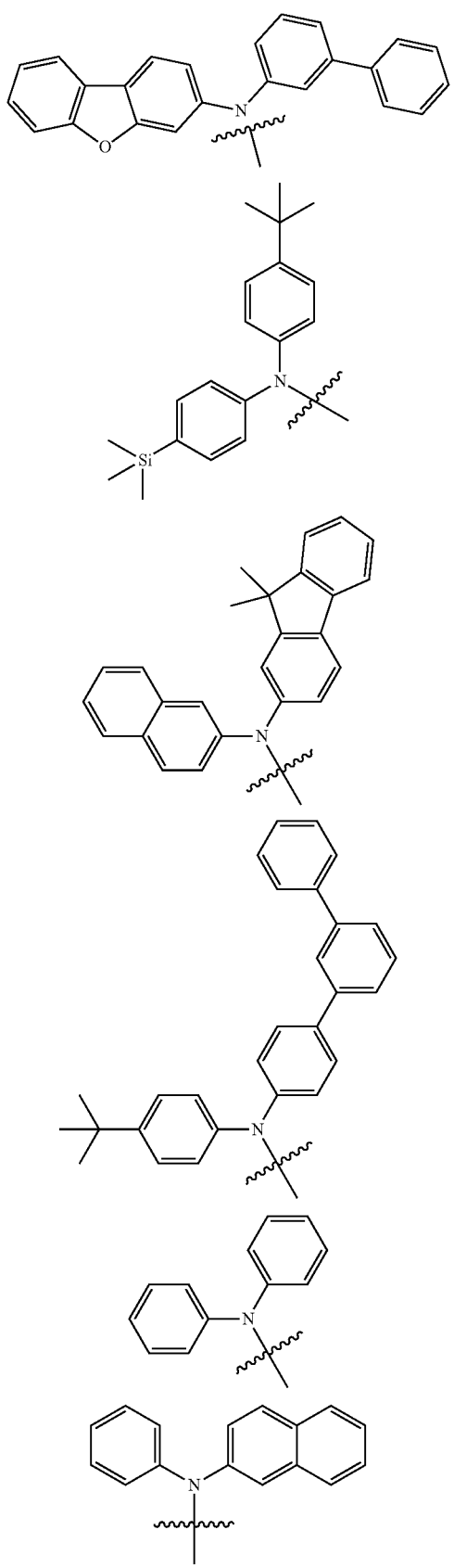
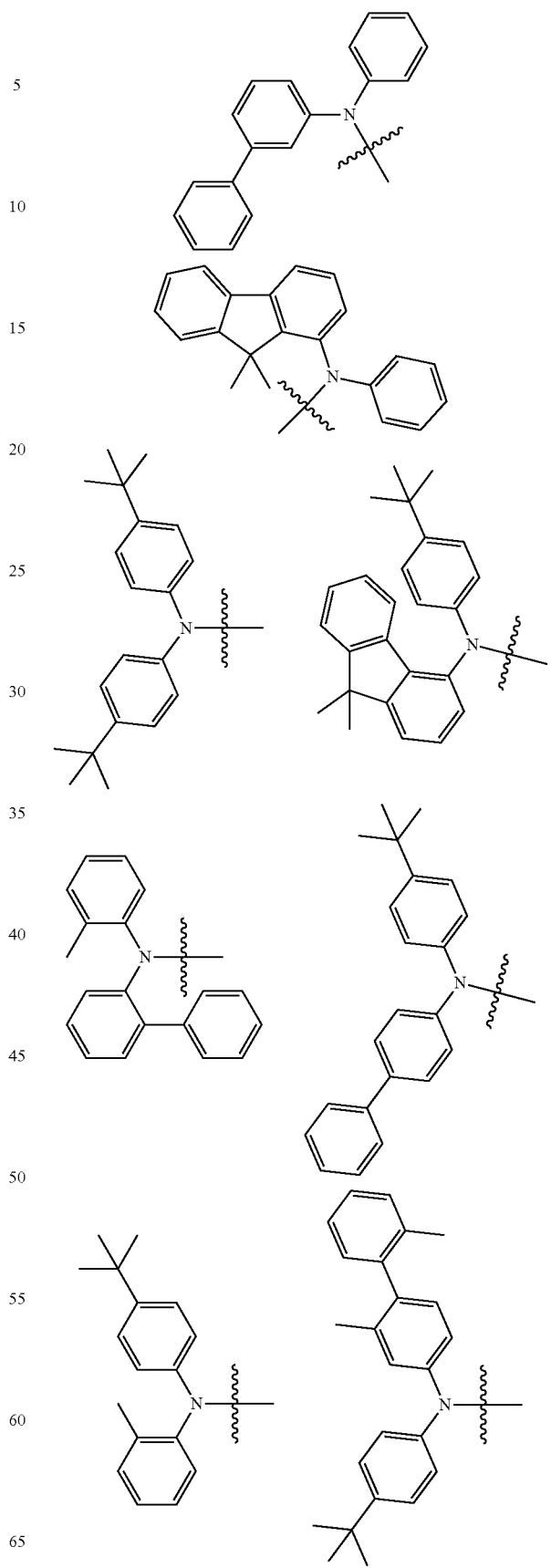

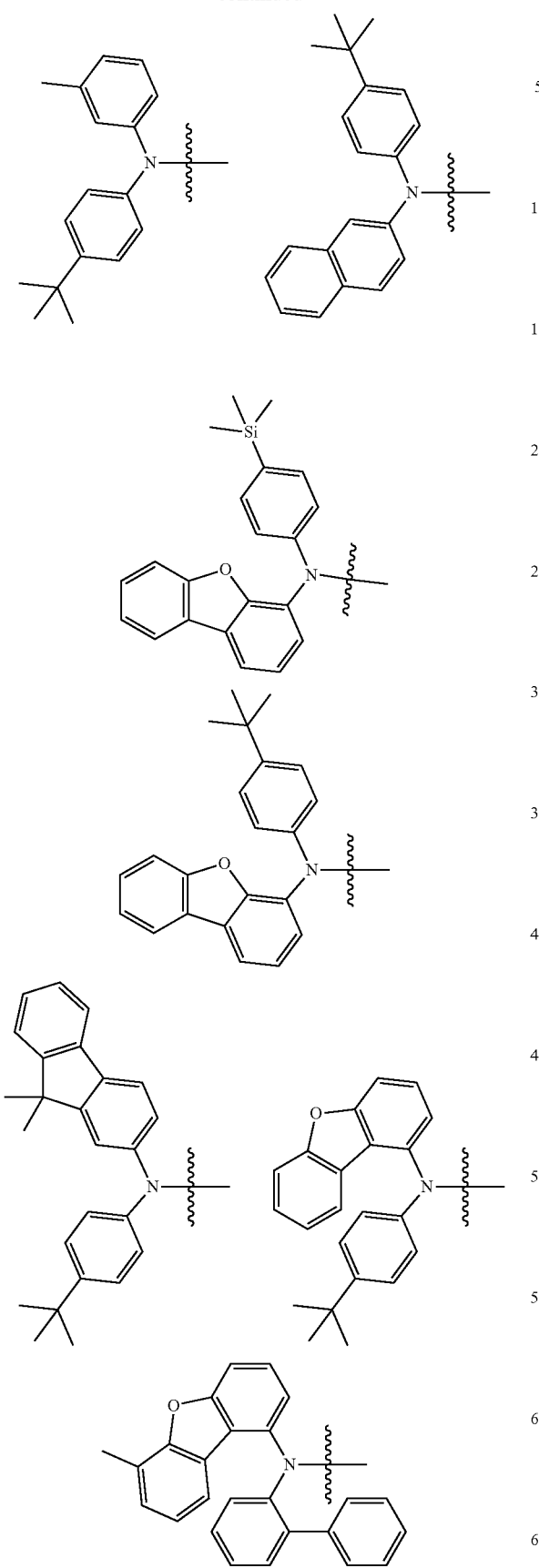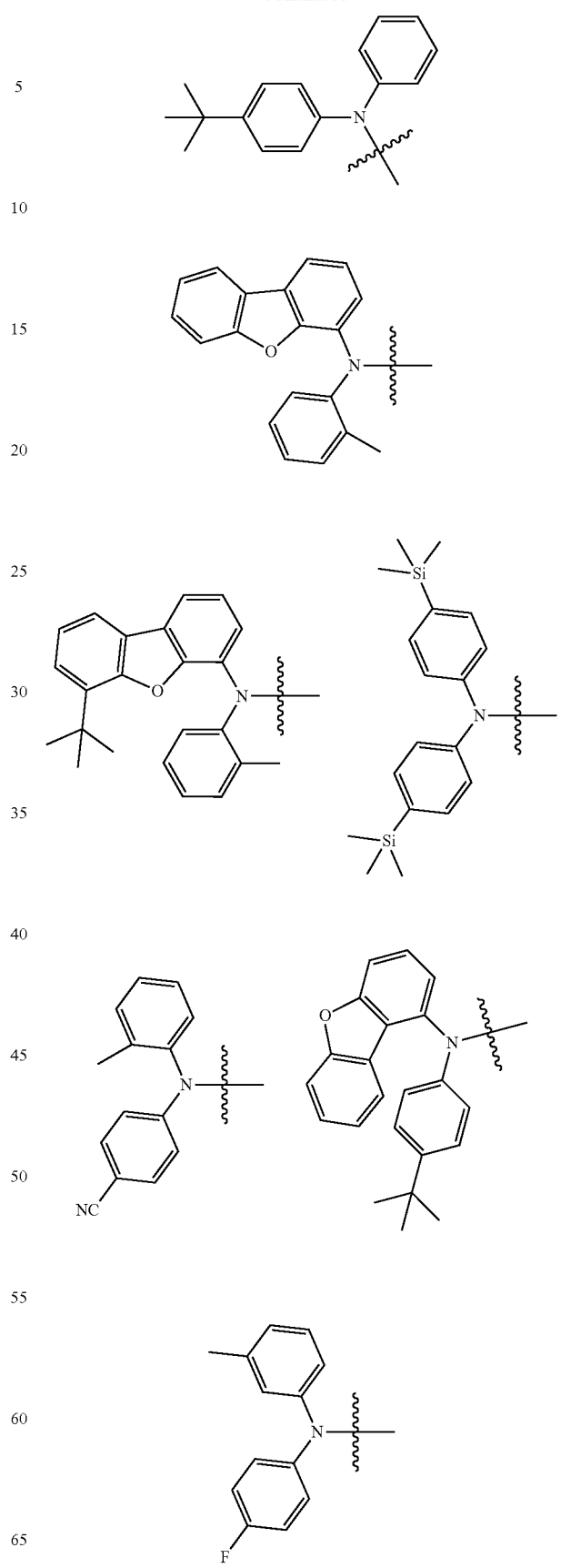

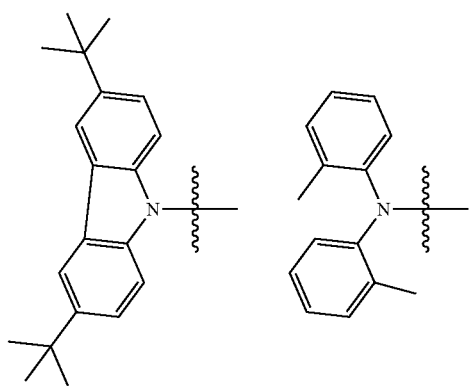
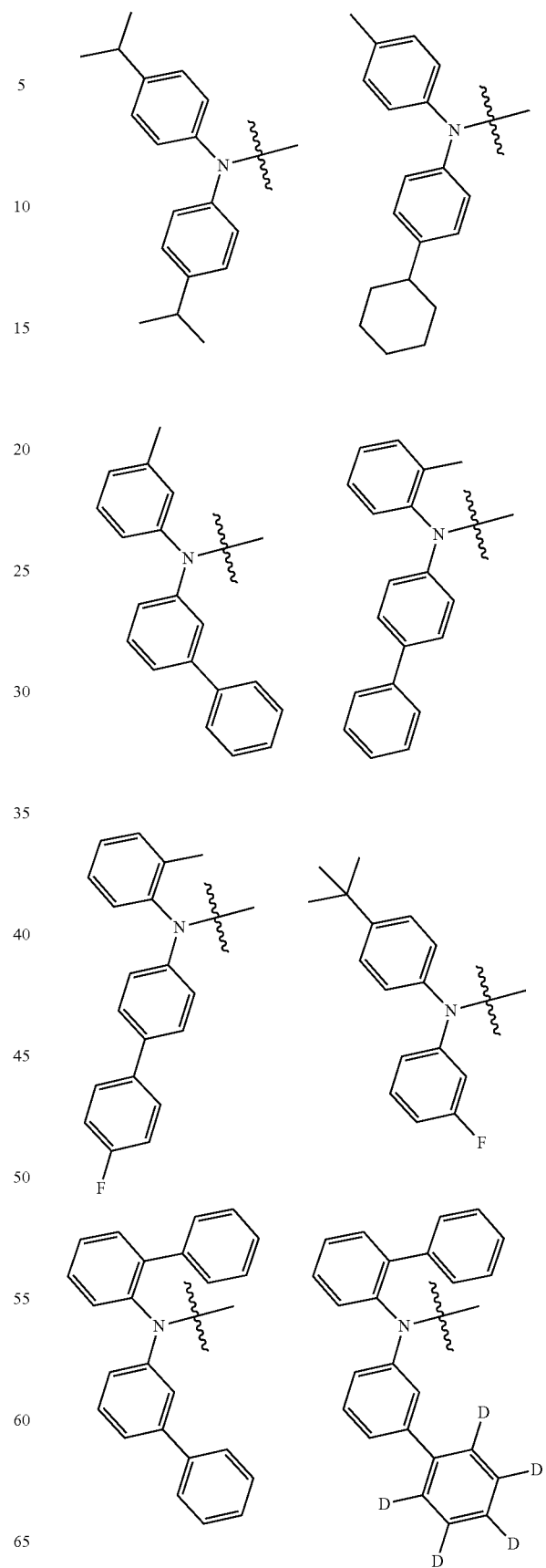

-continued
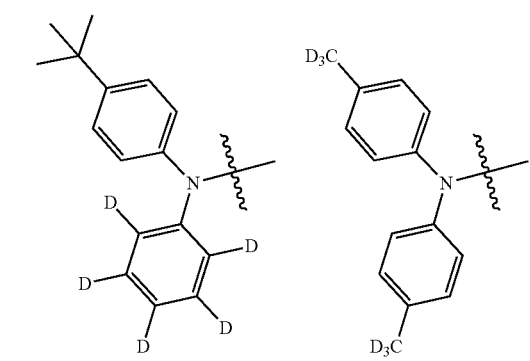
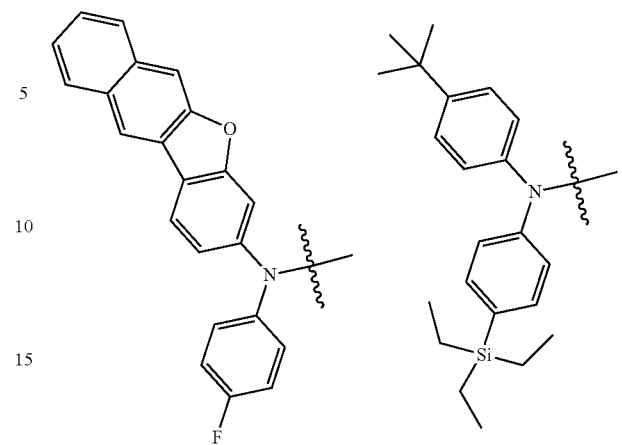
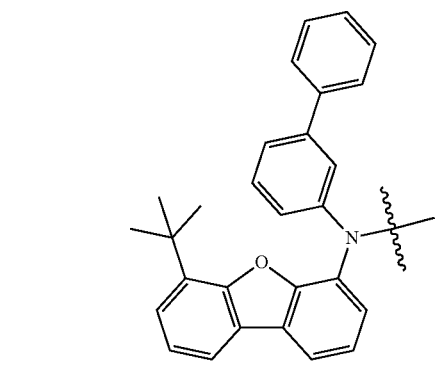
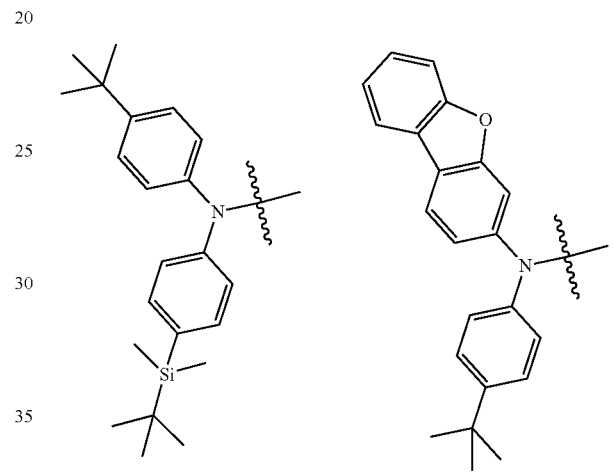
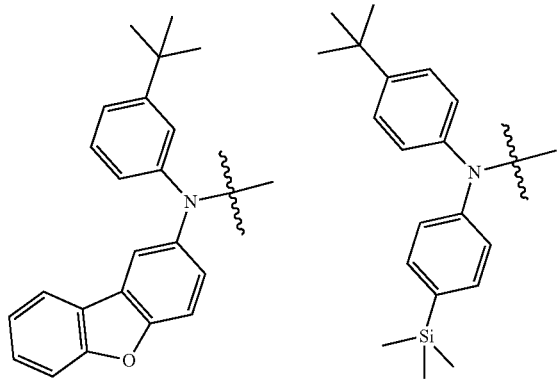
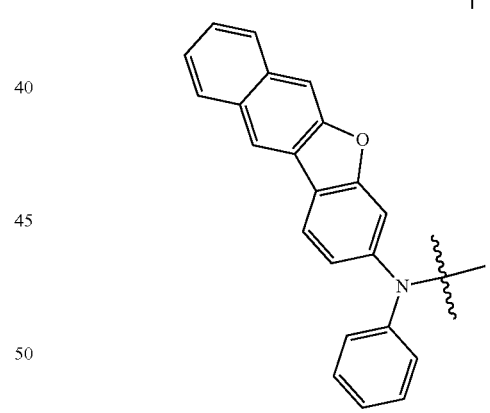
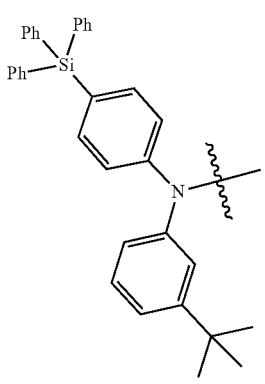
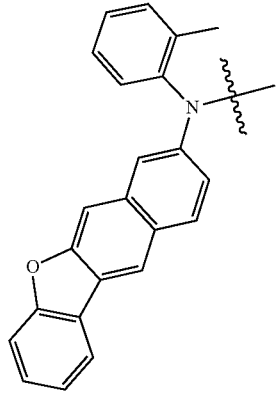
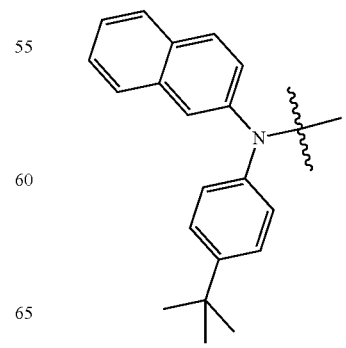
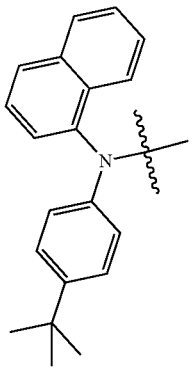

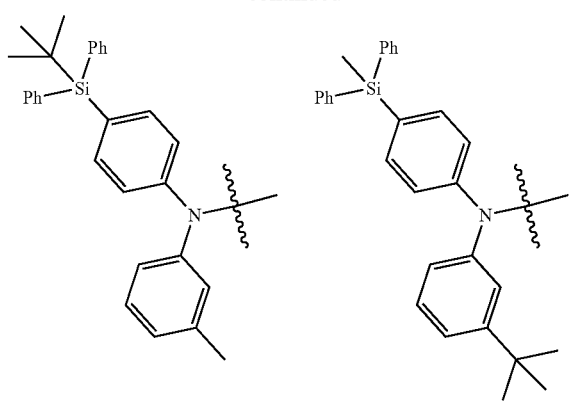
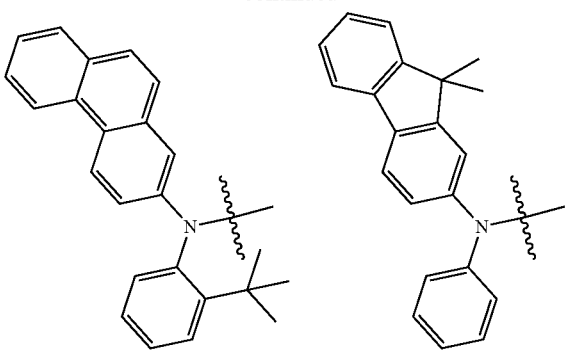
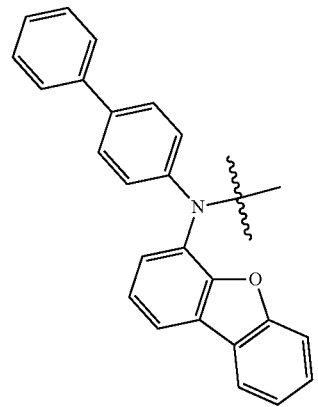
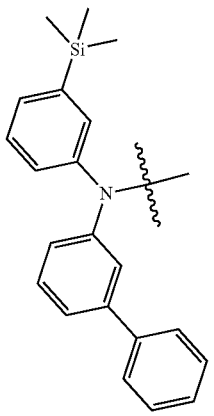
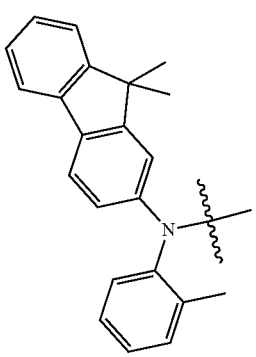
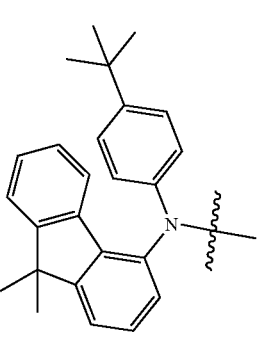
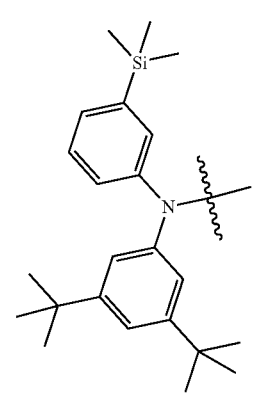
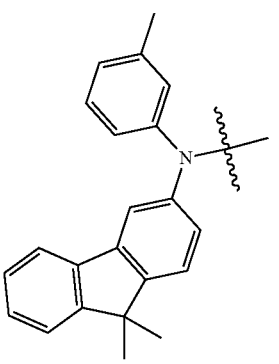
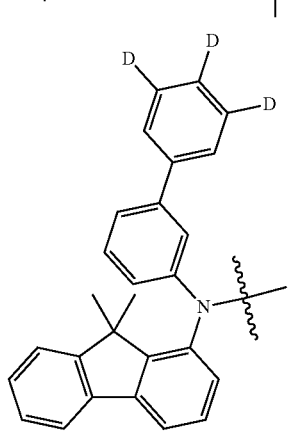
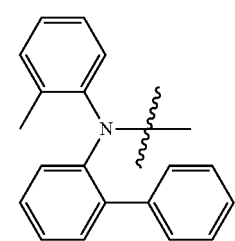
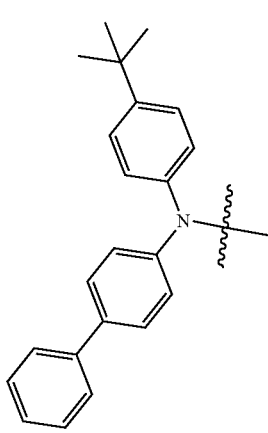

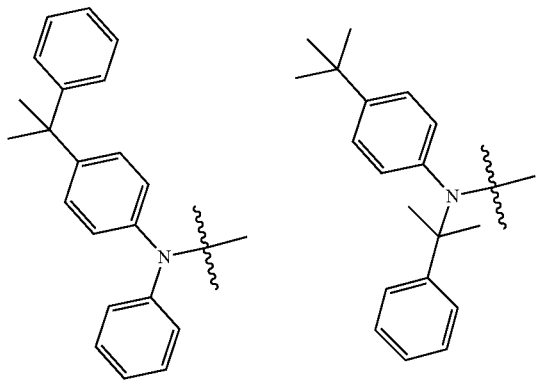
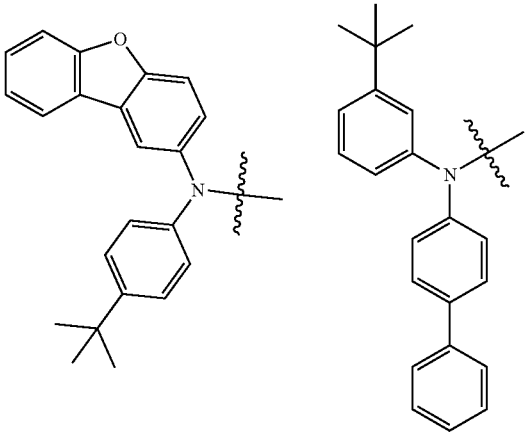
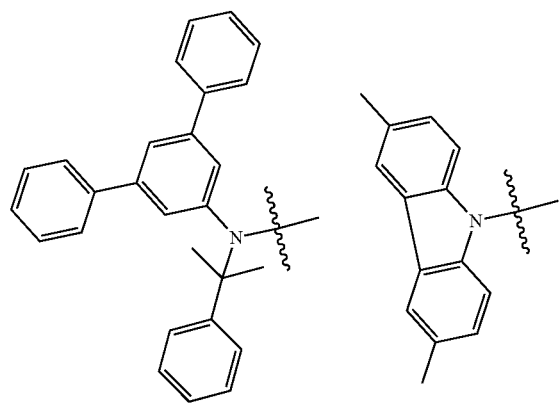
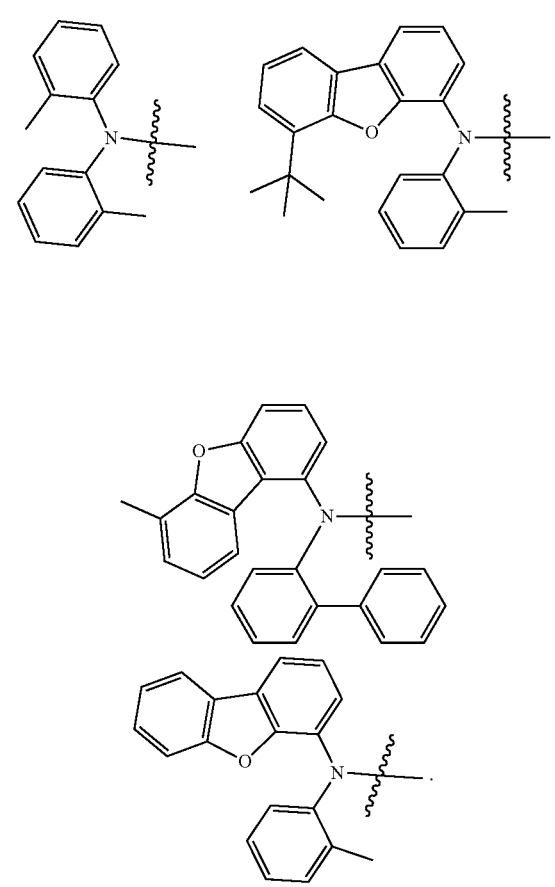
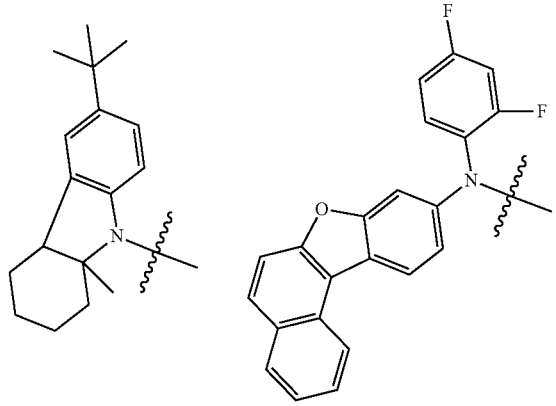
9. The compound according to claim 1, wherein:
R'$_1$ and R'$_2$ are each independently hydrogen or deuterium.
10. The compound according to claim 1, wherein:
the compound of Chemical Formula 1 is any one compound selected from the group consisting of the following compounds:

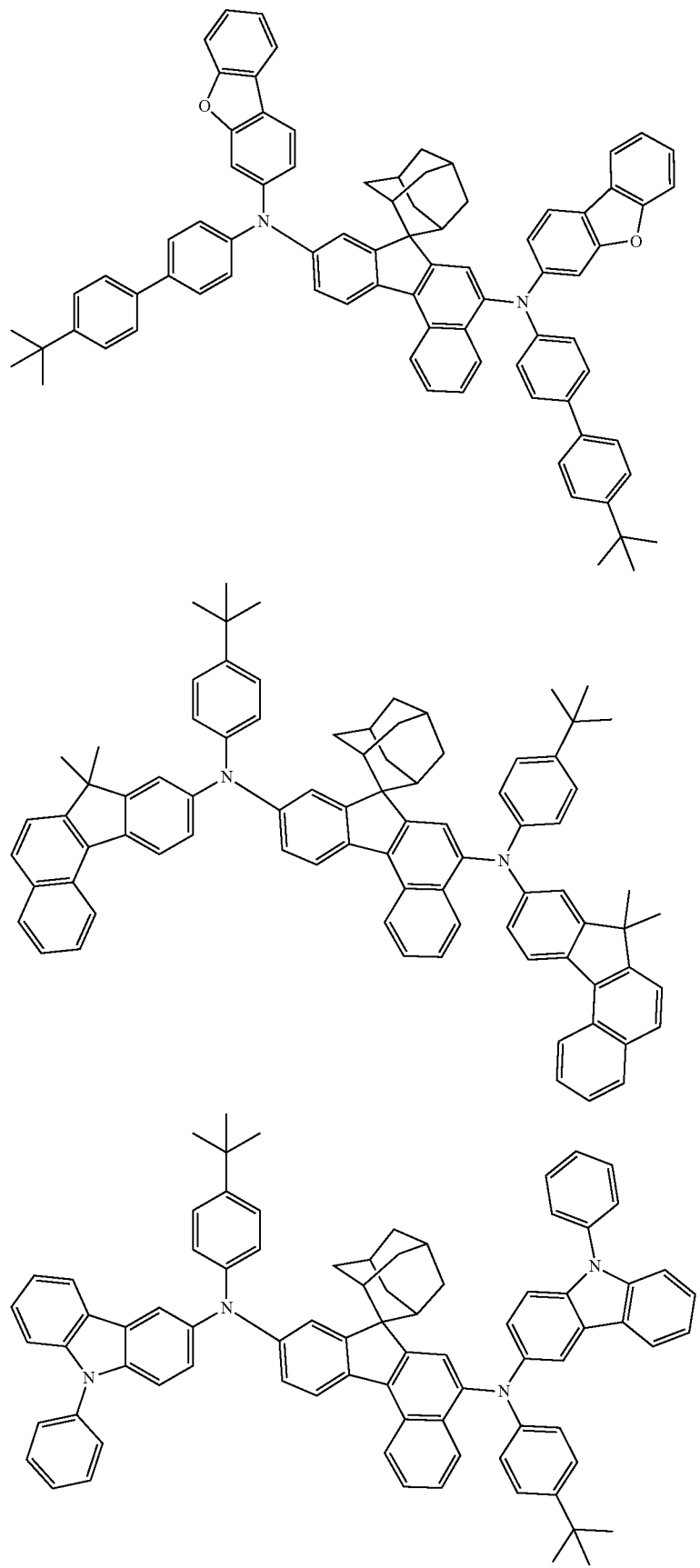

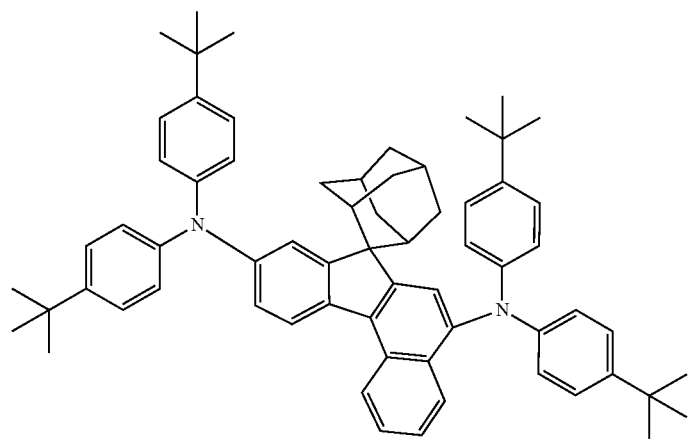
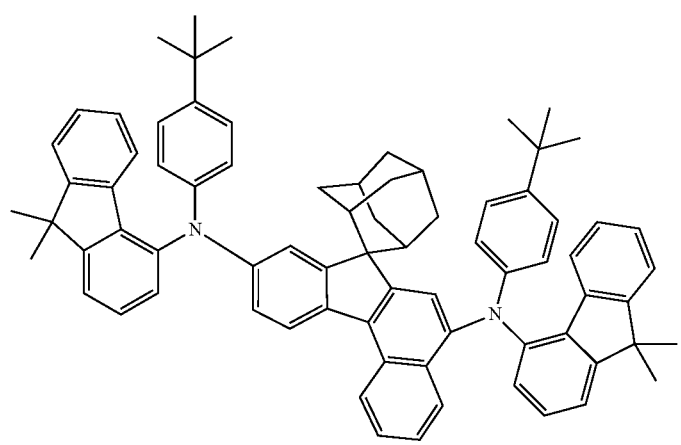
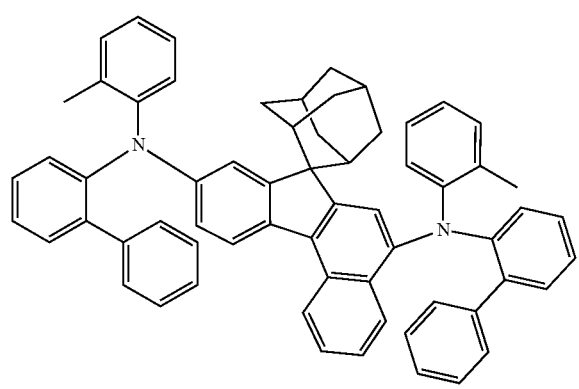

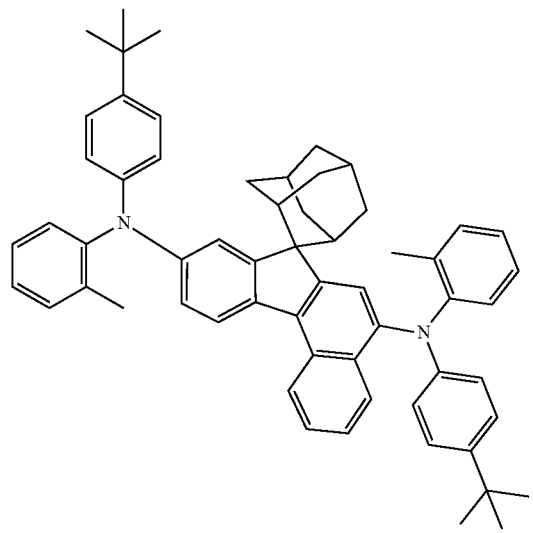
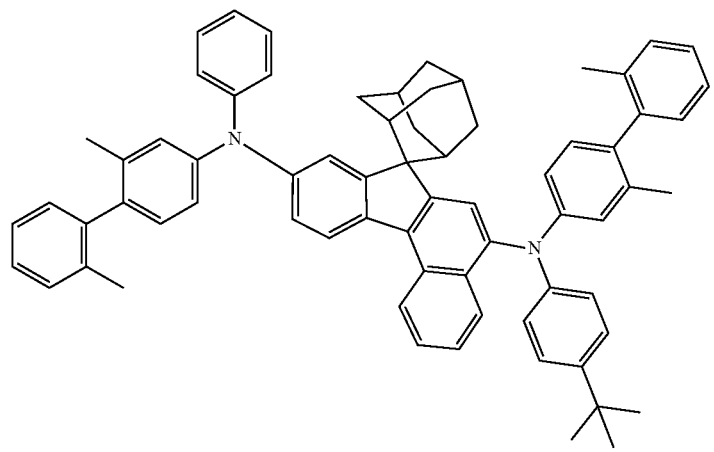
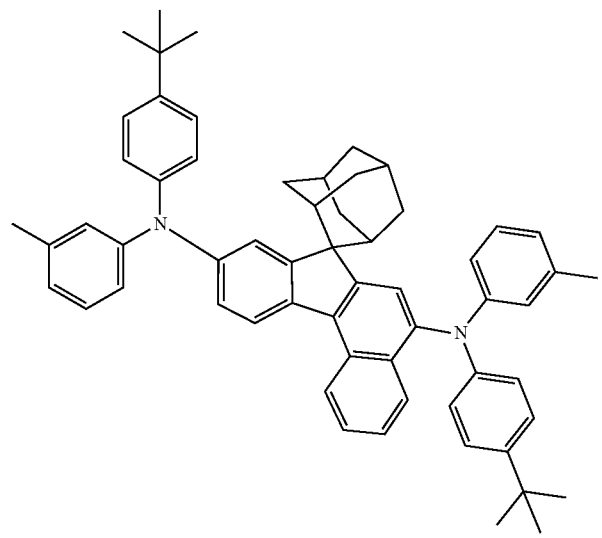

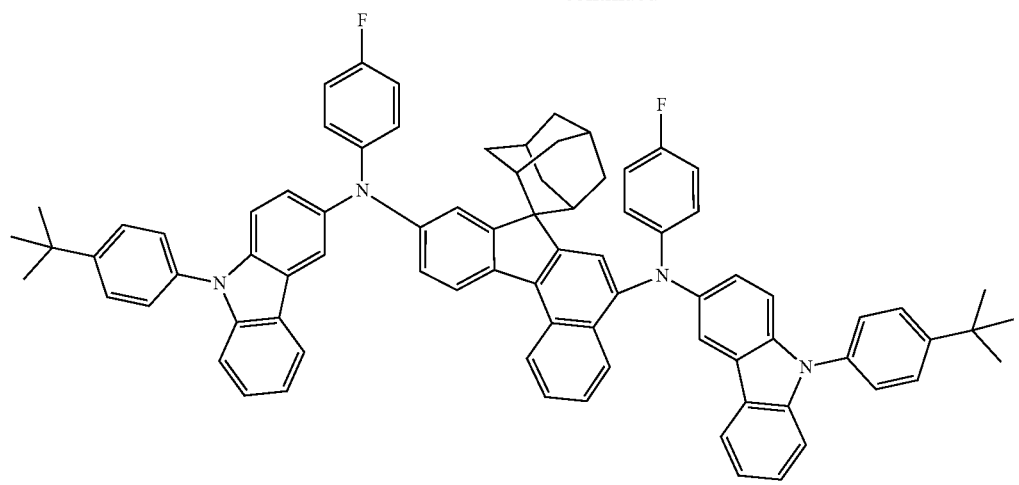
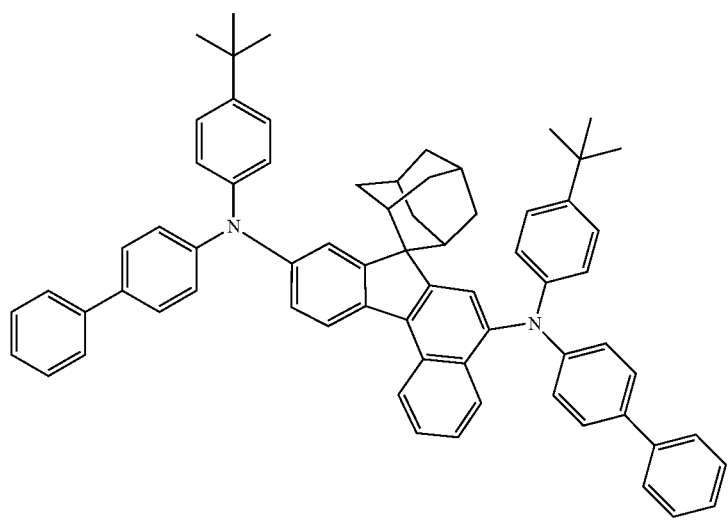
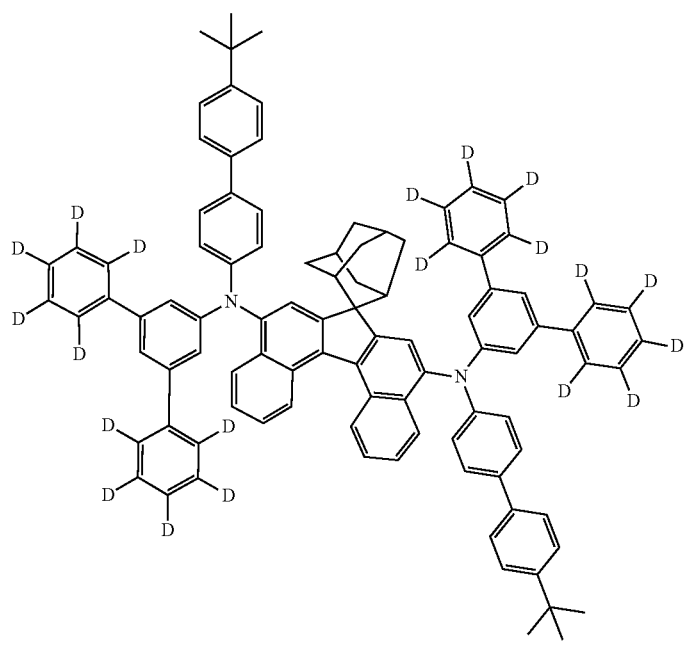

-continued
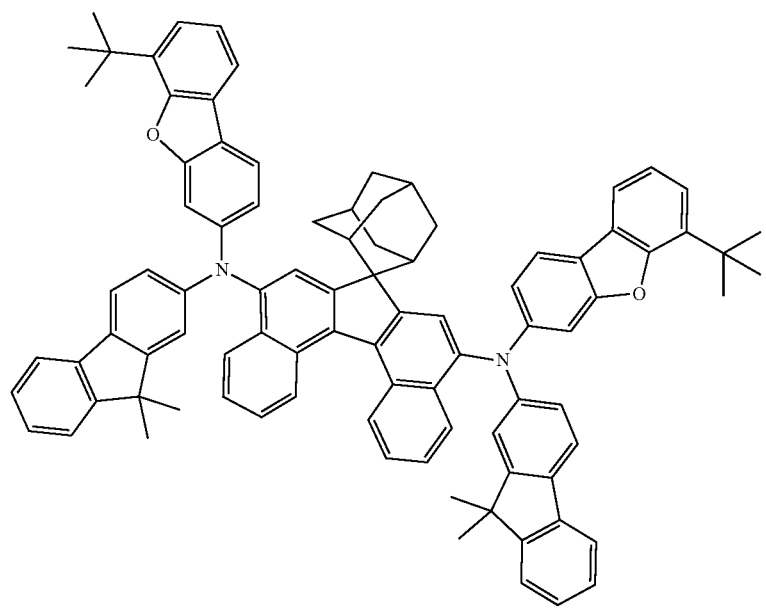
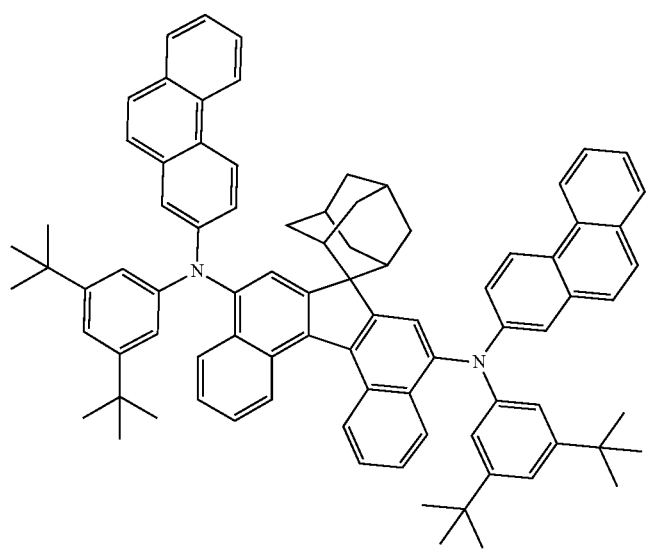

-continued
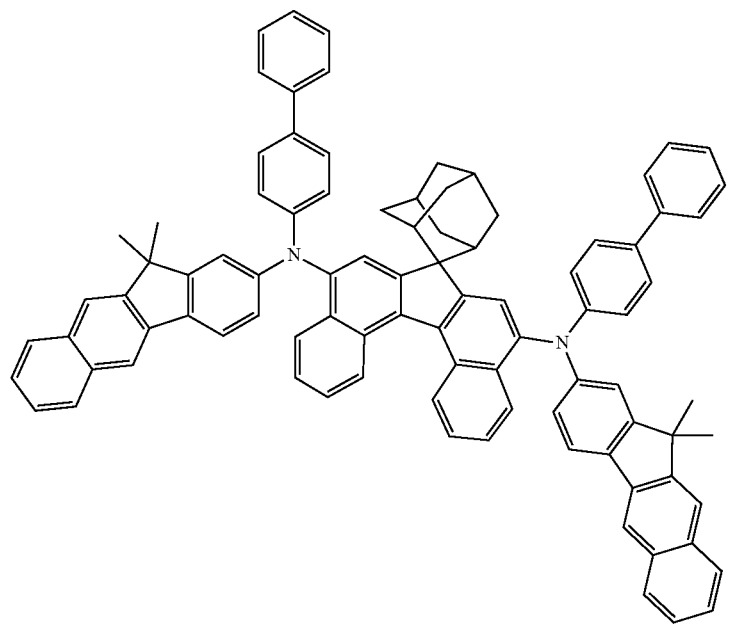
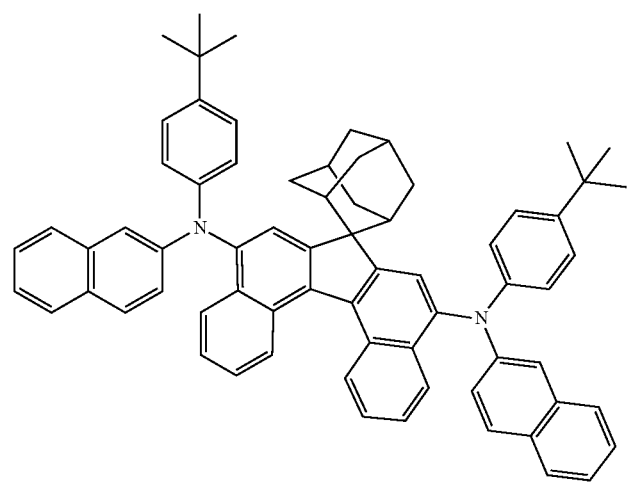
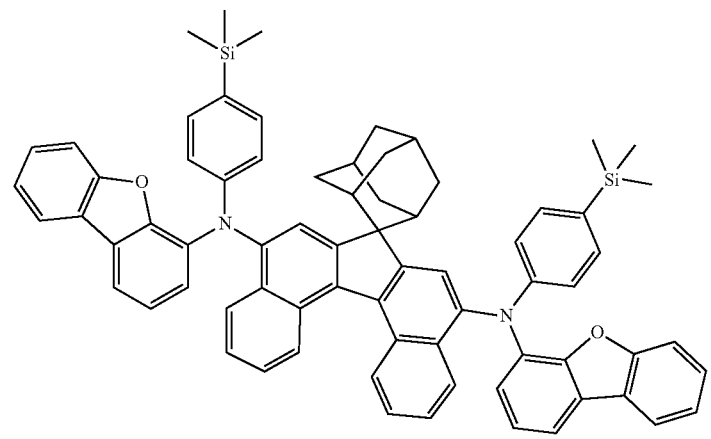

-continued
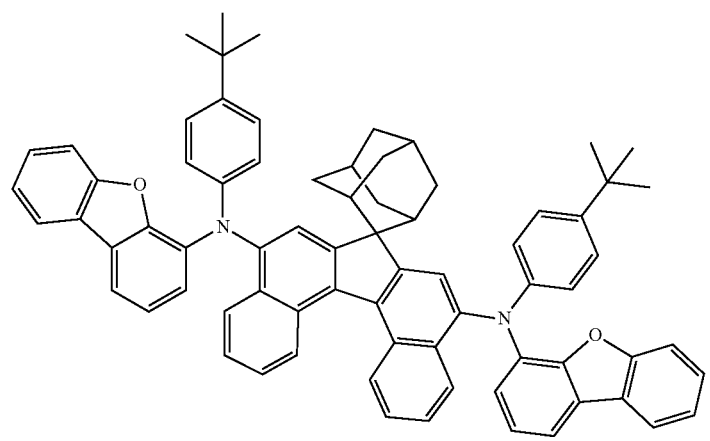
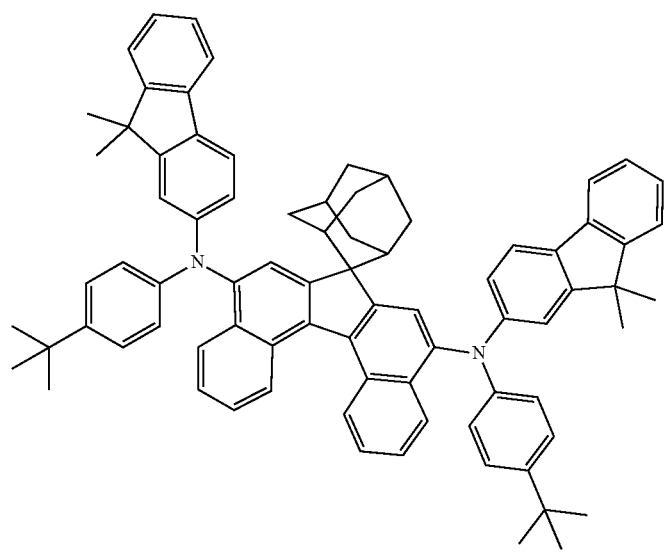
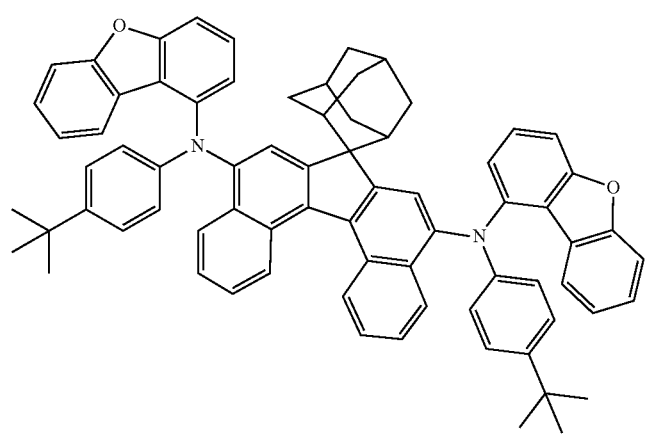

-continued
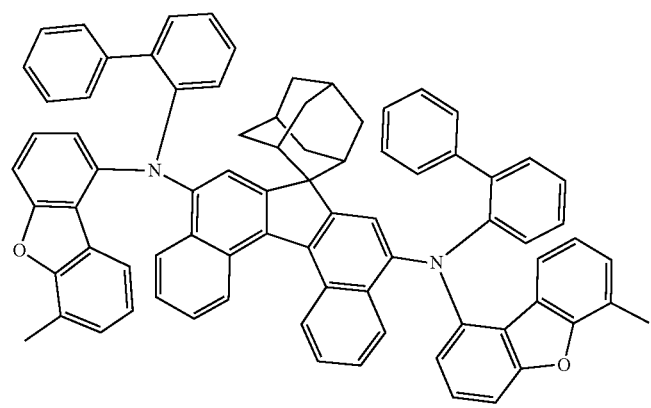
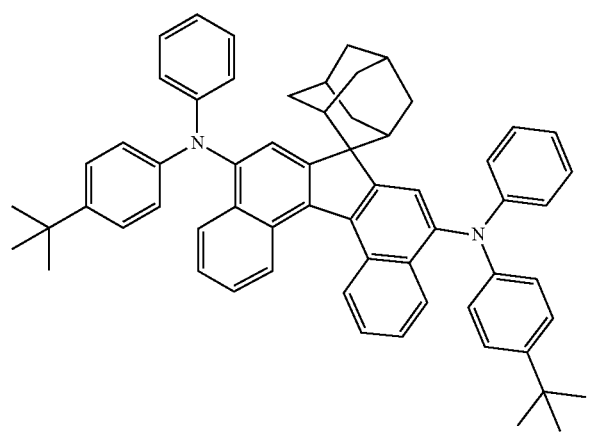
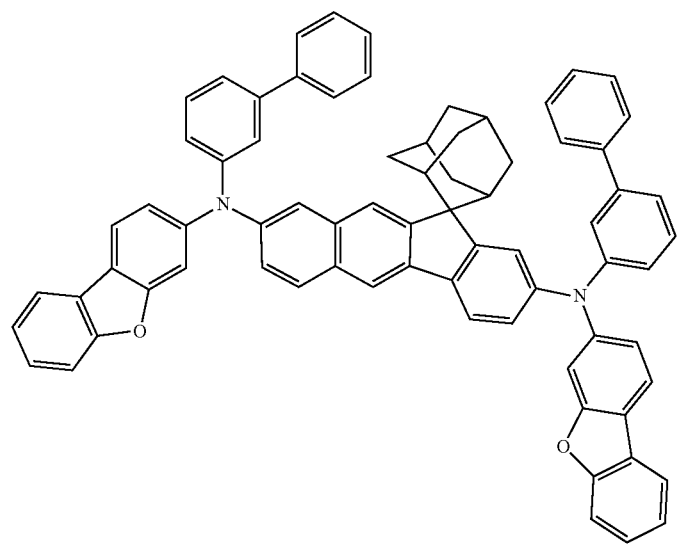

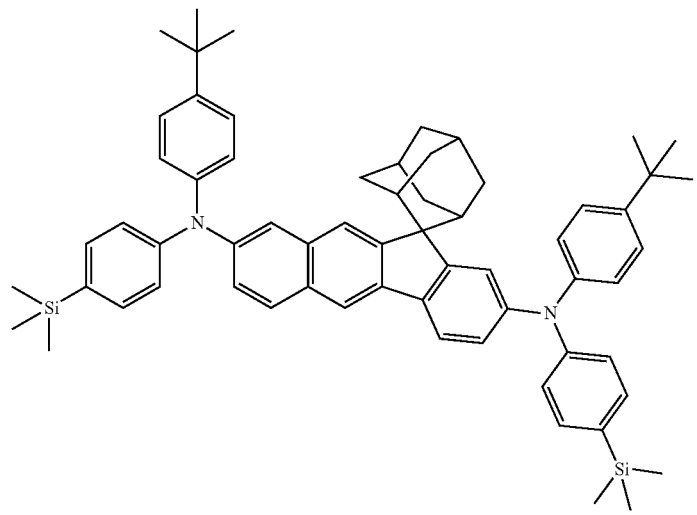
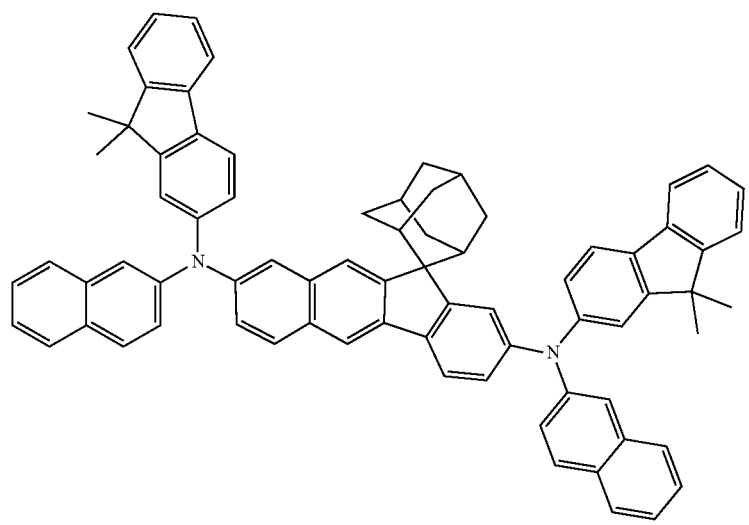
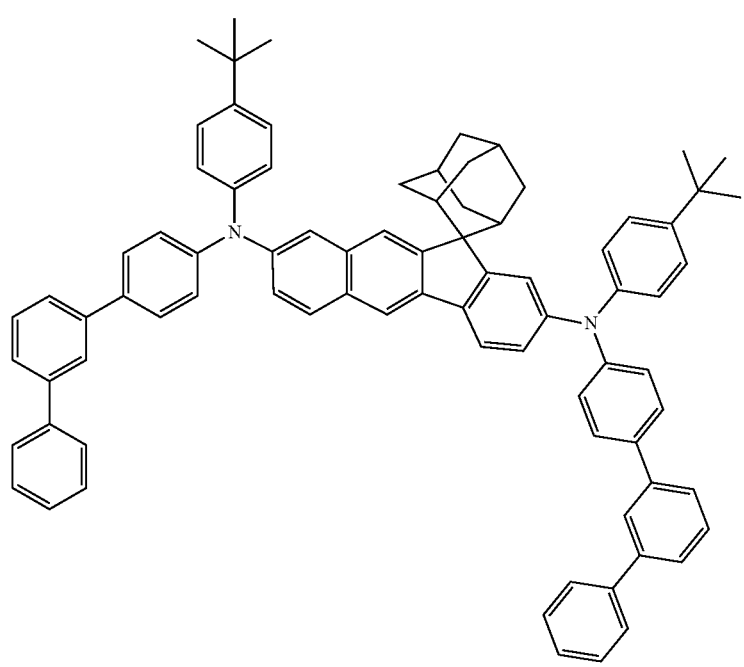

-continued
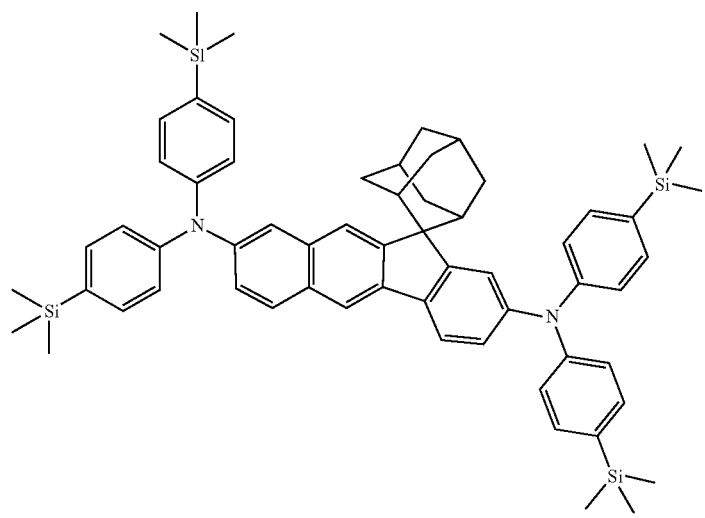
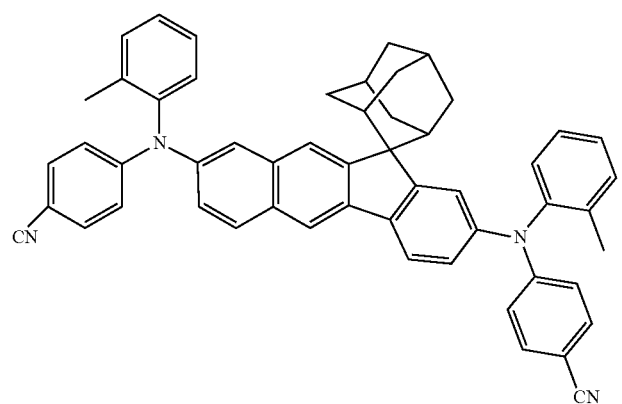
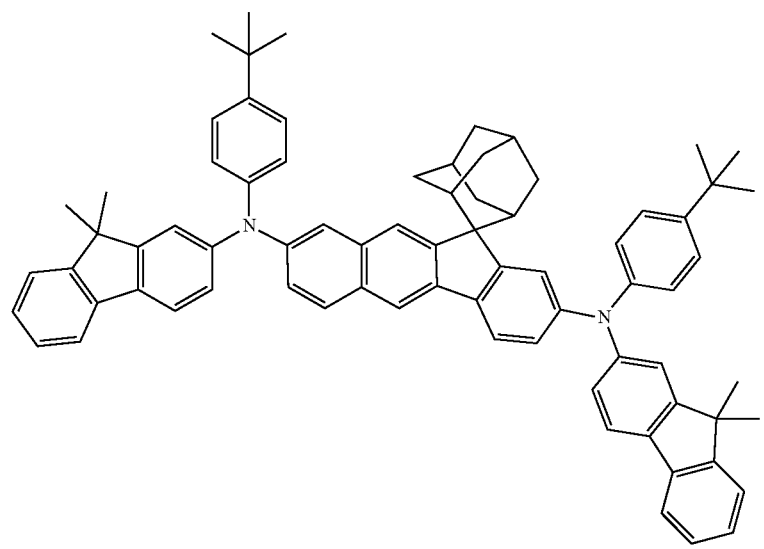

-continued
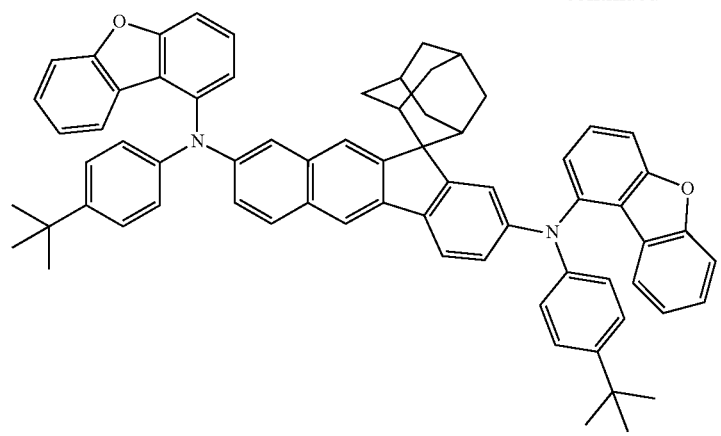
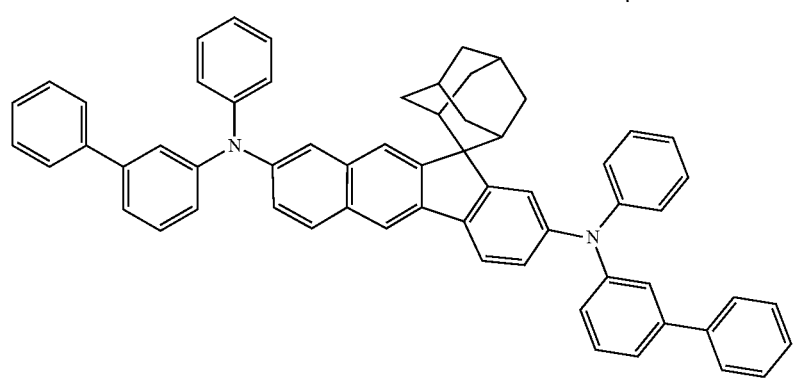
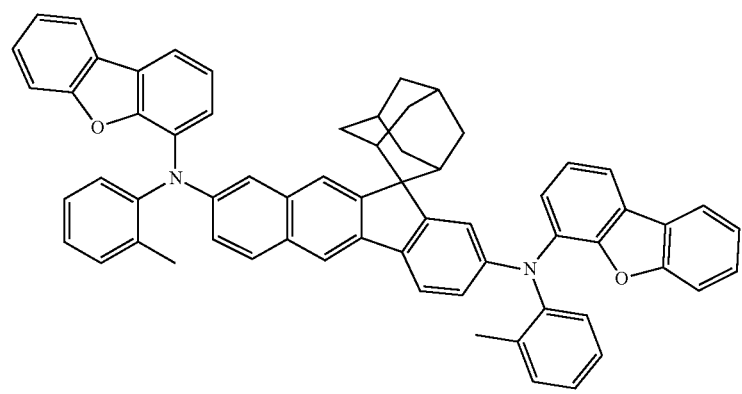
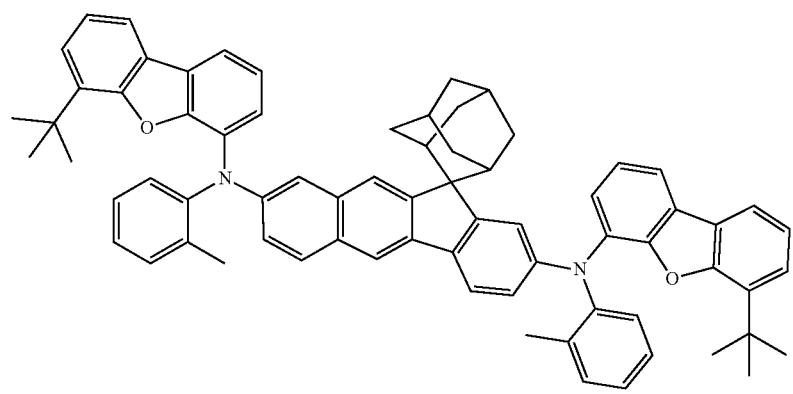 [SMILES: Cc1ccccc1N(c1ccc2c(c1)C1(c3cc4cc(N(c5ccccc5C)c5cccc6c5oc5c(C(C)(C)C)cccc56)ccc4cc3-2)C2CC3CC(C2)CC1C3)c1cccc2c1oc1c(C(C)(C)C)cccc12]

-continued
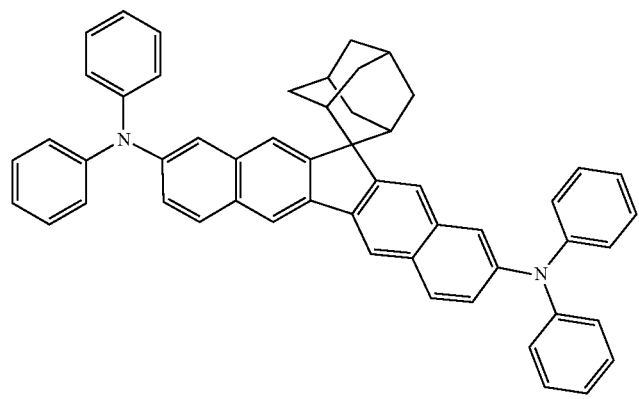
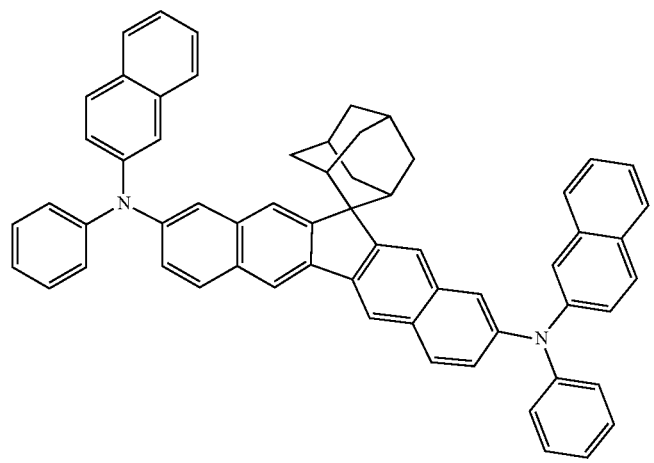
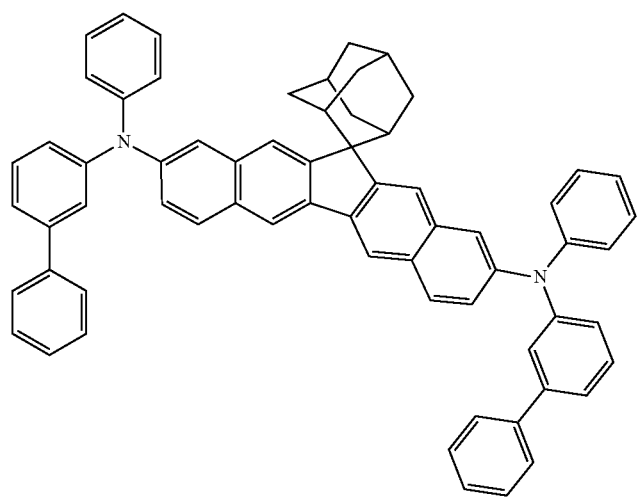

-continued
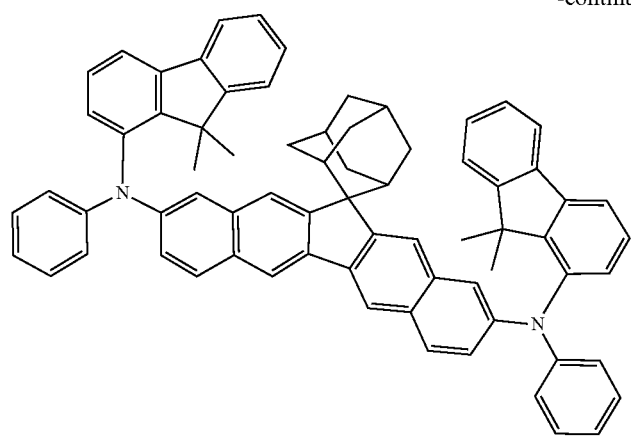
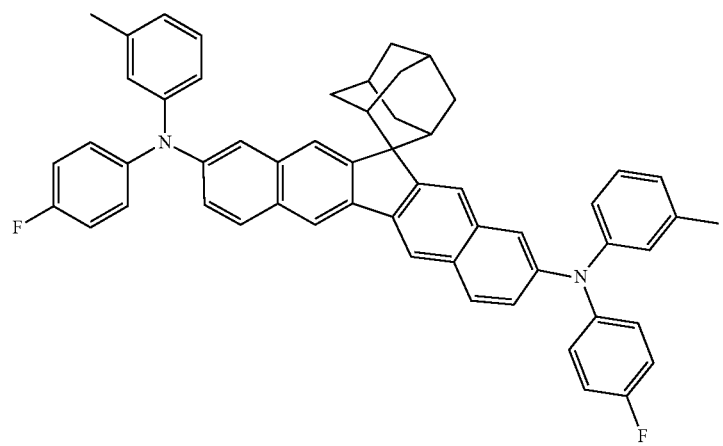
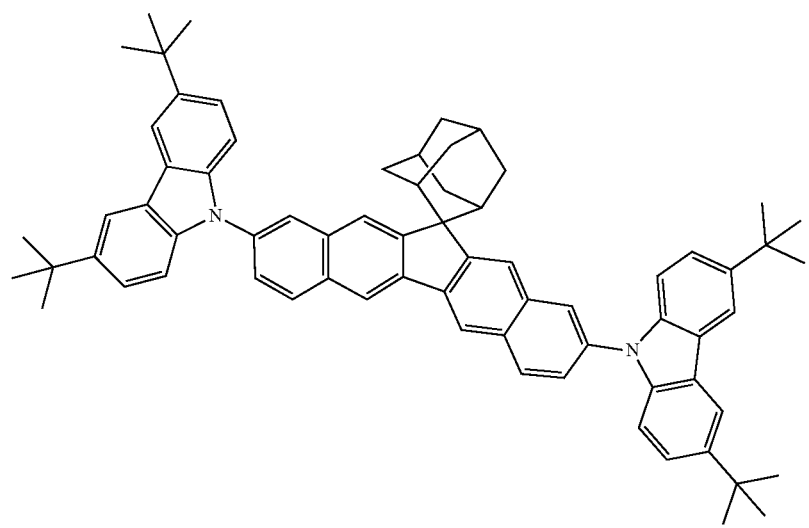

-continued
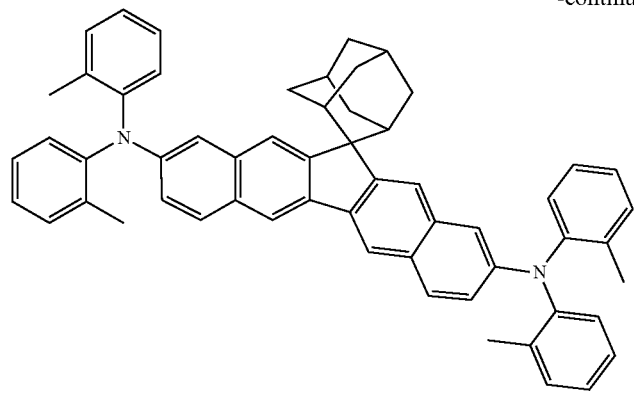
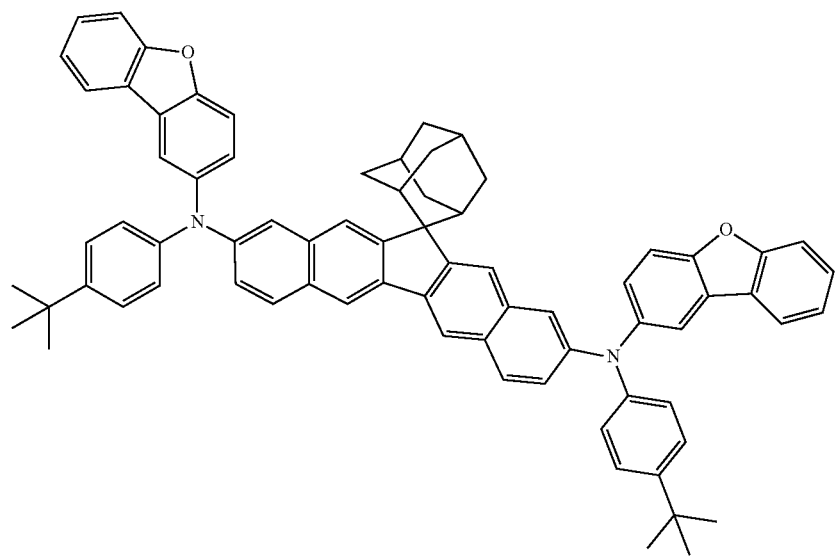
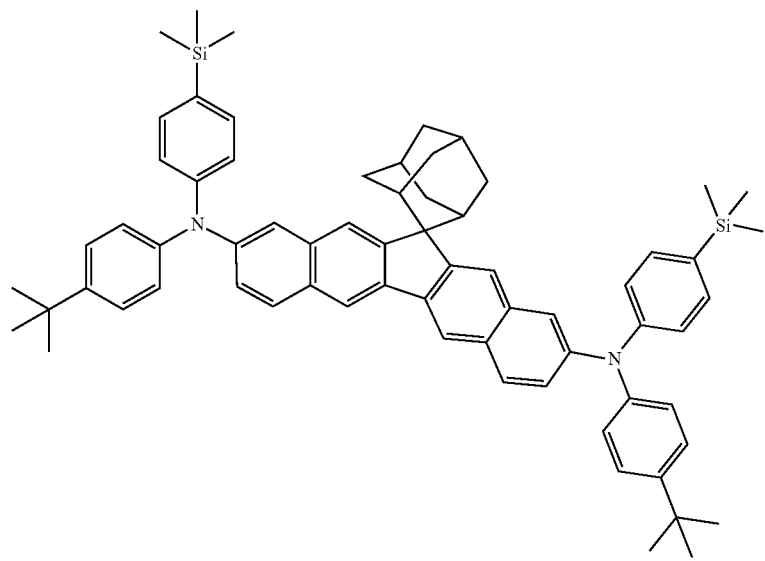

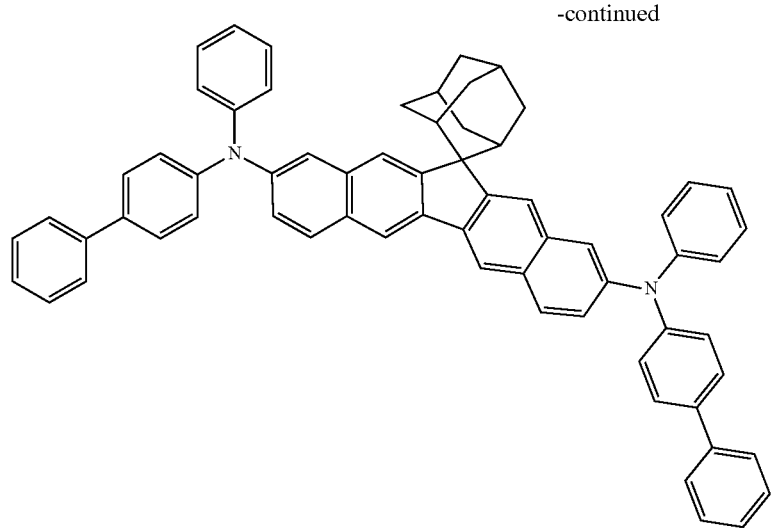
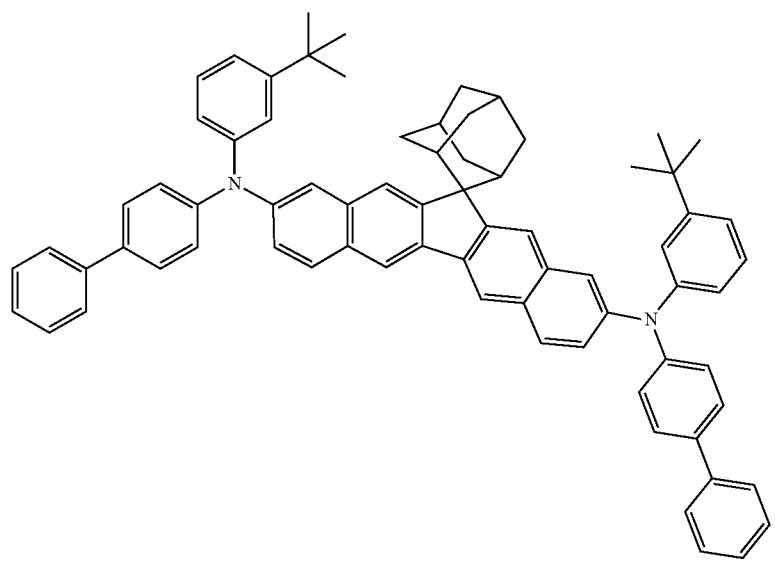
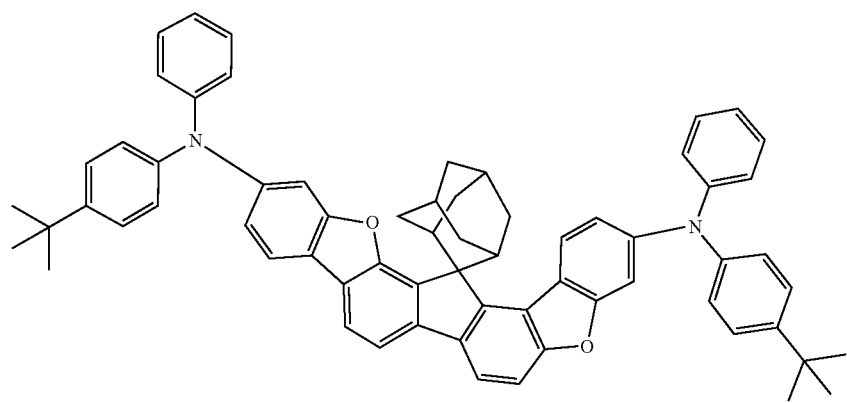

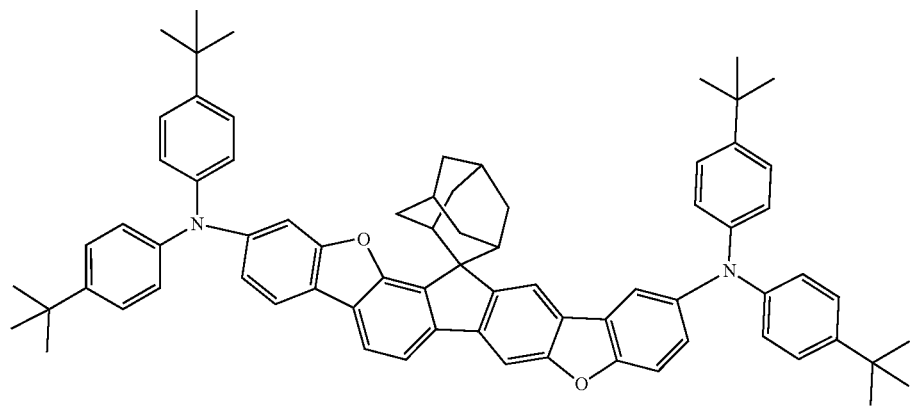
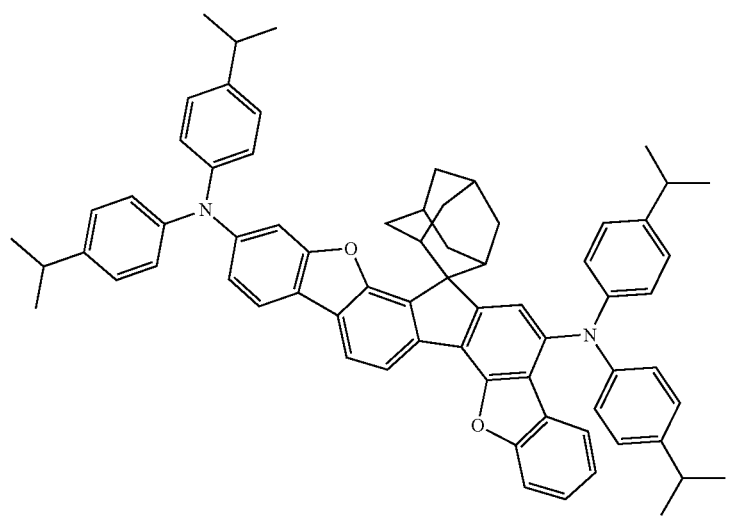
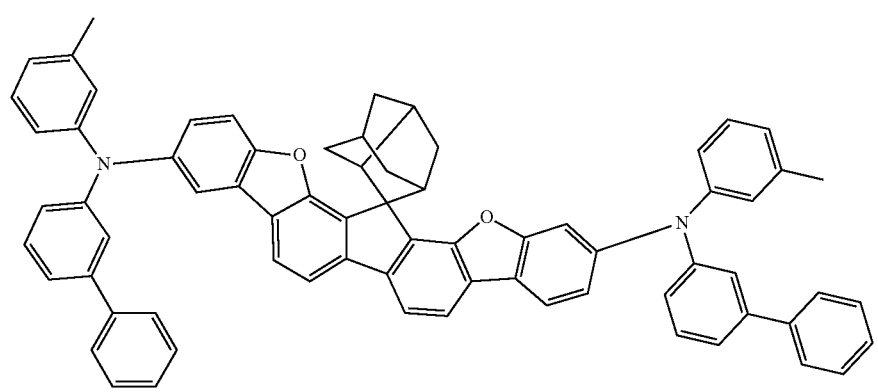

-continued
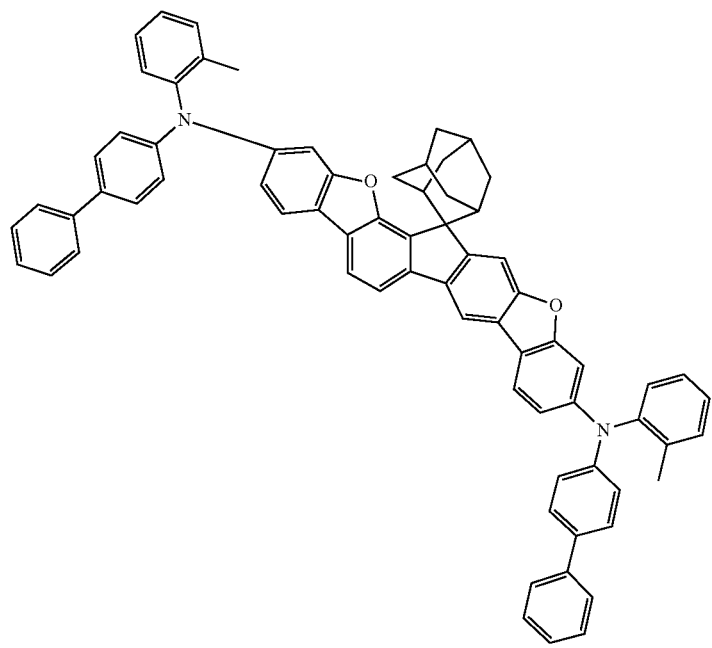
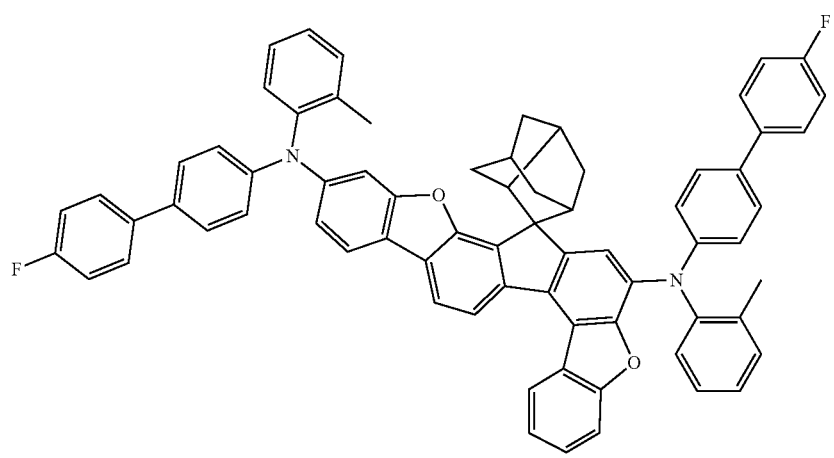
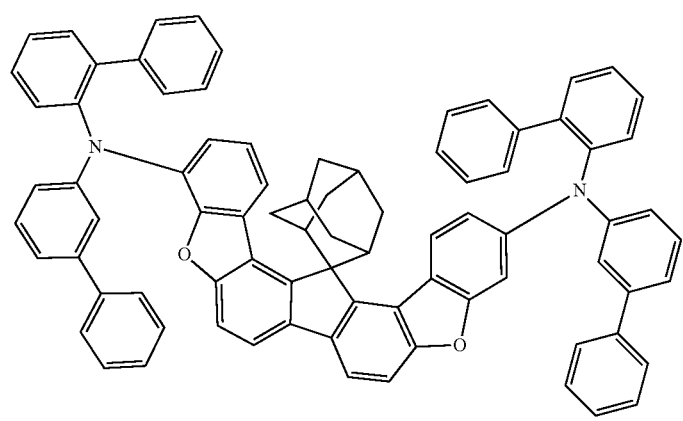

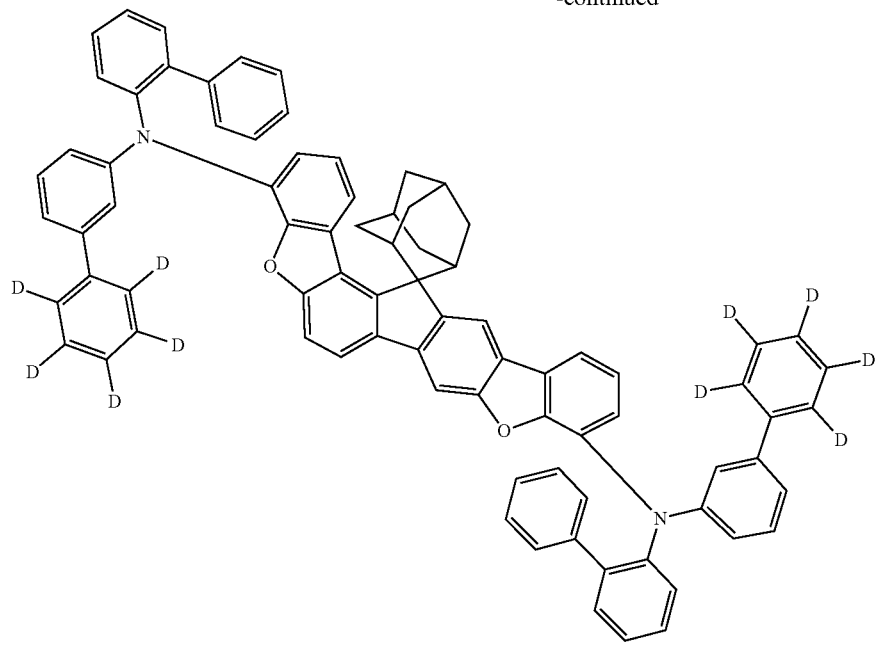
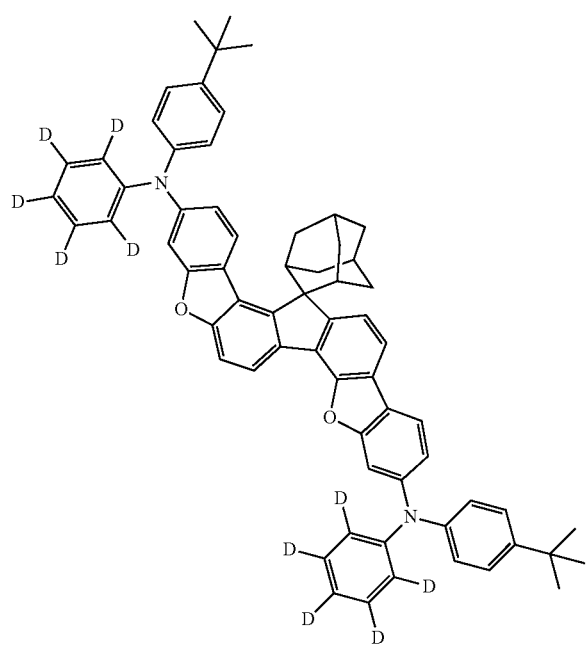

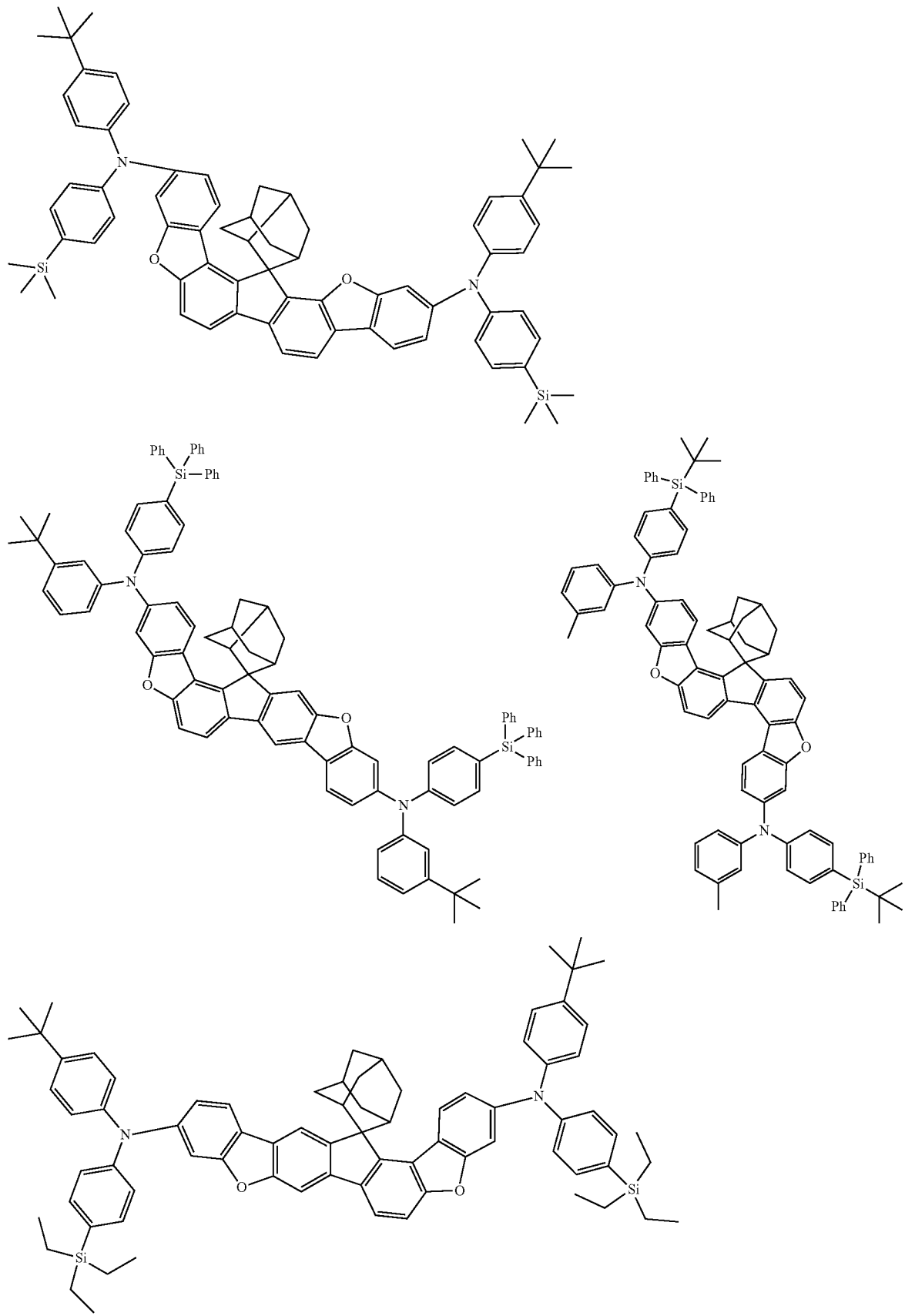

-continued
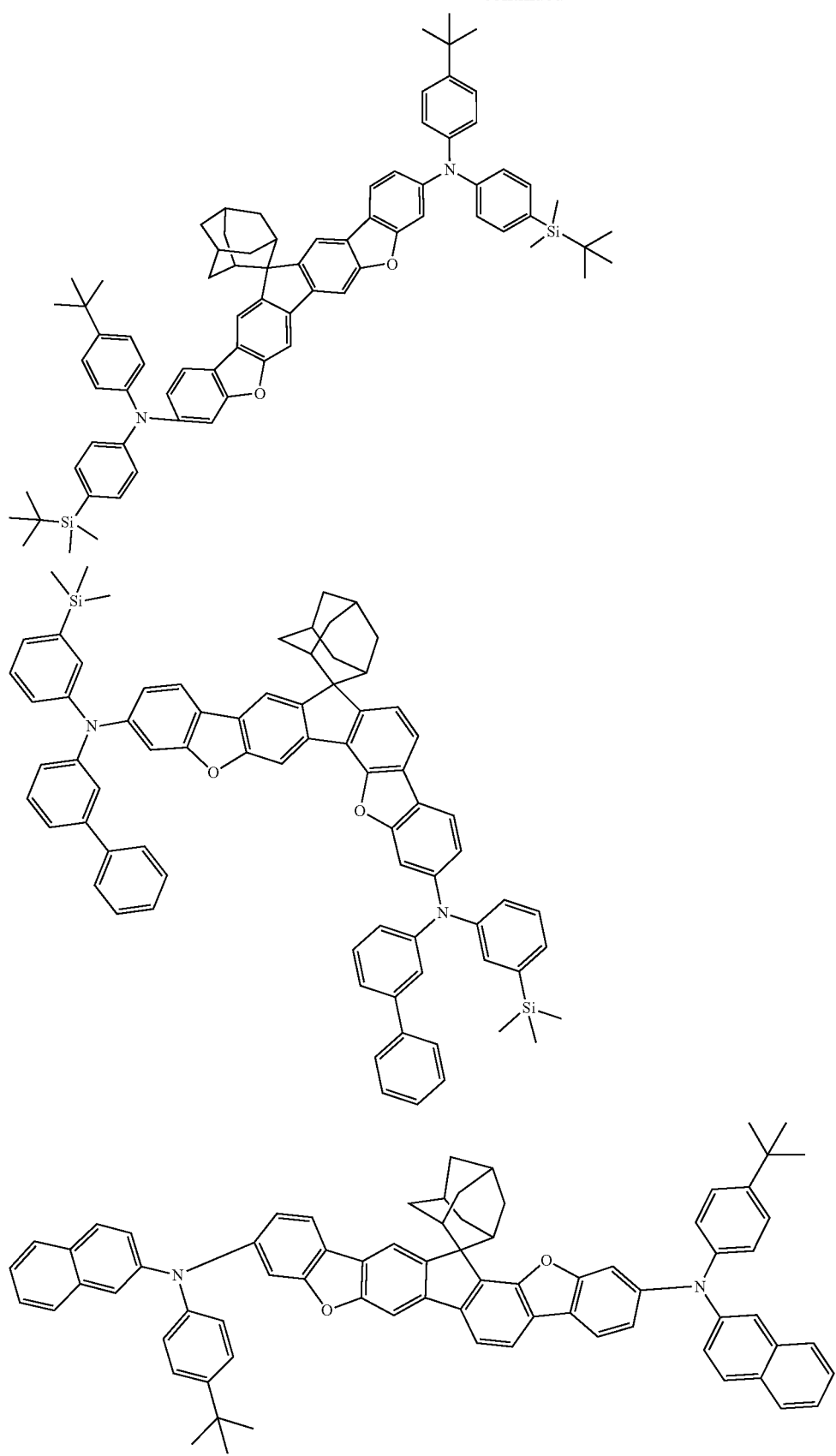

-continued
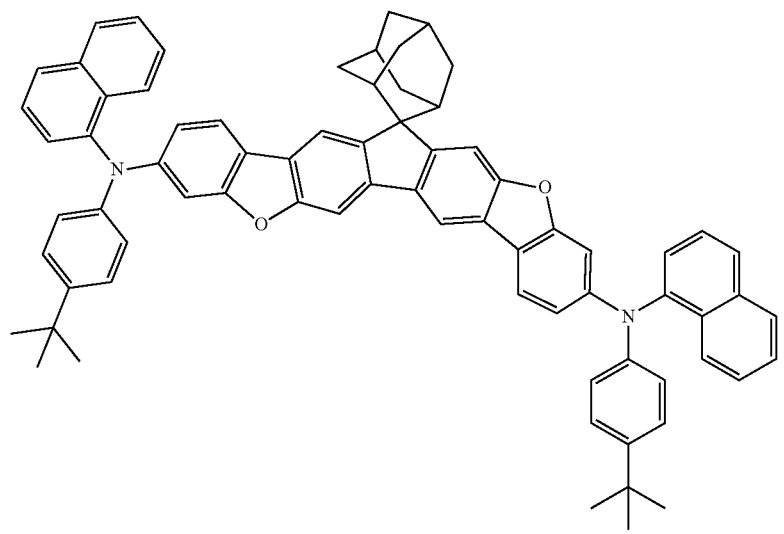
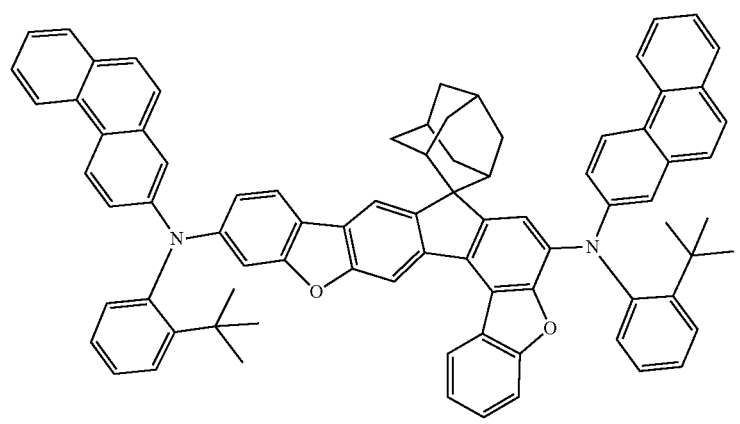
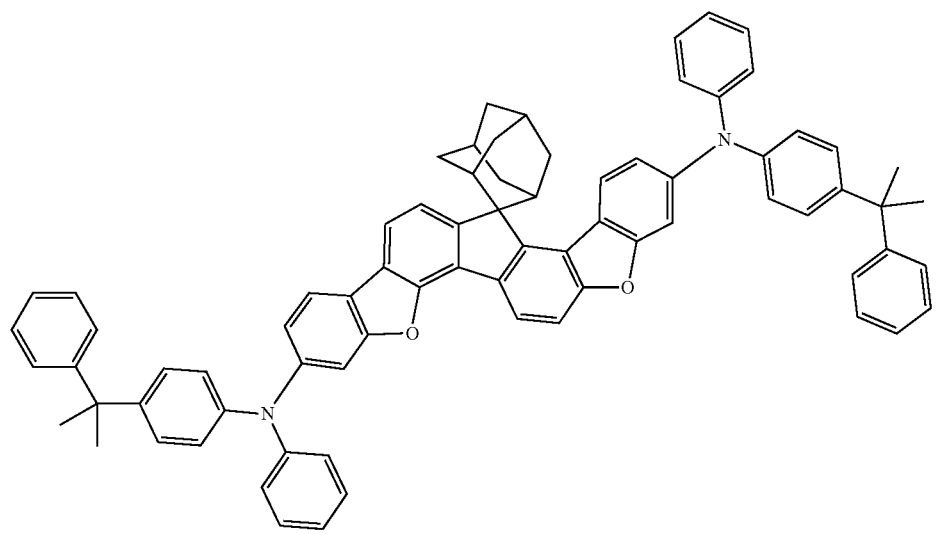

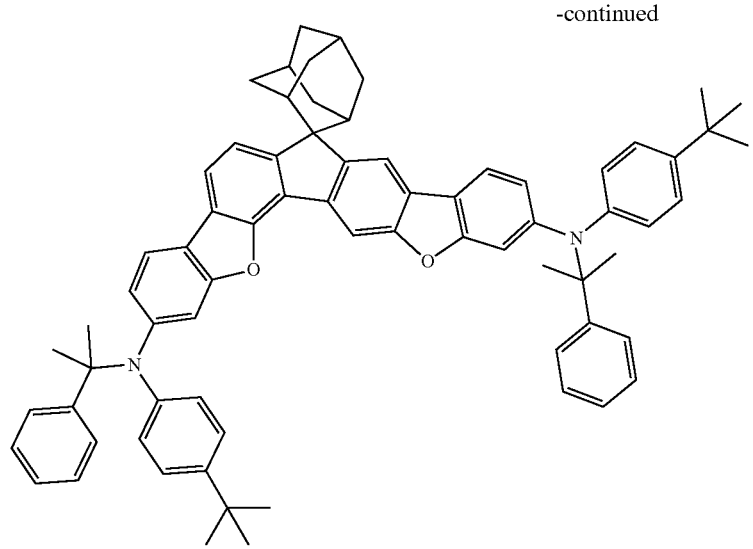
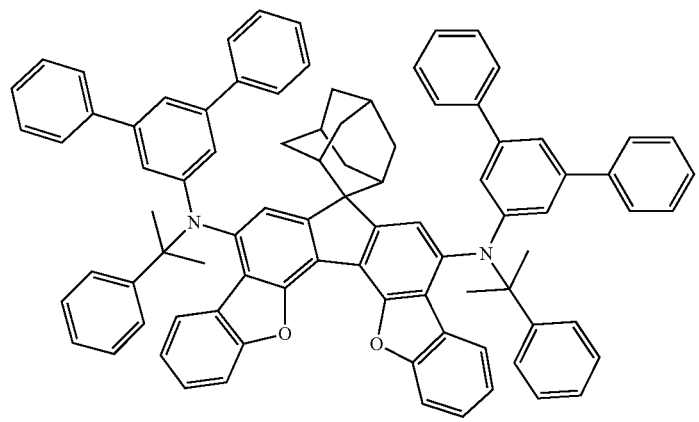
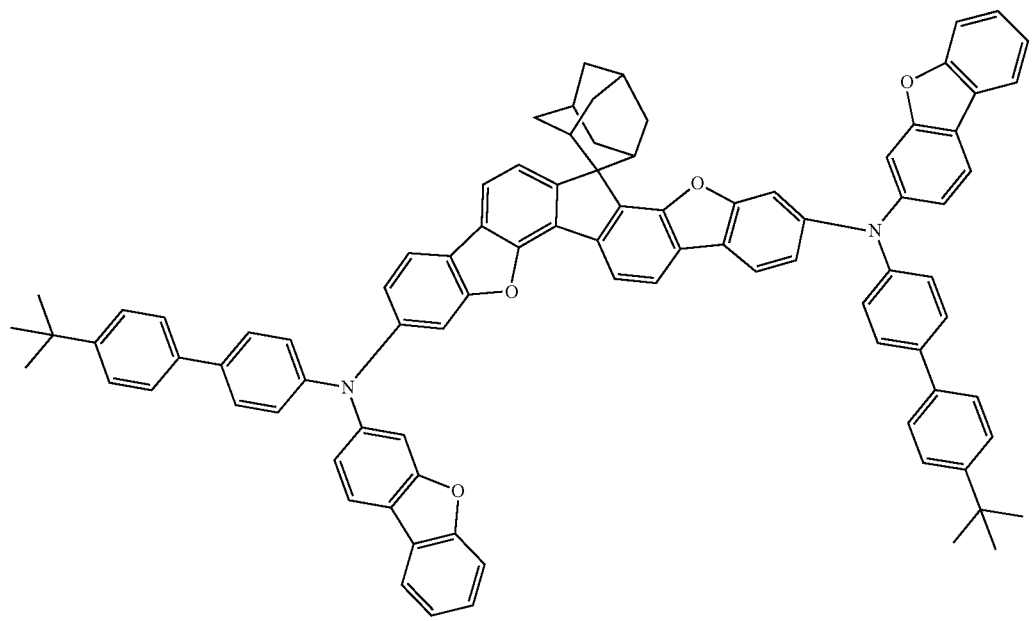

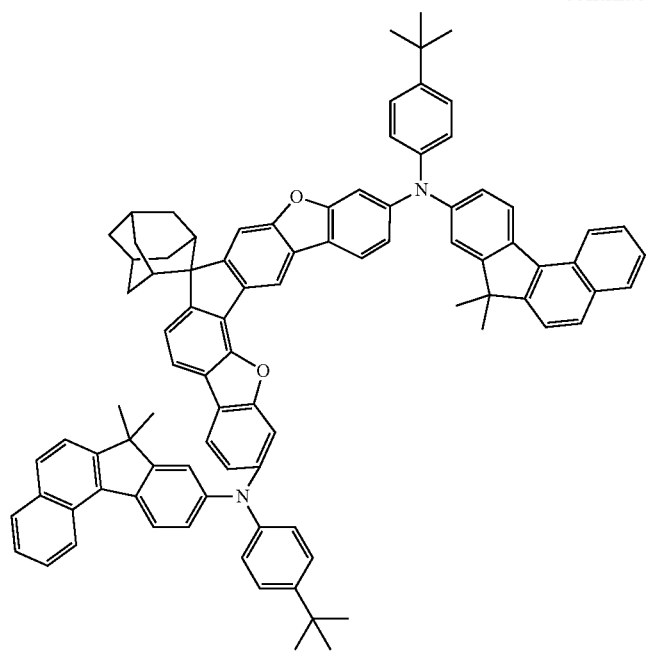
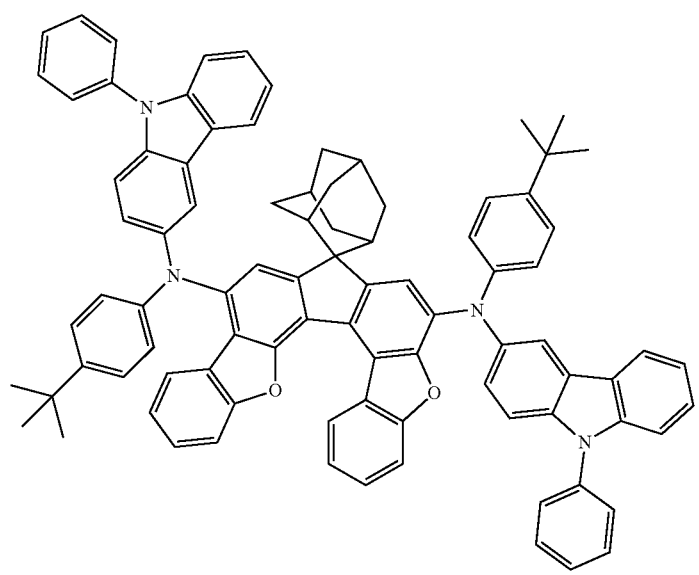

-continued
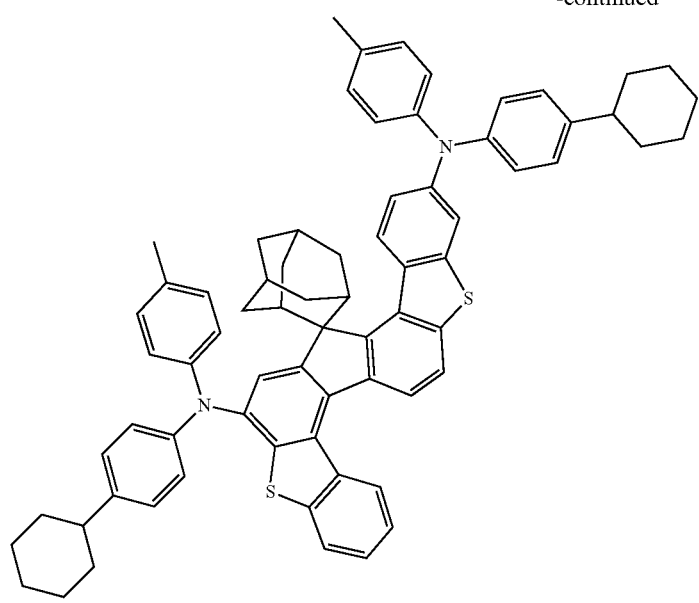
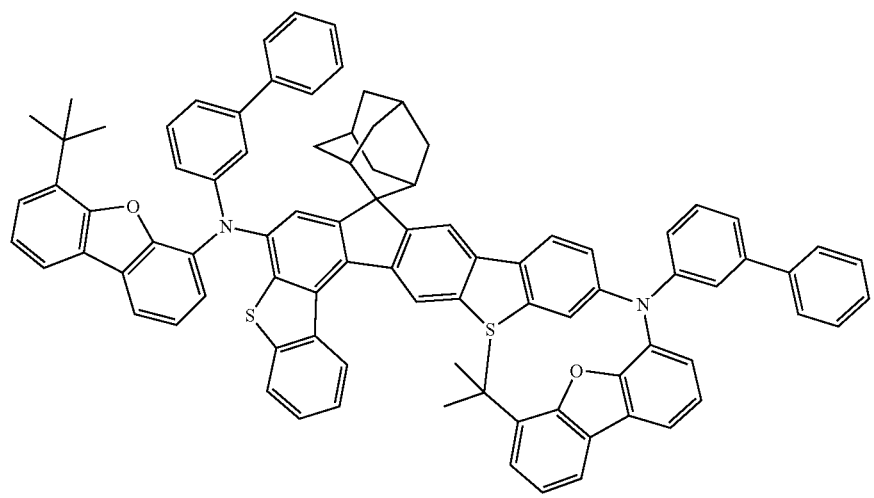
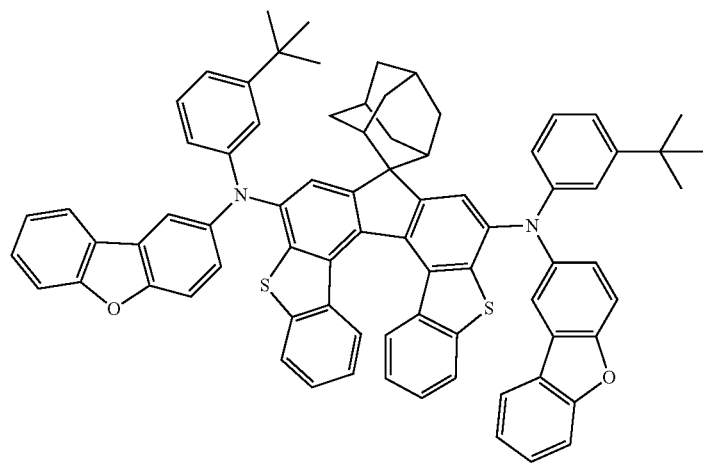

-continued
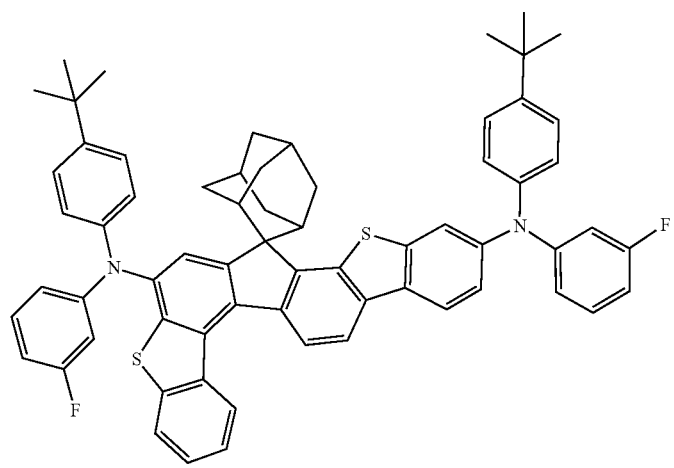
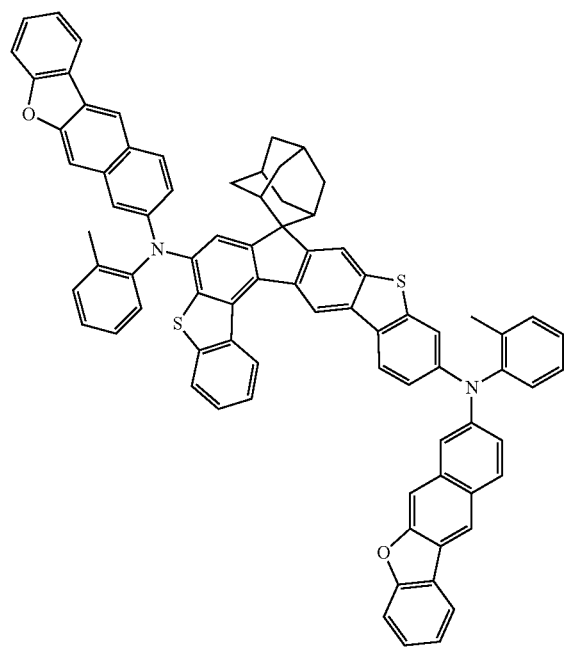
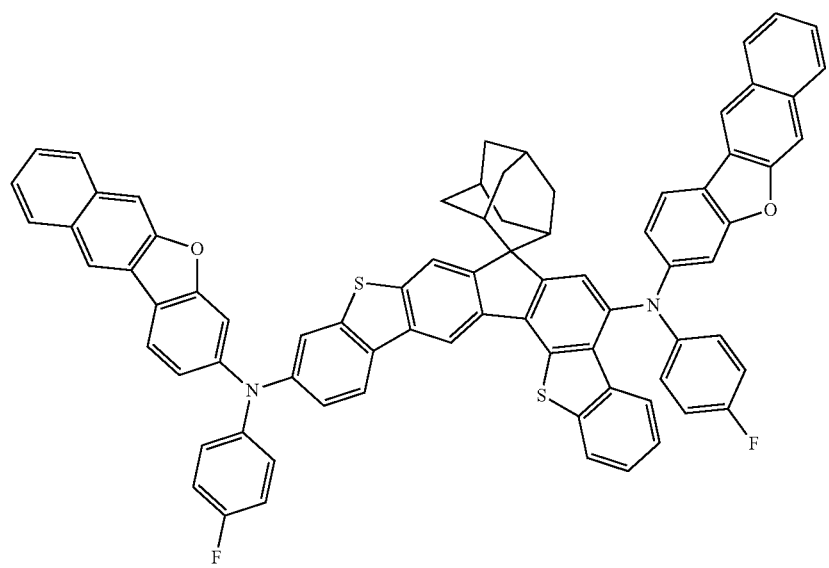

-continued
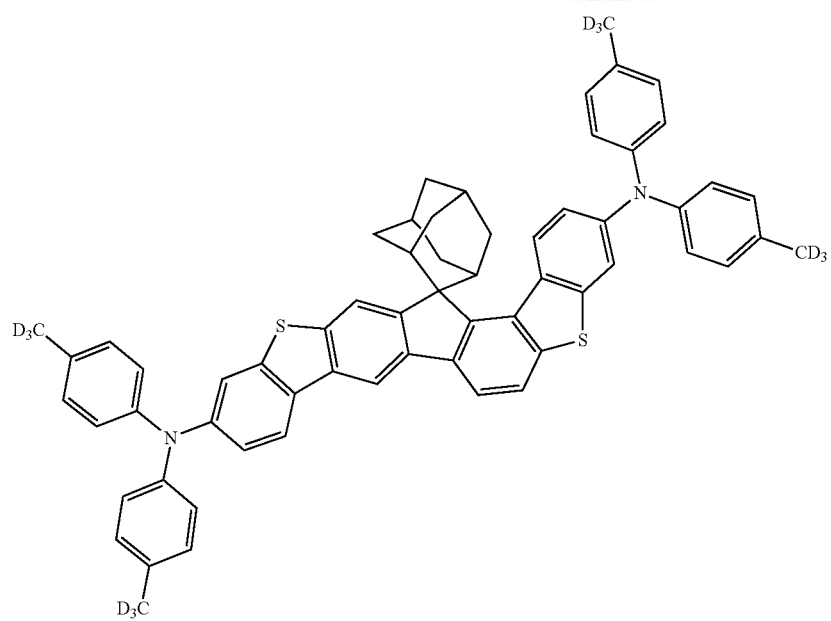
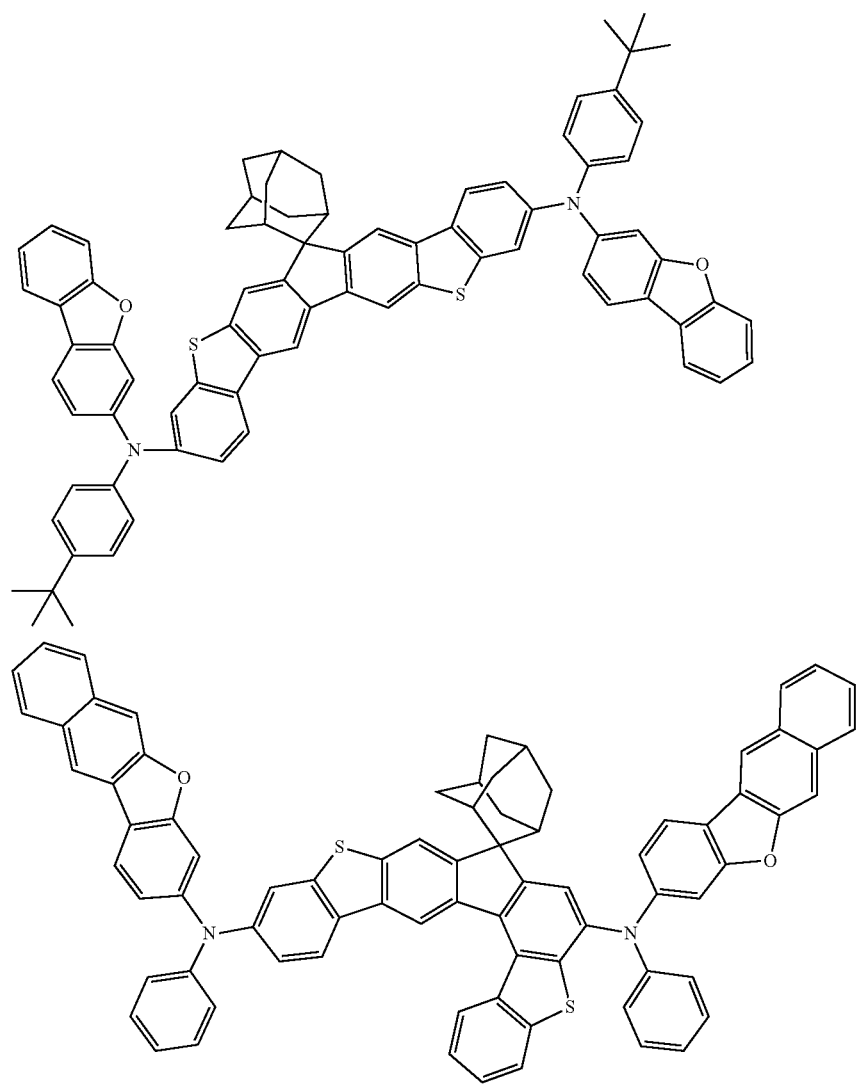

-continued
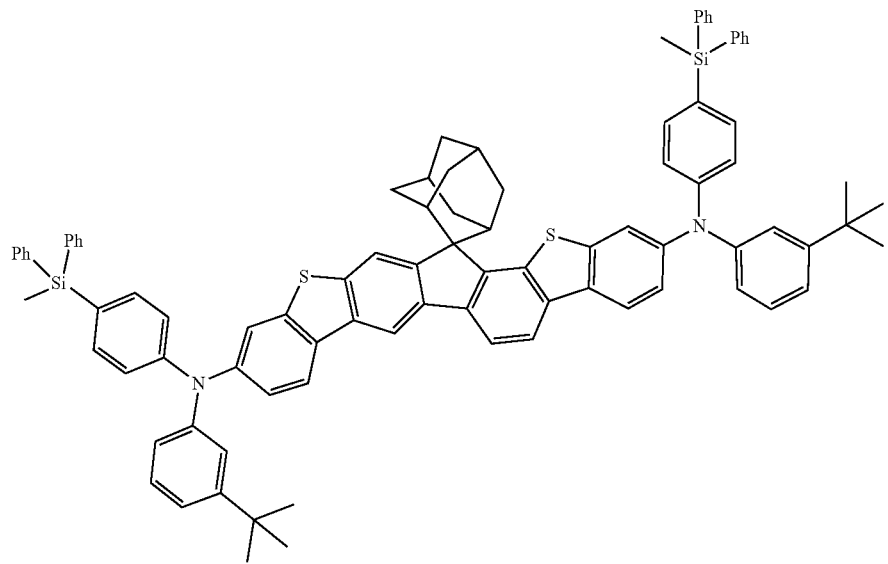
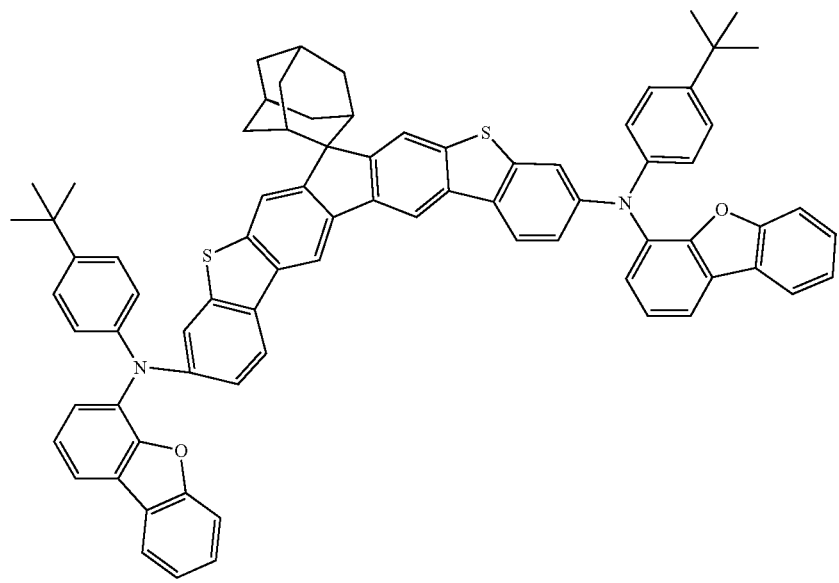
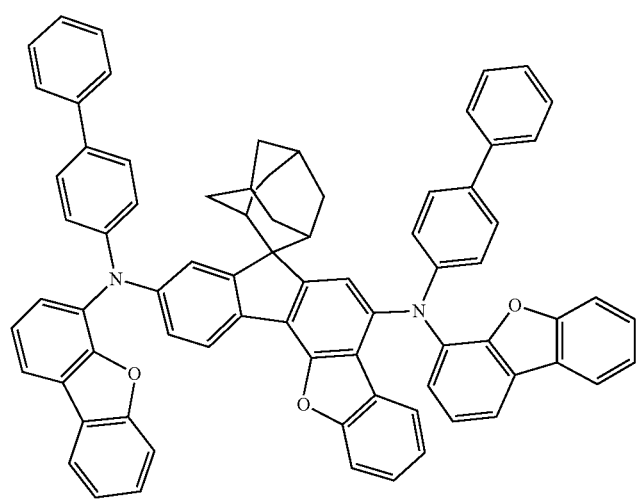

-continued
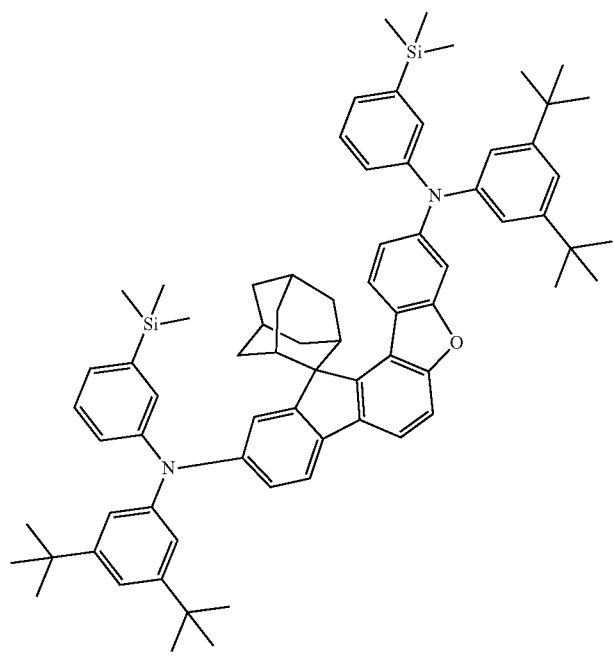
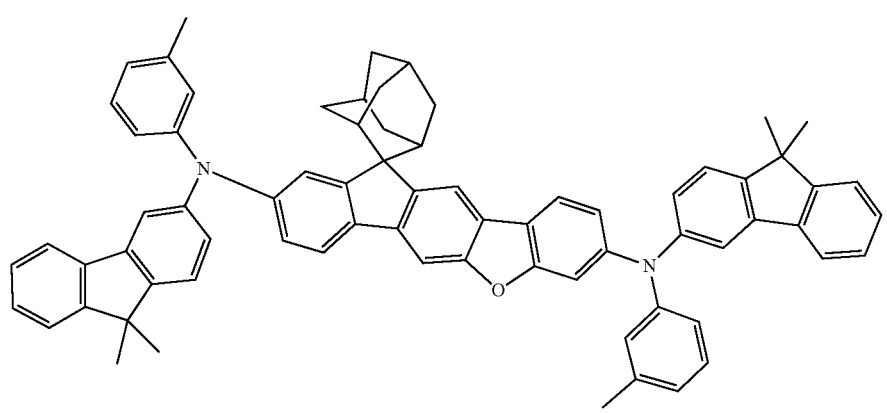
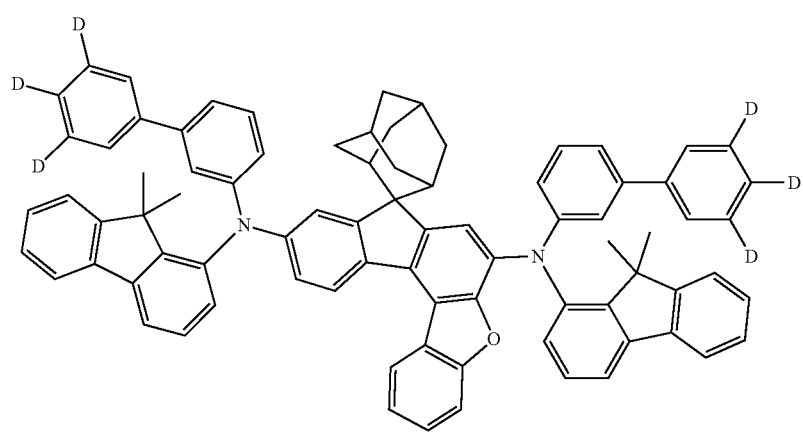

-continued
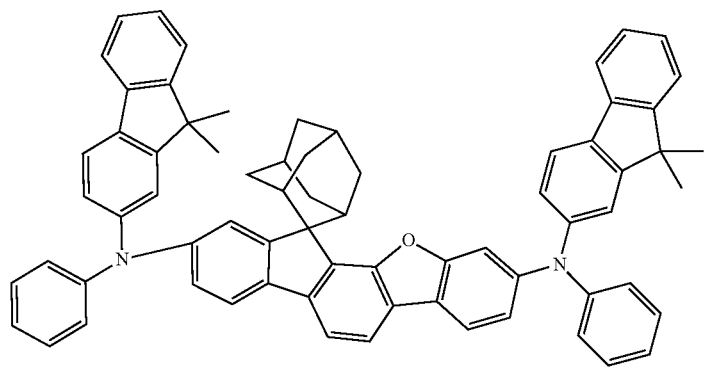

-continued
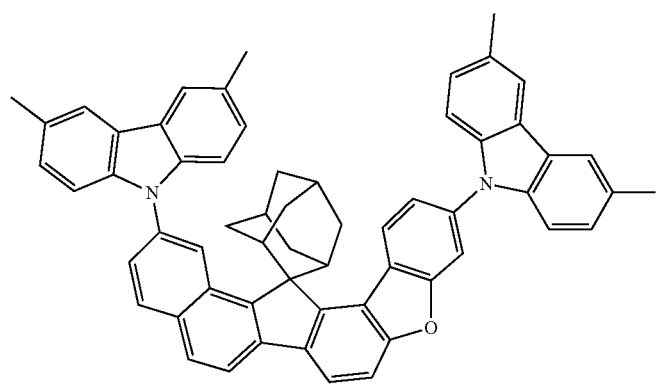
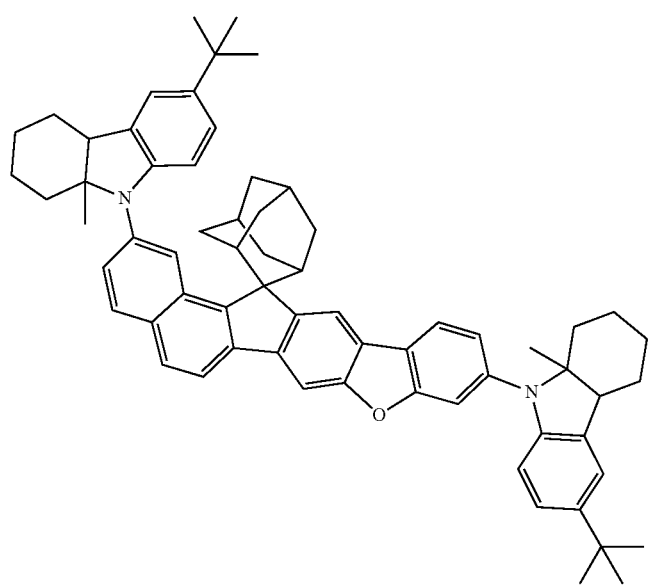
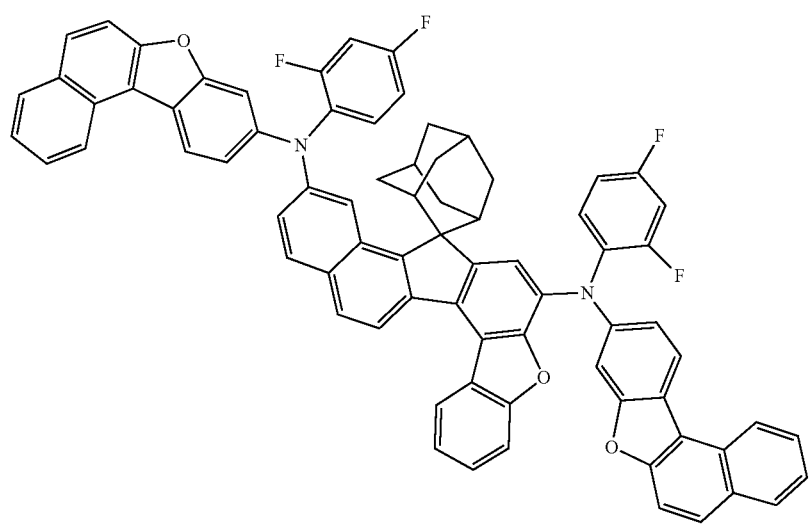

-continued
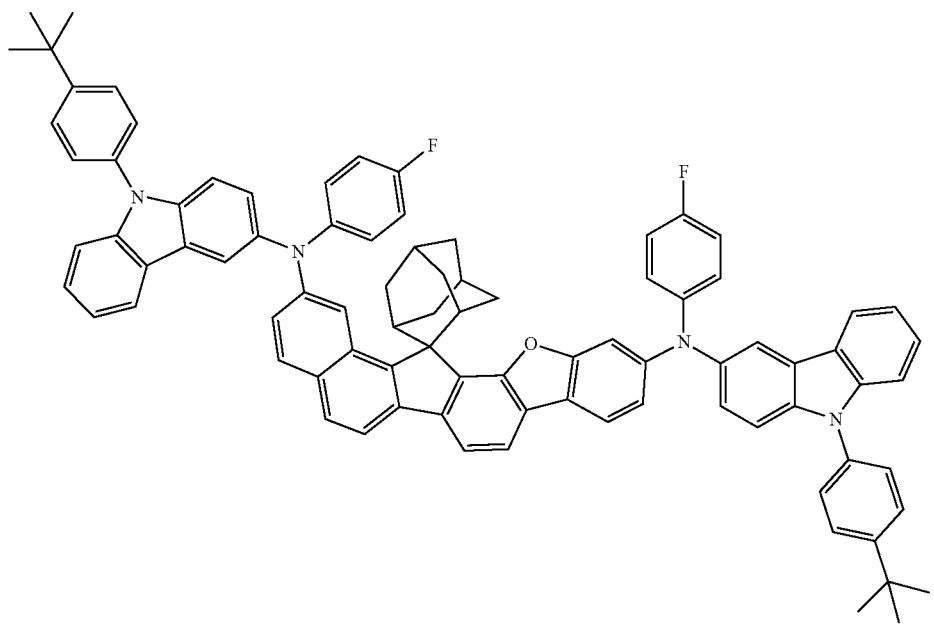
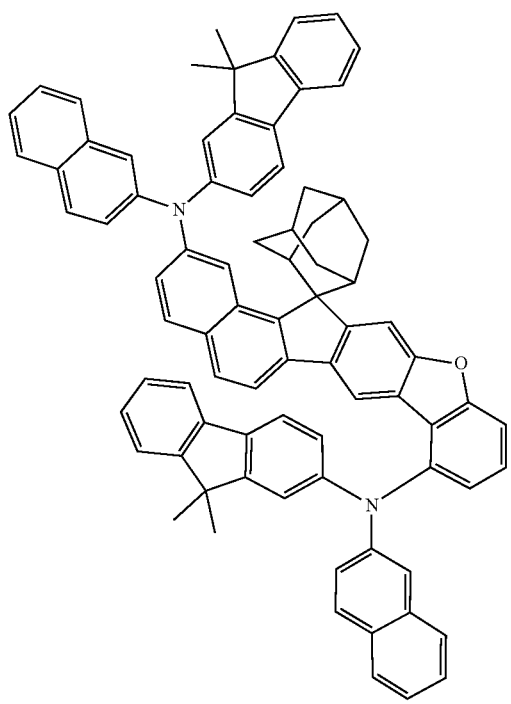

-continued
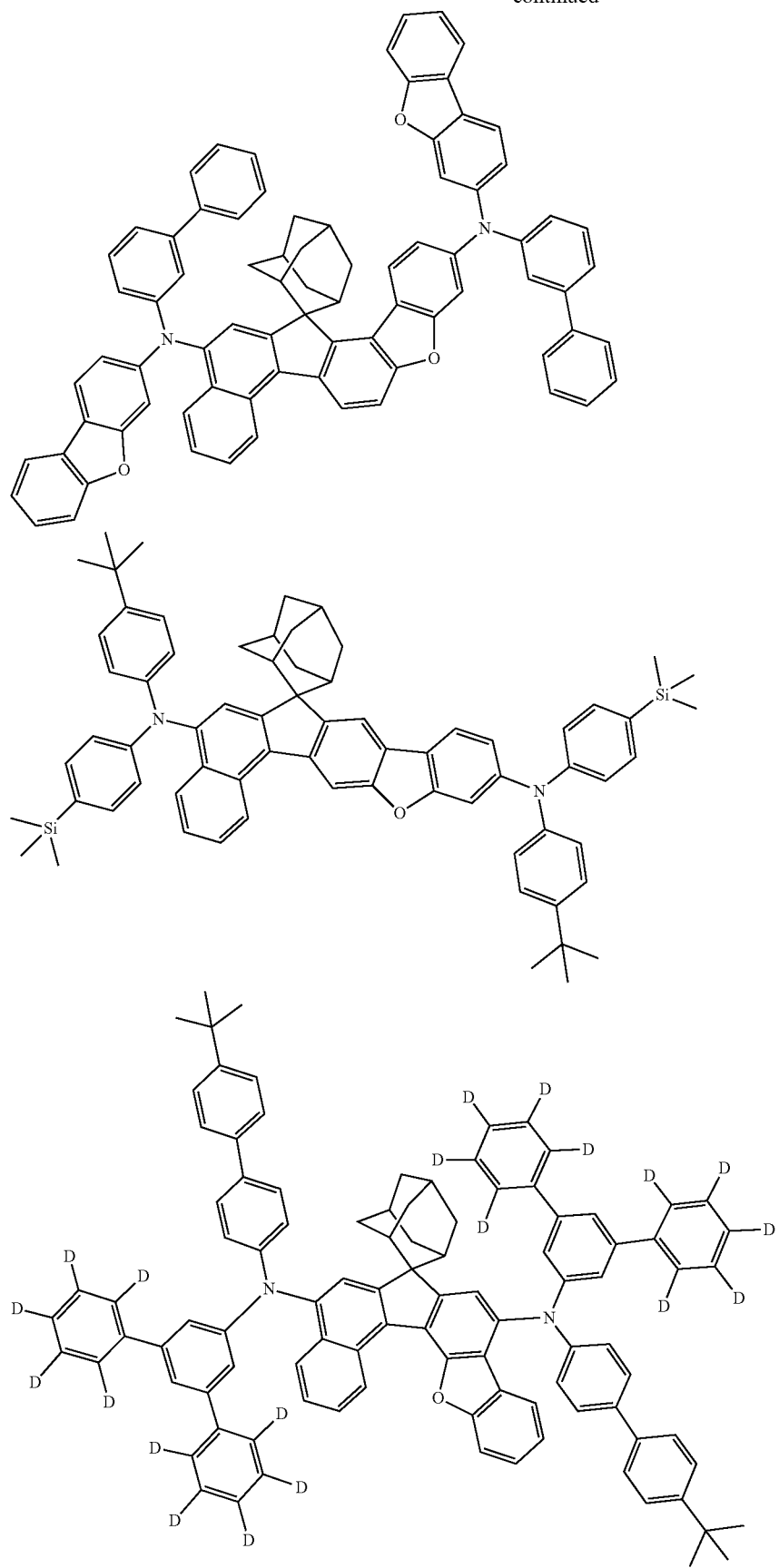

-continued
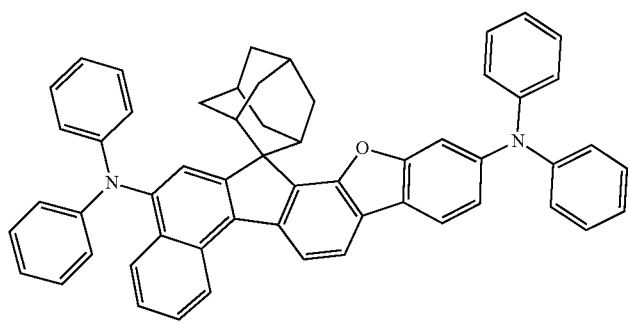
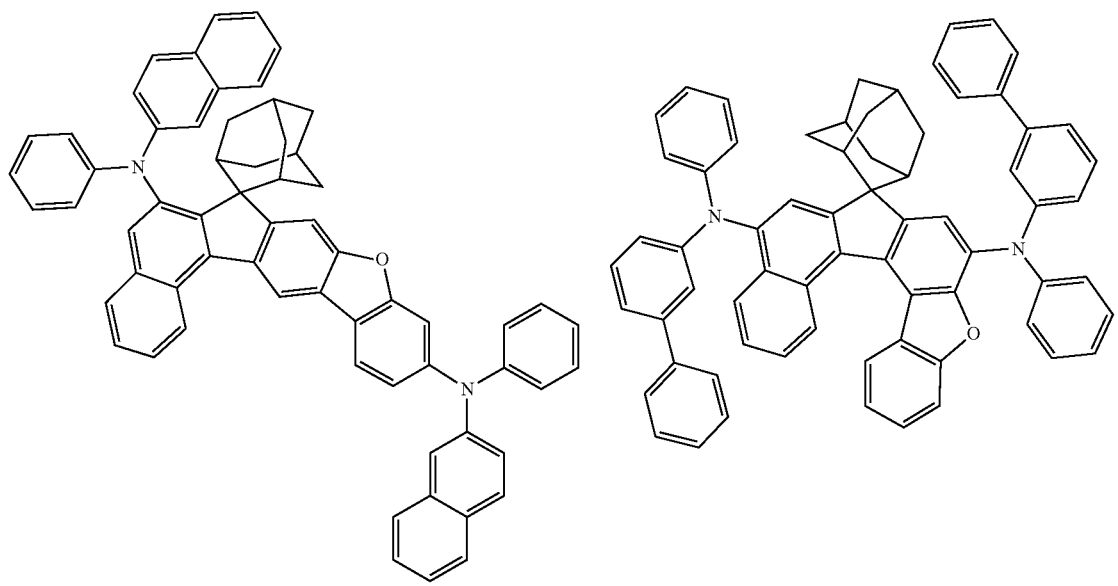
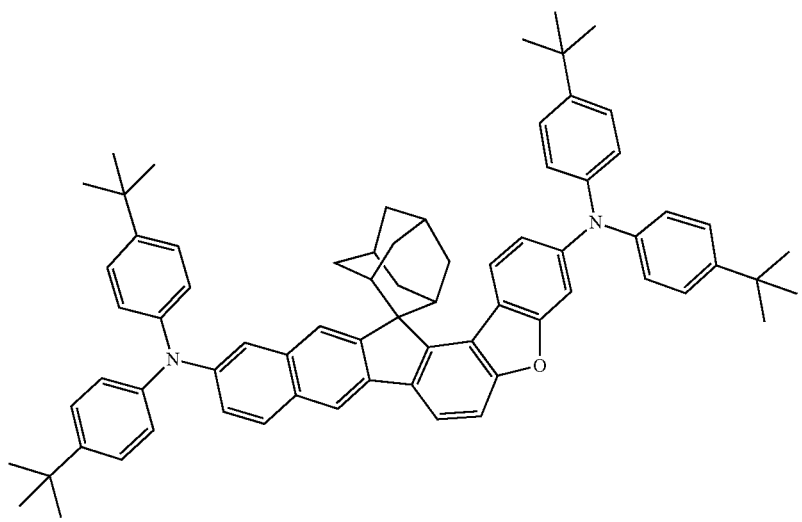

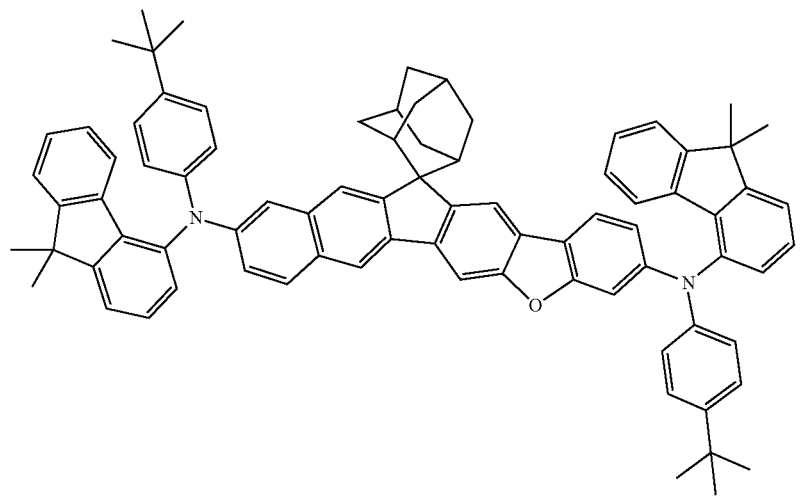
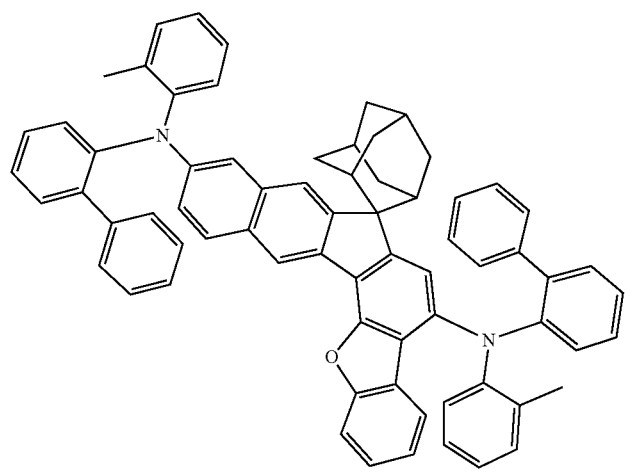
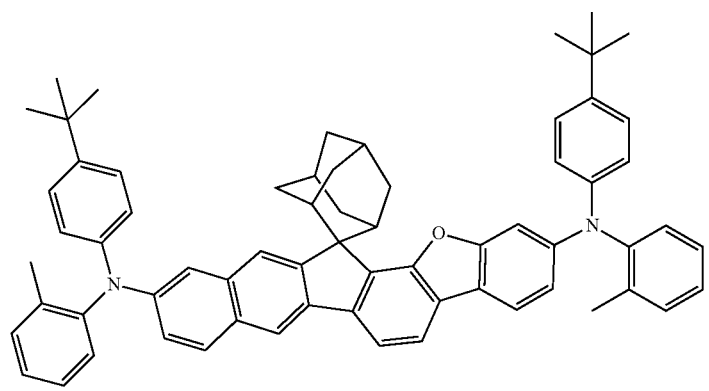

-continued
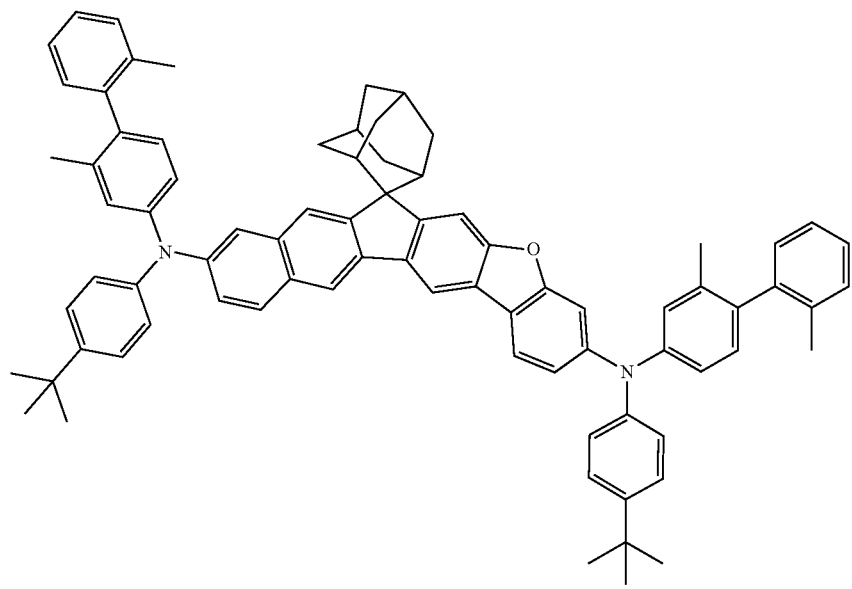
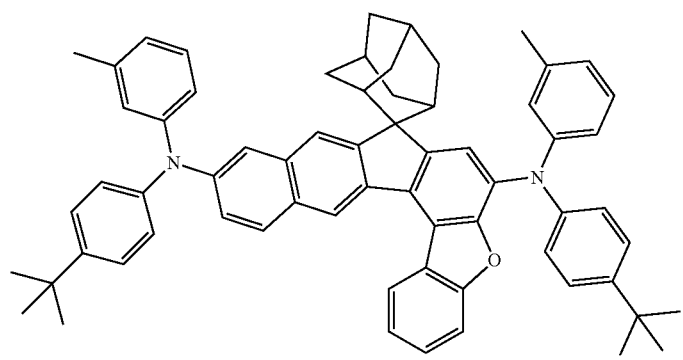
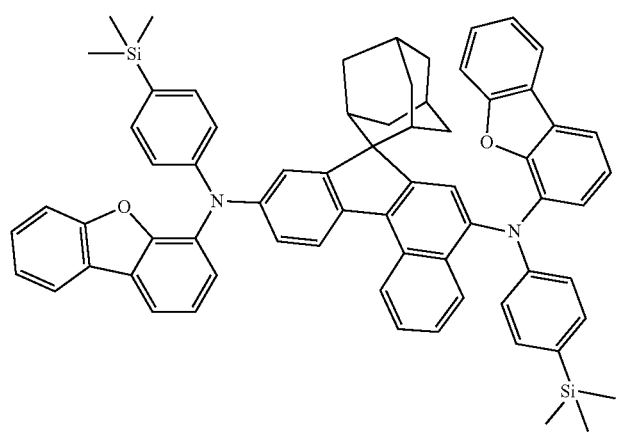

-continued
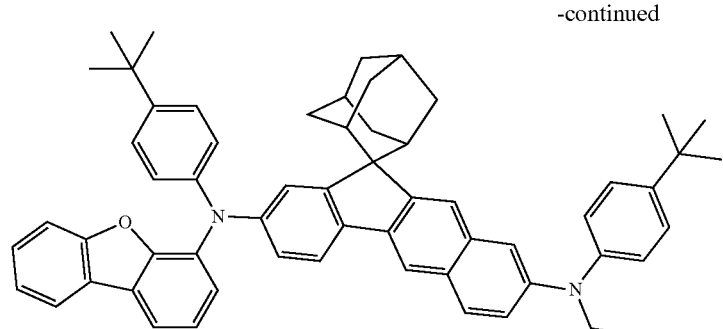
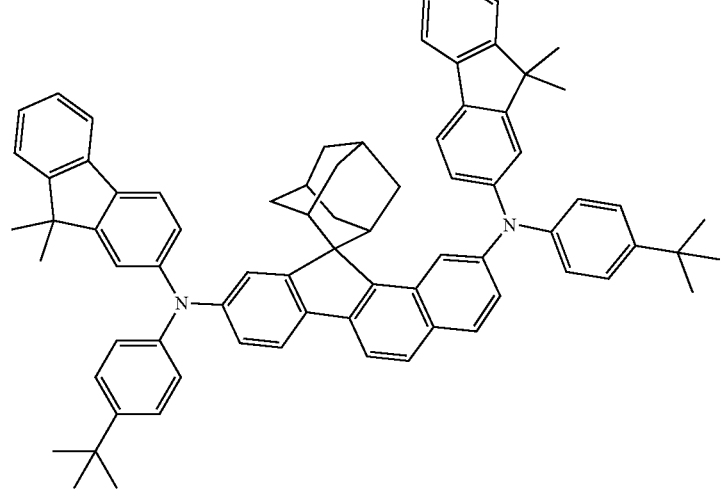
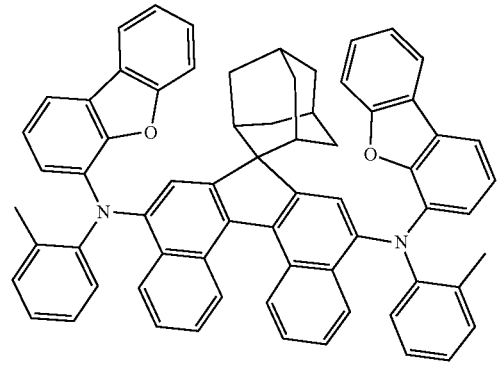
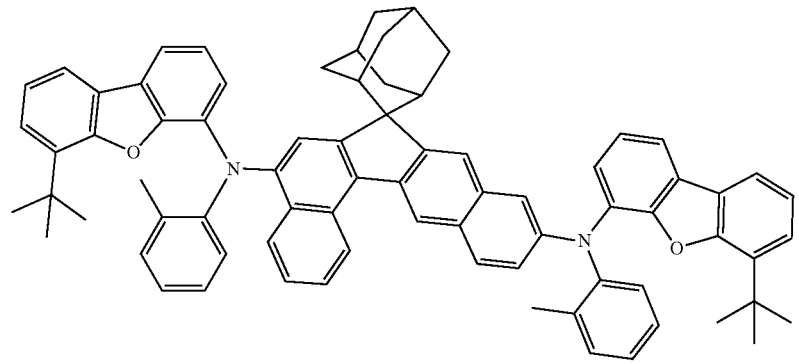

-continued
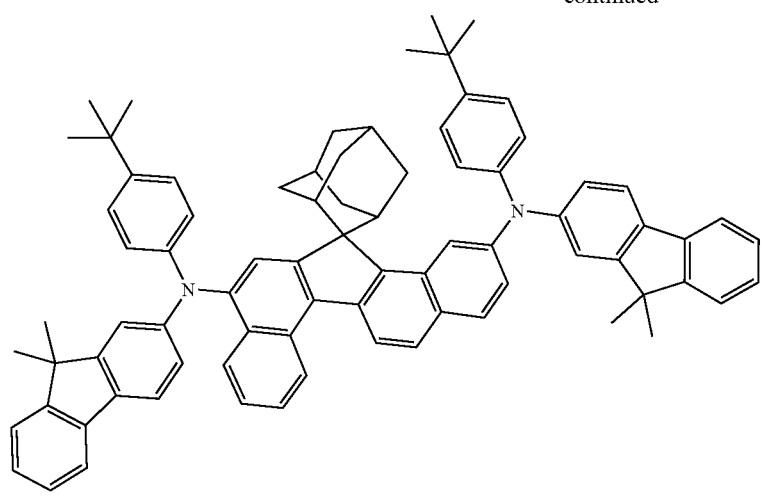
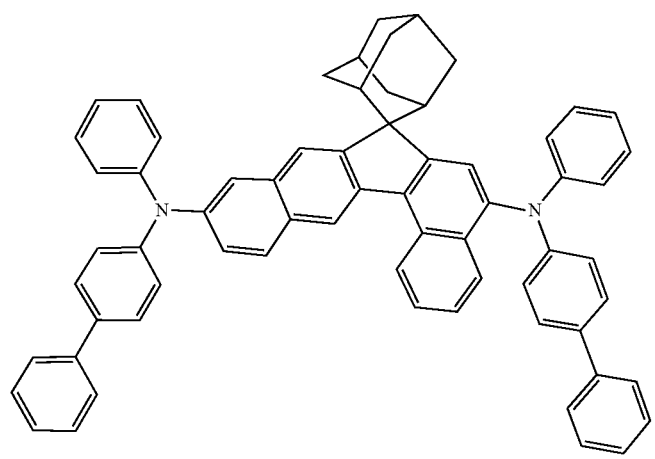
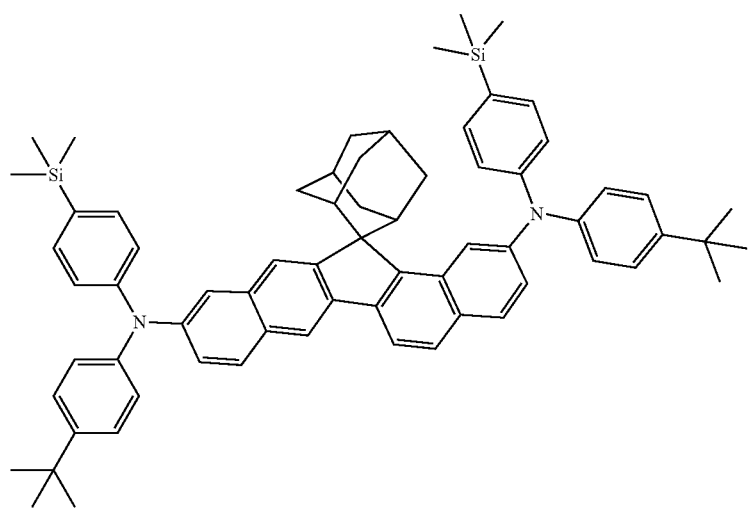

-continued
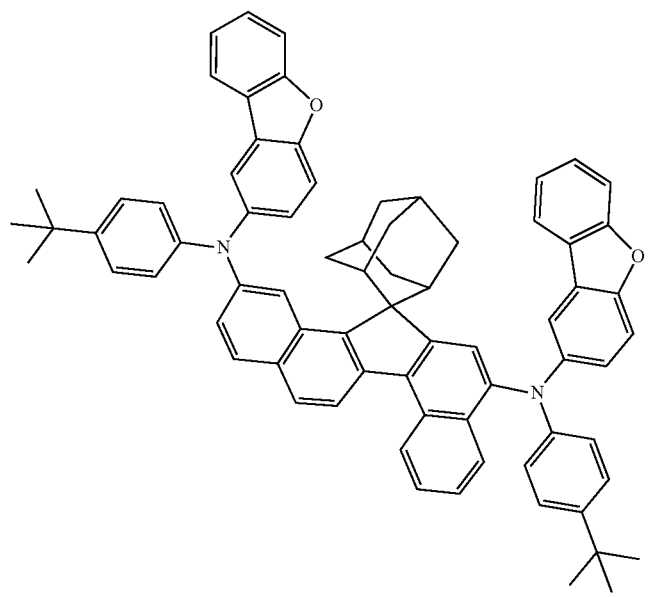
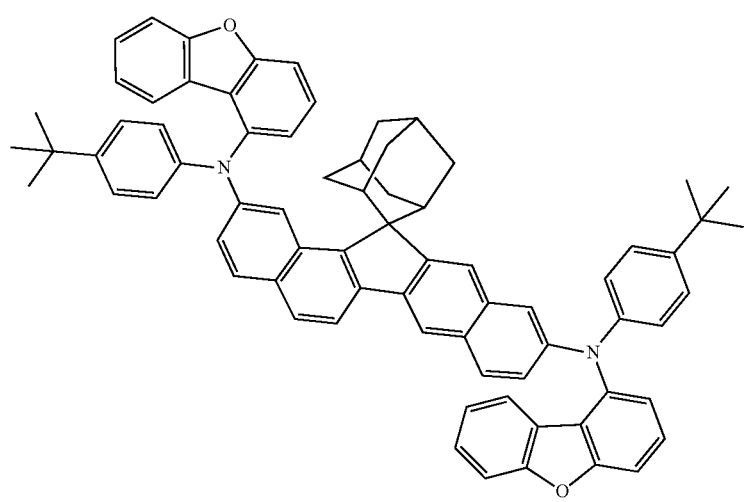
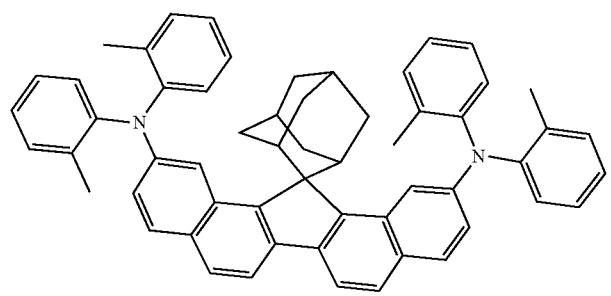

-continued
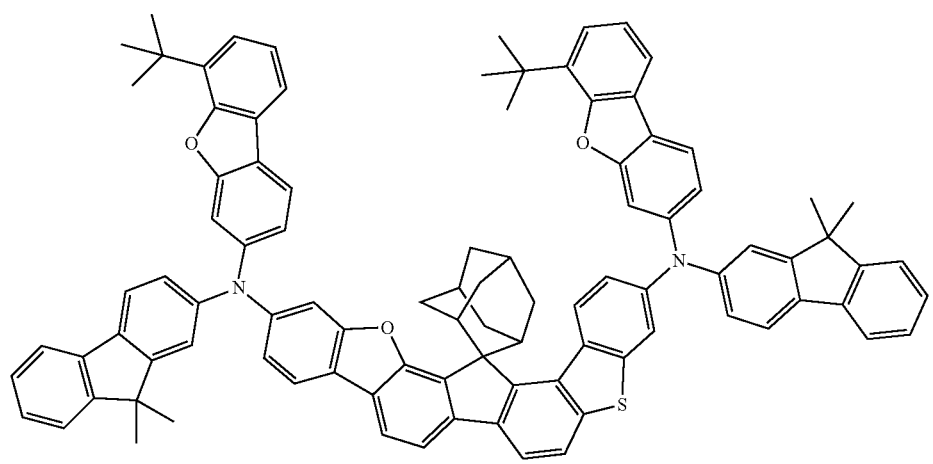
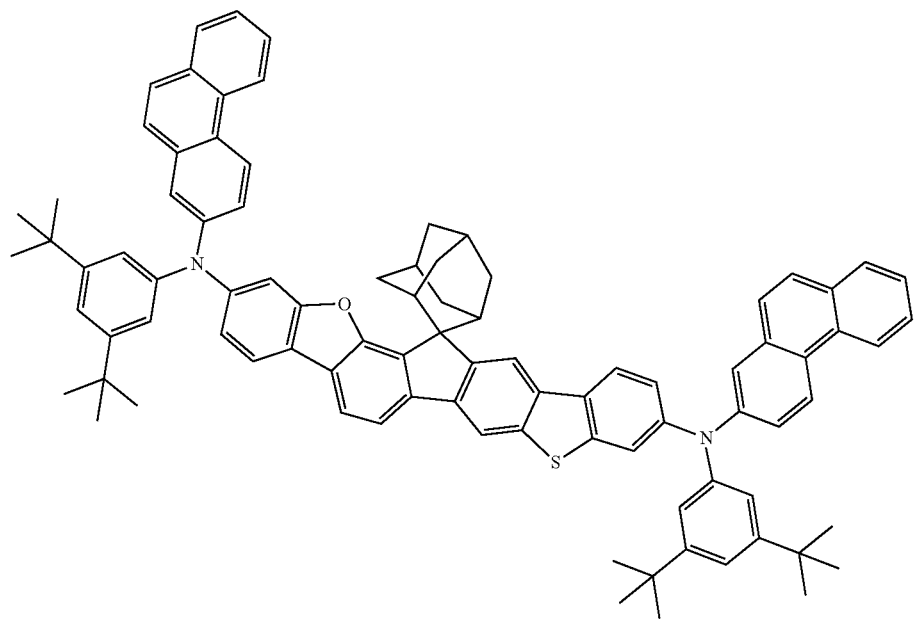
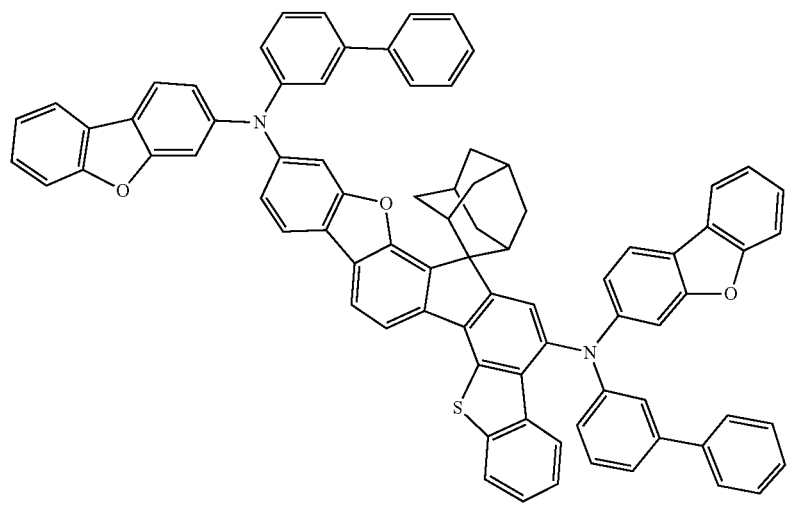

-continued
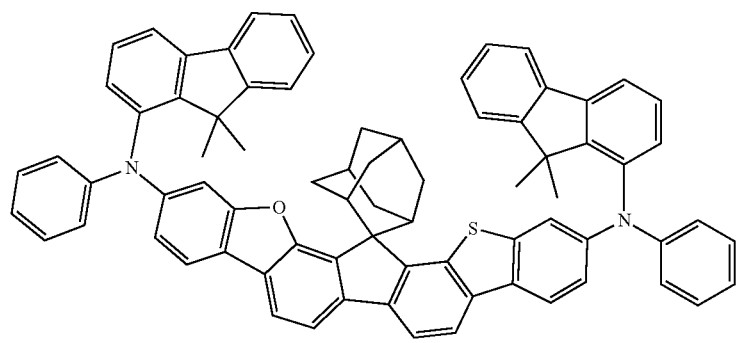
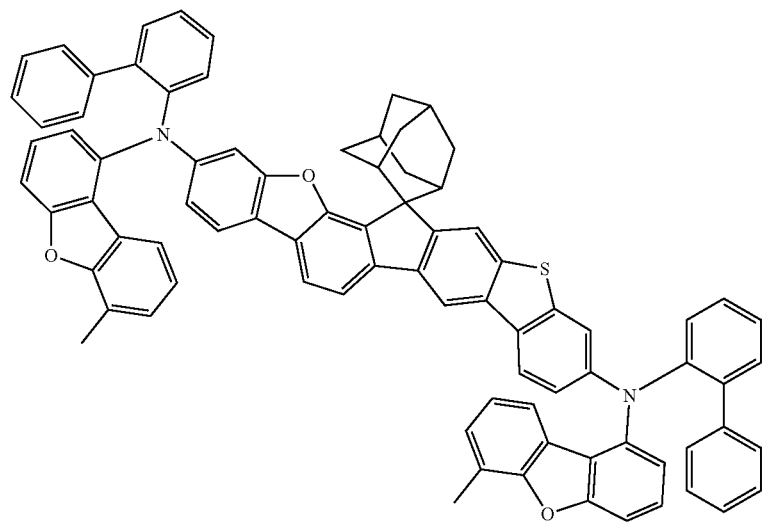
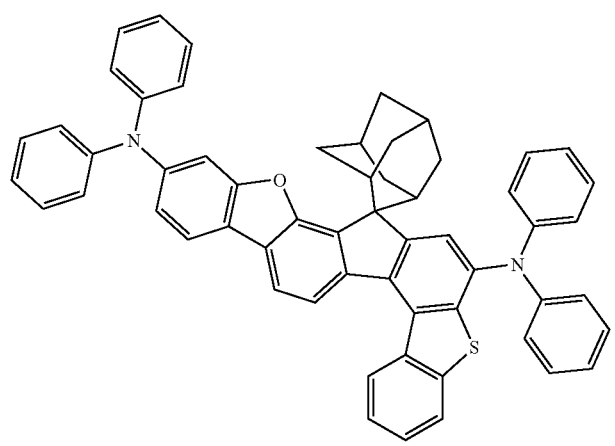

-continued
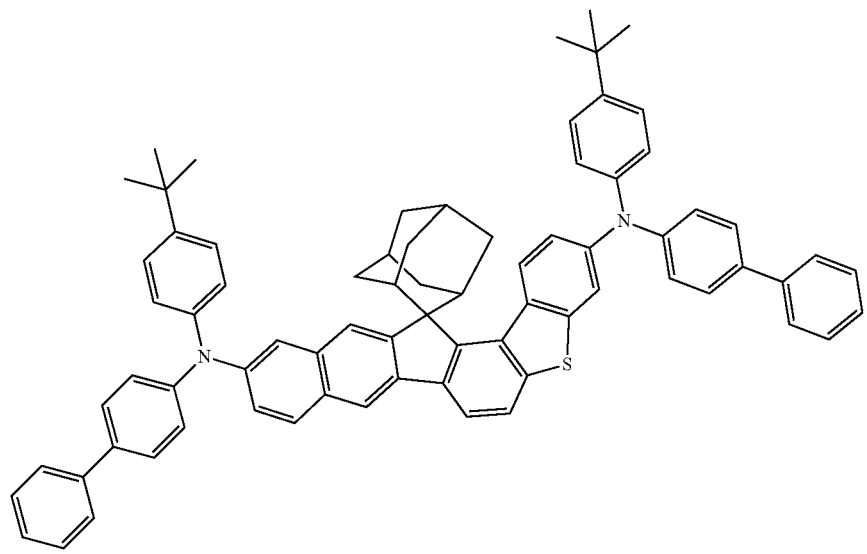
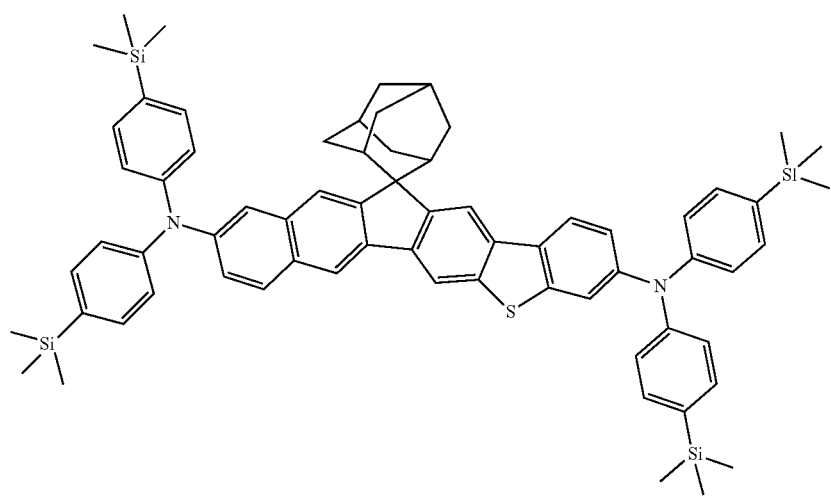
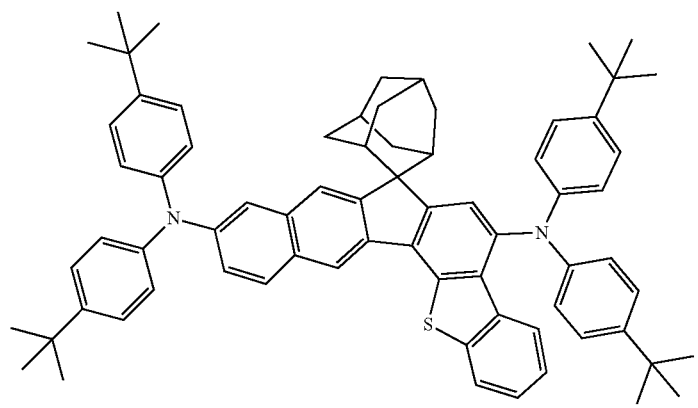

-continued
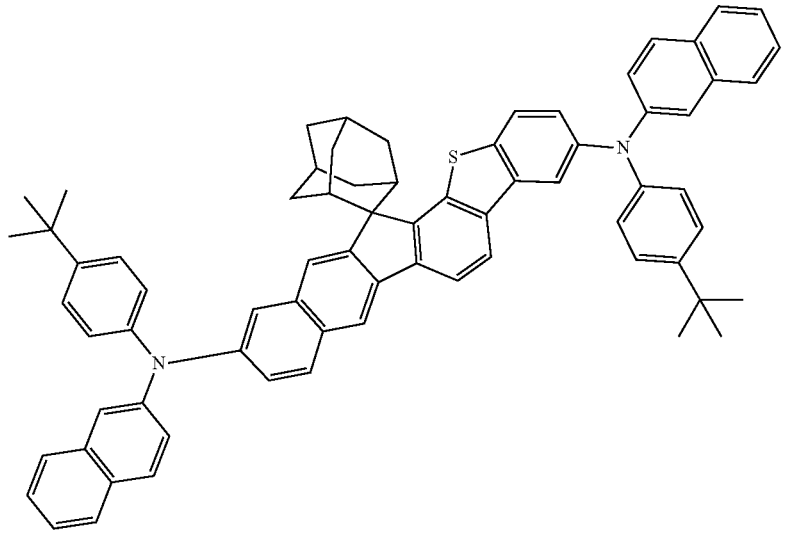
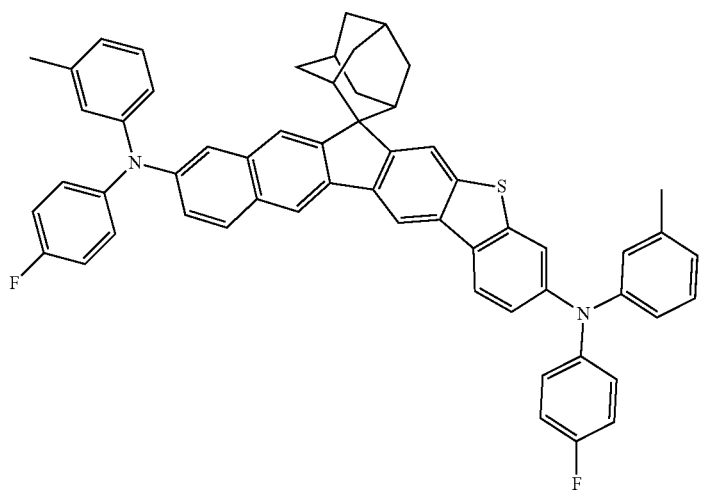
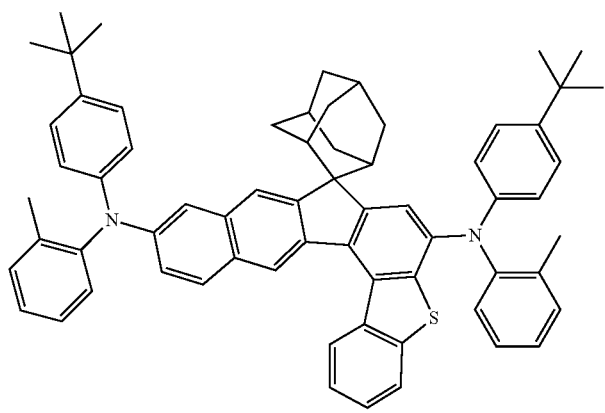

-continued
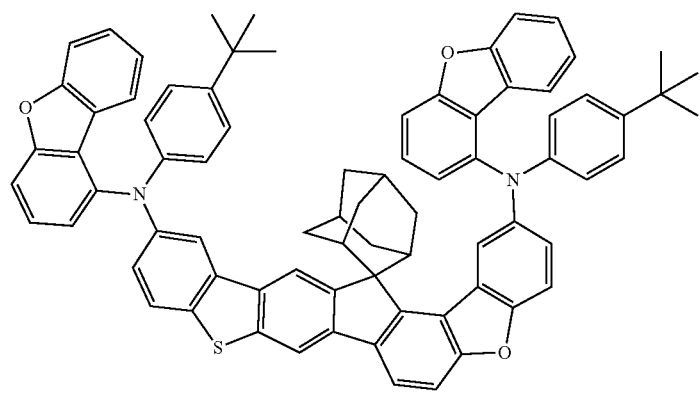
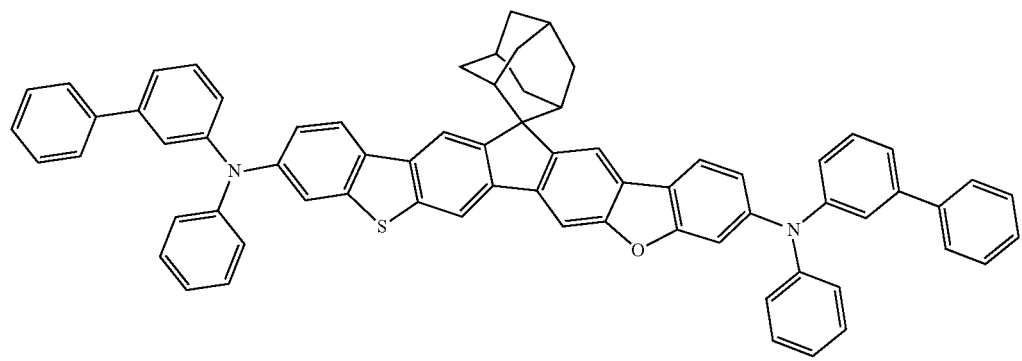
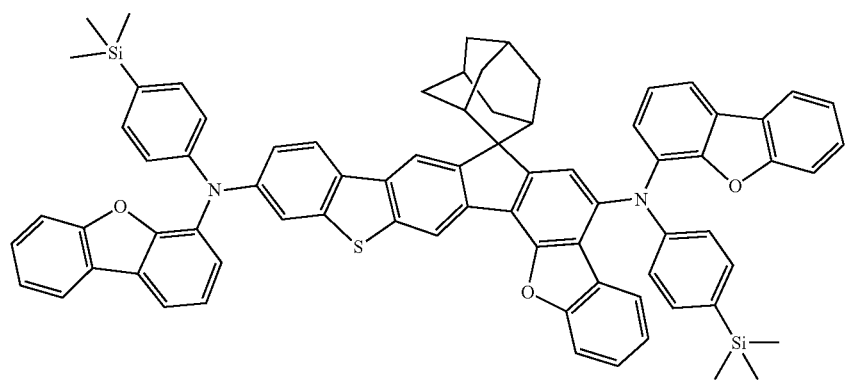
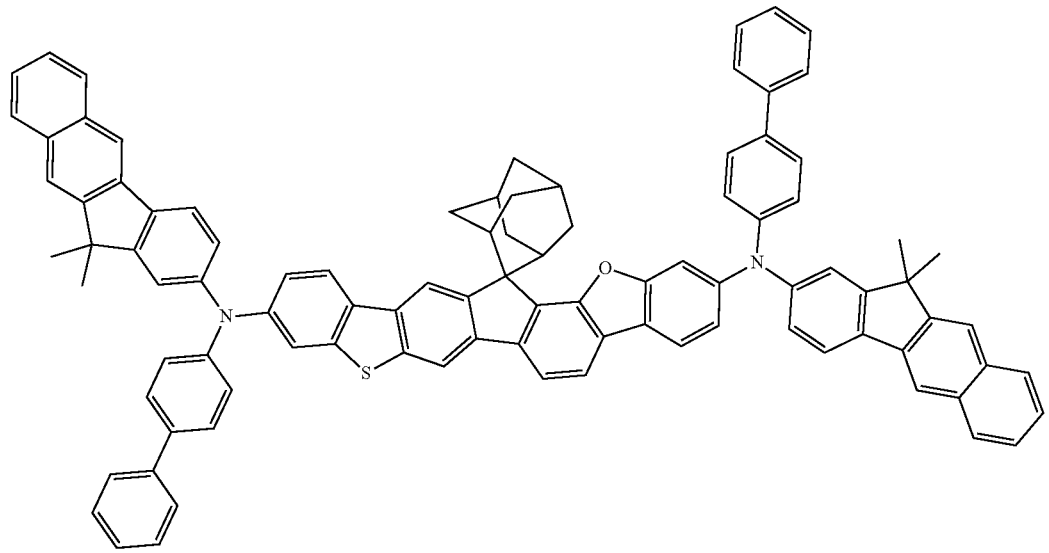

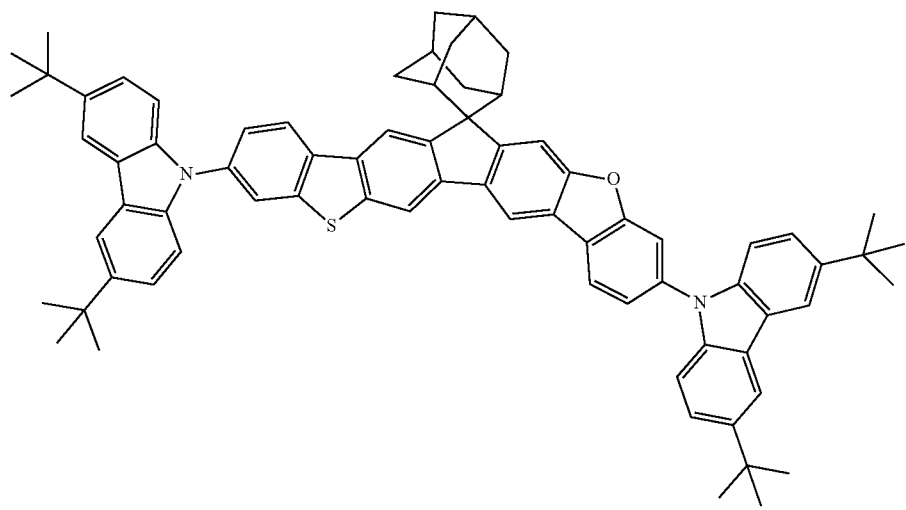
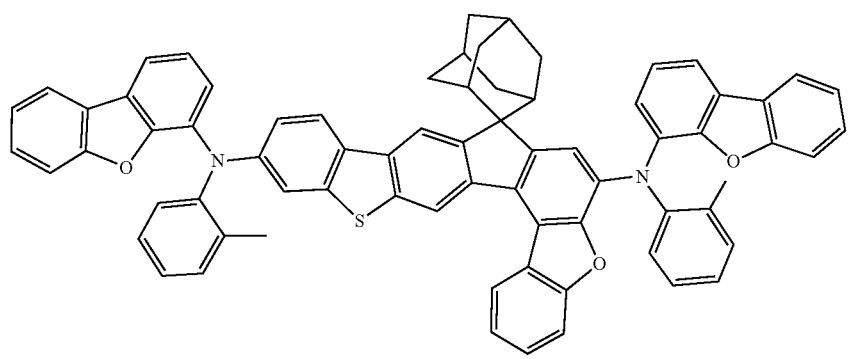
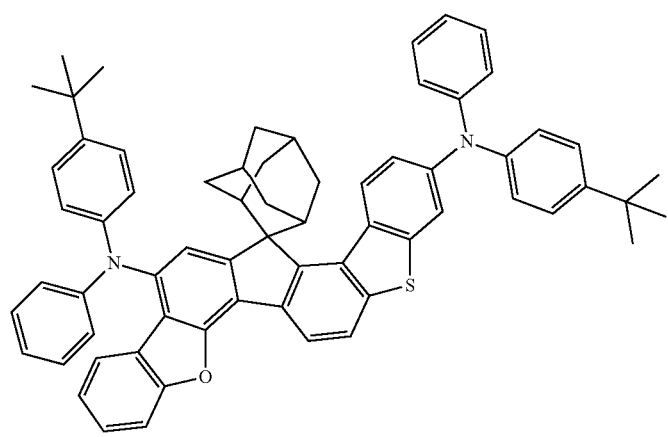

-continued
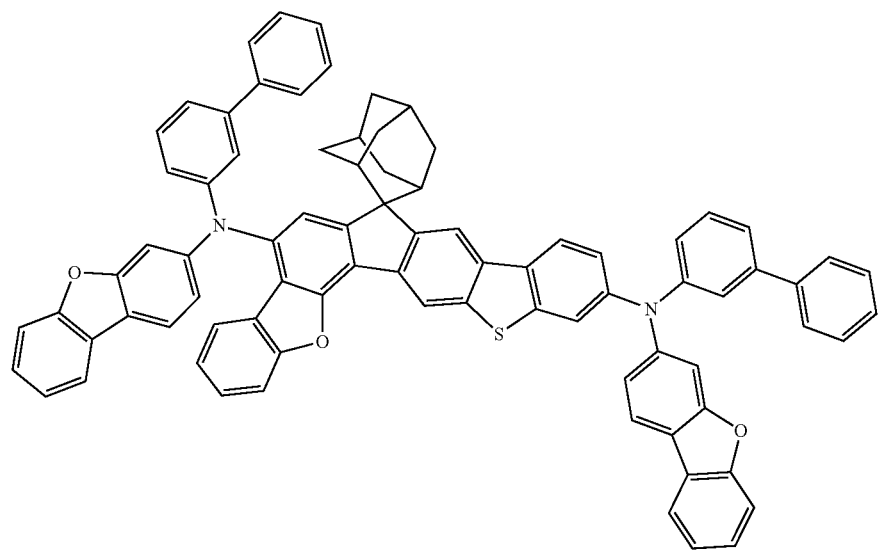
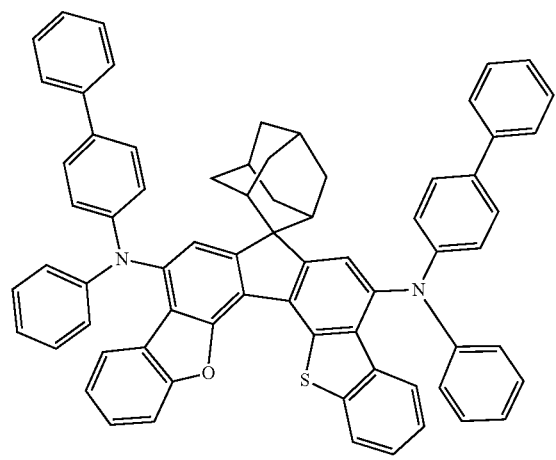
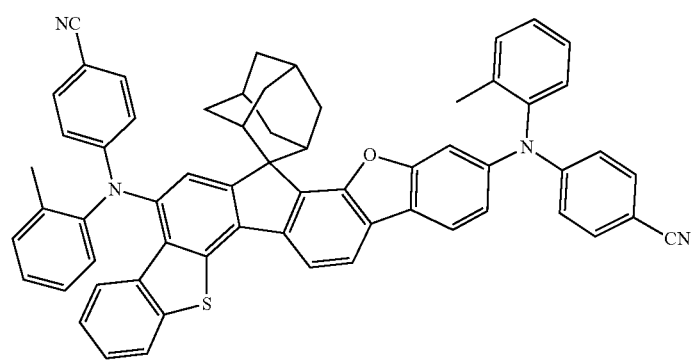

-continued
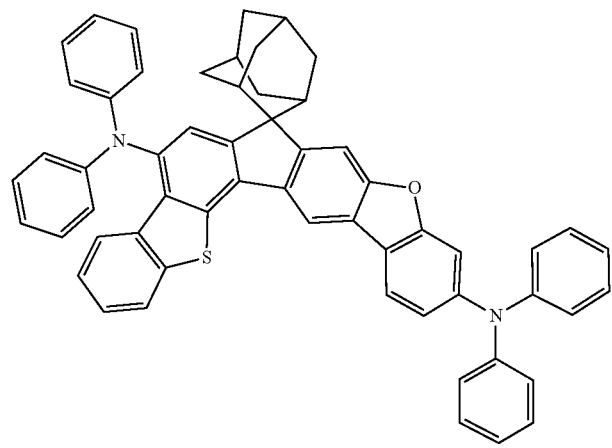
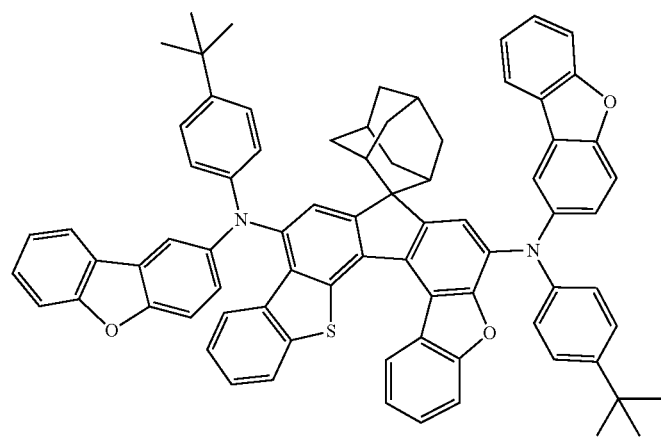
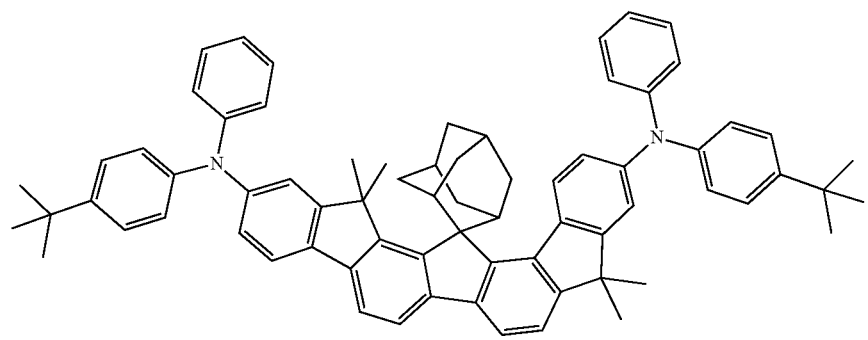

-continued
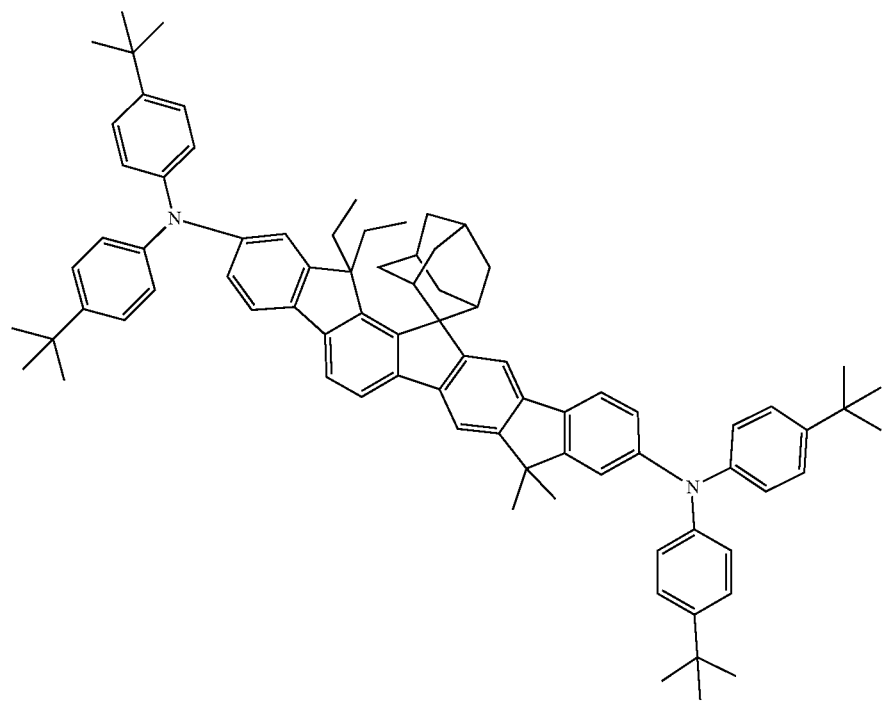
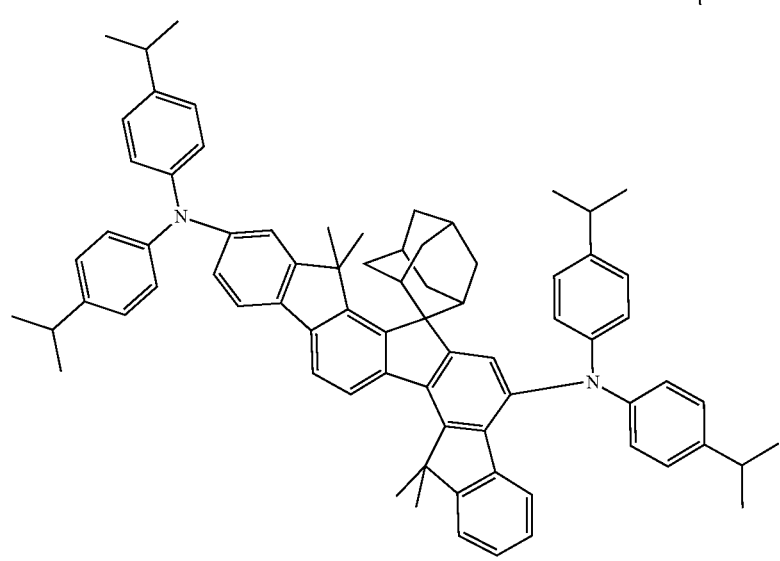
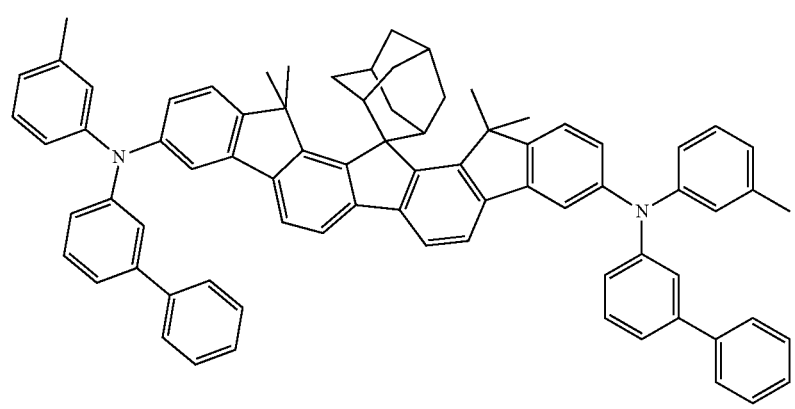

-continued
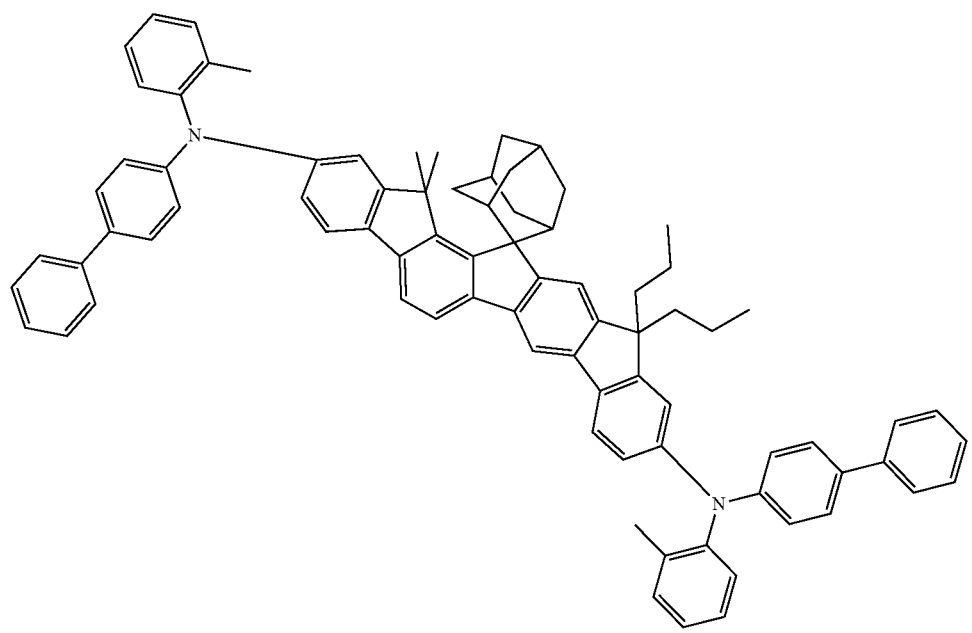
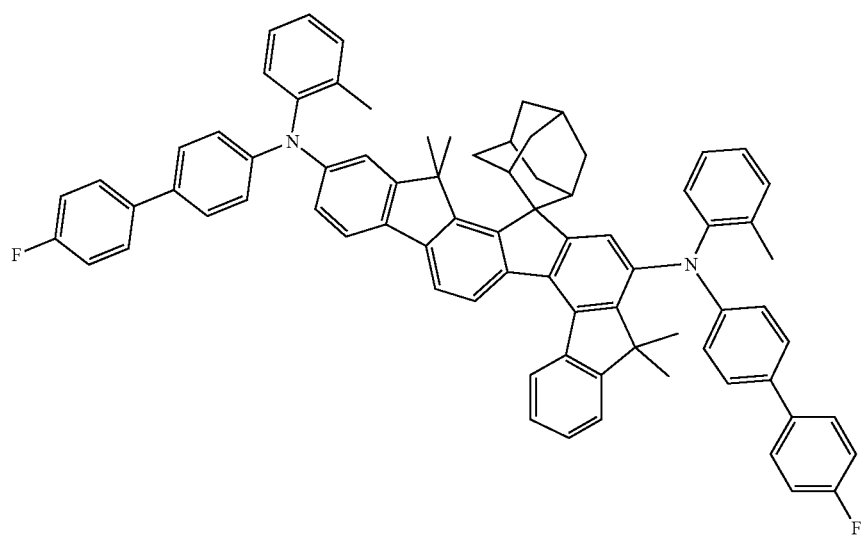
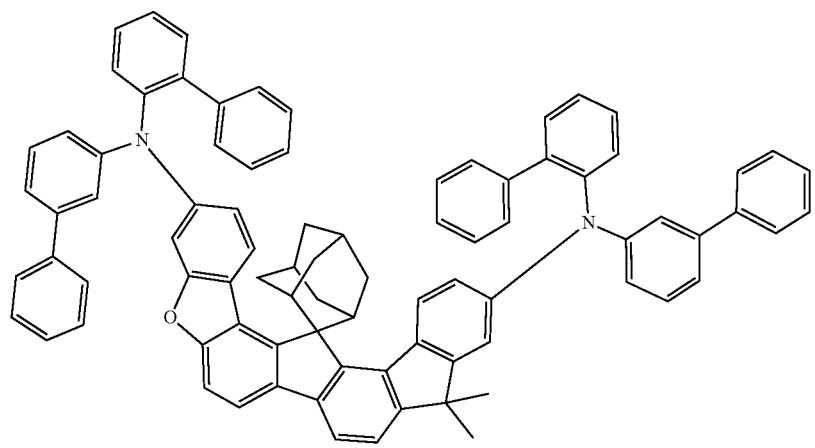

-continued
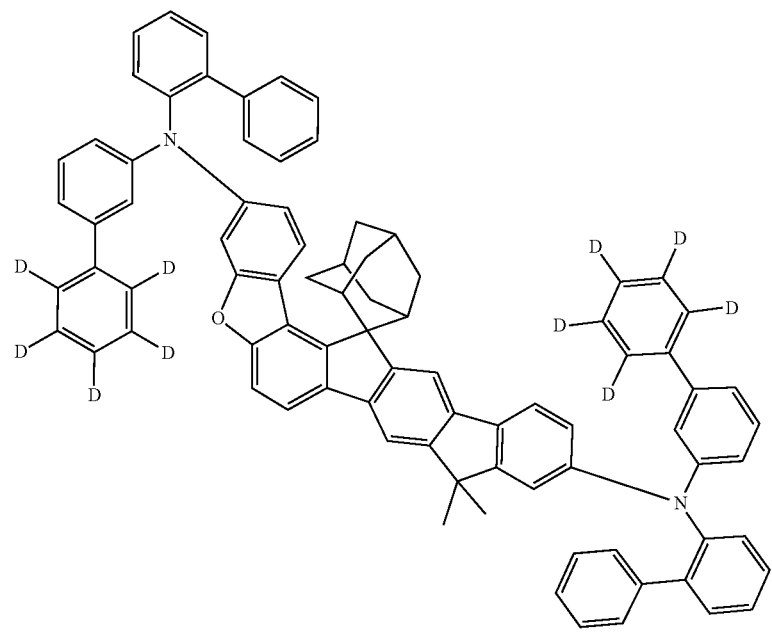
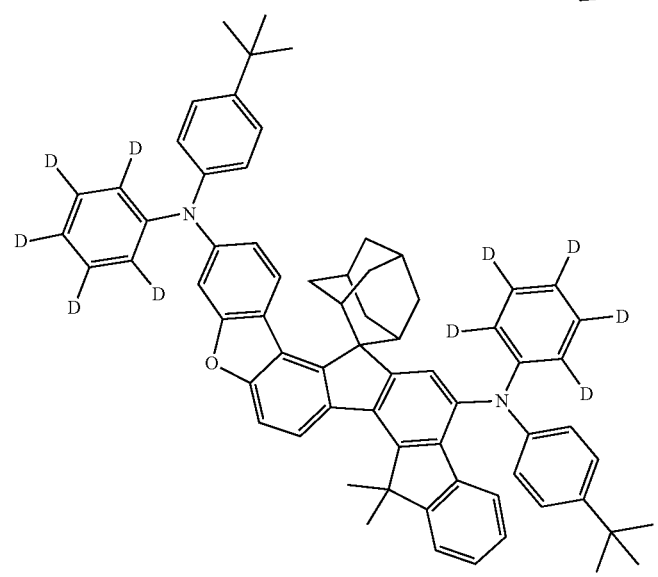
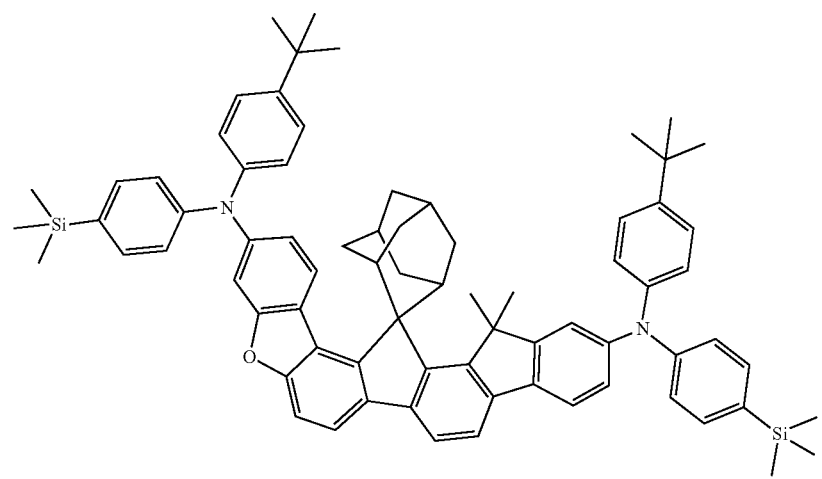

-continued
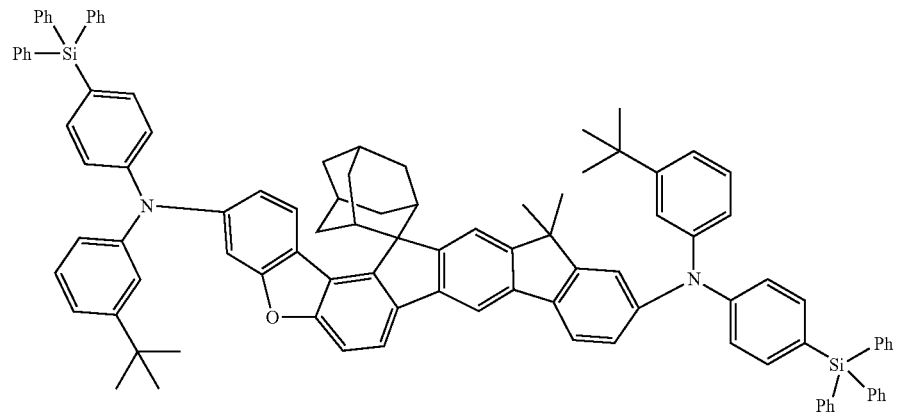
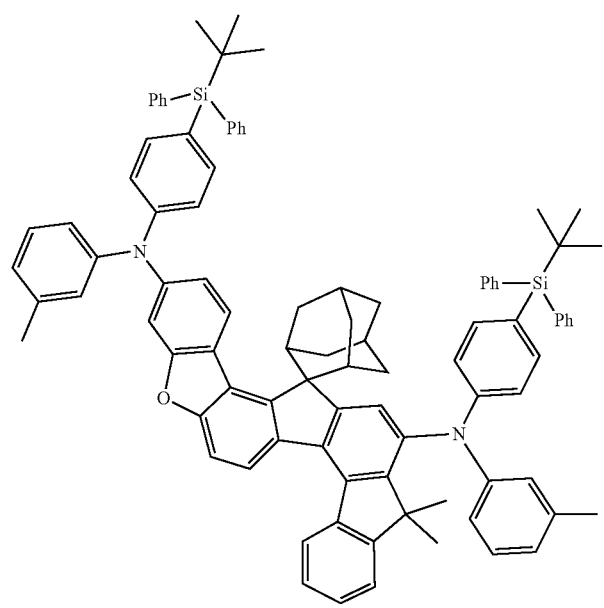
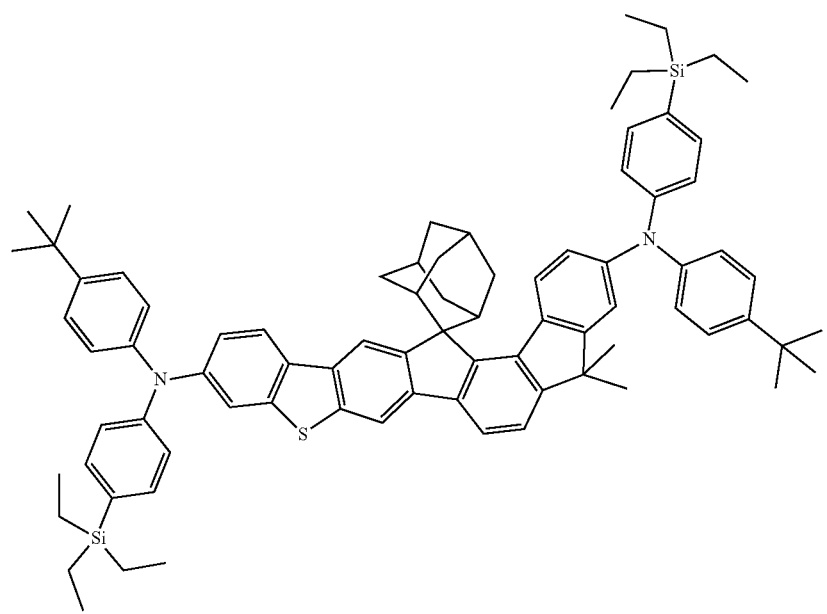

-continued
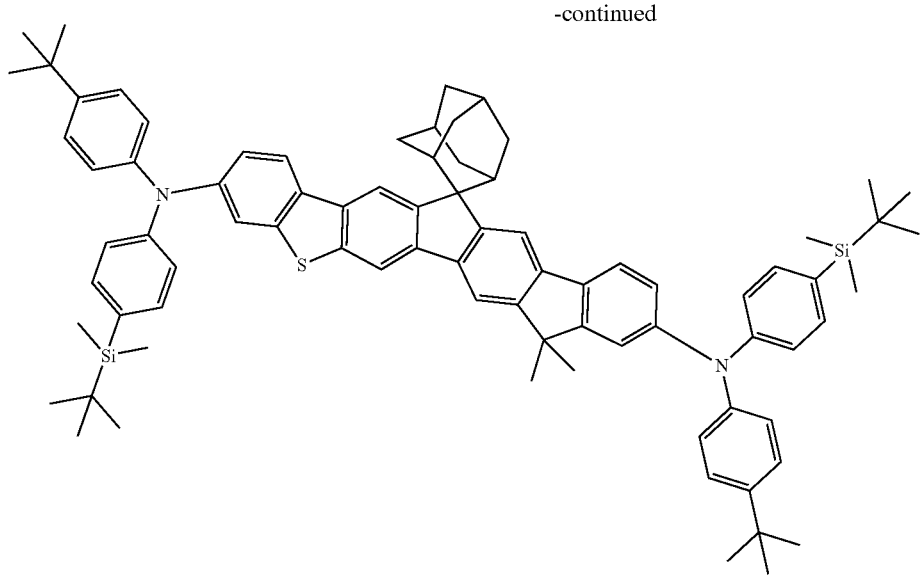
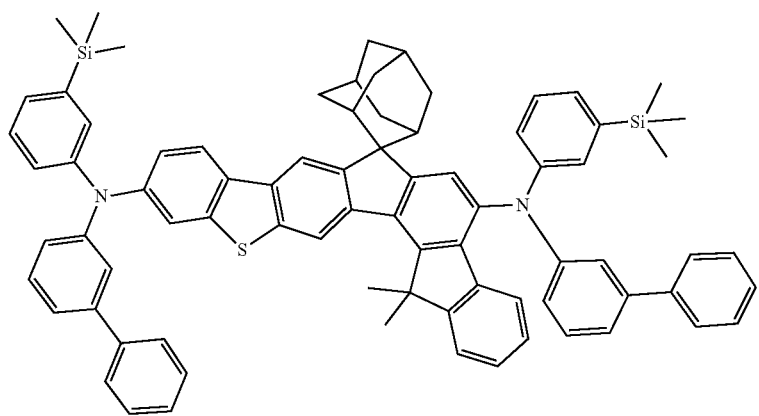
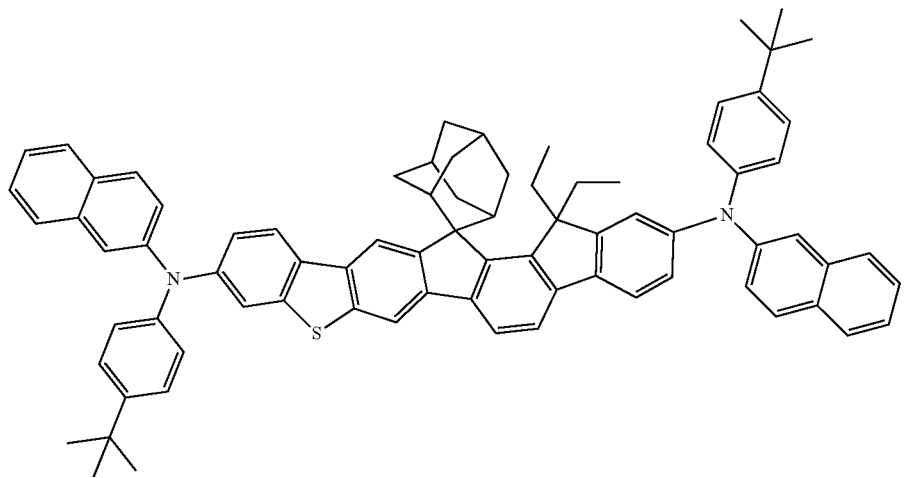

-continued
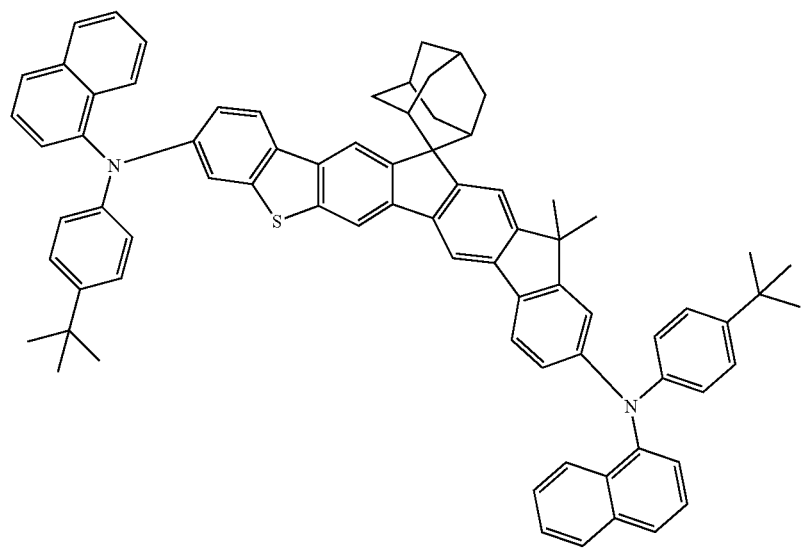
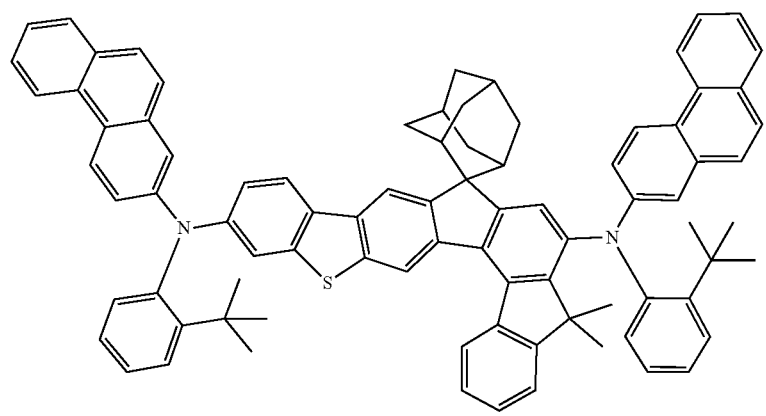
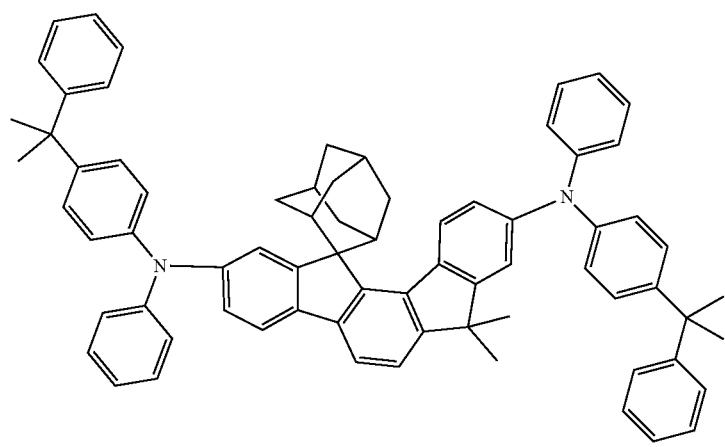

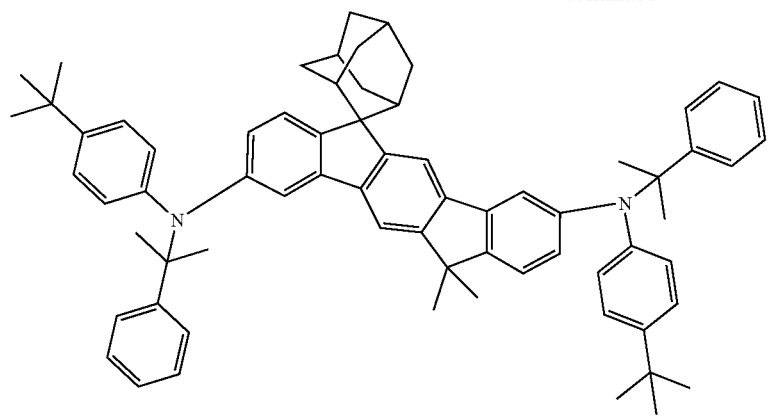
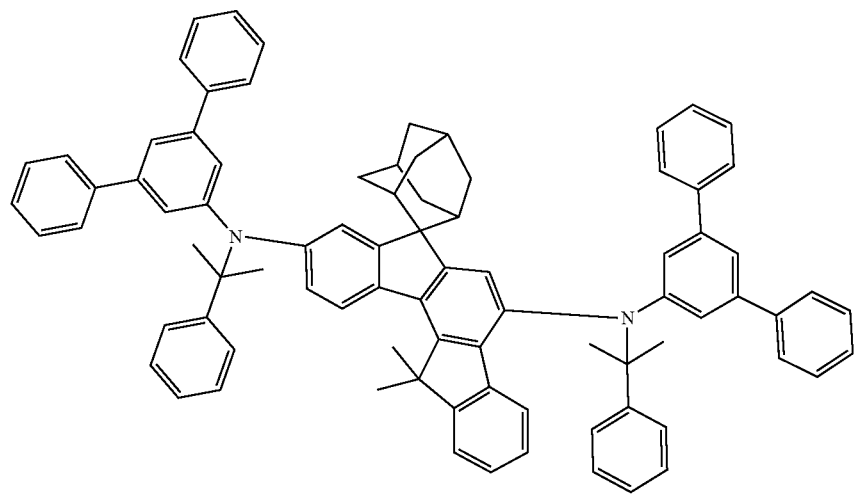
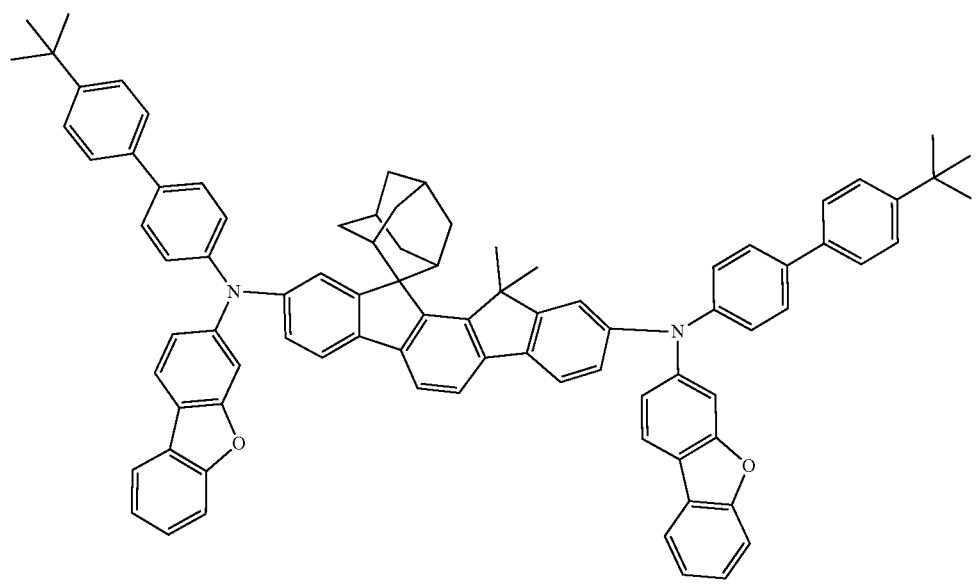

-continued
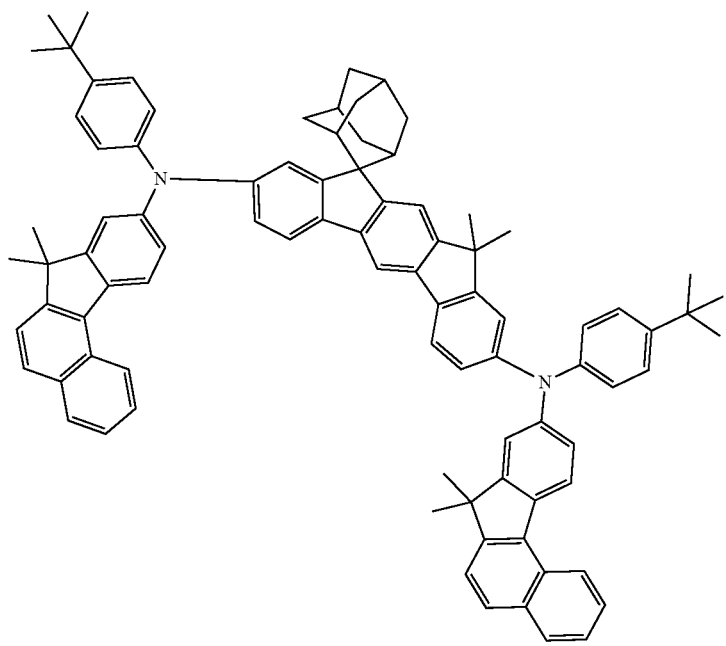

-continued
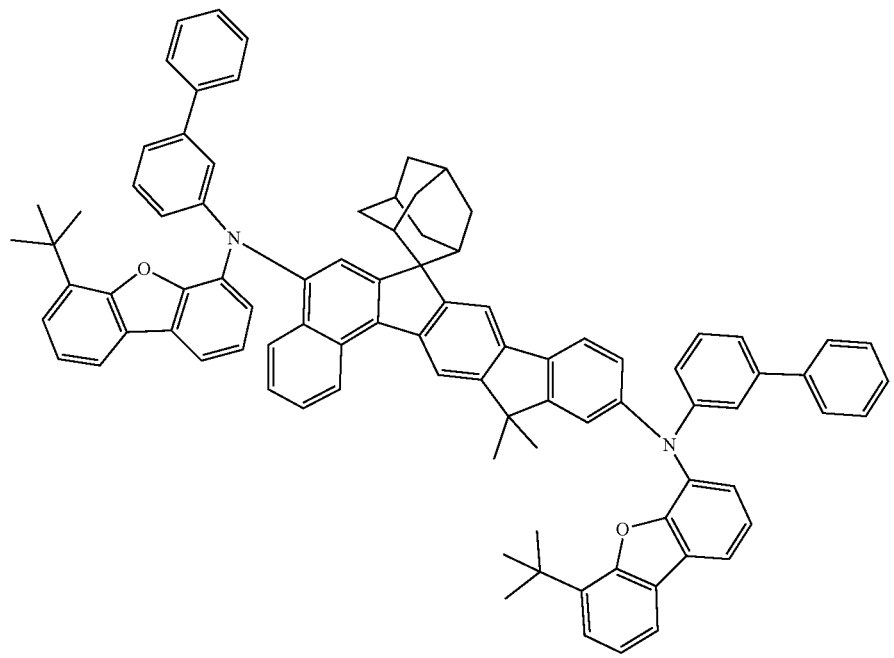
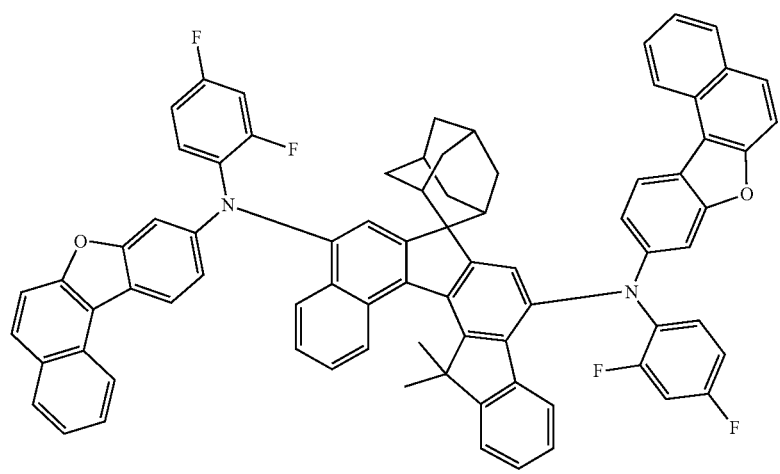
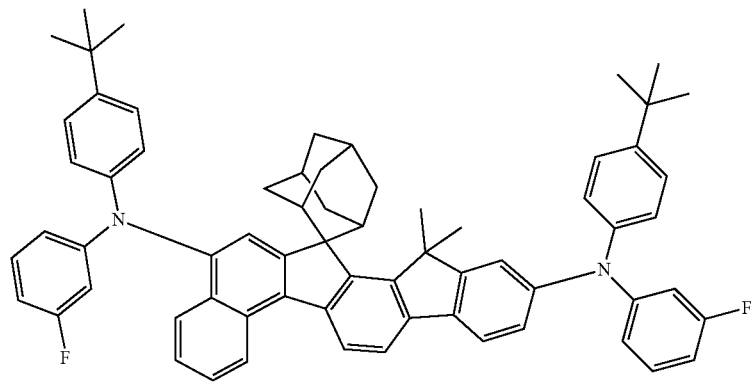

-continued
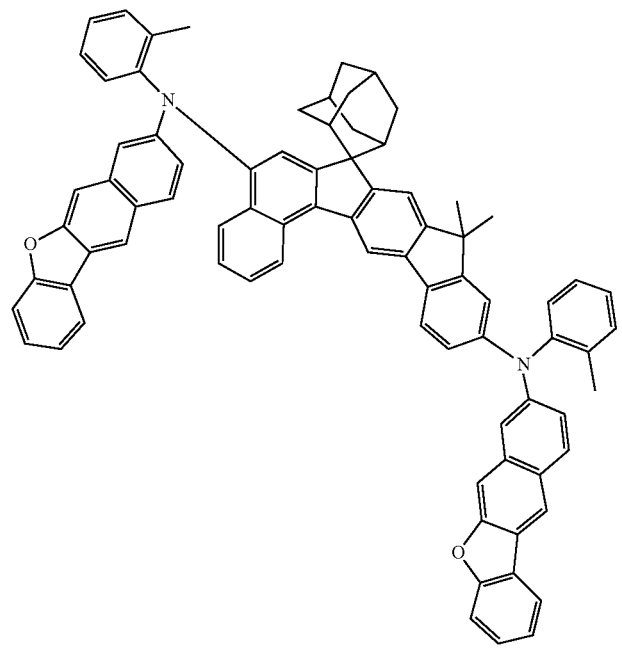
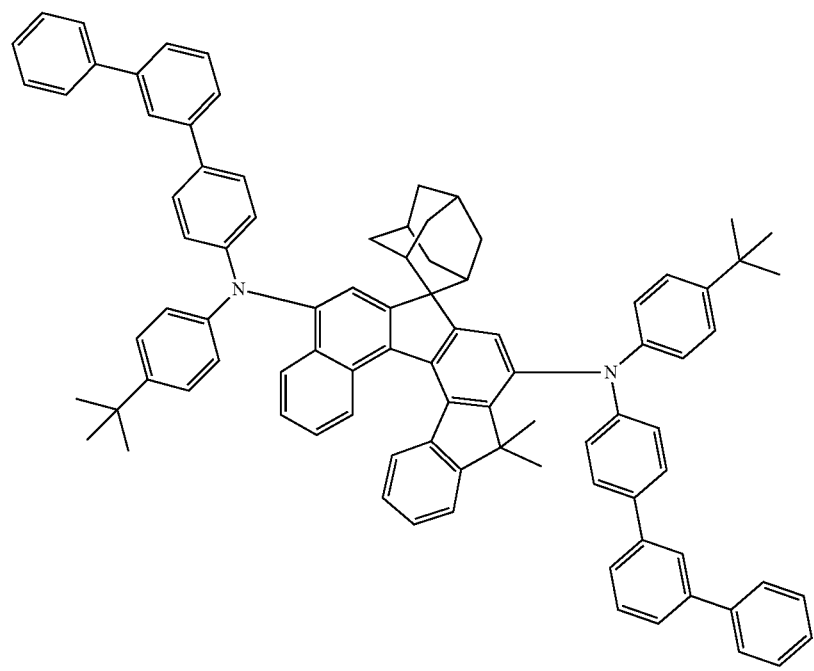
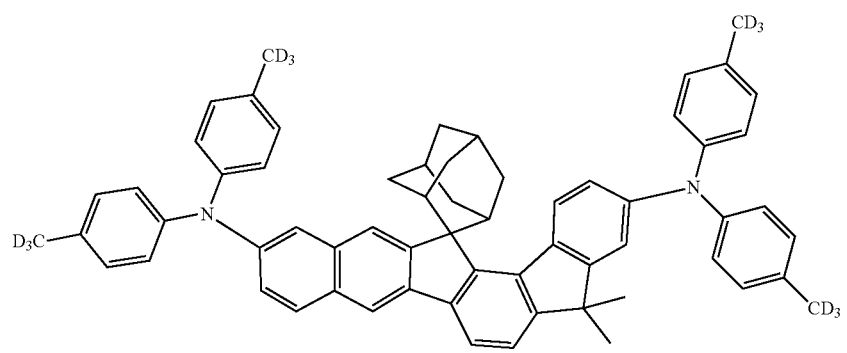

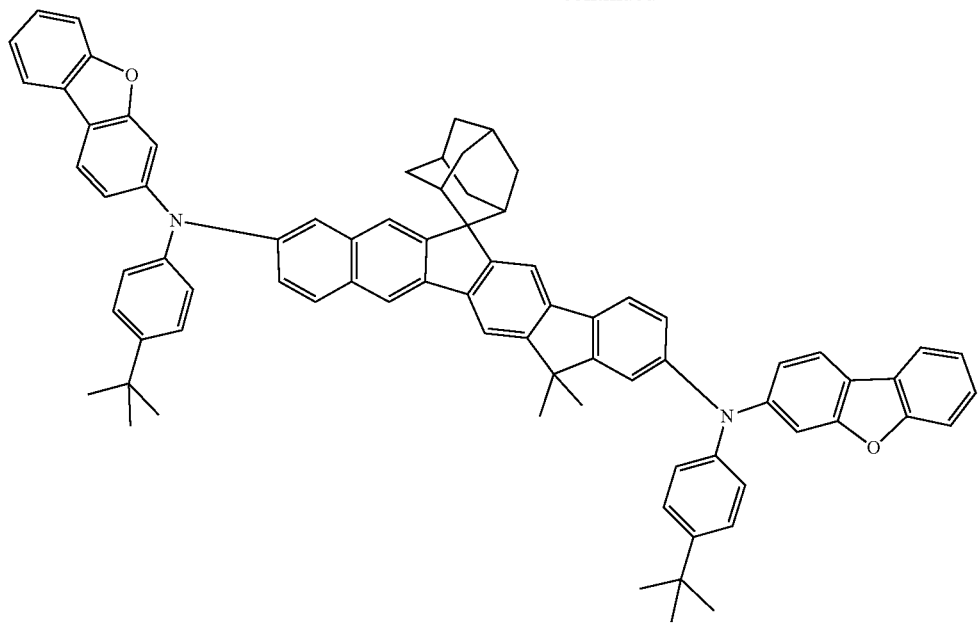
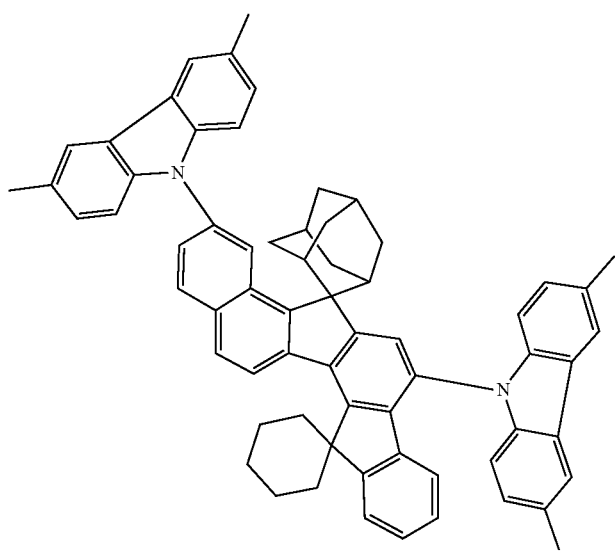
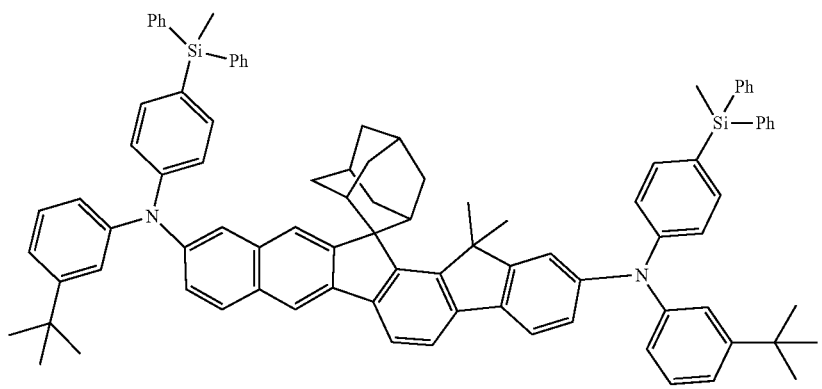

271
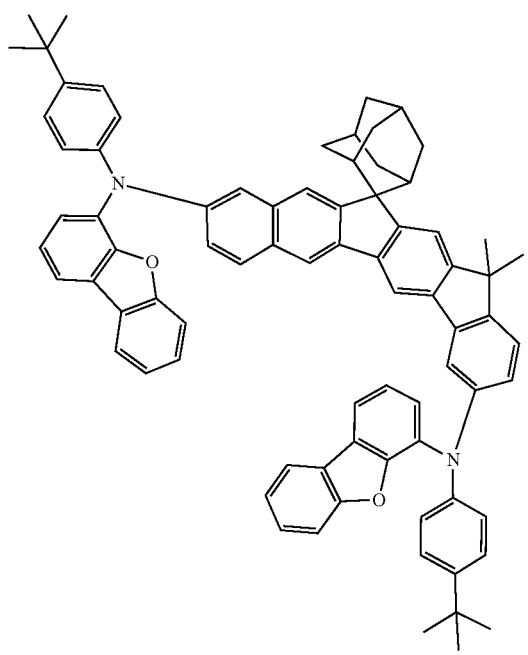
272
-continued
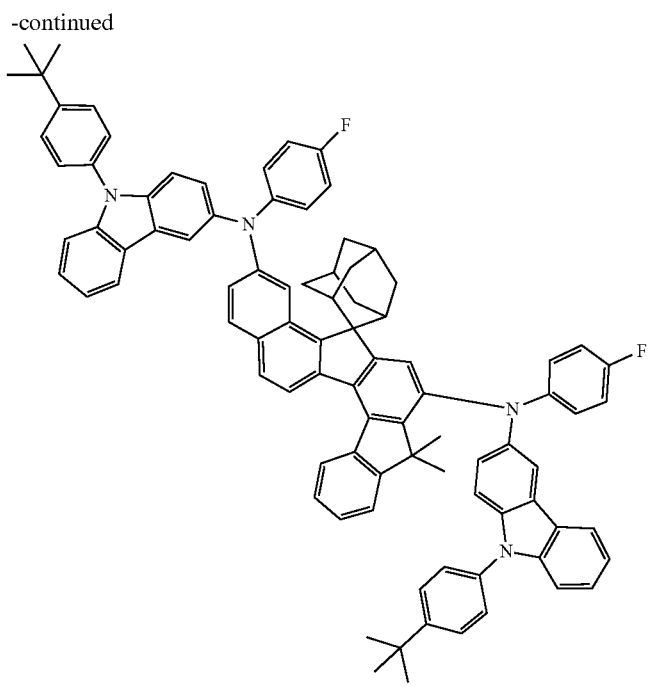
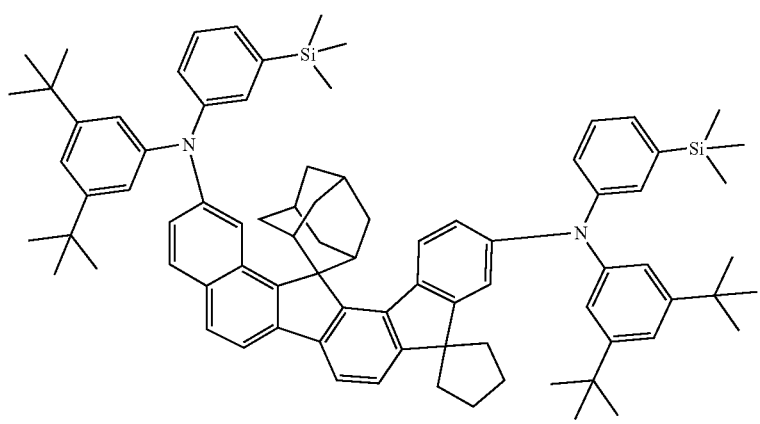
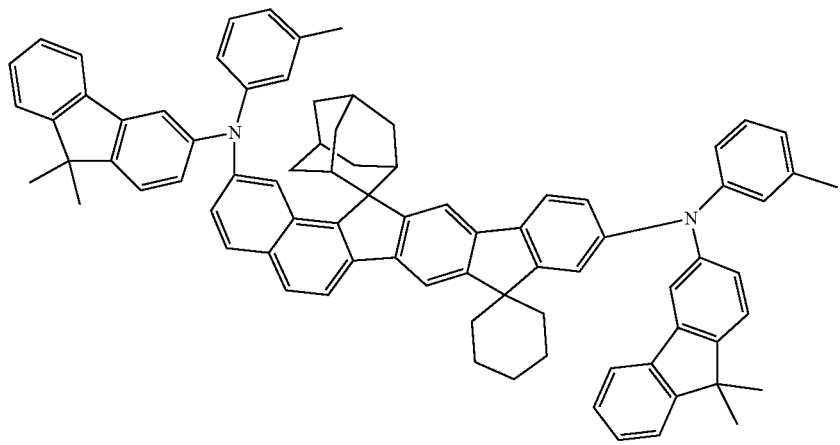

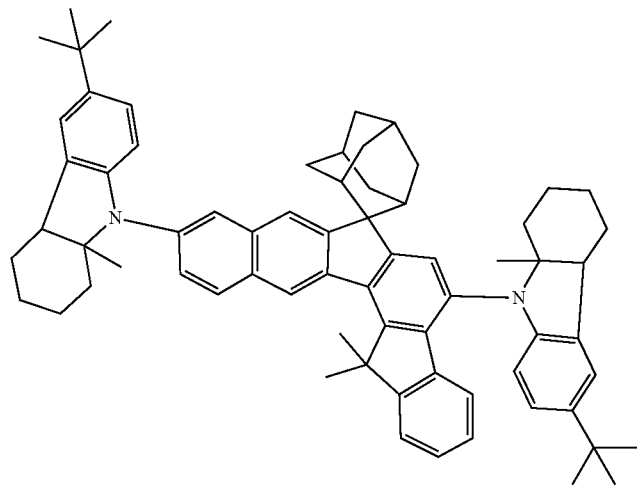
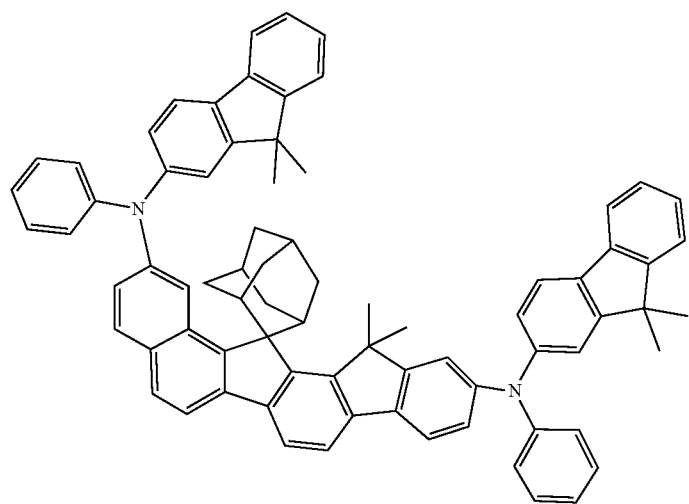
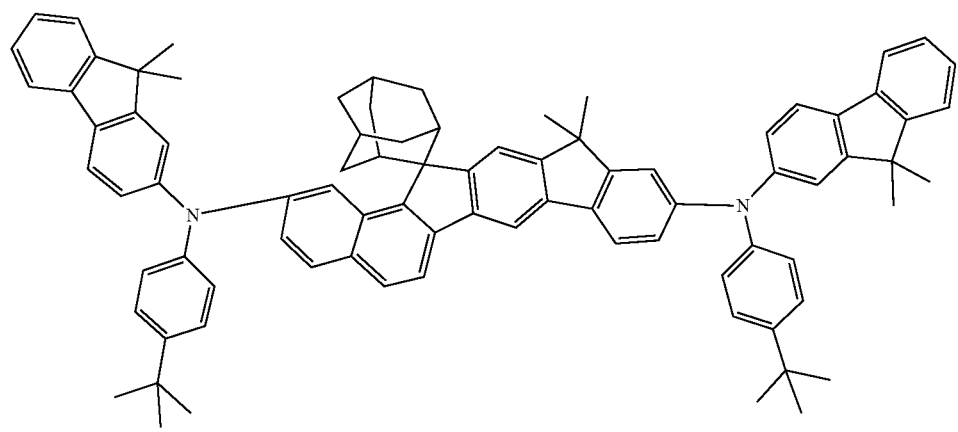

-continued
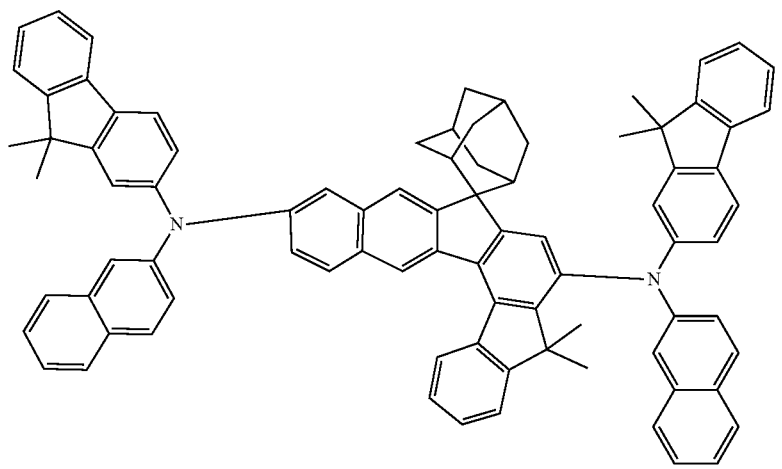
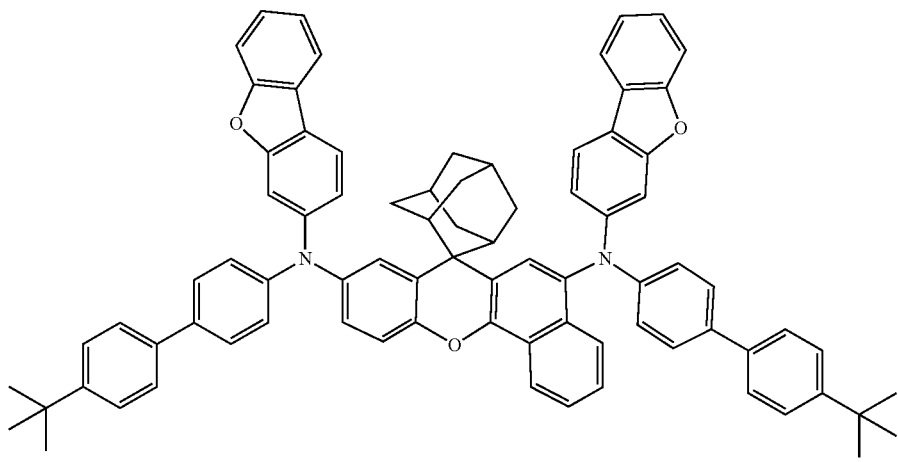
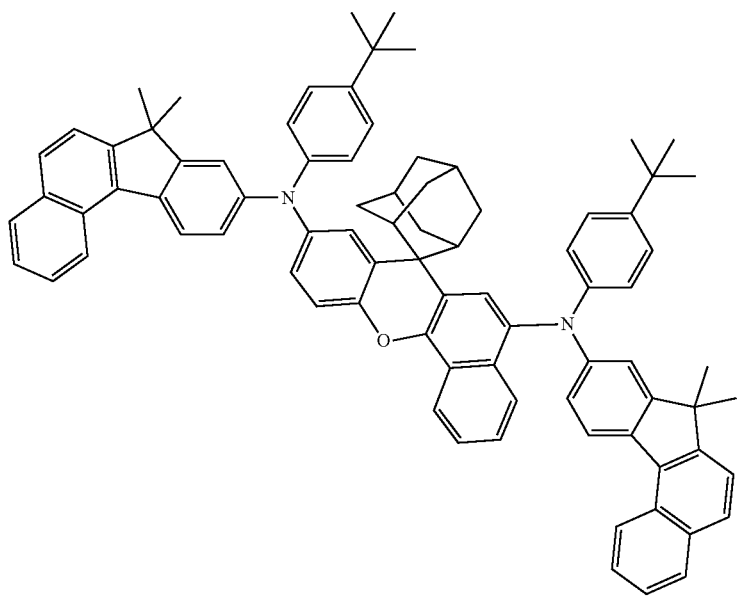

-continued
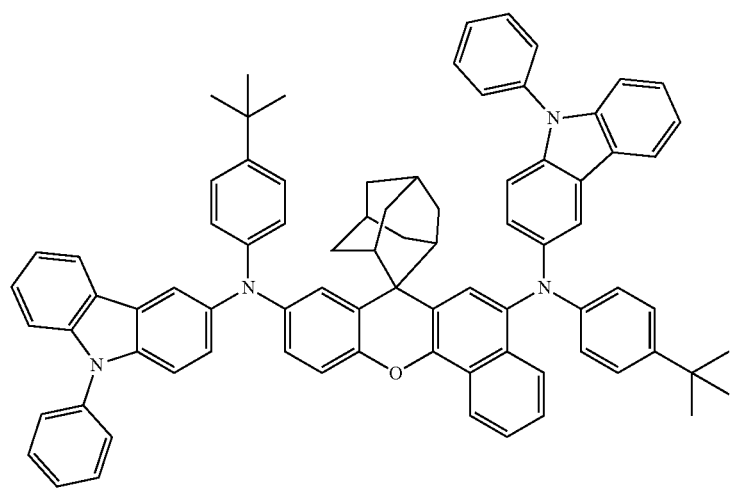
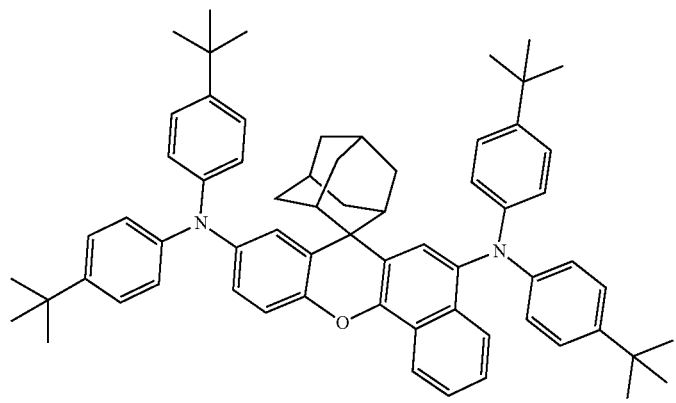
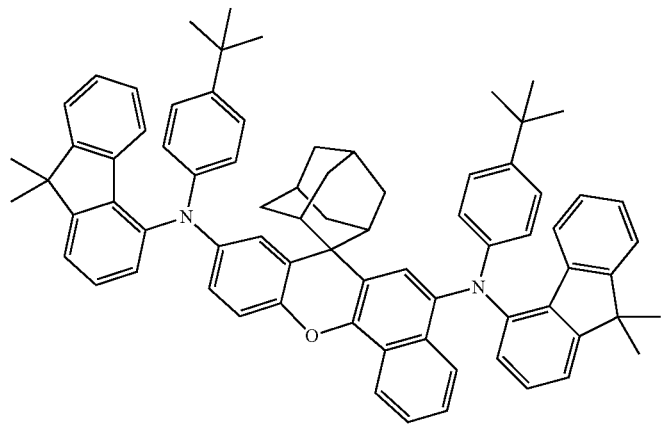
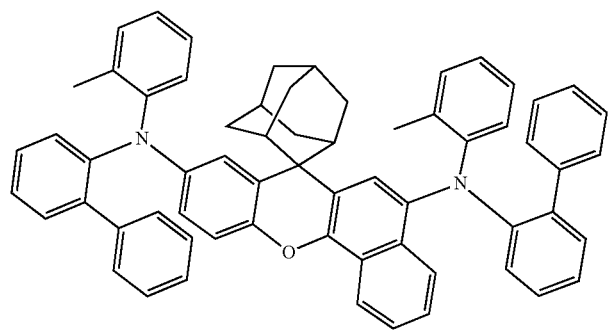

279
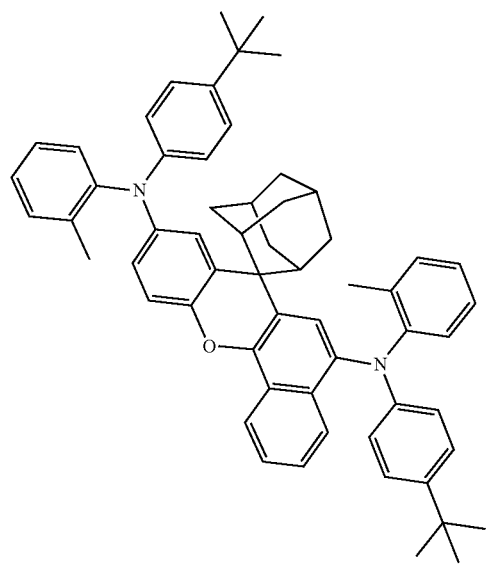
280
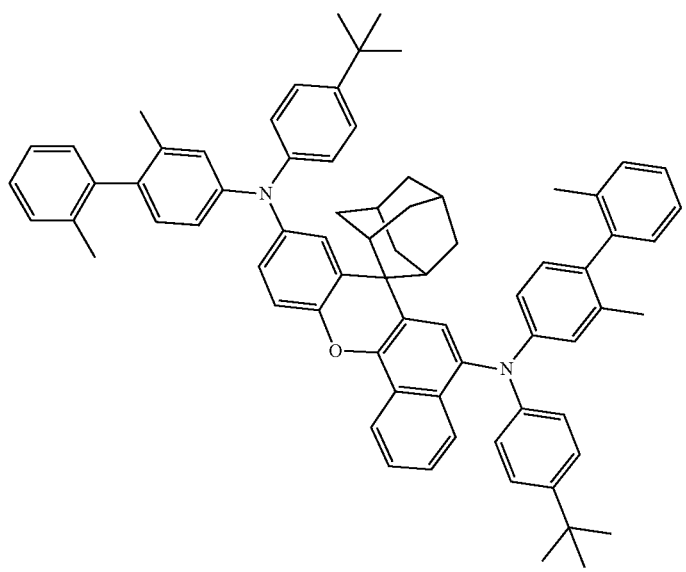
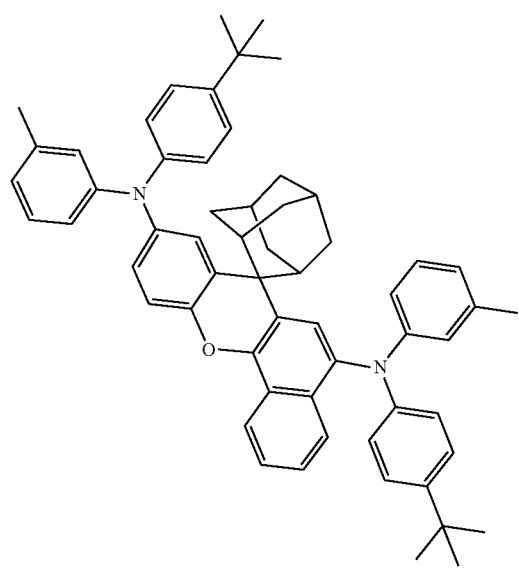

-continued
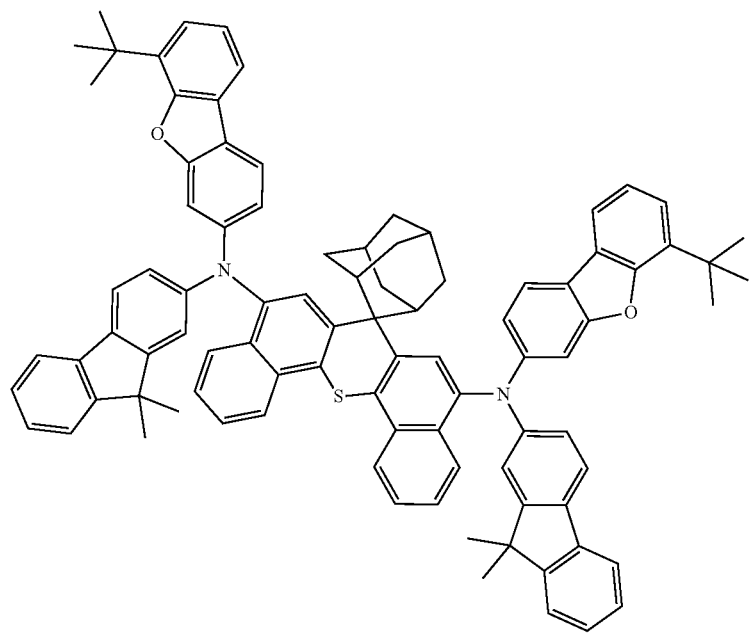

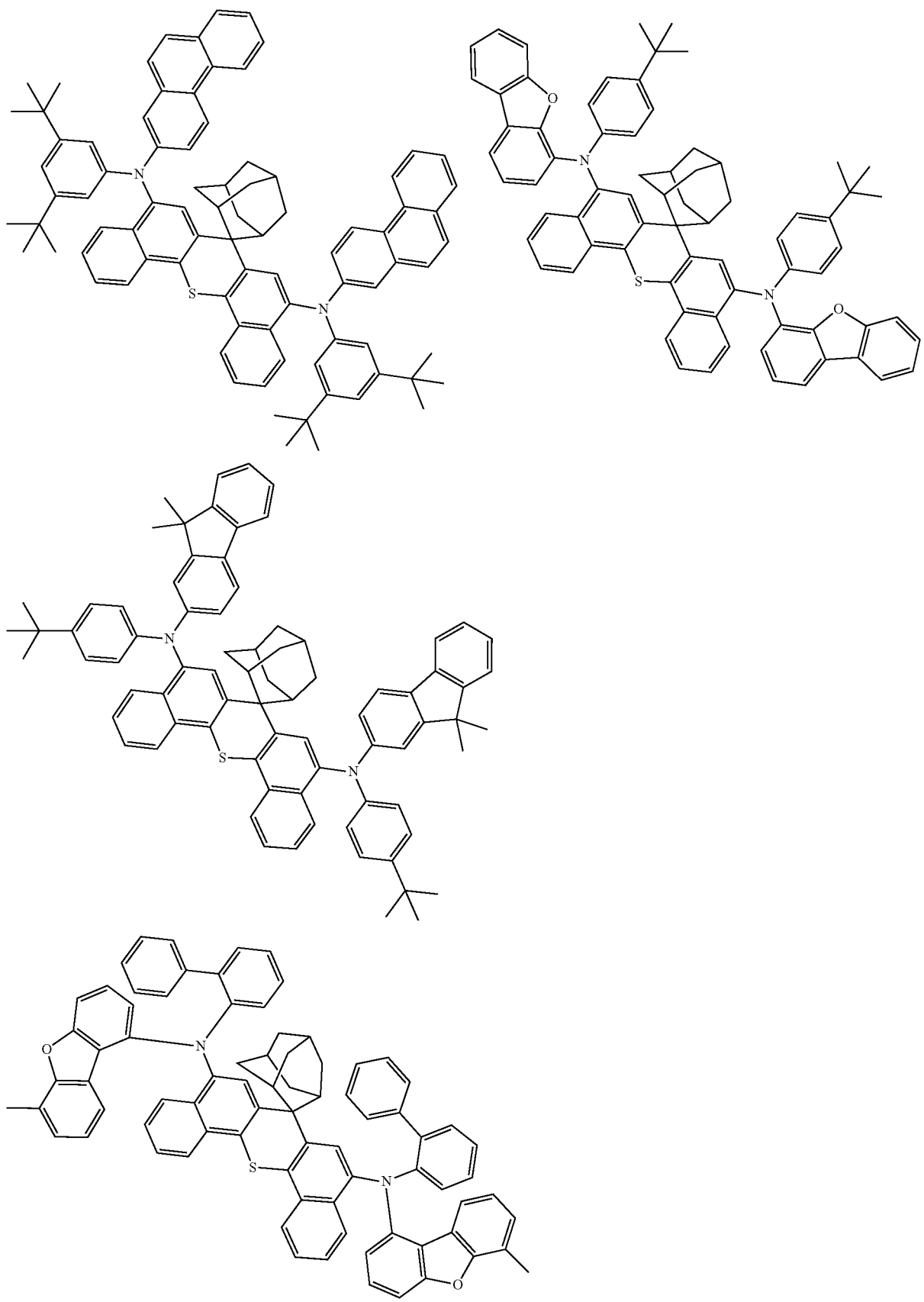

-continued
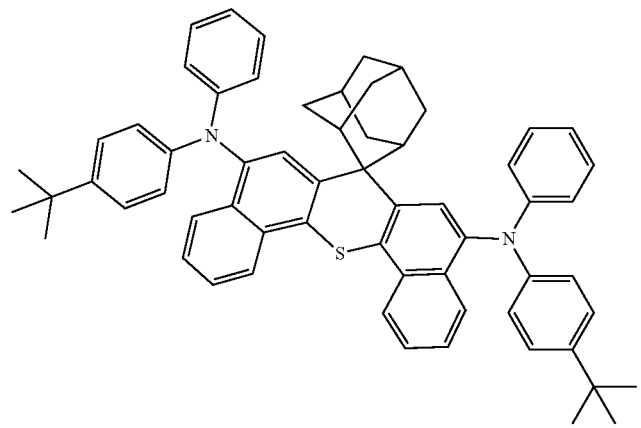
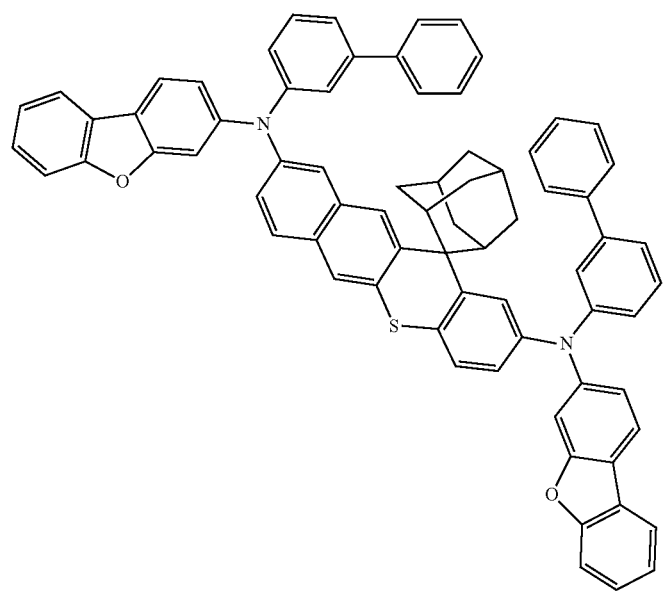
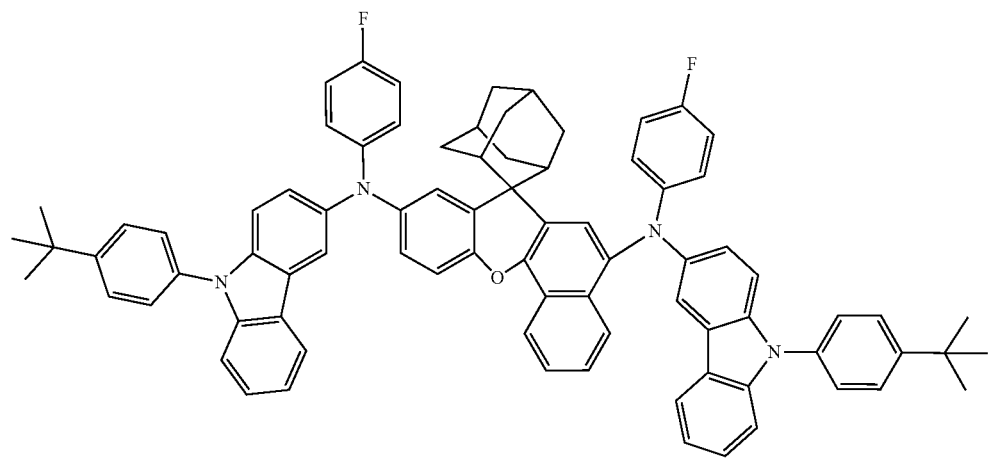

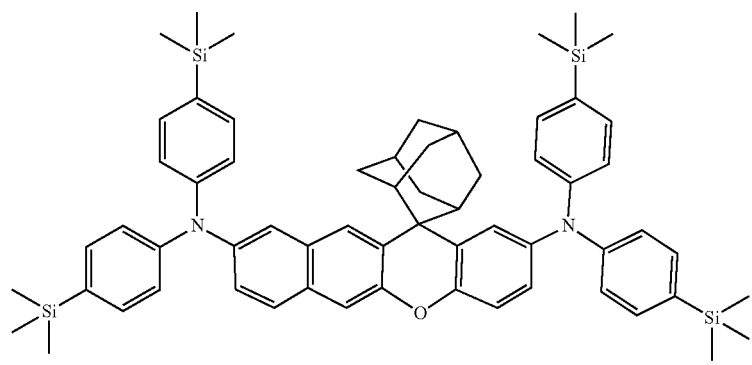
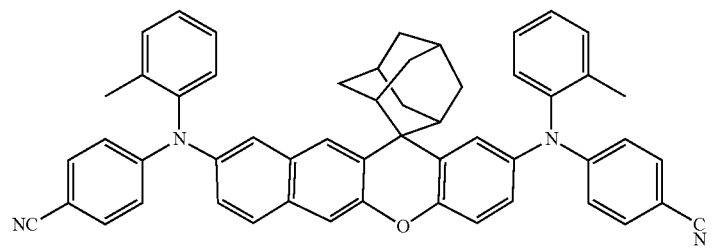
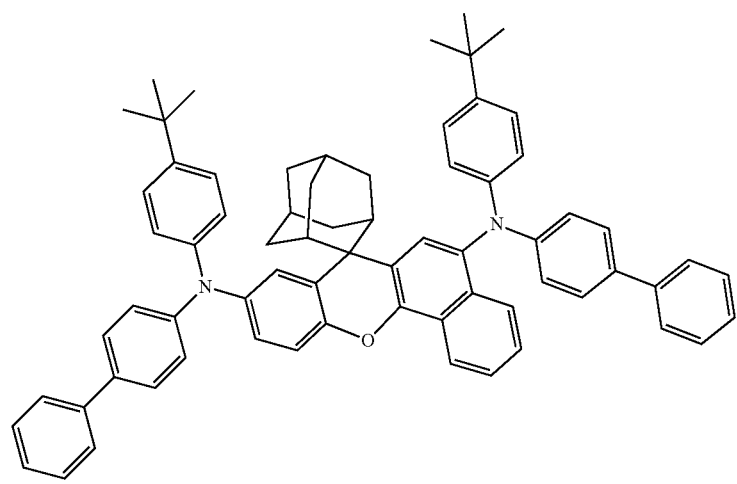
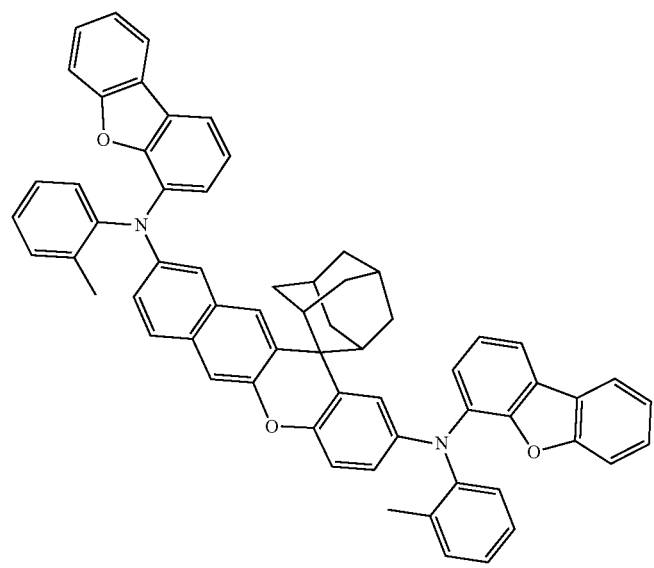

-continued
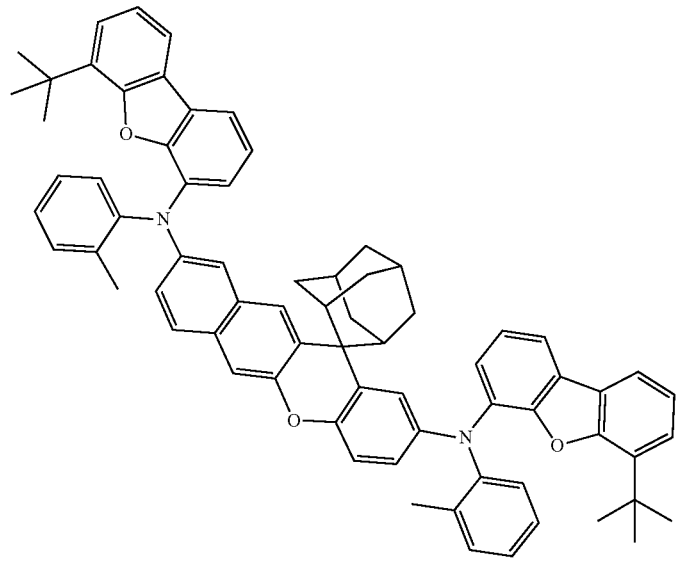
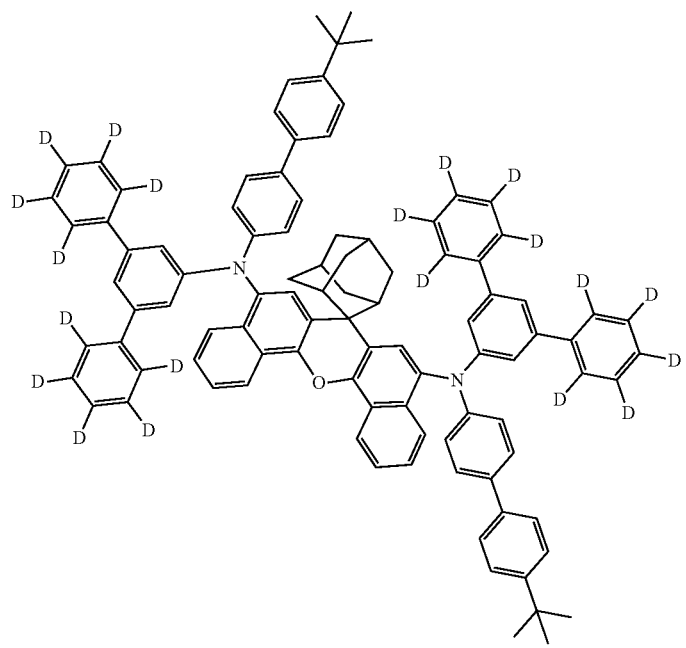
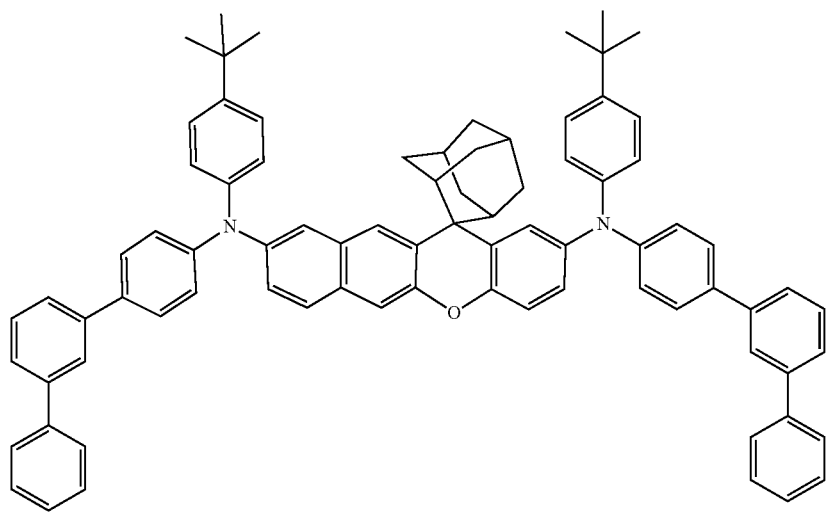

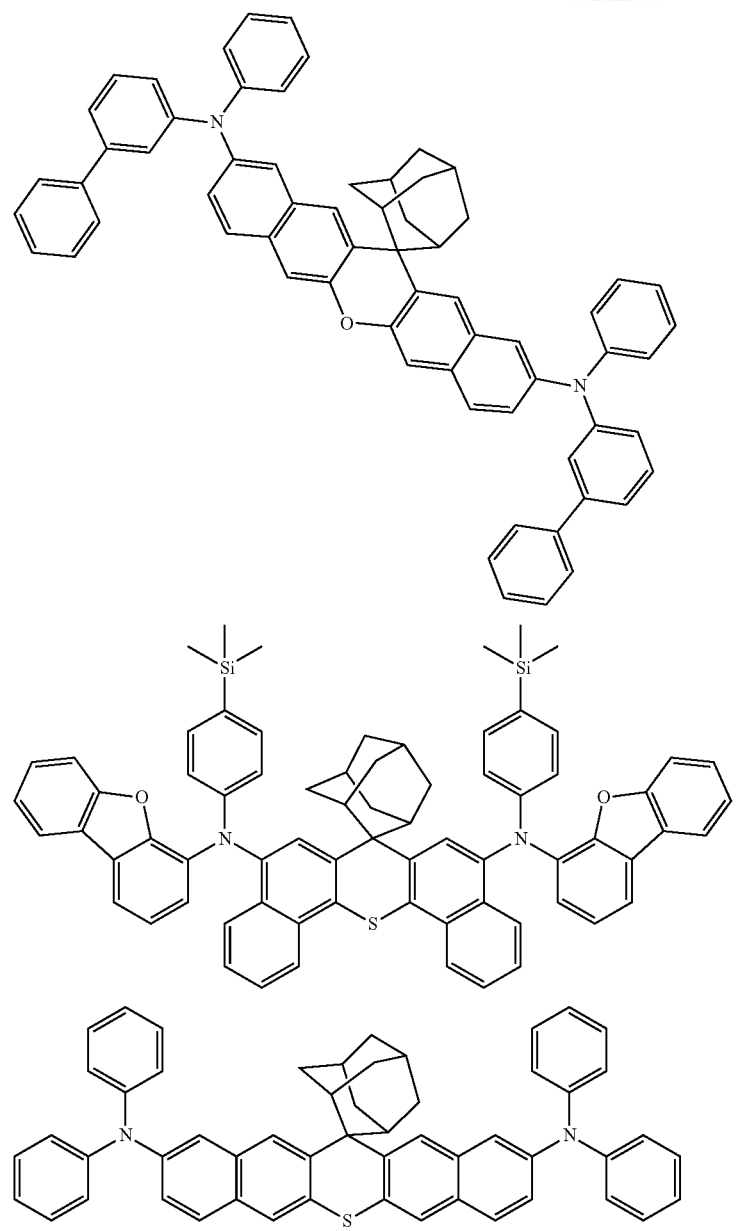
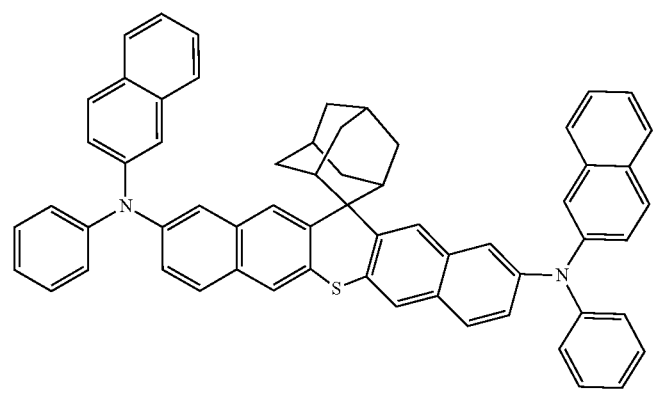

-continued
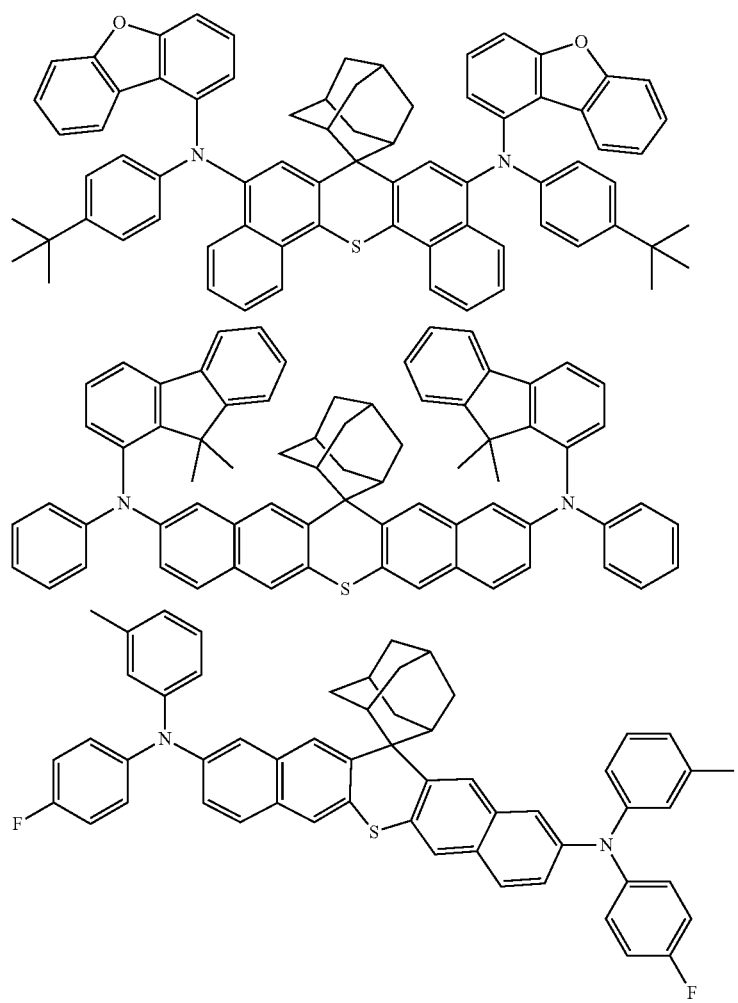
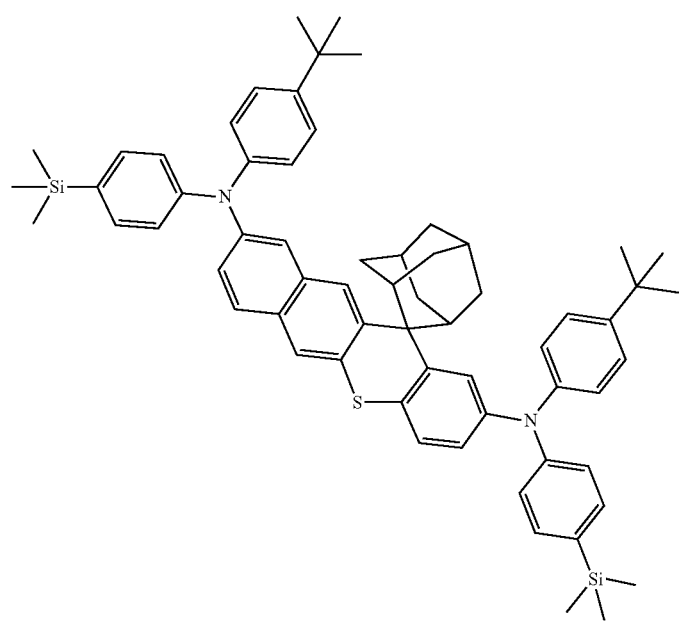

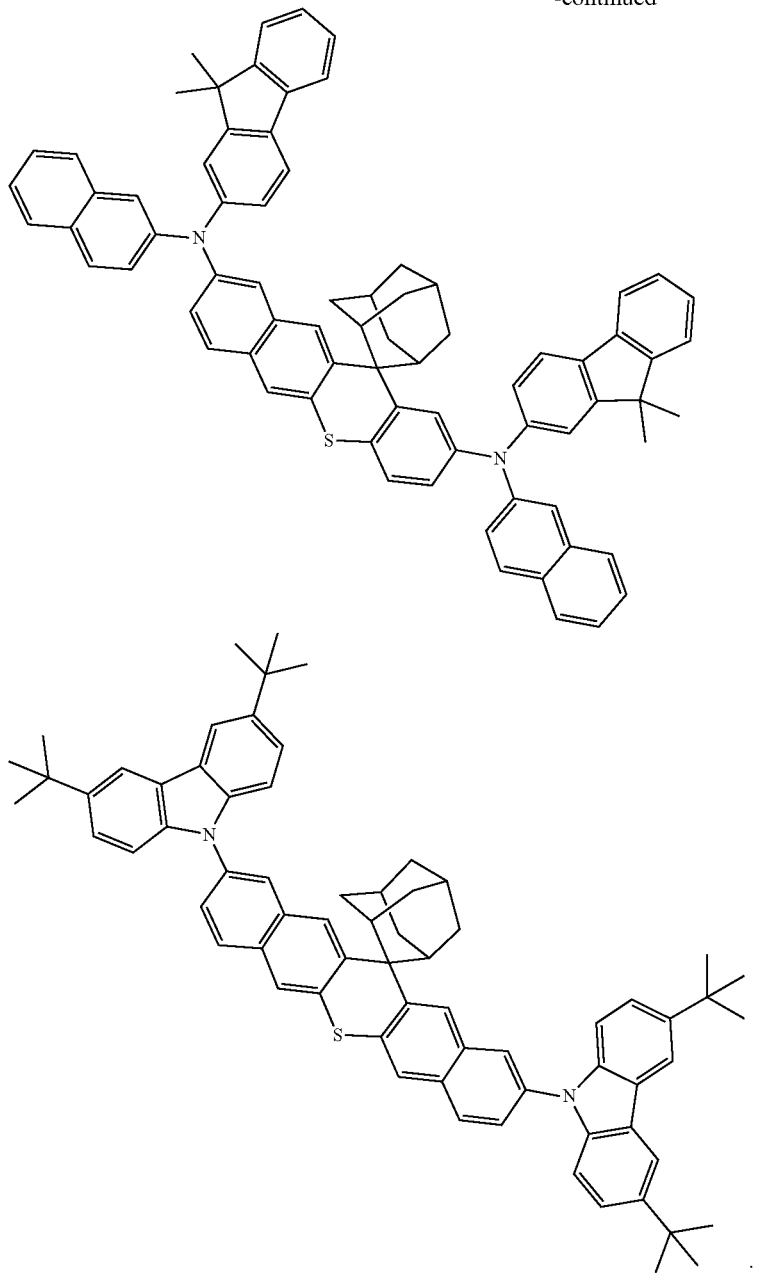
11. An organic light emitting device comprising:
a first electrode;
a second electrode that is opposite to the first electrode; and
one or more organic material layers that are between the first electrode and the second electrode, wherein one or more layers of the organic material layers include the compound of claim 1.
* * * * *

UNITED STATES PATENT AND TRADEMARK OFFICE
CERTIFICATE OF CORRECTION

| | | |
|---|---|---|
| PATENT NO. | : 12,060,372 B2 | Page 1 of 3 |
| APPLICATION NO. | : 17/267560 | |
| DATED | : August 13, 2024 | |
| INVENTOR(S) | : Yoon et al. | |

It is certified that error appears in the above-identified patent and that said Letters Patent is hereby corrected as shown below:

In the Claims

In Claim 8, at Column 143, Lines 8-22, the structure should be:

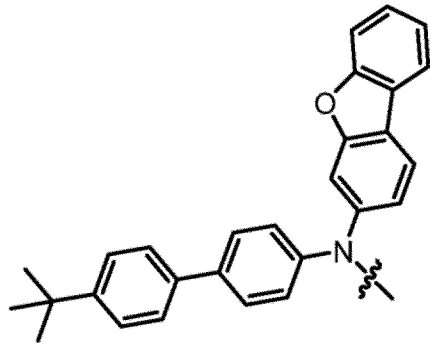

In Claim 8, at Column 143, Lines 39-52, the structure should be:

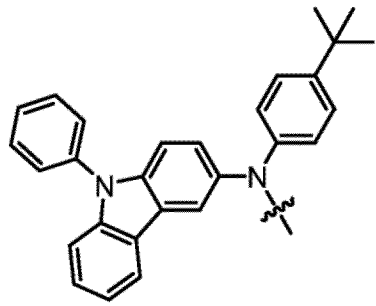

Signed and Sealed this
Twenty-fourth Day of September, 2024

Katherine Kelly Vidal
*Director of the United States Patent and Trademark Office*

In Claim 8, at Column 144, Lines 23-37, the structure should be:
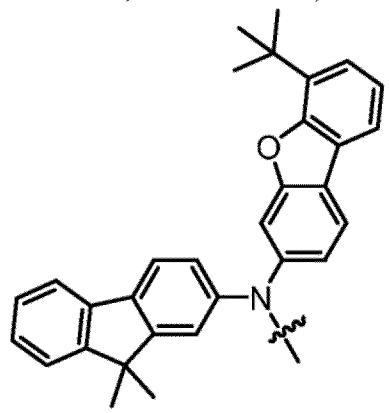
In Claim 8, at Column 145, Lines 2-8, the structure should be:
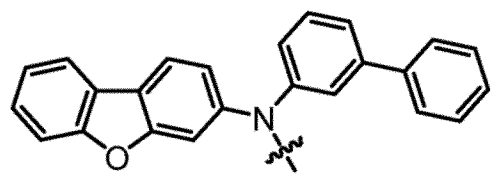
In Claim 10, at Column 161, the structure of the second compound should be:
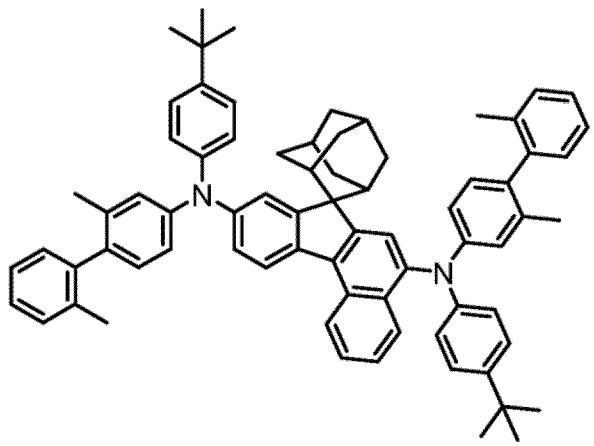

CERTIFICATE OF CORRECTION (continued)
U.S. Pat. No. 12,060,372 B2

In Claim 10, at Column 203, the structure of the second compound should be: